United States Patent
Kastelein et al.

(10) Patent No.: US 12,291,572 B2
(45) Date of Patent: May 6, 2025

(54) IL12 RECEPTOR SYNTHETIC CYTOKINES AND METHODS OF USE

(71) Applicant: Synthekine, Inc., Menlo Park, CA (US)

(72) Inventors: Robert Kastelein, Menlo Park, CA (US); Deepti Rokkam, Menlo Park, CA (US); Patrick J. Lupardus, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

(21) Appl. No.: 18/018,448

(22) PCT Filed: Aug. 5, 2021

(86) PCT No.: PCT/US2021/044855
§ 371 (c)(1),
(2) Date: Jan. 27, 2023

(87) PCT Pub. No.: WO2022/032042
PCT Pub. Date: Feb. 10, 2022

(65) Prior Publication Data
US 2023/0279127 A1   Sep. 7, 2023

Related U.S. Application Data

(60) Provisional application No. 63/135,884, filed on Jan. 11, 2021, provisional application No. 63/078,745, filed on Sep. 15, 2020, provisional application No. 63/061,562, filed on Aug. 5, 2020.

(51) Int. Cl.
| | |
|---|---|
| *C07K 16/28* | (2006.01) |
| *A61K 39/00* | (2006.01) |
| *A61P 37/02* | (2006.01) |
| *C07K 14/715* | (2006.01) |
| *C07K 16/46* | (2006.01) |
| *C07K 19/00* | (2006.01) |
| *C12N 15/63* | (2006.01) |
| *C12N 15/86* | (2006.01) |

(52) U.S. Cl.
CPC .......... *C07K 16/2866* (2013.01); *A61P 37/02* (2018.01); *C07K 14/7155* (2013.01); *C07K 16/2803* (2013.01); *C07K 16/46* (2013.01); *C07K 16/468* (2013.01); *C07K 19/00* (2013.01); *C12N 15/63* (2013.01); *C12N 15/86* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/567* (2013.01); *C07K 2317/569* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 8,258,268 B2 | 9/2012 | Wu et al. | |
| 8,574,573 B2 | 11/2013 | Carballido Herrera et al. | |
| 8,921,528 B2 | 12/2014 | Holt et al. | |
| 8,975,382 B2 | 3/2015 | Revets et al. | |
| 10,927,186 B2 | 2/2021 | Roobrouck et al. | |
| 11,859,001 B2 * | 1/2024 | Kastelein | A61P 37/02 |
| 12,012,457 B1 | 6/2024 | Kastelein et al. | |
| 2006/0024295 A1 | 2/2006 | Brunetta | |
| 2010/0297127 A1 | 11/2010 | Ghilardi et al. | |
| 2011/0028695 A1 | 2/2011 | Revets et al. | |
| 2011/0053865 A1 | 3/2011 | Saunders et al. | |
| 2011/0142831 A1 | 6/2011 | Cua et al. | |
| 2012/0082681 A1 | 4/2012 | Carballido et al. | |
| 2012/0201746 A1 | 8/2012 | Liu et al. | |
| 2012/0316324 A1 | 12/2012 | Adams et al. | |
| 2014/0065142 A1 | 3/2014 | Roschke et al. | |
| 2014/0099708 A1 | 4/2014 | Carballido Herrera et al. | |
| 2014/0170154 A1 | 6/2014 | Presta | |
| 2015/0079088 A1 | 3/2015 | Lowman et al. | |
| 2016/0046730 A1 | 2/2016 | Ghayur et al. | |
| 2016/0251440 A1 | 9/2016 | Roobrouck et al. | |
| 2017/0106051 A1 | 4/2017 | Oh et al. | |
| 2017/0298149 A1 | 10/2017 | Baeuerle et al. | |
| 2018/0362655 A1 | 12/2018 | Wang et al. | |
| 2019/0315864 A1 | 10/2019 | Xu et al. | |
| 2020/0157237 A1 | 5/2020 | Regev et al. | |
| 2023/0272093 A1 * | 8/2023 | Kastelein | C12N 15/63 |
| | | | 530/388.22 |

FOREIGN PATENT DOCUMENTS

| | | |
|---|---|---|
| CN | 103396482 A | 11/2013 |
| CN | 111018985 A | 6/2019 |

(Continued)

OTHER PUBLICATIONS

International Search Report in PCT/US2021/044855, mailed Dec. 16, 2021, 11 pages.
Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.
"PE Anti-Mouse IL-23R Antibody", BioLegend, Available Online at: https://biolegend.com/en-us/global-elements/pdf-popup/pe-anti-mouse-il-23r-antibody-13084?filename=PE%20anti-mouse%20IL-23R%20Antibody.pdf&pdfoen=true, Mar. 28, 2016, 2 pages.
"UniProtKB-A0A066RQT8", Uncharacterized Protein, Available Online at: https://www.uniprot.org/uniprot/A0A066RQT8, Sep. 3, 2014, 3 pages.
U.S. Appl. No. 18/017,065, Non-Final Office Action, Mailed On Sep. 19, 2023, 8 pages.

(Continued)

*Primary Examiner* — Marianne P Allen
(74) *Attorney, Agent, or Firm* — Kilpatrick Townsend & Stockton LLP

(57) ABSTRACT

Provided herein are IL12R binding molecules that bind to IL12Rb1 and IL12Rb2 and comprise an anti-IL12Rb2 sdAb and an anti-IL12Rb2 $V_HH$ antibody.

12 Claims, 6 Drawing Sheets

Specification includes a Sequence Listing.

(56) References Cited

FOREIGN PATENT DOCUMENTS

| WO | 2008/011081 | A2 | | 1/2008 |
|---|---|---|---|---|
| WO | 2009/068631 | A1 | | 6/2009 |
| WO | 2011051327 | A2 | | 5/2011 |
| WO | 2013/006544 | A1 | | 1/2013 |
| WO | 2013/059299 | A1 | | 4/2013 |
| WO | 2016/097313 | A1 | | 6/2016 |
| WO | 2017/198212 | A1 | | 11/2017 |
| WO | 2019/129221 | A1 | | 7/2019 |
| WO | 2020052543 | A1 | | 3/2020 |
| WO | 2020/144164 | A1 | | 7/2020 |
| WO | 2020/187711 | A1 | | 9/2020 |
| WO | WO 2022/031929 | | * | 2/2022 |
| WO | WO 2022/031942 | | * | 2/2022 |
| WO | WO 2022/032042 | | * | 2/2022 |
| WO | WO 2022/055641 | | * | 3/2022 |

OTHER PUBLICATIONS

U.S. Appl. No. 18/017,065, Notice of Allowance, Mailed On Feb. 7, 2024, 8 pages.
U.S. Appl. No. 18/017,282, Notice of Allowance, Mailed On Aug. 24, 2023, 14 pages.
U.S. Appl. No. 18/018,444, Non-Final Office Action, Mailed On Feb. 1, 2024, 14 pages.
Franke et al., "Human and Murine Interleukin 23 Receptors are Novel Substrates for a Disintegrin and Metalloproteases ADAM10 and ADAM17", The Journal of Biological Chemistry, vol. 291, No. 20, May 13, 2016, pp. 10551-10561.
Application No. PCT/US2021/044674, International Preliminary Report on Patentability, Mailed On Feb. 16, 2023, 8 pages.
Application No. PCT/US2021/044674, International Search Report and Written Opinion, Mailed On Jan. 19, 2022, 12 pages.
PCT/US2021/044674, "Invitation To Pay Additional Fees And, Where Applicable, Protest Fee", Nov. 12, 2021, 2 pages.
Application No. PCT/US2021/044698, International Preliminary Report on Patentability, Mailed On Feb. 16, 2023, 9 pages.
Application No. PCT/US2021/044698, International Search Report and Written Opinion, Mailed On Feb. 1, 2022, 13 pages.
PCT/US2021/044698, "Invitation to Pay Additional Fees And, Where Applicable Protest Fee", Nov. 9, 2021, 2 pages.
Application No. PCT/US2021/044835, International Search Report and Written Opinion, Mailed On Feb. 8, 2022, 17 pages.
PCT/US2021/044835, "Invitation to Pay Additional Fees and, Where Applicable, Protest Fee", Nov. 16, 2021, 3 pages.
Application No. PCT/US2021/044850, International Preliminary Report on Patentability, Mailed On Feb. 16, 2023, 6 pages.
Application No. PCT/US2021/044850, International Search Report and Written Opinion, Mailed On Jan. 6, 2022, 9 pages.
Wilton et al., "sdAb-DB: The Single Domain Antibody Database", American Chemical Society Synthetic Biology, vol. 7, No. 11, Nov. 16, 2018, pp. 2480-2484.
U.S. Appl. No. 18/006,528, Notice of Allowance, Mailed On Dec. 20, 2023, 7 pages.
U.S. Appl. No. 18/017,836, Non-Final Office Action, Mailed On May 10, 2024, 11 pages.
U.S. Appl. No. 18/017,838, Non-Final Office Action, Mailed On Jul. 9, 2024, 13 pages.
U.S. Appl. No. 18/018,444, Final Office Action, Mailed On Jun. 14, 2024, 8 pages.
U.S. Appl. No. 18/514,330, Non-Final Office Action, Mailed On Aug. 7, 2024, 15 pages.
Hoey et al., "The Expanded Family of Class II Ctokines that Share the IL-10 Receptor-2 (IL-10R2) Chain", Experimental Biology and Medicine (Maywood), vol. 244, No. 17, Dec. 2019, pp. 1568-1576.

* cited by examiner

```
                              SEQUENCE LISTING

<160> NUMBER OF SEQ ID NOS: 432

<210> SEQ ID NO 1
<211> LENGTH: 662
<212> TYPE: PRT
<213> ORGANISM: Homo sapiens

<400> SEQUENCE: 1

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110
```

Leu Trp Val Glu Ser Trp Ala Arg Asn Gln Thr Glu Lys Ser Pro Glu
            115                 120                 125

Val Thr Leu Gln Leu Tyr Asn Ser Val Lys Tyr Glu Pro Pro Leu Gly
        130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser

```
            530                 535                 540
Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
                580                 585                 590

Pro Gly Gly Lys Glu Thr Trp Gln Trp Ile Asn Pro Val Asp Phe Gln
                595                 600                 605

Glu Glu Ala Ser Leu Gln Glu Ala Leu Val Val Glu Met Ser Trp Asp
                610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
                660

<210> SEQ ID NO 2
<211> LENGTH: 522
<212> TYPE: PRT
<213> ORGANISM: Homo sapiens

<400> SEQUENCE: 2

Cys Arg Thr Ser Glu Cys Cys Phe Gln Asp Pro Tyr Pro Asp Ala
1               5                   10                  15

Asp Ser Gly Ser Ala Ser Gly Pro Arg Asp Leu Arg Cys Tyr Arg Ile
                20                  25                  30

Ser Ser Asp Arg Tyr Glu Cys Ser Trp Gln Tyr Glu Gly Pro Thr Ala
            35                  40                  45

Gly Val Ser His Phe Leu Arg Cys Cys Leu Ser Ser Gly Arg Cys Cys
        50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
                100                 105                 110

Ser Val Lys Tyr Glu Pro Pro Leu Gly Asp Ile Lys Val Ser Lys Leu
            115                 120                 125

Ala Gly Gln Leu Arg Met Glu Trp Glu Thr Pro Asp Asn Gln Val Gly
        130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Thr Glu Ser Cys Leu Cys Pro
                165                 170                 175

Leu Glu Met Asn Val Ala Gln Glu Phe Gln Leu Arg Arg Arg Gln Leu
                180                 185                 190

Gly Ser Gln Gly Ser Ser Trp Ser Lys Trp Ser Ser Pro Val Cys Val
            195                 200                 205

Pro Pro Glu Asn Pro Pro Gln Pro Gln Val Arg Phe Ser Val Glu Gln
        210                 215                 220

Leu Gly Gln Asp Gly Arg Arg Arg Leu Thr Leu Lys Glu Gln Pro Thr
225                 230                 235                 240
```

-continued

```
Gln Leu Glu Leu Pro Glu Gly Cys Gln Gly Leu Ala Pro Gly Thr Glu
            245                 250                 255

Val Thr Tyr Arg Leu Gln Leu His Met Leu Ser Cys Pro Cys Lys Ala
        260                 265                 270

Lys Ala Thr Arg Thr Leu His Leu Gly Lys Met Pro Tyr Leu Ser Gly
    275                 280                 285

Ala Ala Tyr Asn Val Ala Val Ile Ser Ser Asn Gln Phe Gly Pro Gly
290                 295                 300

Leu Asn Gln Thr Trp His Ile Pro Ala Asp Thr His Thr Glu Pro Val
305                 310                 315                 320

Ala Leu Asn Ile Ser Val Gly Thr Asn Gly Thr Thr Met Tyr Trp Pro
                325                 330                 335

Ala Arg Ala Gln Ser Met Thr Tyr Cys Ile Glu Trp Gln Pro Val Gly
            340                 345                 350

Gln Asp Gly Gly Leu Ala Thr Cys Ser Leu Thr Ala Pro Gln Asp Pro
        355                 360                 365

Asp Pro Ala Gly Met Ala Thr Tyr Ser Trp Ser Arg Glu Ser Gly Ala
    370                 375                 380

Met Gly Gln Glu Lys Cys Tyr Tyr Ile Thr Ile Phe Ala Ser Ala His
385                 390                 395                 400

Pro Glu Lys Leu Thr Leu Trp Ser Thr Val Leu Ser Thr Tyr His Phe
                405                 410                 415

Gly Gly Asn Ala Ser Ala Ala Gly Thr Pro His His Val Ser Val Lys
            420                 425                 430

Asn His Ser Leu Asp Ser Val Ser Val Asp Trp Ala Pro Ser Leu Leu
        435                 440                 445

Ser Thr Cys Pro Gly Val Leu Lys Glu Tyr Val Val Arg Cys Arg Asp
    450                 455                 460

Glu Asp Ser Lys Gln Val Ser Glu His Pro Val Gln Pro Thr Glu Thr
465                 470                 475                 480

Gln Val Thr Leu Ser Gly Leu Arg Ala Gly Val Ala Tyr Thr Val Gln
                485                 490                 495

Val Arg Ala Asp Thr Ala Trp Leu Arg Gly Val Trp Ser Gln Pro Gln
            500                 505                 510

Arg Phe Ser Ile Glu Val Gln Val Ser Asp
        515                 520

<210> SEQ ID NO 3
<211> LENGTH: 738
<212> TYPE: PRT
<213> ORGANISM: Mus musculus

<400> SEQUENCE: 3

Met Asp Met Met Gly Leu Ala Gly Thr Ser Lys His Ile Thr Phe Leu
1               5                   10                  15

Leu Leu Cys Gln Leu Gly Ala Ser Gly Pro Gly Asp Gly Cys Cys Val
            20                  25                  30

Glu Lys Thr Ser Phe Pro Glu Gly Ala Ser Gly Ser Pro Leu Gly Pro
        35                  40                  45

Arg Asn Leu Ser Cys Tyr Arg Val Ser Lys Thr Asp Tyr Glu Cys Ser
    50                  55                  60

Trp Gln Tyr Asp Gly Pro Glu Asp Asn Val Ser His Val Leu Trp Cys
65                  70                  75                  80

Cys Phe Val Pro Pro Asn His Thr His Thr Gly Gln Glu Arg Cys Arg
                85                  90                  95
```

-continued

Tyr Phe Ser Ser Gly Pro Asp Arg Thr Val Gln Phe Trp Glu Gln Asp
            100                 105                 110

Gly Ile Pro Val Leu Ser Lys Val Asn Phe Trp Val Glu Ser Arg Leu
            115                 120                 125

Gly Asn Arg Thr Met Lys Ser Gln Lys Ile Ser Gln Tyr Leu Tyr Asn
            130                 135                 140

Trp Thr Lys Thr Thr Pro Pro Leu Gly His Ile Lys Val Ser Gln Ser
145                 150                 155                 160

His Arg Gln Leu Arg Met Asp Trp Asn Val Ser Glu Ala Gly Ala
                165                 170                 175

Glu Val Gln Phe Arg Arg Met Pro Thr Thr Asn Trp Thr Leu Gly
                180                 185                 190

Asp Cys Gly Pro Gln Val Asn Ser Gly Ser Gly Val Leu Gly Asp Ile
            195                 200                 205

Arg Gly Ser Met Ser Glu Ser Cys Leu Cys Pro Ser Glu Asn Met Ala
            210                 215                 220

Gln Glu Ile Gln Ile Arg Arg Arg Arg Leu Ser Ser Gly Ala Pro
225                 230                 235                 240

Gly Gly Pro Trp Ser Asp Trp Ser Met Pro Val Cys Val Pro Pro Glu
            245                 250                 255

Val Leu Pro Gln Ala Lys Ile Lys Phe Leu Val Glu Pro Leu Asn Gln
            260                 265                 270

Gly Gly Arg Arg Arg Leu Thr Met Gln Gly Gln Ser Pro Gln Leu Ala
            275                 280                 285

Val Pro Glu Gly Cys Arg Gly Arg Pro Gly Ala Gln Val Lys Lys His
            290                 295                 300

Leu Val Leu Val Arg Met Leu Ser Cys Arg Cys Gln Ala Gln Thr Ser
305                 310                 315                 320

Lys Thr Val Pro Leu Gly Lys Lys Leu Asn Leu Ser Gly Ala Thr Tyr
            325                 330                 335

Asp Leu Asn Val Leu Ala Lys Thr Arg Phe Gly Arg Ser Thr Ile Gln
            340                 345                 350

Lys Trp His Leu Pro Ala Gln Glu Leu Thr Glu Thr Arg Ala Leu Asn
            355                 360                 365

Val Ser Val Gly Gly Asn Met Thr Ser Met Gln Trp Ala Ala Gln Ala
            370                 375                 380

Pro Gly Thr Thr Tyr Cys Leu Glu Trp Gln Pro Trp Phe Gln His Arg
385                 390                 395                 400

Asn His Thr His Cys Thr Leu Ile Val Pro Glu Glu Asp Pro Ala
            405                 410                 415

Lys Met Val Thr His Ser Trp Ser Ser Lys Pro Thr Leu Glu Gln Glu
            420                 425                 430

Glu Cys Tyr Arg Ile Thr Val Phe Ala Ser Lys Asn Pro Lys Asn Pro
            435                 440                 445

Met Leu Trp Ala Thr Val Leu Ser Ser Tyr Tyr Phe Gly Gly Asn Ala
            450                 455                 460

Ser Arg Ala Gly Thr Pro Arg His Val Ser Val Arg Asn Gln Thr Gly
465                 470                 475                 480

Asp Ser Val Ser Val Glu Trp Thr Ala Ser Gln Leu Ser Thr Cys Pro
            485                 490                 495

Gly Val Leu Thr Gln Tyr Val Val Arg Cys Glu Ala Glu Asp Gly Ala
            500                 505                 510

```
Trp Glu Ser Glu Trp Leu Val Pro Thr Lys Thr Gln Val Thr Leu
            515                 520                 525

Asp Gly Leu Arg Ser Arg Val Met Tyr Lys Val Gln Val Arg Ala Asp
        530                 535                 540

Thr Ala Arg Leu Pro Gly Ala Trp Ser His Pro Gln Arg Phe Ser Phe
545                 550                 555                 560

Glu Val Gln Ile Ser Arg Leu Ser Ile Ile Phe Ala Ser Leu Gly Ser
                565                 570                 575

Phe Ala Ser Val Leu Leu Val Gly Ser Leu Gly Tyr Ile Gly Leu Asn
            580                 585                 590

Arg Ala Ala Trp His Leu Cys Pro Pro Leu Pro Thr Pro Cys Gly Ser
        595                 600                 605

Thr Ala Val Glu Phe Pro Gly Ser Gln Gly Lys Gln Ala Trp Gln Trp
    610                 615                 620

Cys Asn Pro Glu Asp Phe Pro Glu Val Leu Tyr Pro Arg Asp Ala Leu
625                 630                 635                 640

Val Val Glu Met Pro Gly Asp Arg Gly Asp Gly Thr Glu Ser Pro Gln
                645                 650                 655

Ala Ala Pro Glu Cys Ala Leu Asp Thr Arg Arg Pro Leu Glu Thr Gln
            660                 665                 670

Arg Gln Arg Gln Val Gln Ala Leu Ser Glu Ala Arg Arg Leu Gly Leu
        675                 680                 685

Ala Arg Glu Asp Cys Pro Arg Gly Asp Leu Ala His Val Thr Leu Pro
    690                 695                 700

Leu Leu Leu Gly Gly Val Thr Gln Gly Ala Ser Val Leu Asp Asp Leu
705                 710                 715                 720

Trp Arg Thr His Lys Thr Ala Glu Pro Gly Pro Thr Leu Gly Gln
                725                 730                 735

Glu Ala

<210> SEQ ID NO 4
<211> LENGTH: 546
<212> TYPE: PRT
<213> ORGANISM: Mus musculus

<400> SEQUENCE: 4

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140
```

-continued

```
Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Lys Ile Lys Phe Leu Val Glu Pro Leu Asn Gln Gly Gly Arg
                245                 250                 255

Arg Arg Leu Thr Met Gln Gly Gln Ser Pro Gln Leu Ala Val Pro Glu
            260                 265                 270

Gly Cys Arg Gly Arg Pro Gly Ala Gln Val Lys Lys His Leu Val Leu
        275                 280                 285

Val Arg Met Leu Ser Cys Arg Cys Gln Ala Gln Thr Ser Lys Thr Val
    290                 295                 300

Pro Leu Gly Lys Lys Leu Asn Leu Ser Gly Ala Thr Tyr Asp Leu Asn
305                 310                 315                 320

Val Leu Ala Lys Thr Arg Phe Gly Arg Ser Thr Ile Gln Lys Trp His
                325                 330                 335

Leu Pro Ala Gln Glu Leu Thr Glu Thr Arg Ala Leu Asn Val Ser Val
            340                 345                 350

Gly Gly Asn Met Thr Ser Met Gln Trp Ala Ala Gln Ala Pro Gly Thr
        355                 360                 365

Thr Tyr Cys Leu Glu Trp Gln Pro Trp Phe Gln His Arg Asn His Thr
    370                 375                 380

His Cys Thr Leu Ile Val Pro Glu Glu Glu Asp Pro Ala Lys Met Val
385                 390                 395                 400

Thr His Ser Trp Ser Ser Lys Pro Thr Leu Glu Gln Glu Glu Cys Tyr
                405                 410                 415

Arg Ile Thr Val Phe Ala Ser Lys Asn Pro Lys Asn Pro Met Leu Trp
            420                 425                 430

Ala Thr Val Leu Ser Ser Tyr Tyr Phe Gly Gly Asn Ala Ser Arg Ala
        435                 440                 445

Gly Thr Pro Arg His Val Ser Val Arg Asn Gln Thr Gly Asp Ser Val
    450                 455                 460

Ser Val Glu Trp Thr Ala Ser Gln Leu Ser Thr Cys Pro Gly Val Leu
465                 470                 475                 480

Thr Gln Tyr Val Val Arg Cys Glu Ala Glu Asp Gly Ala Trp Glu Ser
                485                 490                 495

Glu Trp Leu Val Pro Pro Thr Lys Thr Gln Val Thr Leu Asp Gly Leu
            500                 505                 510

Arg Ser Arg Val Met Tyr Lys Val Gln Val Arg Ala Asp Thr Ala Arg
        515                 520                 525

Leu Pro Gly Ala Trp Ser His Pro Gln Arg Phe Ser Phe Glu Val Gln
    530                 535                 540

Ile Ser
545
```

<210> SEQ ID NO 5
<211> LENGTH: 862
<212> TYPE: PRT
<213> ORGANISM: Homo sapiens

<400> SEQUENCE: 5

```
Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
            20                  25                  30

Val Thr Val Lys Pro Ser His Val Ile Leu Leu Gly Ser Thr Val Asn
        35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
    210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
        355                 360                 365

Gly Gly Lys Ala Met Thr Gln Asn Ile Thr Gly His Thr Ser Trp Thr
    370                 375                 380
```

```
Thr Val Ile Pro Arg Thr Gly Asn Trp Ala Val Ser Ala Ala
385             390             395             400

Asn Ser Lys Gly Ser Ser Leu Pro Thr Arg Ile Asn Ile Met Asn Leu
        405             410             415

Cys Glu Ala Gly Leu Leu Ala Pro Arg Gln Val Ser Ala Asn Ser Glu
        420             425             430

Gly Met Asp Asn Ile Leu Val Thr Trp Gln Pro Pro Arg Lys Asp Pro
        435             440             445

Ser Ala Val Gln Glu Tyr Val Val Glu Trp Arg Glu Leu His Pro Gly
450             455             460

Gly Asp Thr Gln Val Pro Leu Asn Trp Leu Arg Ser Arg Pro Tyr Asn
465             470             475             480

Val Ser Ala Leu Ile Ser Glu Asn Ile Lys Ser Tyr Ile Cys Tyr Glu
            485             490             495

Ile Arg Val Tyr Ala Leu Ser Gly Asp Gln Gly Gly Cys Ser Ser Ile
            500             505             510

Leu Gly Asn Ser Lys His Lys Ala Pro Leu Ser Gly Pro His Ile Asn
        515             520             525

Ala Ile Thr Glu Glu Lys Gly Ser Ile Leu Ile Ser Trp Asn Ser Ile
530             535             540

Pro Val Gln Glu Gln Met Gly Cys Leu Leu His Tyr Arg Ile Tyr Trp
545             550             555             560

Lys Glu Arg Asp Ser Asn Ser Gln Pro Gln Leu Cys Glu Ile Pro Tyr
                565             570             575

Arg Val Ser Gln Asn Ser His Pro Ile Asn Ser Leu Gln Pro Arg Val
            580             585             590

Thr Tyr Val Leu Trp Met Thr Ala Leu Thr Ala Ala Gly Glu Ser Ser
            595             600             605

His Gly Asn Glu Arg Glu Phe Cys Leu Gln Gly Lys Ala Asn Trp Met
        610             615             620

Ala Phe Val Ala Pro Ser Ile Cys Ile Ala Ile Ile Met Val Gly Ile
625             630             635             640

Phe Ser Thr His Tyr Phe Gln Gln Lys Val Phe Val Leu Leu Ala Ala
            645             650             655

Leu Arg Pro Gln Trp Cys Ser Arg Glu Ile Pro Asp Pro Ala Asn Ser
            660             665             670

Thr Cys Ala Lys Lys Tyr Pro Ile Ala Glu Glu Lys Thr Gln Leu Pro
        675             680             685

Leu Asp Arg Leu Leu Ile Asp Trp Pro Thr Pro Glu Asp Pro Glu Pro
690             695             700

Leu Val Ile Ser Glu Val Leu His Gln Val Thr Pro Val Phe Arg His
705             710             715             720

Pro Pro Cys Ser Asn Trp Pro Gln Arg Glu Lys Gly Ile Gln Gly His
            725             730             735

Gln Ala Ser Glu Lys Asp Met Met His Ser Ala Ser Ser Pro Pro Pro
        740             745             750

Pro Arg Ala Leu Gln Ala Glu Ser Arg Gln Leu Val Asp Leu Tyr Lys
        755             760             765

Val Leu Glu Ser Arg Gly Ser Asp Pro Lys Pro Glu Asn Pro Ala Cys
        770             775             780

Pro Trp Thr Val Leu Pro Ala Gly Asp Leu Pro Thr His Asp Gly Tyr
785             790             795             800

Leu Pro Ser Asn Ile Asp Asp Leu Pro Ser His Glu Ala Pro Leu Ala
```

```
                805                 810                 815
Asp Ser Leu Glu Glu Leu Glu Pro Gln His Ile Ser Leu Ser Val Phe
        820                 825                 830

Pro Ser Ser Ser Leu His Pro Leu Thr Phe Ser Cys Gly Asp Lys Leu
        835                 840                 845

Thr Leu Asp Gln Leu Lys Met Arg Cys Asp Ser Leu Met Leu
        850                 855                 860

<210> SEQ ID NO 6
<211> LENGTH: 599
<212> TYPE: PRT
<213> ORGANISM: Homo sapiens

<400> SEQUENCE: 6

Lys Ile Asp Ala Cys Lys Arg Gly Asp Val Thr Val Lys Pro Ser His
1               5                   10                  15

Val Ile Leu Leu Gly Ser Thr Val Asn Ile Thr Cys Ser Leu Lys Pro
            20                  25                  30

Arg Gln Gly Cys Phe His Tyr Ser Arg Arg Asn Lys Leu Ile Leu Tyr
        35                  40                  45

Lys Phe Asp Arg Arg Ile Asn Phe His His Gly His Ser Leu Asn Ser
    50                  55                  60

Gln Val Thr Gly Leu Pro Leu Gly Thr Thr Leu Phe Val Cys Lys Leu
65                  70                  75                  80

Ala Cys Ile Asn Ser Asp Glu Ile Gln Ile Cys Gly Ala Glu Ile Phe
                85                  90                  95

Val Gly Val Ala Pro Glu Gln Pro Gln Asn Leu Ser Cys Ile Gln Lys
            100                 105                 110

Gly Glu Gln Gly Thr Val Ala Cys Thr Trp Glu Arg Gly Arg Asp Thr
        115                 120                 125

His Leu Tyr Thr Glu Tyr Thr Leu Gln Leu Ser Gly Pro Lys Asn Leu
    130                 135                 140

Thr Trp Gln Lys Gln Cys Lys Asp Ile Tyr Cys Asp Tyr Leu Asp Phe
145                 150                 155                 160

Gly Ile Asn Leu Thr Pro Glu Ser Pro Glu Ser Asn Phe Thr Ala Lys
                165                 170                 175

Val Thr Ala Val Asn Ser Leu Gly Ser Ser Ser Ser Leu Pro Ser Thr
            180                 185                 190

Phe Thr Phe Leu Asp Ile Val Arg Pro Leu Pro Pro Trp Asp Ile Arg
        195                 200                 205

Ile Lys Phe Gln Lys Ala Ser Val Ser Arg Cys Thr Leu Tyr Trp Arg
    210                 215                 220

Asp Glu Gly Leu Val Leu Leu Asn Arg Leu Arg Tyr Arg Pro Ser Asn
225                 230                 235                 240

Ser Arg Leu Trp Asn Met Val Asn Val Thr Lys Ala Lys Gly Arg His
                245                 250                 255

Asp Leu Leu Asp Leu Lys Pro Phe Thr Glu Tyr Glu Phe Gln Ile Ser
            260                 265                 270

Ser Lys Leu His Leu Tyr Lys Gly Ser Trp Ser Asp Trp Ser Glu Ser
        275                 280                 285

Leu Arg Ala Gln Thr Pro Glu Glu Pro Thr Gly Met Leu Asp Val
    290                 295                 300

Trp Tyr Met Lys Arg His Ile Asp Tyr Ser Arg Gln Gln Ile Ser Leu
305                 310                 315                 320
```

```
Phe Trp Lys Asn Leu Ser Val Ser Glu Ala Arg Gly Lys Ile Leu His
                325                 330                 335

Tyr Gln Val Thr Leu Gln Glu Leu Thr Gly Gly Lys Ala Met Thr Gln
            340                 345                 350

Asn Ile Thr Gly His Thr Ser Trp Thr Thr Val Ile Pro Arg Thr Gly
        355                 360                 365

Asn Trp Ala Val Ala Val Ser Ala Ala Asn Ser Lys Gly Ser Ser Leu
370                 375                 380

Pro Thr Arg Ile Asn Ile Met Asn Leu Cys Glu Ala Gly Leu Leu Ala
385                 390                 395                 400

Pro Arg Gln Val Ser Ala Asn Ser Glu Gly Met Asp Asn Ile Leu Val
                405                 410                 415

Thr Trp Gln Pro Pro Arg Lys Asp Pro Ser Ala Val Gln Glu Tyr Val
            420                 425                 430

Val Glu Trp Arg Glu Leu His Pro Gly Gly Asp Thr Gln Val Pro Leu
        435                 440                 445

Asn Trp Leu Arg Ser Arg Pro Tyr Asn Val Ser Ala Leu Ile Ser Glu
    450                 455                 460

Asn Ile Lys Ser Tyr Ile Cys Tyr Glu Ile Arg Val Tyr Ala Leu Ser
465                 470                 475                 480

Gly Asp Gln Gly Gly Cys Ser Ser Ile Leu Gly Asn Ser Lys His Lys
                485                 490                 495

Ala Pro Leu Ser Gly Pro His Ile Asn Ala Ile Thr Glu Glu Lys Gly
            500                 505                 510

Ser Ile Leu Ile Ser Trp Asn Ser Ile Pro Val Gln Glu Gln Met Gly
        515                 520                 525

Cys Leu Leu His Tyr Arg Ile Tyr Trp Lys Glu Arg Asp Ser Asn Ser
    530                 535                 540

Gln Pro Gln Leu Cys Glu Ile Pro Tyr Arg Val Ser Gln Asn Ser His
545                 550                 555                 560

Pro Ile Asn Ser Leu Gln Pro Arg Val Thr Tyr Val Leu Trp Met Thr
                565                 570                 575

Ala Leu Thr Ala Ala Gly Glu Ser Ser His Gly Asn Glu Arg Glu Phe
            580                 585                 590

Cys Leu Gln Gly Lys Ala Asn
            595

<210> SEQ ID NO 7
<211> LENGTH: 874
<212> TYPE: PRT
<213> ORGANISM: Mus musculus

<400> SEQUENCE: 7

Met Ala Gln Thr Val Arg Glu Cys Ser Leu Ala Leu Leu Phe Leu Phe
1               5                   10                  15

Met Trp Leu Leu Ile Lys Ala Asn Ile Asp Val Cys Lys Leu Gly Thr
            20                  25                  30

Val Thr Val Gln Pro Ala Pro Val Ile Pro Leu Gly Ser Ala Ala Asn
        35                  40                  45

Ile Ser Cys Ser Leu Asn Pro Lys Gln Gly Cys Ser His Tyr Pro Ser
    50                  55                  60

Ser Asn Glu Leu Ile Leu Leu Lys Phe Val Asn Asp Val Leu Val Glu
65                  70                  75                  80

Asn Leu His Gly Lys Lys Val His Asp His Thr Gly His Ser Ser Thr
                85                  90                  95
```

```
Phe Gln Val Thr Asn Leu Ser Leu Gly Met Thr Leu Phe Val Cys Lys
            100                 105                 110

Leu Asn Cys Ser Asn Ser Gln Lys Lys Pro Val Pro Val Cys Gly
            115                 120                 125

Val Glu Ile Ser Val Gly Val Ala Pro Glu Pro Gln Asn Ile Ser
130                 135                 140

Cys Val Gln Glu Gly Glu Asn Gly Thr Val Ala Cys Ser Trp Asn Ser
145                 150                 155                 160

Gly Lys Val Thr Tyr Leu Lys Thr Asn Tyr Thr Leu Gln Leu Ser Gly
                165                 170                 175

Pro Asn Asn Leu Thr Cys Gln Lys Gln Cys Phe Ser Asp Asn Arg Gln
            180                 185                 190

Asn Cys Asn Arg Leu Asp Leu Gly Ile Asn Leu Ser Pro Asp Leu Ala
            195                 200                 205

Glu Ser Arg Phe Ile Val Arg Val Thr Ala Ile Asn Asp Leu Gly Asn
210                 215                 220

Ser Ser Ser Leu Pro His Thr Phe Thr Phe Leu Asp Ile Val Ile Pro
225                 230                 235                 240

Leu Pro Pro Trp Asp Ile Arg Ile Asn Phe Leu Asn Ala Ser Gly Ser
                245                 250                 255

Arg Gly Thr Leu Gln Trp Glu Asp Glu Gly Gln Val Val Leu Asn Gln
            260                 265                 270

Leu Arg Tyr Gln Pro Leu Asn Ser Thr Ser Trp Asn Met Val Asn Ala
            275                 280                 285

Thr Asn Ala Lys Gly Lys Tyr Asp Leu Arg Asp Leu Arg Pro Phe Thr
290                 295                 300

Glu Tyr Glu Phe Gln Ile Ser Ser Lys Leu His Leu Ser Gly Gly Ser
305                 310                 315                 320

Trp Ser Asn Trp Ser Glu Ser Leu Arg Thr Arg Thr Pro Glu Glu Glu
                325                 330                 335

Pro Val Gly Ile Leu Asp Ile Trp Tyr Met Lys Gln Asp Ile Asp Tyr
            340                 345                 350

Asp Arg Gln Gln Ile Ser Leu Phe Trp Lys Ser Leu Asn Pro Ser Glu
            355                 360                 365

Ala Arg Gly Lys Ile Leu His Tyr Gln Val Thr Leu Gln Glu Val Thr
370                 375                 380

Lys Lys Thr Thr Leu Gln Asn Thr Thr Arg His Thr Ser Trp Thr Arg
385                 390                 395                 400

Val Ile Pro Arg Thr Gly Ala Trp Thr Ala Ser Val Ser Ala Ala Asn
                405                 410                 415

Ser Lys Gly Ala Ser Ala Pro Thr His Ile Asn Ile Val Asp Leu Cys
            420                 425                 430

Gly Thr Gly Leu Leu Ala Pro His Gln Val Ser Ala Lys Ser Glu Asn
            435                 440                 445

Met Asp Asn Ile Leu Val Thr Trp Gln Pro Pro Lys Lys Ala Asp Ser
450                 455                 460

Ala Val Arg Glu Tyr Ile Val Glu Trp Arg Ala Leu Gln Pro Gly Ser
465                 470                 475                 480

Ile Thr Lys Phe Pro Pro His Trp Leu Arg Ile Pro Pro Asp Asn Met
                485                 490                 495

Ser Ala Leu Ile Ser Glu Asn Ile Lys Pro Tyr Ile Cys Tyr Glu Ile
            500                 505                 510
```

```
Arg Val His Ala Leu Ser Glu Ser Gln Gly Gly Cys Ser Ser Ile Arg
            515                 520                 525

Gly Asp Ser Lys His Lys Ala Pro Val Ser Gly Pro His Ile Thr Ala
        530                 535                 540

Ile Thr Glu Lys Lys Glu Arg Leu Phe Ile Ser Trp Thr His Ile Pro
545                 550                 555                 560

Phe Pro Glu Gln Arg Gly Cys Ile Leu His Tyr Arg Ile Tyr Trp Lys
                565                 570                 575

Glu Arg Asp Ser Thr Ala Gln Pro Glu Leu Cys Glu Ile Gln Tyr Arg
            580                 585                 590

Arg Ser Gln Asn Ser His Pro Ile Ser Ser Leu Gln Pro Arg Val Thr
        595                 600                 605

Tyr Val Leu Trp Met Thr Ala Val Thr Ala Ala Gly Glu Ser Pro Gln
    610                 615                 620

Gly Asn Glu Arg Glu Phe Cys Pro Gln Gly Lys Ala Asn Trp Lys Ala
625                 630                 635                 640

Phe Val Ile Ser Ser Ile Cys Ile Ala Ile Ile Thr Val Gly Thr Phe
                645                 650                 655

Ser Ile Arg Tyr Phe Arg Gln Lys Ala Phe Thr Leu Leu Ser Thr Leu
            660                 665                 670

Lys Pro Gln Trp Tyr Ser Arg Thr Ile Pro Asp Pro Ala Asn Ser Thr
        675                 680                 685

Trp Val Lys Lys Tyr Pro Ile Leu Glu Lys Ile Gln Leu Pro Thr
    690                 695                 700

Asp Asn Leu Leu Met Ala Trp Pro Thr Pro Glu Glu Pro Glu Pro Leu
705                 710                 715                 720

Ile Ile His Glu Val Leu Tyr His Met Ile Pro Val Val Arg Gln Pro
                725                 730                 735

Tyr Tyr Phe Lys Arg Gly Gln Gly Phe Gln Gly Tyr Ser Thr Ser Lys
            740                 745                 750

Gln Asp Ala Met Tyr Ile Ala Asn Pro Gln Ala Thr Gly Thr Leu Thr
        755                 760                 765

Ala Glu Thr Arg Gln Leu Val Asn Leu Tyr Lys Val Leu Glu Ser Arg
770                 775                 780

Asp Pro Asp Ser Lys Leu Ala Asn Leu Thr Ser Pro Leu Thr Val Thr
785                 790                 795                 800

Pro Val Asn Tyr Leu Pro Ser His Glu Gly Tyr Leu Pro Ser Asn Ile
                805                 810                 815

Glu Asp Leu Ser Pro His Glu Ala Asp Pro Thr Asp Ser Phe Asp Leu
            820                 825                 830

Glu His Gln His Ile Ser Leu Ser Ile Phe Ala Ser Ser Ser Leu Arg
        835                 840                 845

Pro Leu Ile Phe Gly Gly Glu Arg Leu Thr Leu Asp Arg Leu Lys Met
850                 855                 860

Gly Tyr Asp Ser Leu Met Ser Asn Glu Ala
865                 870

<210> SEQ ID NO 8
<211> LENGTH: 614
<212> TYPE: PRT
<213> ORGANISM: Mus musculus

<400> SEQUENCE: 8

Asn Ile Asp Val Cys Lys Leu Gly Thr Val Thr Val Gln Pro Ala Pro
1               5                   10                  15
```

```
Val Ile Pro Leu Gly Ser Ala Ala Asn Ile Ser Cys Ser Leu Asn Pro
             20                  25                  30

Lys Gln Gly Cys Ser His Tyr Pro Ser Ser Asn Glu Leu Ile Leu Leu
         35                  40                  45

Lys Phe Val Asn Asp Val Leu Val Glu Asn Leu His Gly Lys Lys Val
     50                  55                  60

His Asp His Thr Gly His Ser Ser Thr Phe Gln Val Thr Asn Leu Ser
 65                  70                  75                  80

Leu Gly Met Thr Leu Phe Val Cys Lys Leu Asn Cys Ser Asn Ser Gln
                 85                  90                  95

Lys Lys Pro Pro Val Pro Val Cys Gly Val Glu Ile Ser Val Gly Val
            100                 105                 110

Ala Pro Glu Pro Pro Gln Asn Ile Ser Cys Val Gln Glu Gly Glu Asn
        115                 120                 125

Gly Thr Val Ala Cys Ser Trp Asn Ser Gly Lys Val Thr Tyr Leu Lys
130                 135                 140

Thr Asn Tyr Thr Leu Gln Leu Ser Gly Pro Asn Asn Leu Thr Cys Gln
145                 150                 155                 160

Lys Gln Cys Phe Ser Asp Asn Arg Gln Asn Cys Asn Arg Leu Asp Leu
                165                 170                 175

Gly Ile Asn Leu Ser Pro Asp Leu Ala Glu Ser Arg Phe Ile Val Arg
            180                 185                 190

Val Thr Ala Ile Asn Asp Leu Gly Asn Ser Ser Ser Leu Pro His Thr
        195                 200                 205

Phe Thr Phe Leu Asp Ile Val Ile Pro Leu Pro Pro Trp Asp Ile Arg
210                 215                 220

Ile Asn Phe Leu Asn Ala Ser Gly Ser Arg Gly Thr Leu Gln Trp Glu
225                 230                 235                 240

Asp Glu Gly Gln Val Val Leu Asn Gln Leu Arg Tyr Gln Pro Leu Asn
                245                 250                 255

Ser Thr Ser Trp Asn Met Val Asn Ala Thr Asn Ala Lys Gly Lys Tyr
            260                 265                 270

Asp Leu Arg Asp Leu Arg Pro Phe Thr Glu Tyr Glu Phe Gln Ile Ser
        275                 280                 285

Ser Lys Leu His Leu Ser Gly Gly Ser Trp Ser Asn Trp Ser Glu Ser
290                 295                 300

Leu Arg Thr Arg Thr Pro Glu Glu Pro Val Gly Ile Leu Asp Ile
305                 310                 315                 320

Trp Tyr Met Lys Gln Asp Ile Asp Tyr Asp Arg Gln Gln Ile Ser Leu
                325                 330                 335

Phe Trp Lys Ser Leu Asn Pro Ser Glu Ala Arg Gly Lys Ile Leu His
        340                 345                 350

Tyr Gln Val Thr Leu Gln Glu Val Thr Lys Lys Thr Thr Leu Gln Asn
    355                 360                 365

Thr Thr Arg His Thr Ser Trp Thr Arg Val Ile Pro Arg Thr Gly Ala
370                 375                 380

Trp Thr Ala Ser Val Ser Ala Ala Asn Ser Lys Gly Ala Ser Ala Pro
385                 390                 395                 400

Thr His Ile Asn Ile Val Asp Leu Cys Gly Thr Gly Leu Leu Ala Pro
                405                 410                 415

His Gln Val Ser Ala Lys Ser Glu Asn Met Asp Asn Ile Leu Val Thr
        420                 425                 430
```

-continued

```
Trp Gln Pro Pro Lys Lys Ala Asp Ser Ala Val Arg Glu Tyr Ile Val
        435                 440                 445
Glu Trp Arg Ala Leu Gln Pro Gly Ser Ile Thr Lys Phe Pro Pro His
450                 455                 460
Trp Leu Arg Ile Pro Pro Asp Asn Met Ser Ala Leu Ile Ser Glu Asn
465                 470                 475                 480
Ile Lys Pro Tyr Ile Cys Tyr Glu Ile Arg Val His Ala Leu Ser Glu
                485                 490                 495
Ser Gln Gly Gly Cys Ser Ser Ile Arg Gly Asp Ser Lys His Lys Ala
            500                 505                 510
Pro Val Ser Gly Pro His Ile Thr Ala Ile Thr Glu Lys Lys Glu Arg
        515                 520                 525
Leu Phe Ile Ser Trp Thr His Ile Pro Phe Pro Glu Gln Arg Gly Cys
    530                 535                 540
Ile Leu His Tyr Arg Ile Tyr Trp Lys Glu Arg Asp Ser Thr Ala Gln
545                 550                 555                 560
Pro Glu Leu Cys Glu Ile Gln Tyr Arg Arg Ser Gln Asn Ser His Pro
                565                 570                 575
Ile Ser Ser Leu Gln Pro Arg Val Thr Tyr Val Leu Trp Met Thr Ala
            580                 585                 590
Val Thr Ala Ala Gly Glu Ser Pro Gln Gly Asn Glu Arg Glu Phe Cys
        595                 600                 605
Pro Gln Gly Lys Ala Asn
        610

<210> SEQ ID NO 9
<211> LENGTH: 219
<212> TYPE: PRT
<213> ORGANISM: Homo sapiens

<400> SEQUENCE: 9

Met Cys Pro Ala Arg Ser Leu Leu Leu Val Ala Thr Leu Val Leu Leu
1               5                   10                  15
Asp His Leu Ser Leu Ala Arg Asn Leu Pro Val Ala Thr Pro Asp Pro
                20                  25                  30
Gly Met Phe Pro Cys Leu His His Ser Gln Asn Leu Leu Arg Ala Val
            35                  40                  45
Ser Asn Met Leu Gln Lys Ala Arg Gln Thr Leu Glu Phe Tyr Pro Cys
        50                  55                  60
Thr Ser Glu Glu Ile Asp His Glu Asp Ile Thr Lys Asp Lys Thr Ser
65                  70                  75                  80
Thr Val Glu Ala Cys Leu Pro Leu Glu Leu Thr Lys Asn Glu Ser Cys
                85                  90                  95
Leu Asn Ser Arg Glu Thr Ser Phe Ile Thr Asn Gly Ser Cys Leu Ala
            100                 105                 110
Ser Arg Lys Thr Ser Phe Met Met Ala Leu Cys Leu Ser Ser Ile Tyr
        115                 120                 125
Glu Asp Leu Lys Met Tyr Gln Val Glu Phe Lys Thr Met Asn Ala Lys
    130                 135                 140
Leu Leu Met Asp Pro Lys Arg Gln Ile Phe Leu Asp Gln Asn Met Leu
145                 150                 155                 160
Ala Val Ile Asp Glu Leu Met Gln Ala Leu Asn Phe Asn Ser Glu Thr
                165                 170                 175
Val Pro Gln Lys Ser Ser Leu Glu Glu Pro Asp Phe Tyr Lys Thr Lys
            180                 185                 190
```

```
Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 10
<211> LENGTH: 215
<212> TYPE: PRT
<213> ORGANISM: Mus musculus

<400> SEQUENCE: 10

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215

<210> SEQ ID NO 11
<211> LENGTH: 328
<212> TYPE: PRT
<213> ORGANISM: Homo sapiens

<400> SEQUENCE: 11

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80
```

Glu Phe Gly Asp Ala Gly Gln Tyr Thr Cys His Lys Gly Gly Glu Val
                85                  90                  95
Leu Ser His Ser Leu Leu Leu His Lys Lys Glu Asp Gly Ile Trp
            100                 105                 110
Ser Thr Asp Ile Leu Lys Asp Gln Lys Glu Pro Lys Asn Lys Thr Phe
            115                 120                 125
Leu Arg Cys Glu Ala Lys Asn Tyr Ser Gly Arg Phe Thr Cys Trp Trp
        130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Asn Lys Glu Tyr Glu Tyr Ser Val Glu
            180                 185                 190
Cys Gln Glu Asp Ser Ala Cys Pro Ala Ala Glu Glu Ser Leu Pro Ile
        195                 200                 205
Glu Val Met Val Asp Ala Val His Lys Leu Lys Tyr Glu Asn Tyr Thr
            210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
            260                 265                 270
Phe Cys Val Gln Val Gln Gly Lys Ser Lys Arg Glu Lys Lys Asp Arg
        275                 280                 285
Val Phe Thr Asp Lys Thr Ser Ala Thr Val Ile Cys Arg Lys Asn Ala
        290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser
                325

<210> SEQ ID NO 12
<211> LENGTH: 335
<212> TYPE: PRT
<213> ORGANISM: Mus musculus

<400> SEQUENCE: 12

Met Cys Pro Gln Lys Leu Thr Ile Ser Trp Phe Ala Ile Val Leu Leu
1               5                   10                  15
Val Ser Pro Leu Met Ala Met Trp Glu Leu Glu Lys Asp Val Tyr Val
            20                  25                  30
Val Glu Val Asp Trp Thr Pro Asp Ala Pro Gly Glu Thr Val Asn Leu
        35                  40                  45
Thr Cys Asp Thr Pro Glu Glu Asp Asp Ile Thr Trp Thr Ser Asp Gln
    50                  55                  60
Arg His Gly Val Ile Gly Ser Gly Lys Thr Leu Thr Ile Thr Val Lys
65                  70                  75                  80
Glu Phe Leu Asp Ala Gly Gln Tyr Thr Cys His Lys Gly Gly Glu Thr
                85                  90                  95
Leu Ser His Ser His Leu Leu Leu His Lys Lys Glu Asn Gly Ile Trp
            100                 105                 110
Ser Thr Glu Ile Leu Lys Asn Phe Lys Asn Lys Thr Phe Leu Lys Cys

```
                  115                 120                 125
Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Ser
1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Gly Gly Ser Gly
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Ser Gly Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Gly Ser Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Gly Gly Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Ser Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ser Ser Ser Gly
1               5

<210> SEQ ID NO 21
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Gly Gly Ser Gly Gly Gly Ser Gly
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Ser Gly Gly Gly Ser Gly Gly Gly Ser Gly
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Ser Gly Gly Gly Ser Gly Gly Gly Ser Gly Gly Gly Ser Gly
1               5                   10                  15

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Ser Gly Gly Gly Ser Gly Gly Gly Ser Gly Gly Gly Ser Gly
1               5                   10                  15

Gly Gly Ser Gly
            20

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Gly Tyr Cys Gly Tyr Asp Met Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

Tyr Thr Tyr Ser Ser Ala Phe Met Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Ser Tyr Cys Gly Tyr Asp Met Met
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Gly Tyr Cys Gly Tyr Asp Met Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Gly Tyr Cys Gly Tyr Asp Met Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Thr Tyr Thr Asn Asn Phe Met Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Asp Tyr Cys Gly Tyr Asp Val Arg
1               5

<210> SEQ ID NO 32
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 32

Tyr Ser Tyr Cys Gly Tyr Asp Met Met
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Ser Tyr Cys Gly Tyr Asp Met Met
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Asp Tyr Cys Gly Tyr Asp Val Arg
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Asp Tyr Cys Gly Tyr Asp Val Arg
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Thr Tyr Ser Ser Ala Phe Met Ala
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Gly Tyr Cys Gly Tyr Asp Met Ser
1               5
```

```
<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Asp Tyr Cys Gly Tyr Asp Val Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Asp Tyr Cys Gly Tyr Asp Val Arg
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Thr Tyr Ser Ser Ala Phe Met Ala
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Gly Tyr Cys Gly Tyr Asp Met Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Thr Tyr Thr Asn Asn Phe Met Ala
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

Tyr Asp Tyr Cys Gly Tyr Asp Val Arg
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Thr Tyr Ser Ser Ala Phe Met Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Thr Tyr Ser Ser Ala Phe Met Ala
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Thr Tyr Ser Ser Ala Phe Met Ala
1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Ile Thr Ser Asp Arg Ser Ile Ser Tyr Glu Asp Ser Val Lys Ala
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Ile Tyr Thr Arg Asp Gly Gly Thr Val Tyr Ala Asp Ser Val Lys
1               5                   10                  15
Gly

<210> SEQ ID NO 49
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Ile Thr Ser Asp Tyr Ser Ile Arg Tyr Glu Asp Ser Val Glu Gly
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Ile Thr Ser Asp Arg Ile Ala Ser Tyr Glu Asp Ser Val Lys Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Ile Thr Ser Asp Arg Ser Val Ser Tyr Glu Asp Ser Val Lys Gly
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ile Tyr Thr Gly Asp Gly Tyr Ala Tyr Tyr Phe Tyr Ser Val Lys
1               5                   10                  15

Gly

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ile Asp Ser Asp Gly Ser Thr Ser Tyr Ala Asp Ser Val Lys Gly
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

```
Leu Ile Thr Ser Asp Tyr Ser Ile Arg Tyr Glu Asp Ser Val Glu Gly
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ile Thr Ser Asp Tyr Ser Ile Arg Tyr Glu Asp Ser Val Glu Gly
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ile Asp Ser Asp Gly Ser Thr Ser Tyr Ala Asp Ser Val Lys Gly
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ile Asp Ser Asp Gly Ser Thr Ser Tyr Ala Asp Ser Val Lys Gly
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ile Tyr Thr Arg Asp Gly Gly Thr Val Tyr Ala Asp Ser Val Lys
1               5                   10                  15

Gly

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Ile Thr Ser Glu Arg Val Ile Ser Tyr Glu Asp Ser Val Lys Gly
1               5                   10                  15

<210> SEQ ID NO 60
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ile Asp Ser Asp Gly Ser Thr Ser Tyr Ala Asp Ser Val Lys Gly
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ile Asn Ser Asp Gly Ser Thr Ser Tyr Ala Asp Ser Val Lys Gly
1               5                   10                  15

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Met Tyr Thr Arg Asp Gly Gly Thr Val Tyr Ala Asp Ser Val Lys
1               5                   10                  15

Gly

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ile Thr Ser Asp Arg Ser Val Ser Tyr Glu Asp Ser Val Lys Gly
1               5                   10                  15

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ile Tyr Thr Gly Asp Gly Tyr Ala Tyr Tyr Phe Asp Ser Val Lys
1               5                   10                  15

Gly

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 65

Gly Ile Asn Ser Asp Gly Ser Thr Ser Tyr Ala Asp Ser Val Lys Gly
1               5                   10                  15

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ile Tyr Thr Arg Asp Gly Ser Pro Val Tyr Ala Asp Ser Leu Lys
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Met Tyr Thr Arg Asp Gly Gly Thr Val Tyr Ala Asp Ser Val Lys
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ile Tyr Thr Arg Asp Gly Gly Thr Val Tyr Ala Asp Ser Val Lys
1               5                   10                  15

Gly

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Ala Ala Ala Arg Glu Ser Ser Trp Cys Arg Ser Arg Tyr Arg Val
1               5                   10                  15

Ala Ser

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 70

Lys Ile Pro Gln Pro Gly Arg Ala Ser Leu Leu Asp Ser Gln Thr Tyr
1               5                   10                  15

Asp Tyr

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Thr Ala Ala Arg Glu Ser Ser Trp Cys Arg Ser Arg Tyr Arg Val
1               5                   10                  15

Ala Ser

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ala Ala Ala Arg Glu Asn Ser Trp Cys Arg Ser Arg Tyr Arg Val
1               5                   10                  15

Ala Ser

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Thr Ala Ala Arg Glu Asn Asn Trp Cys Arg Ser Arg Tyr Arg Ile
1               5                   10                  15

Ala Tyr

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Met Glu Arg Arg Ile Gly Thr Arg Arg Met Thr Glu Asn Ala Glu Tyr
1               5                   10                  15

Lys Tyr

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 75

Glu Ser Pro Ala Gly Glu Ser Ala Trp Cys Arg Asn Phe Arg Gly Met
1               5                   10                  15

Asp Tyr

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Thr Ala Ala Arg Glu Ser Ser Trp Cys Arg Ser Arg Tyr Arg Val
1               5                   10                  15

Ala Ser

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Thr Ala Ala Arg Glu Ser Gly Trp Cys Arg Ser Arg Tyr Arg Val
1               5                   10                  15

Ala Ser

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Ser Pro Ala Gly Glu Ser Ala Trp Cys Arg Asn Phe Arg Gly Met
1               5                   10                  15

Asp Tyr

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Ser Pro Ala Gly Glu Ser Ala Trp Cys Arg Asn Phe Arg Gly Met
1               5                   10                  15

Asp Tyr

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
                                 peptide

<400> SEQUENCE: 80

Lys Met Pro Gln Pro Gly Arg Ala Ser Leu Leu Asp Ser Gln Thr Tyr
1               5                   10                  15

Asp Tyr

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Ala Ala Ala Arg Glu Ser Ser Trp Cys Arg Ser Arg Tyr Arg Val
1               5                   10                  15

Ala Ser

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Ser Pro Ala Gly Glu Ser Ala Trp Cys Arg Asn Phe Arg Gly Met
1               5                   10                  15

Asp Tyr

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu Ser Pro Ala Gly Glu Ser Ala Trp Cys Arg Asn Phe Arg Gly Met
1               5                   10                  15

Asp Tyr

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Ile Pro Gln Pro Gly Arg Ala Ser Leu Leu Asp Ser Gln Thr Tyr
1               5                   10                  15

Asp Tyr

<210> SEQ ID NO 85
<211> LENGTH: 18
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 85

Ser Thr Ala Ala Arg Glu Asn Asn Trp Cys Arg Ser Arg Tyr Arg Ile
1               5                   10                  15

Ala Ser

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 86

Met Glu Arg Arg Ser Gly Arg Arg Arg Met Thr Glu Asn Ala Glu Tyr
1               5                   10                  15

Lys Tyr

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 87

Glu Gly Pro Ala Gly Glu Ser Ala Trp Cys Arg Asn Phe Arg Gly Met
1               5                   10                  15

Asp Tyr

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 88

Lys Ile Pro Glu Pro Gly Arg Ile Ser Leu Leu Asp Ser Gln Thr Tyr
1               5                   10                  15

Asp Tyr

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 89

Lys Ile Pro Gln Pro Gly Arg Ala Ser Leu Leu Asp Ser Gln Thr Tyr
1               5                   10                  15

Asp Tyr

<210> SEQ ID NO 90
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 90

Lys Ile Pro Gln Pro Gly Arg Ala Ser Leu Leu Asp Ser Gln Thr Tyr
1               5                   10                  15

Asp Tyr

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Thr Tyr Ser Ser Ala Phe Met Ala
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Tyr Asp Tyr Cys Gly Tyr Asp Val Arg
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Ser Tyr Cys Gly Tyr Asp Met Met
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Tyr Thr Tyr Thr Asn Asn Phe Met Ala
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Thr Ile Asp Asp Ser Glu Met Gly
```

```
<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Thr Tyr Ser Ser Ala Phe Met Ala
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Tyr Asp Tyr Cys Gly Tyr Asp Val Arg
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Tyr Gly Tyr Cys Gly Tyr Asp Met Ser
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Gly Tyr Cys Gly Tyr Asp Met Ser
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Asp Tyr Cys Gly Tyr Asp Val Arg
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 101

Tyr Ser Tyr Cys Gly Tyr Asp Met Met
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Tyr Thr Tyr Thr Asn Asn Phe Met Ala
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Ser Tyr Cys Gly Tyr Asp Met Met
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Tyr Asp Tyr Cys Gly Tyr Asp Val Arg
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Tyr Gly Tyr Cys Gly Tyr Asp Met Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Asp Tyr Cys Gly Tyr Asp Val Arg
1               5

<210> SEQ ID NO 107

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Thr Tyr Ser Ser Ala Phe Met Ala
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Thr Tyr Ser Ser Ala Phe Met Ala
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Gly Tyr Cys Gly Tyr Asp Met Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Tyr Gly Tyr Cys Gly Tyr Asp Met Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Asp Tyr Cys Gly Tyr Asp Val Arg
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112
```

Tyr Thr Tyr Ser Ser Ala Phe Met Ala
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Tyr Thr Tyr Ser Ser Ala Phe Met Ala
1               5

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Ile Tyr Thr Arg Asp Gly Gly Thr Val Tyr Ala Asp Ser Val Lys
1               5                   10                  15
Gly

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Ile Asp Ser Asp Gly Ser Thr Ser Tyr Ala Asp Ser Val Lys Gly
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Leu Ile Thr Ser Asp Tyr Ser Ile Arg Tyr Glu Asp Ser Val Glu Gly
1               5                   10                  15

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Ile Tyr Thr Gly Asp Gly Tyr Ala Tyr Tyr Phe Asp Ser Val Lys
1               5                   10                  15
Gly

<210> SEQ ID NO 118

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ser Gly Ser Ser Asp Asp Thr Tyr Tyr Val Asp Ser Val Lys Gly
1               5                   10                  15

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Ile Tyr Thr Arg Asp Gly Ser Pro Val Tyr Ala Asp Ser Leu Lys
1               5                   10                  15

Gly

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ile Asp Ser Asp Gly Ser Thr Ser Tyr Ala Asp Ser Val Lys Gly
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Ile Thr Ser Glu Arg Val Ile Ser Tyr Glu Asp Ser Val Lys Gly
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Ile Thr Ser Asp Arg Ser Ile Ser Tyr Glu Asp Ser Val Lys Ala
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 123

Gly Ile Asp Ser Asp Gly Ser Thr Ser Tyr Ala Asp Ser Val Lys Gly
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Ile Thr Ser Asp Tyr Ser Ile Arg Tyr Glu Asp Ser Val Glu Gly
1               5                   10                  15

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ile Tyr Thr Gly Asp Gly Tyr Ala Tyr Tyr Phe Tyr Ser Val Lys
1               5                   10                  15

Gly

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Ile Thr Ser Asp Tyr Ser Ile Arg Tyr Glu Asp Ser Val Glu Gly
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Ile Asn Ser Asp Gly Ser Thr Ser Tyr Ala Asp Ser Val Lys Gly
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Ile Thr Ser Asp Arg Ser Val Ser Tyr Glu Asp Ser Val Lys Gly
1               5                   10                  15

<210> SEQ ID NO 129
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Ile Asn Ser Asp Gly Ser Thr Ser Tyr Ala Asp Ser Val Lys Gly
1               5                   10                  15

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Met Tyr Thr Arg Asp Gly Gly Thr Val Tyr Ala Asp Ser Val Lys
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Met Tyr Thr Arg Asp Gly Gly Thr Val Tyr Ala Asp Ser Val Lys
1               5                   10                  15

Gly

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Leu Ile Thr Ser Asp Arg Ser Val Ser Tyr Glu Asp Ser Val Lys Gly
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Leu Ile Thr Ser Asp Arg Ile Ala Ser Tyr Glu Asp Ser Val Lys Gly
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
              peptide

<400> SEQUENCE: 134

Gly Ile Asp Ser Asp Gly Ser Thr Ser Tyr Ala Asp Ser Val Lys Gly
1               5                   10                  15

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ile Tyr Thr Arg Asp Gly Gly Thr Val Tyr Ala Asp Ser Val Lys
1               5                   10                  15

Gly

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ile Tyr Thr Arg Asp Gly Gly Thr Val Tyr Ala Asp Ser Val Lys
1               5                   10                  15

Gly

<210> SEQ ID NO 137
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Ile Pro Gln Pro Gly Arg Ala Ser Leu Leu Asp Ser Gln Thr Tyr
1               5                   10                  15

Asp Tyr

<210> SEQ ID NO 138
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Glu Ser Pro Ala Gly Glu Ser Ala Trp Cys Arg Asn Phe Arg Gly Met
1               5                   10                  15

Asp Tyr

<210> SEQ ID NO 139
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 139

Ser Thr Ala Ala Arg Glu Ser Ser Trp Cys Arg Ser Arg Tyr Arg Val
1               5                   10                  15

Ala Ser

<210> SEQ ID NO 140
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Met Glu Arg Arg Ser Gly Arg Arg Met Thr Glu Asn Ala Glu Tyr
1               5                   10                  15

Lys Tyr

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Pro Thr Tyr Pro Pro Lys Asp Gly Asp Cys Ala His
1               5                   10

<210> SEQ ID NO 142
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Lys Ile Pro Glu Pro Gly Arg Ile Ser Leu Leu Asp Ser Gln Thr Tyr
1               5                   10                  15

Asp Tyr

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Ser Pro Ala Gly Glu Ser Ala Trp Cys Arg Asn Phe Arg Gly Met
1               5                   10                  15

Asp Tyr

<210> SEQ ID NO 144
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 144

Ser Ala Ala Ala Arg Glu Ser Ser Trp Cys Arg Ser Arg Tyr Arg Val
1               5                   10                  15

Ala Ser

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Ala Ala Ala Arg Glu Ser Ser Trp Cys Arg Ser Arg Tyr Arg Val
1               5                   10                  15

Ala Ser

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Glu Ser Pro Ala Gly Glu Ser Ala Trp Cys Arg Asn Phe Arg Gly Met
1               5                   10                  15

Asp Tyr

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Thr Ala Ala Arg Glu Ser Ser Trp Cys Arg Ser Arg Tyr Arg Val
1               5                   10                  15

Ala Ser

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Met Glu Arg Arg Ile Gly Thr Arg Arg Met Thr Glu Asn Ala Glu Tyr
1               5                   10                  15

Lys Tyr

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Thr Ala Ala Arg Glu Ser Gly Trp Cys Arg Ser Arg Tyr Arg Val
1               5                   10                  15
Ala Ser

<210> SEQ ID NO 150
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Glu Ser Pro Ala Gly Glu Ser Ala Trp Cys Arg Asn Phe Arg Gly Met
1               5                   10                  15
Asp Tyr

<210> SEQ ID NO 151
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Thr Ala Ala Arg Glu Asn Asn Trp Cys Arg Ser Arg Tyr Arg Ile
1               5                   10                  15
Ala Tyr

<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Glu Gly Pro Ala Gly Glu Ser Ala Trp Cys Arg Asn Phe Arg Gly Met
1               5                   10                  15
Asp Tyr

<210> SEQ ID NO 153
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Lys Ile Pro Gln Pro Gly Arg Ala Ser Leu Leu Asp Ser Gln Thr Tyr
1               5                   10                  15
Asp Tyr

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic -continued

```
                peptide

<400> SEQUENCE: 154

Lys Ile Pro Gln Pro Gly Arg Ala Ser Leu Leu Asp Ser Gln Thr Tyr
1               5                   10                  15

Asp Tyr

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Thr Ala Ala Arg Glu Asn Asn Trp Cys Arg Ser Arg Tyr Arg Ile
1               5                   10                  15

Ala Ser

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ser Ala Ala Ala Arg Glu Asn Ser Trp Cys Arg Ser Arg Tyr Arg Val
1               5                   10                  15

Ala Ser

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Ser Pro Ala Gly Glu Ser Ala Trp Cys Arg Asn Phe Arg Gly Met
1               5                   10                  15

Asp Tyr

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Lys Ile Pro Gln Pro Gly Arg Ala Ser Leu Leu Asp Ser Gln Thr Tyr
1               5                   10                  15

Asp Tyr

<210> SEQ ID NO 159
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 159

Lys Met Pro Gln Pro Gly Arg Ala Ser Leu Leu Asp Ser Gln Thr Tyr
1               5                   10                  15

Asp Tyr

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Phe Thr Val Thr Arg Tyr Cys Met Gly
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Phe Thr Ile Ser Arg Tyr Cys Met Gly
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Leu Thr Phe Asp Asp Val Glu Met Ala
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Phe Thr Ile Ser Arg Tyr Cys Met Gly
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Phe Thr Phe Ser Thr Tyr Ala Met Ser
1               5
```

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Tyr Thr Tyr Gly Leu Phe Cys Met Gly
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Val Thr Tyr Ser Arg Tyr Cys Met Gly
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Phe Thr Val Ser Arg Tyr Cys Met Gly
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Phe Thr Ile Ser Arg Tyr Cys Met Gly
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Phe Thr Val Thr Arg Tyr Cys Met Gly
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 170

Phe Thr Val Ser Arg Tyr Cys Met Gly
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Thr Tyr Ser Arg Tyr Cys Met Gly
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Phe Thr Ile Ser Lys Tyr Cys Met Gly
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Val Thr Tyr Ser Arg Tyr Cys Met Gly
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Phe Thr Ile Ser Arg Tyr Cys Met Gly
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Val Thr Tyr Ser Arg Tyr Cys Met Gly
1               5

<210> SEQ ID NO 176
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Leu Thr Ile Ser Arg Tyr Cys Met Gly
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Phe Thr Val Asp Asp Phe Ala Met Gly
1               5

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ile Ile Glu Arg Asp Gly Arg Thr Gly Tyr Ala Asp Ser Val Lys Gly
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ile Ile Glu Arg Asp Gly Arg Thr Gly Tyr Ala Asp Ser Val Lys Gly
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Ile Asn Thr Asp Ser Arg Val Tyr Tyr Val Asp Ser Val Lys Asp
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ile Ile Glu Arg Asp Gly Arg Thr Gly Tyr Ala Asp Ser Val Lys Gly
```

```
<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Ile Ser Ser Gly Gly Gly Asn Thr Tyr Tyr Ala Asp Ala Val Lys
1               5                   10                  15
Gly

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Val Val Asp Ser Pro Gly Gly Arg His Val Ala Asp Ser Leu Lys Gly
1               5                   10                  15

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Thr Ile Tyr Ser Arg Gly Ile Ile Thr Tyr Tyr Thr Asp Ser Val Lys
1               5                   10                  15
Gly

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ile Ile Glu Arg Glu Gly Arg Thr Gly Tyr Ala Asp Ser Val Lys Gly
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Ile Glu Arg Asp Gly Arg Thr Gly Tyr Ala Asp Ser Val Lys Gly
1               5                   10                  15

<210> SEQ ID NO 187
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Ile Glu Arg Asp Gly Arg Thr Gly Tyr Ala Asp Ser Val Lys Gly
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ile Ile Glu Arg Asp Gly Arg Thr Gly Tyr Ala Asp Ser Val Lys Gly
1               5                   10                  15

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Thr Ile Tyr Ser Arg Gly Ile Ile Thr Tyr Tyr Thr Asp Ser Val Lys
1               5                   10                  15

Gly

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ile Ile Glu Arg Asp Gly Arg Thr Gly Tyr Ala Asp Ser Val Lys Gly
1               5                   10                  15

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

His Ile Tyr Ser Arg Gly Ile Ile Thr Tyr Tyr Thr Asp Ser Val Lys
1               5                   10                  15

Gly

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 192

Ile Ile Glu Arg Asp Gly Arg Thr Gly Tyr Ala Asp Ser Val Lys Gly
1               5                   10                  15

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

His Ile Tyr Ser Arg Gly Ile Ile Thr Tyr Tyr Thr Asp Ser Val Lys
1               5                   10                  15

Gly

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ile Ile Glu Arg Asp Gly Arg Thr Gly Tyr Ala Asp Ser Val Lys Gly
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Ile Ser Ser Gly Gly Ser Thr Tyr Tyr Ala Asp Ser Val Lys Gly
1               5                   10                  15

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ile Glu Gly Ser Cys Arg Pro Asp Phe Gly Tyr
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ile Glu Gly Ser Cys Arg Pro Asp Phe Gly Tyr
1               5                   10
```

```
<210> SEQ ID NO 198
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Asp Pro Trp Gly Gly Asp Leu Arg Gly Tyr Pro Asn Tyr
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ile Glu Gly Ser Cys Arg Pro Asp Phe Gly Tyr
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asp Asp Tyr Tyr Gly Gly Ser Trp His Pro Ile Ser
1               5                   10

<210> SEQ ID NO 201
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Asp Pro Glu Lys Tyr Cys Phe Leu Phe Ser Asp Ala Gly Tyr Gln Tyr
1               5                   10                  15

<210> SEQ ID NO 202
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Thr Arg Glu Thr Tyr Gly Gly Ser Gly Asp Cys Asp Tyr Glu Ser Val
1               5                   10                  15

Tyr Asn Tyr

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 203

Ile Glu Gly Ser Cys Arg Pro Asp Phe Gly Tyr
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ile Glu Gly Ser Cys Arg Pro Asp Phe Gly Tyr
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ile Glu Gly Ser Cys Arg Pro Asp Phe Gly Tyr
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ile Glu Gly Ser Cys Arg Pro Asp Phe Gly Tyr
1               5                   10

<210> SEQ ID NO 207
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Thr Arg Glu Thr Tyr Gly Gly Ser Gly Asp Cys Asp Tyr Glu Ser Val
1               5                   10                  15

Tyr Asn Tyr

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ile Glu Gly Ser Cys Arg Pro Asp Phe Gly Tyr
1               5                   10

```
<210> SEQ ID NO 209
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Thr Arg Glu Thr Tyr Gly Gly Ser Gly Asp Cys Gly Tyr Glu Ser Val
1               5                   10                  15

Tyr Asn Tyr

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ile Glu Gly Ser Cys Arg Pro Asp Leu Gly Tyr
1               5                   10

<210> SEQ ID NO 211
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Thr Arg Glu Thr Tyr Gly Gly Ser Gly Asp Cys Ser Tyr Glu Ser Val
1               5                   10                  15

Tyr Asn His

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ile Glu Gly Ser Cys Arg Pro Asp Phe Gly Tyr
1               5                   10

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Ser Val Gly Cys Pro Leu Gly Tyr
1               5

<210> SEQ ID NO 214
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 214

Tyr Thr Tyr Ser Asn Arg His Met Gly
1               5

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Val Thr Tyr Gly Ser Tyr Tyr Met Ala Ala
1               5                   10

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Phe Thr Tyr Ser Ser Ser Cys Leu Gly
1               5

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Lys Leu Tyr Gly Gly Ala
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ile Thr Tyr Arg Gly Val Trp Met Gly
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Lys Ala Tyr Gly Gly Ala
1               5

```
<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asn Pro Tyr Gly Gly Ala
1               5

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Lys Ala Tyr Gly Gly Ala
1               5

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Lys Ala Phe Gly Gly Ala
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Tyr Thr Phe Ser Asn His His Met Gly
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Tyr Thr Phe Ser Asn His His Met Gly
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225
```

```
Tyr Thr Phe Ser Asn His His Met Gly
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Thr Phe Ser Asn His His Met Gly
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Thr Asn Ser Asn Arg His Met Gly
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Asp Ile Tyr Ala Arg Asn Cys Met Gly
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Thr Asn Ser Asn Arg His Met Gly
1               5

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Ile Tyr Thr Gly Gly Gly Ser Thr Tyr Tyr Ala Asp Ser Val Lys
1               5                   10                  15

Asp

<210> SEQ ID NO 231
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ser Ile Tyr Gly Gly Ser Asp Ser Thr Tyr Tyr Ala Asp Ser Val Leu
1               5                   10                  15
Gly

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Thr Ile Tyr Pro Ala Gly Gly Asn Ile Phe Tyr Ala Asp Ser Val Lys
1               5                   10                  15
Gly

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Ile Trp Ile Gly Thr Gly Thr Thr Phe Tyr Ala Asp Ser Val Lys
1               5                   10                  15
Gly

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Thr Ile Tyr Thr Gly Ser Gly His Thr Tyr Tyr Ala Asp Ser Val Lys
1               5                   10                  15
Gly

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Ile Trp Ile Gly Thr Gly Thr Thr Phe Tyr Ala Asp Ser Val Lys
1               5                   10                  15
Gly

<210> SEQ ID NO 236
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Ile Trp Leu Gly Thr Gly Thr Thr Phe Tyr Ala Asp Ser Val Lys
1               5                   10                  15

Gly

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Ile Trp Ile Gly Thr Gly Thr Thr Phe Tyr Ala Asp Ser Val Lys
1               5                   10                  15

Gly

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ala Ile Trp Ile Gly Thr Gly Thr Thr Phe Tyr Ala Asp Ser Val Lys
1               5                   10                  15

Gly

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Ile Tyr Thr Gly Ala Gly Asn Ile Tyr Tyr Ala Asp Ser Val Lys
1               5                   10                  15

Asp

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Ile Tyr Thr Gly Ala Gly Asn Ile Tyr Tyr Ala Asp Ser Val Lys
1               5                   10                  15

Asp
```

```
<210> SEQ ID NO 241
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Ile Tyr Thr Gly Ala Gly Asn Ile Tyr Tyr Ala Asp Ser Val Lys
1               5                   10                  15

Asp

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Ile Tyr Thr Gly Ala Gly Asn Ile Tyr Tyr Ala Asp Ser Val Lys
1               5                   10                  15

Asp

<210> SEQ ID NO 243
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Ile Tyr Thr Gly Tyr Thr Gly Gly Gly Asn Thr Tyr Tyr Ala Asp
1               5                   10                  15

Ser Val Arg Asp
            20

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Val Ala Asp Thr Gly Gly Arg Ser Pro Tyr Tyr Ala Asp Ser Val Lys
1               5                   10                  15

Gly

<210> SEQ ID NO 245
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ala Ile Tyr Thr Gly Tyr Thr Gly Gly Gly Asn Thr Tyr Tyr Ala Asp
1               5                   10                  15

Ser Val Lys Asp
```

```
            20

<210> SEQ ID NO 246
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asp Leu Thr Arg Trp Tyr Ser Gly Gly Trp Arg Asp Pro Arg Gly Tyr
1               5                   10                  15

Lys Tyr

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ala Pro Pro Gly Lys Trp Phe Leu Lys Arg Leu Glu Gly His Asn Tyr
1               5                   10                  15

Ser Tyr

<210> SEQ ID NO 248
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Arg Gly Gly Gln Thr Trp Gly Ser Gly Gly Asn Arg Cys Ser Leu Trp
1               5                   10                  15

Leu Pro Ala Tyr Asn Tyr
            20

<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asp Asp Arg Pro Gly Tyr Arg Asp Pro Leu Ala Pro Val Ser Tyr Asn
1               5                   10                  15

His

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Arg Thr Val Gly Gly Thr Phe Tyr Thr Leu Ala Ala Asp Ser Phe Asn
```

-continued

```
1               5                   10                  15
Thr

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asp Asp Arg Pro Gly Tyr Arg Asp Pro Leu Ala Pro Val Ser Tyr Asn
1               5                   10                  15

His

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Asp Asp Arg Pro Gly Tyr Arg Asp Pro Leu Ala Pro Val Ser Tyr Asn
1               5                   10                  15

His

<210> SEQ ID NO 253
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asp Asp Arg Pro Gly Tyr Arg Asp Pro Leu Ala Pro Val Ser Tyr Asn
1               5                   10                  15

His

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Asp Arg Pro Gly Tyr Arg Asp Pro Leu Ala Pro Val Ser Tyr Asn
1               5                   10                  15

His

<210> SEQ ID NO 255
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255
```

Asp Leu Thr Arg Trp Tyr Ser Gly Gly Trp Arg Asp Pro Arg Gly Tyr
1               5                   10                  15

Lys Tyr

<210> SEQ ID NO 256
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asp Leu Thr Arg Trp Tyr Ser Gly Gly Trp Arg Asp Pro Arg Gly Tyr
1               5                   10                  15

Lys Tyr

<210> SEQ ID NO 257
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asp Leu Thr Arg Trp Tyr Ser Gly Gly Trp Arg Asp Pro Arg Gly Tyr
1               5                   10                  15

Lys Tyr

<210> SEQ ID NO 258
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asp Leu Thr Arg Trp Tyr Ser Gly Gly Trp Arg Asp Pro Arg Gly Tyr
1               5                   10                  15

Lys Tyr

<210> SEQ ID NO 259
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Asp Leu Thr Arg Trp Tyr Ser Gly Gly Trp Arg Asp Pro Arg Gly Tyr
1               5                   10                  15

Lys Tyr

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

-continued

Gly Pro Leu Val Pro Val Val Asn Thr Ala Ala Arg Cys Val Tyr Glu
1               5                   10                  15

Tyr

<210> SEQ ID NO 261
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asp Leu Thr Arg Trp Tyr Ser Gly Gly Trp Arg Asp Pro Arg Gly Tyr
1               5                   10                  15

Lys Tyr

<210> SEQ ID NO 262
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Gly Tyr Cys Gly Tyr
                20                  25                  30

Asp Met Ser Trp Tyr Arg Gln Ala Pro Gly Lys Glu Arg Glu Phe Val
            35                  40                  45

Ala Leu Ile Thr Ser Asp Arg Ser Ile Ser Tyr Glu Asp Ser Val Lys
        50                  55                  60

Ala Arg Phe Ile Ile Ser Arg Asp Asn Ala Ala Asn Thr Gly Tyr Leu
65                  70                  75                  80

Asp Met Thr Arg Leu Thr Pro Asp Asp Thr Ala Ile Tyr Tyr Cys Lys
                85                  90                  95

Thr Ser Ala Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 263
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
                20                  25                  30

Phe Met Ala Trp Phe Arg Gln Ala Pro Gly Lys Glu Arg Glu Gly Val
            35                  40                  45

Ala Ala Ile Tyr Thr Arg Asp Gly Gly Thr Val Tyr Ala Asp Ser Val
        50                  55                  60

Lys Gly Arg Phe Thr Ile Ser Gln Asp Asn Ala Lys Asn Ile Leu Tyr
65                  70                  75                  80

Leu Gln Met Asn Ser Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 264
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 265
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Gly Tyr Cys Gly Tyr
            20                  25                  30

Asp Met Ser Trp Tyr Arg Gln Thr Pro Gly Lys Glu Arg Glu Phe Val
        35                  40                  45

Ala Leu Ile Thr Ser Asp Arg Ile Ala Ser Tyr Glu Asp Ser Val Lys
    50                  55                  60

Gly Arg Phe Ile Ile Ser Arg Asp Asn Ala Lys Asn Thr Gly Tyr Leu
65                  70                  75                  80

Asp Met Thr Arg Val Thr Pro Asp Asp Thr Ala Ile Tyr Tyr Cys Lys
                85                  90                  95

Thr Ser Ala Ala Ala Arg Glu Asn Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 266
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gln Val Gln Leu Gln Glu Ser Gly Gly Ser Val Gln Ala Gly Gly
1               5                   10                  15

Phe Leu Arg Leu Ser Cys Val Ala Ser Gly Tyr Gly Tyr Cys Gly Tyr
            20                  25                  30

Asp Met Ser Trp Tyr Arg Gln Val Pro Gly Lys Glu Arg Glu Phe Val
        35                  40                  45

Ala Leu Ile Thr Ser Asp Arg Ser Val Ser Tyr Glu Asp Ser Val Lys
    50                  55                  60

Gly Arg Phe Ser Ile Ser Arg Asp Asn Ala Lys Asn Thr Ala Tyr Leu
65                  70                  75                  80

Glu Met Asn Arg Leu Thr Pro Asp Asp Thr Ala Val Tyr Tyr Cys Lys
                85                  90                  95

Thr Ser Thr Ala Ala Arg Glu Asn Asn Trp Cys Arg Ser Arg Tyr Arg
            100                 105                 110

Ile Ala Tyr Trp Gly Gln Gly Thr Gln Val Thr Val Ser Ser
        115                 120                 125

<210> SEQ ID NO 267
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
            20                  25                  30

Phe Met Ala Trp Phe Arg Gln Ala Pro Gly Lys Glu Arg Glu Gly Val
        35                  40                  45

Ala Ala Ile Tyr Thr Gly Asp Gly Tyr Ala Tyr Tyr Phe Tyr Ser Val
    50                  55                  60

Lys Gly Arg Phe Thr Ile Ser Gln Asp Asn Asp Glu Asn Met Leu Tyr
65                  70                  75                  80

Leu Gln Met Asn Ser Leu Lys Pro Glu Asp Thr Ala Met Tyr Tyr Cys
                85                  90                  95

Ala Ala Met Glu Arg Arg Ile Gly Thr Arg Arg Met Thr Glu Asn Ala
            100                 105                 110

Glu Tyr Lys Tyr Trp Gly Gln Gly Thr Gln Val Thr Val Ser Ser
        115                 120                 125

<210> SEQ ID NO 268
<211> LENGTH: 126
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 268

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Arg Ala Pro Gly Lys Glu Arg Glu Phe Val
        35                  40                  45

Ser Gly Ile Asp Ser Asp Gly Ser Thr Ser Tyr Ala Asp Ser Val Lys
50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 269
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 270
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gln Val Gln Leu Gln Glu Ser Gly Gly Gly Ser Val Gln Ala Gly Gly
1               5                   10                  15
```

```
Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Gly Trp Cys Arg Ser Arg Tyr Arg
            100                 105                 110

Val Ala Ser Trp Gly Gln Gly Thr Gln Val Thr Val Ser Ser
            115                 120                 125

<210> SEQ ID NO 271
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125

<210> SEQ ID NO 272
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60
```

```
Gly Arg Phe Thr Ile Ser Gln Asp Asn Ala Glu Asn Thr Ser Tyr Leu
 65                  70                  75                  80

His Met Phe Ser Leu Lys Pro Glu Asp Thr Ala Met Tyr Tyr Cys Lys
                 85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125
```

<210> SEQ ID NO 273
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

```
Gln Val Gln Leu Gln Glu Ser Gly Gly Gly Ser Val Gln Ala Gly Gly
  1               5                  10                  15

Ser Leu Arg Leu Ser Cys Thr Ala Ser Gly Tyr Thr Tyr Ser Ser Ala
                 20                  25                  30

Phe Met Ala Trp Phe Arg Gln Ala Pro Gly Lys Glu Arg Glu Gly Val
             35                  40                  45

Ala Ala Ile Tyr Thr Arg Asp Gly Gly Thr Val Tyr Ala Asp Ser Val
         50                  55                  60

Lys Gly Arg Phe Thr Ile Ser Gln Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Ala Lys Met Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125
```

<210> SEQ ID NO 274
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

```
Gln Val Gln Leu Gln Glu Ser Gly Gly Gly Ser Val Gln Ala Gly Gly
  1               5                  10                  15

Phe Leu Arg Leu Ser Cys Val Ala Ser Gly Tyr Gly Tyr Cys Gly Tyr
                 20                  25                  30

Asp Met Ser Trp Tyr Arg Gln Ala Pro Gly Lys Glu Arg Glu Phe Val
             35                  40                  45

Ala Leu Ile Thr Ser Glu Arg Val Ile Ser Tyr Glu Asp Ser Val Lys
         50                  55                  60

Gly Arg Phe Ser Ile Ser Arg Asp Asn Ala Glu Asn Thr Gly Tyr Leu
 65                  70                  75                  80

Glu Met Asn Arg Leu Thr Pro Asp Asp Thr Ala Ile Tyr Tyr Cys Lys
                 85                  90                  95

Thr Ser Ala Ala Ala Arg Glu Ser Ser Trp Cys Arg Ser Arg Tyr Arg
            100                 105                 110
```

```
Val Ala Ser Trp Gly Gln Gly Thr Gln Val Thr Val Ser Ser
            115                 120                 125
```

<210> SEQ ID NO 275
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

```
Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Ala Pro Gly Lys Glu Arg Glu Phe Val
            35                  40                  45

Ser Gly Ile Asp Ser Asp Gly Ser Thr Ser Tyr Ala Asp Ser Val Lys
        50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125
```

<210> SEQ ID NO 276
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

```
Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
            35                  40                  45

Ser Gly Ile Asn Ser Asp Gly Ser Thr Ser Tyr Ala Asp Ser Val Lys
        50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125
```

<210> SEQ ID NO 277
<211> LENGTH: 127
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 277

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Met Tyr Thr Arg Asp Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Ile His Thr Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125
```

<210> SEQ ID NO 278
<211> LENGTH: 126
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 278

```
Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
            20                  25                  30

Asp Met Ser Trp Tyr Arg Gln Val Pro Gly Lys Glu Arg Glu Phe Val
        35                  40                  45

Ala Leu Ile Thr Ser Asp Arg Ser Val Ser Tyr Glu Asp Ser Val Lys
    50                  55                  60

Gly Arg Phe Ser Ile Ser Arg Asp Asn Ala Lys Asn Thr Ala Tyr Leu
65                  70                  75                  80

Glu Met Asn Arg Leu Thr Pro Asp Asp Thr Ala Ile Tyr Tyr Cys Lys
                85                  90                  95

Thr Ser Thr Ala Ala Arg Glu Asn Asn Trp Cys Arg Ser Arg Tyr Arg
            100                 105                 110

Ile Ala Ser Trp Gly Gln Gly Thr Gln Val Thr Val Ser Ser
        115                 120                 125
```

<210> SEQ ID NO 279
<211> LENGTH: 127
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 279

```
Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
```

```
                    20                  25                  30
Phe Met Ala Trp Phe Arg Gln Ala Pro Gly Lys Glu Arg Glu Gly Val
                35                  40                  45
Ala Ala Ile Tyr Thr Gly Asp Gly Tyr Ala Tyr Tyr Phe Asp Ser Val
            50                  55                  60
Lys Gly Arg Phe Thr Ile Ser Gln Asp Asn Asp Lys Asn Met Leu Tyr
65                  70                  75                  80
Leu Gln Met Asn Ser Leu Lys Pro Glu Asp Thr Ala Met Tyr Tyr Cys
                    85                  90                  95
Ala Ala Met Glu Arg Arg Ser Gly Arg Arg Arg Met Thr Glu Asn Ala
                100                 105                 110
Glu Tyr Lys Tyr Trp Gly Gln Gly Thr Gln Val Thr Val Ser Ser
                115                 120                 125

<210> SEQ ID NO 280
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Gln Val Gln Leu Gln Glu Ser Gly Gly Gly Ser Val Gln Ala Gly Gly
1               5                   10                  15
Ser Leu Arg Leu Ser Cys Ala Val Ser Gly Tyr Asp Tyr Cys Gly Tyr
                20                  25                  30
Asp Val Arg Trp Tyr Arg Gln Ala Pro Gly Lys Glu Arg Glu Phe Val
                35                  40                  45
Ser Gly Ile Asn Ser Asp Gly Ser Thr Ser Tyr Ala Asp Ser Val Lys
            50                  55                  60
Gly Arg Phe Thr Ile Ser Gln Asp Asn Ala Glu Asn Thr Ser Tyr Leu
65                  70                  75                  80
His Met Phe Ser Leu Lys Pro Glu Asp Thr Ala Met Tyr Tyr Cys Lys
                    85                  90                  95
Thr Glu Gly Pro Ala Gly Glu Ser Ala Trp Cys Arg Asn Phe Arg Gly
                100                 105                 110
Met Asp Tyr Trp Gly Lys Gly Thr Gln Val Thr Val Ser Ser
            115                 120                 125

<210> SEQ ID NO 281
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gln Val Gln Leu Gln Glu Ser Gly Gly Gly Ser Val Gln Ala Gly Gly
1               5                   10                  15
Ser Leu Arg Leu Ser Cys Thr Ala Ser Gly Tyr Thr Tyr Ser Ser Ala
                20                  25                  30
Phe Met Ala Trp Phe Arg Gln Ala Pro Gly Lys Glu Arg Glu Gly Val
                35                  40                  45
Ala Ala Ile Tyr Thr Arg Asp Gly Ser Pro Val Tyr Ala Asp Ser Leu
            50                  55                  60
Lys Gly Arg Phe Thr Ile Ser Gln Asp Asn Ala Lys Asn Thr Leu His
```

```
            65                  70                  75                  80
Leu Gln Met Asn Ser Leu Lys Pro Glu Asp Thr Ala Met Tyr Tyr Cys
                    85                  90                  95

Ala Ala Lys Ile Pro Glu Pro Gly Arg Ile Ser Leu Leu Asp Ser Gln
                100                 105                 110

Thr Tyr Asp Tyr Trp Gly His Gly Thr Gln Val Thr Val Ser Ser
            115                 120                 125

<210> SEQ ID NO 282
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Met Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Thr Glu Asp Thr Ala Met Tyr Tyr Cys
                85                  90                  95

Ala Ala Lys Ile Pro Gln Pro Gly Arg Ala Ser Leu Leu Asp Ser Gln
                100                 105                 110

Thr Tyr Asp Tyr Trp Gly Gln Gly Thr Gln Val Thr Val Ser Ser
            115                 120                 125

<210> SEQ ID NO 283
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Ile Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
                100                 105                 110

Thr Tyr Asp Tyr Trp Gly Gln Gly Thr Gln Val Thr Val Ser Ser
```

```
            115                 120                 125

<210> SEQ ID NO 284
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Ile Tyr Thr Arg Asp Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 285
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 286
<211> LENGTH: 126
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 286

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 287
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
            20                  25                  30

Phe Met Ala Trp Phe Arg Gln Ala Pro Gly Lys Glu Arg Glu Gly Val
        35                  40                  45

Ala Ala Ile Tyr Thr Gly Asp Gly Tyr Ala Tyr Tyr Phe Asp Ser Val
    50                  55                  60

Lys Gly Arg Phe Thr Ile Ser Gln Asp Asn Asp Lys Asn Met Leu Tyr
65                  70                  75                  80

Leu Gln Met Asn Ser Leu Lys Pro Glu Asp Thr Ala Met Tyr Tyr Cys
                85                  90                  95

Ala Ala Met Glu Arg Arg Ser Gly Arg Arg Met Thr Glu Asn Ala
            100                 105                 110

Glu Tyr Lys Tyr Trp Gly Gln Gly Thr Gln Val Thr Val Ser Ser
        115                 120                 125

<210> SEQ ID NO 288
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Gln Val Gln Leu Gln Glu Ser Gly Gly Gly Ser Val Gln Ala Gly Glu
1               5                   10                  15

Thr Leu Arg Leu Ser Cys Thr Val Ser Gly Phe Thr Ile Asp Asp Ser
            20                  25                  30
```

Glu Met Gly Trp Tyr Arg Gln Ala Pro Gly His Glu Cys Glu Leu Val
           35                  40                  45

Ala Ser Gly Ser Ser Asp Asp Thr Tyr Tyr Val Asp Ser Val Lys
        50                  55                  60

Gly Arg Phe Thr Ile Ser Leu Asp Asn Ala Lys Asn Met Val Tyr Leu
65                   70                  75                  80

Gln Met Asn Ser Leu Lys Pro Glu Asp Thr Ala Val Tyr Tyr Cys Ala
                85                  90                  95

Thr Gly Pro Thr Tyr Pro Pro Lys Asp Gly Asp Cys Ala His Trp Gly
               100                 105                 110

Gln Gly Thr Gln Val Thr Val Ser Ser
               115                 120

<210> SEQ ID NO 289
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
           35                  40                  45

Ala Ala Ile Tyr Thr Arg Asp Gly Ser Pro Val Tyr Ala Asp Ser Leu
        50                  55                  60

Lys Gly Arg Phe Thr Ile Ser Gln Asp Asn Ala Lys Asn Thr Leu His
65                   70                  75                  80

Leu Gln Met Asn Ser Leu Lys Pro Glu Asp Thr Ala Met Tyr Tyr Cys
                85                  90                  95

Ala Ala Lys Ile Pro Glu Pro Gly Arg Ile Ser Leu Leu Asp Ser Gln
               100                 105                 110

Thr Tyr Asp Tyr Trp Gly His Gly Thr Gln Val Thr Val Ser Ser
               115                 120                 125

<210> SEQ ID NO 290
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Arg Ala Pro Gly Lys Glu Arg Glu Phe Val
           35                  40                  45

Ser Gly Ile Asp Ser Asp Gly Ser Thr Ser Tyr Ala Asp Ser Val Lys
        50                  55                  60

Gly Arg Phe Thr Ile Ser Gln Asp Asn Ala Glu Asn Thr Ser Tyr Leu
65                   70                  75                  80

```
His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 291
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
            20                  25                  30

Asp Met Ser Trp Tyr Arg Gln Ala Pro Gly Lys Glu Arg Glu Phe Val
        35                  40                  45

Ala Leu Ile Thr Ser Glu Arg Val Ile Ser Tyr Glu Asp Ser Val Lys
    50                  55                  60

Gly Arg Phe Ser Ile Ser Arg Asp Asn Ala Glu Asn Thr Gly Tyr Leu
65                  70                  75                  80

Glu Met Asn Arg Leu Thr Pro Asp Asp Thr Ala Ile Tyr Tyr Cys Lys
                85                  90                  95

Thr Ser Ala Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 292
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Gly Tyr Cys Gly Tyr
            20                  25                  30

Asp Met Ser Trp Tyr Arg Gln Ala Pro Gly Lys Glu Arg Glu Phe Val
        35                  40                  45

Ala Leu Ile Thr Ser Asp Arg Ser Ile Ser Tyr Glu Asp Ser Val Lys
    50                  55                  60

Ala Arg Phe Ile Ile Ser Arg Asp Asn Ala Ala Asn Thr Gly Tyr Leu
65                  70                  75                  80

Asp Met Thr Arg Leu Thr Pro Asp Asp Thr Ala Ile Tyr Tyr Cys Lys
                85                  90                  95

Thr Ser Ala Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125
```

<210> SEQ ID NO 293
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 293

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 294
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 294

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 295
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 295

Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
            20                  25                  30

Phe Met Ala Trp Phe Arg Gln Ala Pro Gly Lys Glu Arg Glu Gly Val
        35                  40                  45

Ala Ala Ile Tyr Thr Gly Asp Gly Tyr Ala Tyr Tyr Phe Tyr Ser Val
    50                  55                  60

Lys Gly Arg Phe Thr Ile Ser Gln Asp Asn Asp Glu Asn Met Leu Tyr
65                  70                  75                  80

Leu Gln Met Asn Ser Leu Lys Pro Glu Asp Thr Ala Met Tyr Tyr Cys
                85                  90                  95

Ala Ala Met Glu Arg Arg Ile Gly Thr Arg Arg Met Thr Glu Asn Ala
            100                 105                 110

Glu Tyr Lys Tyr Trp Gly Gln Gly Thr Gln Val Thr Val Ser Ser
        115                 120                 125

<210> SEQ ID NO 296
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Gly Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 297
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

-continued

Asp Val Arg Trp Tyr Arg Gln Ala Pro Gly Lys Glu Arg Glu Phe Val
            35                  40                  45

Ser Gly Ile Asn Ser Asp Gly Ser Thr Ser Tyr Ala Asp Ser Val Lys
 50                  55                  60

Gly Arg Phe Thr Ile Ser Gln Asp Asn Ala Glu Asn Thr Ser Tyr Leu
 65                  70                  75                  80

His Met Phe Ser Leu Lys Pro Glu Asp Thr Ala Met Tyr Tyr Cys Lys
                 85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125

<210> SEQ ID NO 298
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Val Gln Leu Gln Glu Ser Gly Gly Gly Ser Val Gln Ala Gly Gly
 1               5                  10                  15

Phe Leu Arg Leu Ser Cys Val Ala Ser Gly Tyr Gly Tyr Cys Gly Tyr
                 20                  25                  30

Asp Met Ser Trp Tyr Arg Gln Val Pro Gly Lys Glu Arg Glu Phe Val
            35                  40                  45

Ala Leu Ile Thr Ser Asp Arg Ser Val Ser Tyr Glu Asp Ser Val Lys
 50                  55                  60

Gly Arg Phe Ser Ile Ser Arg Asp Asn Ala Lys Asn Thr Ala Tyr Leu
 65                  70                  75                  80

Glu Met Asn Arg Leu Thr Pro Asp Asp Thr Ala Val Tyr Tyr Cys Lys
                 85                  90                  95

Thr Ser Thr Ala Ala Arg Glu Asn Asn Trp Cys Arg Ser Arg Tyr Arg
            100                 105                 110

Ile Ala Tyr Trp Gly Gln Gly Thr Gln Val Thr Val Ser Ser
            115                 120                 125

<210> SEQ ID NO 299
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Gln Val Gln Leu Gln Glu Ser Gly Gly Gly Ser Val Gln Ala Gly Gly
 1               5                  10                  15

Ser Leu Arg Leu Ser Cys Ala Val Ser Gly Tyr Asp Tyr Cys Gly Tyr
                 20                  25                  30

Asp Val Arg Trp Tyr Arg Gln Ala Pro Gly Lys Glu Arg Glu Phe Val
            35                  40                  45

Ser Gly Ile Asn Ser Asp Gly Ser Thr Ser Tyr Ala Asp Ser Val Lys
 50                  55                  60

Gly Arg Phe Thr Ile Ser Gln Asp Asn Ala Glu Asn Thr Ser Tyr Leu
 65                  70                  75                  80

His Met Phe Ser Leu Lys Pro Glu Asp Thr Ala Met Tyr Tyr Cys Lys
            85                  90                  95

Thr Glu Gly Pro Ala Gly Glu Ser Ala Trp Cys Arg Asn Phe Arg Gly
        100                 105                 110

Met Asp Tyr Trp Gly Lys Gly Thr Gln Val Thr Val Ser Ser
    115                 120                 125

<210> SEQ ID NO 300
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Met Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Ile His Thr Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 301
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Met Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Thr Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 302
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
                20                  25                  30

Asp Met Ser Trp Tyr Arg Gln Val Pro Gly Lys Glu Arg Glu Phe Val
            35                  40                  45

Ala Leu Ile Thr Ser Asp Arg Ser Val Ser Tyr Glu Asp Ser Val Lys
    50                  55                  60

Gly Arg Phe Ser Ile Ser Arg Asp Asn Ala Lys Asn Thr Ala Tyr Leu
65                  70                  75                  80

Glu Met Asn Arg Leu Thr Pro Asp Asp Thr Ala Ile Tyr Tyr Cys Lys
                85                  90                  95

Thr Ser Thr Ala Ala Arg Glu Asn Asn Trp Cys Arg Ser Arg Tyr Arg
                100                 105                 110

Ile Ala Ser Trp Gly Gln Gly Thr Gln Val Thr Val Ser Ser
            115                 120                 125

<210> SEQ ID NO 303
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Gly Tyr Cys Gly Tyr
                20                  25                  30

Asp Met Ser Trp Tyr Arg Gln Thr Pro Gly Lys Glu Arg Glu Phe Val
            35                  40                  45

Ala Leu Ile Thr Ser Asp Arg Ile Ala Ser Tyr Glu Asp Ser Val Lys
    50                  55                  60

Gly Arg Phe Ile Ile Ser Arg Asp Asn Ala Lys Asn Thr Gly Tyr Leu
65                  70                  75                  80

Asp Met Thr Arg Val Thr Pro Asp Asp Thr Ala Ile Tyr Tyr Cys Lys
                85                  90                  95

Thr Ser Ala Ala Ala Arg Glu Asn Ser Trp Cys Arg Ser Arg Tyr Arg
                100                 105                 110

Val Ala Ser Trp Gly Gln Gly Thr Gln Val Thr Val Ser Ser
            115                 120                 125

<210> SEQ ID NO 304
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 304

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
                20                  25                  30

Asp Val Arg Trp Tyr Arg Arg Ala Pro Gly Lys Glu Arg Glu Phe Val
            35                  40                  45

Ser Gly Ile Asp Ser Asp Gly Ser Thr Ser Tyr Ala Asp Ser Val Lys
        50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 305
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
                20                  25                  30

Phe Met Ala Trp Phe Arg Gln Ala Pro Gly Lys Glu Arg Glu Gly Val
            35                  40                  45

Ala Ala Ile Tyr Thr Arg Asp Gly Gly Thr Val Tyr Ala Asp Ser Val
        50                  55                  60

Lys Gly Arg Phe Thr Ile Ser Gln Asp Asn Ala Lys Asn Ile Leu Tyr
65                  70                  75                  80

Leu Gln Met Asn Ser Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 306
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
                20                  25                  30

Phe Met Ala Trp Phe Arg Gln Ala Pro Gly Lys Glu Arg Glu Gly Val
```

```
            35                  40                  45

Ala Ala Ile Tyr Thr Arg Asp Gly Gly Thr Val Tyr Ala Asp Ser Val
        50                  55                  60

Lys Gly Arg Phe Thr Ile Ser Gln Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Ala Lys Met Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 307
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Phe Thr Val Thr Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
        50                  55                  60

Gly Arg Phe Thr Ile Ser Lys Asp Asn Ala Lys Asn Thr Leu Tyr Leu
 65                  70                  75                  80

Gln Met Asn Ser Leu Lys Pro Glu Asp Thr Ala Met Tyr Tyr Cys Gly
                 85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 308
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Phe Thr Ile Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
        50                  55                  60

Gly Arg Phe Thr Ile Ser Lys Asp Asn Ala Lys Asn Thr Leu Tyr Leu
 65                  70                  75                  80

Gln Met Asn Ser Leu Lys Pro Glu Asp Thr Ala Met Tyr Tyr Cys Gly
```

```
Ala Ile Glu Gly Ser Cys Arg Pro Asp Phe Gly Tyr Arg Gly Gln Gly
                100                 105                 110

Thr Gln Val Thr Val Ser Ser
        115
```

<210> SEQ ID NO 309
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Leu Thr Phe Asp Asp Val
            20                  25                  30

Glu Met Ala Trp Tyr Arg Gln Gly Pro Gly Asp Asp Tyr Asp Leu Val
        35                  40                  45

Ser Ser Ile Asn Thr Asp Ser Arg Val Tyr Tyr Val Asp Ser Val Lys
    50                  55                  60

Asp Arg Phe Thr Ile Ser Arg Asp Asn Ala Lys Asn Thr Leu Tyr Leu
65                  70                  75                  80

Gln Met Asn Asn Leu Lys Pro Glu Asp Thr Ala Val Tyr Tyr Cys Ala
                85                  90                  95

Ala Asp Pro Trp Gly Gly Asp Leu Arg Gly Tyr Pro Asn Tyr Trp Gly
                100                 105                 110

Gln Gly Thr Gln Val Thr Val Ser Ser
        115                 120
```

<210> SEQ ID NO 310
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

```
Gln Val Gln Leu Gln Glu Ser Gly Gly Gly Ser Val Gln Ala Gly Gly
1               5                   10                  15

Ser Leu Arg Leu Ser Cys Val Ala Ser Gly Phe Thr Ile Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Gly Asp Thr Ala Met Tyr Tyr Cys Gly
                85                  90                  95

Ala Ile Glu Gly Ser Cys Arg Pro Asp Phe Gly Tyr Arg Gly Gln Gly
                100                 105                 110

Thr Gln Val Thr Val Ser Ser
        115
```

<210> SEQ ID NO 311
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Ala Pro Gly Lys Glu Pro Glu Trp Ile
        35                  40                  45

Ser Arg Ile Ser Ser Gly Gly Gly Asn Thr Tyr Tyr Ala Asp Ala Val
    50                  55                  60

Lys Gly Arg Phe Ala Ile Ser Arg Asp Asn Ala Lys Asn Thr Leu Tyr
65                  70                  75                  80

Leu Gln Leu Asn Ser Leu Lys Thr Glu Asp Thr Ala Ile Tyr Val Cys
                85                  90                  95

Thr Met Asp Asp Tyr Tyr Gly Ser Trp His Pro Ile Ser Arg Gly
            100                 105                 110

His Gly Thr Gln Val Thr Val Ser Ser
        115                 120

<210> SEQ ID NO 312
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Gln Val Gln Leu Gln Glu Ser Gly Gly Gly Leu Val Gln Ala Gly Gly
1               5                   10                  15

Ser Leu Arg Leu Ser Cys Gln Ala Ser Gly Tyr Thr Tyr Gly Leu Phe
            20                  25                  30

Cys Met Gly Trp Phe Arg Gln Val Ser Gly Lys Lys Arg Glu Gly Val
        35                  40                  45

Ala Val Val Asp Ser Pro Gly Gly Arg His Val Ala Asp Ser Leu Lys
    50                  55                  60

Gly Arg Phe Thr Ile Ser Lys Asp Asn Ala Asn Asn Ile Leu Tyr Leu
65                  70                  75                  80

Asp Met Thr Asn Leu Lys Ser Glu Asp Thr Ala Thr Tyr Tyr Cys Ala
                85                  90                  95

Ala Asp Pro Glu Lys Tyr Cys Phe Leu Phe Ser Asp Ala Gly Tyr Gln
            100                 105                 110

Tyr Trp Gly Gln Gly Thr Gln Val Thr Val Ser Ser
        115                 120

<210> SEQ ID NO 313
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
            20                  25                  30

Cys Met Gly Trp Phe Arg Gln Ala Pro Gly Leu Glu Arg Glu Arg Val
        35                  40                  45

Ala Thr Ile Tyr Ser Arg Gly Ile Ile Thr Tyr Tyr Thr Asp Ser Val
    50                  55                  60

Lys Gly Arg Phe Thr Ile Ser Gln Asp Ser Ala Lys Lys Thr Val Tyr
65                  70                  75                  80

Leu Gln Met Asn Ser Leu Lys Pro Glu Asp Thr Ala Met Tyr Tyr Cys
            85                  90                  95

Ala Ala Thr Arg Glu Thr Tyr Gly Gly Ser Gly Asp Cys Asp Tyr Glu
            100                 105                 110

Ser Val Tyr Asn Tyr Trp Ala Gln Gly Thr Gln Val Thr Val Ser Ser
            115                 120                 125

<210> SEQ ID NO 314
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Val Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Glu Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
            85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 315
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ile Ser Arg Tyr
            20                  25                  30

Cys Met Gly Trp Leu Arg Gln Ala Pro Gly Lys Gln Arg Glu Gly Val
        35                  40                  45
```

```
Ala Ile Ile Glu Arg Asp Gly Arg Thr Gly Tyr Ala Asp Ser Val Lys
            50                  55                  60

Gly Arg Phe Thr Ile Ser Lys Asp Asn Ala Lys Asn Thr Leu Tyr Leu
 65                  70                  75                  80

Gln Met Asn Ser Leu Lys Pro Glu Asp Thr Ala Met Tyr Phe Cys Gly
                 85                  90                  95

Ala Ile Glu Gly Ser Cys Arg Pro Asp Phe Gly Tyr Arg Gly Gln Gly
                100                 105                 110

Thr Gln Val Thr Val Ser Ser
            115
```

<210> SEQ ID NO 316
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 316

```
Gln Val Gln Leu Gln Glu Ser Gly Gly Gly Ser Val Gln Ala Gly Gly
 1               5                  10                  15

Ser Leu Arg Leu Ser Cys Ala Ala Ser Gly Phe Thr Val Thr Arg Tyr
            20                  25                  30

Cys Met Gly Trp Leu Arg Gln Ala Pro Gly Lys Gln Arg Glu Gly Val
            35                  40                  45

Ala Ile Ile Glu Arg Asp Gly Arg Thr Gly Tyr Ala Asp Ser Val Lys
            50                  55                  60

Gly Arg Phe Thr Ile Ser Lys Asp Asn Ala Lys Asn Thr Leu Tyr Leu
 65                  70                  75                  80

Gln Met Asn Ser Leu Lys Pro Glu Asp Thr Ala Met Tyr Tyr Cys Gly
                 85                  90                  95

Ala Ile Glu Gly Ser Cys Arg Pro Asp Phe Gly Tyr Arg Gly Gln Gly
                100                 105                 110

Thr Gln Val Thr Val Ser Ser
            115
```

<210> SEQ ID NO 317
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 317

```
Gln Val Gln Leu Gln Glu Ser Gly Gly Gly Ser Val Gln Ala Gly Gly
 1               5                  10                  15

Ser Leu Arg Leu Ser Cys Ala Ala Ser Gly Phe Thr Val Ser Arg Tyr
            20                  25                  30

Cys Met Gly Trp Leu Arg Gln Ala Pro Gly Lys Gln Arg Glu Gly Val
            35                  40                  45

Ala Ile Ile Glu Arg Asp Gly Arg Thr Gly Tyr Ala Asp Ser Val Lys
            50                  55                  60

Gly Arg Phe Thr Ile Ser Lys Asp Asp Ala Lys Asn Thr Leu Tyr Leu
 65                  70                  75                  80

Gln Met Asn Ser Leu Lys Pro Glu Asp Thr Ala Met Tyr Tyr Cys Gly
                 85                  90                  95
```

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 318
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
            20                  25                  30

Cys Met Gly Trp Phe Arg Gln Ala Pro Gly Leu Glu Arg Glu Arg Val
        35                  40                  45

Ala Thr Ile Tyr Ser Arg Gly Ile Ile Thr Tyr Tyr Thr Asp Ser Val
    50                  55                  60

Lys Gly Arg Phe Thr Ile Ser Gln Asp Ser Ala Lys Lys Thr Val Tyr
65                  70                  75                  80

Leu Gln Met Asn Met Leu Lys Pro Glu Asp Thr Ala Met Tyr Tyr Cys
                85                  90                  95

Ala Ala Thr Arg Glu Thr Tyr Gly Gly Ser Gly Asp Cys Asp Tyr Glu
            100                 105                 110

Ser Val Tyr Asn Tyr Trp Ala Gln Gly Thr Gln Val Thr Val Ser Ser
        115                 120                 125

<210> SEQ ID NO 319
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ile Ser Lys Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 320

<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
            20                  25                  30

Cys Met Gly Trp Phe Arg Gln Ala Pro Gly Leu Glu Arg Glu Arg Val
        35                  40                  45

Ala His Ile Tyr Ser Arg Gly Ile Ile Thr Tyr Tyr Thr Asp Ser Val
    50                  55                  60

Lys Gly Arg Phe Thr Ile Ser Gln Asp Ser Ala Lys Lys Thr Val Tyr
65                  70                  75                  80

Leu Gln Met Asn Ser Leu Lys Pro Glu Asp Thr Ala Met Tyr Tyr Cys
                85                  90                  95

Ala Ala Thr Arg Glu Thr Tyr Gly Gly Ser Gly Asp Cys Gly Tyr Glu
            100                 105                 110

Ser Val Tyr Asn Tyr Trp Ala Gln Gly Thr Gln Val Thr Val Ser Ser
        115                 120                 125

<210> SEQ ID NO 321
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ile Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Leu Gly Tyr Arg Gly Gln Gly
            100                 105                 110

Thr Gln Val Thr Val Ser Ser
        115

<210> SEQ ID NO 322
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
            20                  25                  30

Cys Met Gly Trp Phe Arg Gln Ala Pro Gly Leu Glu Arg Glu Arg Val
        35                  40                  45

Ala His Ile Tyr Ser Arg Gly Ile Ile Thr Tyr Tyr Thr Asp Ser Val
    50                  55                  60

Lys Gly Arg Phe Thr Ile Ser Gln Asp Ser Ala Lys Thr Val Tyr
65                  70                  75                  80

Leu Gln Met Asn Ser Leu Lys Pro Glu Asp Thr Ala Met Tyr Tyr Cys
                85                  90                  95

Ala Ala Thr Arg Glu Thr Tyr Gly Gly Ser Gly Asp Cys Ser Tyr Glu
            100                 105                 110

Ser Val Tyr Asn His Trp Ala Gln Gly Thr Gln Val Thr Val Ser Ser
        115                 120                 125

<210> SEQ ID NO 323
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Gln Val Gln Leu Gln Glu Ser Gly Gly Gly Ser Val Gln Ala Gly Gly
1               5                   10                  15

Ser Leu Arg Leu Ser Cys Ala Ala Ser Gly Leu Thr Ile Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 324
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Gln Val Gln Leu Gln Glu Ser Gly Gly Gly Ser Val Gln Ala Gly Gly
1               5                   10                  15

Ser Leu Arg Leu Ser Cys Ser Ala Ser Gly Phe Thr Val Asp Asp Phe
            20                  25                  30

Ala Met Gly Trp Tyr Arg Gln Ala Pro Gly Asn Glu Cys Glu Leu Val
        35                  40                  45

```
Ser Thr Ile Ser Ser Gly Gly Ser Thr Tyr Tyr Ala Asp Ser Val Lys
    50              55                  60

Gly Arg Phe Thr Ile Ser Gln Asp Ser Ala Lys Asn Thr Val Tyr Leu
 65              70                  75                  80

Gln Met Asn Ser Leu Lys Pro Glu Asp Thr Ala Val Tyr Tyr Cys Ala
                85                  90                  95

Pro Ser Ser Val Gly Cys Pro Leu Gly Tyr Trp Gly Gln Gly Thr Gln
                100                 105                 110

Val Thr Val Ser Ser
            115

<210> SEQ ID NO 325
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr Tyr Ser Asn Arg
                20                  25                  30

His Met Gly Trp Phe Arg Gln Ala Pro Gly Lys Glu Arg Glu Gly Val
            35                  40                  45

Ala Ala Ile Tyr Thr Gly Gly Ser Thr Tyr Tyr Ala Asp Ser Val
    50              55                  60

Lys Asp Arg Phe Thr Ile Ser Gln Asp Asn Ala Lys Asn Thr Leu Tyr
 65              70                  75                  80

Leu Gln Met Asn Ser Leu Thr Pro Glu Asp Thr Ala Met Tyr Tyr Cys
                85                  90                  95

Ala Ala Asp Leu Thr Arg Trp Tyr Ser Gly Gly Trp Arg Asp Pro Arg
                100                 105                 110

Gly Tyr Lys Tyr Trp Gly Gln Gly Thr Gln Val Thr Val Ser
            115                 120                 125

<210> SEQ ID NO 326
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Val Thr Tyr Gly Ser Tyr
                20                  25                  30

Tyr Met Ala Ala Trp Phe Arg Gln Ala Pro Gly Lys Glu Arg Glu Gly
            35                  40                  45

Val Ala Ser Ile Tyr Gly Gly Ser Asp Ser Thr Tyr Tyr Ala Asp Ser
    50              55                  60

Val Leu Gly Arg Phe Thr Ile Ser Gln Asp Asn Gly Lys Asn Thr Leu
 65              70                  75                  80

Tyr Leu Gln Met Asn Ser Leu Lys Pro Asp Asp Thr Ala Met Tyr Tyr
                85                  90                  95
```

```
Cys Ala Ala Ala Pro Pro Gly Lys Trp Phe Leu Lys Arg Leu Glu Gly
            100                 105                 110

His Asn Tyr Ser Tyr Trp Gly Gln Gly Thr Gln Val Thr Val Ser Ser
        115                 120                 125
```

<210> SEQ ID NO 327
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

```
Gln Val Gln Leu Gln Glu Ser Gly Gly Gly Ser Val Gln Val Gly Gly
1               5                   10                  15

Ser Leu Arg Leu Ser Cys Ala Ala Ser Gly Phe Thr Tyr Ser Ser Ser
            20                  25                  30

Cys Leu Gly Trp Phe Arg Gln Ala Pro Gly Lys Glu Arg Glu Gly Val
        35                  40                  45

Ala Thr Ile Tyr Pro Ala Gly Gly Asn Ile Phe Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Arg Gly Gly Gln Thr Trp Gly Ser Gly Gly Asn Arg Cys Ser
            100                 105                 110

Leu Trp Leu Pro Ala Tyr Asn Tyr Trp Gly Gln Gly Thr Gln Val Thr
        115                 120                 125

Val Ser Ser
    130
```

<210> SEQ ID NO 328
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

```
Gln Val Gln Leu Gln Glu Ser Gly Gly Gly Ser Val Gln Val Gly Gly
1               5                   10                  15

Ser Leu Arg Leu Ser Cys Ala Val Ser Gly Lys Leu Tyr Gly Gly Ala
            20                  25                  30

Trp Phe Arg Gln Ala Gln Gly Lys Gly Arg Glu Gly Val Ala Ala Ile
        35                  40                  45

Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Glu Asp Thr Ala Leu Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120
```

<210> SEQ ID NO 329
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ile Thr Tyr Arg Gly Val
            20                  25                  30

Trp Met Gly Trp Phe Arg Gln Ala Pro Gly Lys Glu Arg Glu Gly Val
        35                  40                  45

Ala Thr Ile Tyr Thr Gly Ser Gly His Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Thr Val Gly Gly Thr Phe Tyr Thr Leu Ala Ala Asp Ser
            100                 105                 110

Phe Asn Thr Trp Gly Gln Gly Thr Gln Val Thr Val Ser Ser
        115                 120                 125

<210> SEQ ID NO 330
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Gln Val Gln Leu Gln Glu Ser Gly Gly Gly Ser Val Gln Ala Gly Gly
1               5                   10                  15

Ser Leu Arg Leu Ser Cys Ala Val Ser Gly Lys Ala Tyr Gly Gly Ala
            20                  25                  30

Trp Phe Arg Gln Ala Gln Gly Lys Gly Arg Glu Gly Val Ala Ala Ile
        35                  40                  45

Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Glu Asp Thr Ala Val Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120

<210> SEQ ID NO 331
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Gln Val Gln Leu Gln Glu Ser Gly Gly Gly Ser Val Gln Ala Gly Gly
1               5                   10                  15

Ser Leu Lys Leu Ser Cys Ala Val Ser Gly Asn Pro Tyr Gly Gly Ala
            20                  25                  30

Trp Phe Arg Gln Ala Gln Gly Lys Ser Arg Glu Gly Val Ala Ala Ile
        35                  40                  45

Trp Leu Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Val Gln Ile
65                  70                  75                  80

Asp Gly Leu Lys Pro Glu Asp Thr Ala Met Tyr Tyr Cys Ala Ala Asp
                85                  90                  95

Asp Arg Pro Gly Tyr Arg Asp Pro Leu Ala Pro Val Ser Tyr Asn His
                100                 105                 110

Trp Gly Gln Gly Thr Gln Val Thr Val Ser Ser
            115                 120

<210> SEQ ID NO 332
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Gln Val Gln Leu Gln Glu Ser Gly Gly Gly Ser Val Gln Ala Gly Gly
1               5                   10                  15

Ser Leu Arg Leu Ser Cys Val Val Ser Gly Lys Ala Tyr Gly Gly Ala
            20                  25                  30

Trp Phe Arg Gln Ala Gln Gly Lys Ser Arg Glu Gly Val Ala Ala Ile
        35                  40                  45

Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Glu Asp Thr Ala Met Tyr Tyr Cys Ala Ala Asp
                85                  90                  95

Asp Arg Pro Gly Tyr Arg Asp Pro Leu Ala Pro Val Ser Tyr Asn His
                100                 105                 110

Trp Gly Gln Gly Thr Gln Val Thr Val Ser Ser
            115                 120

<210> SEQ ID NO 333
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Val Gln Leu Gln Glu Ser Gly Gly Gly Ser Val Gln Ala Gly Gly
1               5                   10                  15

Ser Leu Thr Leu Ser Cys Val Val Ser Gly Lys Ala Phe Gly Gly Ala
            20                  25                  30

Trp Phe Arg Gln Ala Gln Gly Lys Gly Arg Glu Gly Val Ala Ala Ile

```
            35                  40                  45
Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Asp Asp Thr Ala Met Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120

<210> SEQ ID NO 334
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Phe Ser Asn His
            20                  25                  30

His Met Gly Trp Phe Arg Gln Ala Pro Gly Lys Glu Arg Glu Gly Val
        35                  40                  45

Ala Ala Ile Tyr Thr Gly Ala Gly Asn Ile Tyr Tyr Ala Asp Ser Val
    50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
                85                  90                  95

Ala Ala Asp Leu Thr Arg Trp Tyr Ser Gly Gly Trp Arg Asp Pro Arg
            100                 105                 110

Gly Tyr Lys Tyr Trp Gly Gln Gly Thr Gln Val Thr Val Ser Ser
        115                 120                 125

<210> SEQ ID NO 335
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gln Val Gln Leu Gln Glu Ser Gly Gly Gly Pro Val Gln Ala Gly Gly
1               5                   10                  15

Ser Leu Arg Leu Ser Cys Ala Ala Ser Gly Tyr Thr Phe Ser Asn His
            20                  25                  30

His Met Gly Trp Phe Arg Gln Ala Pro Gly Lys Glu Arg Glu Gly Val
        35                  40                  45

Ala Ala Ile Tyr Thr Gly Ala Gly Asn Ile Tyr Tyr Ala Asp Ser Val
    50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
```

```
                    85                  90                  95
Ala Ala Asp Leu Thr Arg Trp Tyr Ser Gly Gly Trp Arg Asp Pro Arg
                100                 105                 110

Gly Tyr Lys Tyr Trp Gly Gln Gly Thr Gln Val Thr Val Ser Ser
            115                 120                 125

<210> SEQ ID NO 336
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Gln Val Gln Leu Gln Glu Ser Gly Gly Gly Val Val Gln Pro Gly Gly
1               5                   10                  15

Ser Leu Arg Leu Ser Cys Ala Ala Ser Gly Tyr Thr Phe Ser Asn His
            20                  25                  30

His Met Gly Trp Phe Arg Gln Ala Pro Gly Lys Glu Arg Glu Gly Val
        35                  40                  45

Ala Ala Ile Tyr Thr Gly Ala Gly Asn Ile Tyr Tyr Ala Asp Ser Val
    50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
                85                  90                  95

Ala Ala Asp Leu Thr Arg Trp Tyr Ser Gly Gly Trp Arg Asp Pro Arg
                100                 105                 110

Gly Tyr Lys Tyr Trp Gly Gln Gly Thr Gln Val Thr Val Ser Ser
            115                 120                 125

<210> SEQ ID NO 337
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Phe Ser Asn His
            20                  25                  30

His Met Gly Trp Phe Arg Gln Ala Pro Gly Lys Glu Arg Glu Gly Val
        35                  40                  45

Ala Ala Ile Tyr Thr Gly Ala Gly Asn Ile Tyr Tyr Ala Asp Ser Val
    50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
                85                  90                  95

Ala Ala Asp Leu Thr Arg Trp Tyr Ser Gly Gly Trp Arg Asp Pro Arg
                100                 105                 110

Gly Tyr Lys Tyr Trp Gly Gln Gly Thr Gln Val Thr Val Ser Ser
            115                 120                 125
```

-continued

```
<210> SEQ ID NO 338
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ala Thr Asn Ser Asn Arg
            20                  25                  30

His Met Gly Trp Phe Arg Gln Ala Pro Gly Lys Glu Arg Glu Gly Val
        35                  40                  45

Ala Ala Ile Tyr Thr Gly Tyr Thr Gly Gly Asn Thr Tyr Tyr Ala
    50                  55                  60

Asp Ser Val Arg Asp Arg Phe Thr Ile Ser Gln Asp Asn Ala Lys Asn
65                  70                  75                  80

Thr Leu Tyr Leu Gln Met Asn Ser Leu Thr Pro Glu Asp Thr Ala Met
                85                  90                  95

Tyr Tyr Cys Ala Ala Asp Leu Thr Arg Trp Tyr Ser Gly Gly Trp Arg
            100                 105                 110

Asp Pro Arg Gly Tyr Lys Tyr Trp Gly Gln Gly Thr Gln Val Thr Val
        115                 120                 125

Ser Ser
    130

<210> SEQ ID NO 339
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gln Val Gln Leu Gln Glu Ser Gly Gly Gly Ser Val Gln Asp Gly Gly
1               5                   10                  15

Ser Leu Arg Leu Ser Cys Ala Ala Ser Gly Asp Ile Tyr Ala Arg Asn
            20                  25                  30

Cys Met Gly Trp Phe Arg Gln Ala Pro Gly Lys Glu Arg Glu Lys Ile
        35                  40                  45

Ala Val Ala Asp Thr Gly Gly Arg Ser Pro Tyr Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Val Tyr Tyr Cys
                85                  90                  95

Ala Ala Gly Pro Leu Val Pro Val Asn Thr Ala Ala Arg Cys Val
            100                 105                 110

Tyr Glu Tyr Trp Gly Gln Gly Thr Gln Val Thr Val Ser Ser
        115                 120                 125

<210> SEQ ID NO 340
<211> LENGTH: 130
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 340

```
Gln Val Gln Leu Gln Glu Ser Gly Gly Gly Ser Val Gln Ala Gly Gly
1               5                   10                  15
Ser Leu Arg Leu Ser Cys Ala Ala Ser Gly Ala Thr Asn Ser Asn Arg
            20                  25                  30
His Met Gly Trp Phe Arg Gln Ala Pro Gly Lys Glu Arg Glu Gly Val
        35                  40                  45
Ala Ala Ile Tyr Thr Gly Tyr Thr Gly Gly Asn Thr Tyr Tyr Ala
    50                  55                  60
Asp Ser Val Lys Asp Arg Phe Thr Ile Ser Gln Asp Asn Ala Lys Asn
65                  70                  75                  80
Thr Leu Tyr Leu Gln Met Asn Ser Leu Thr Pro Glu Asp Thr Ala Met
                85                  90                  95
Tyr Tyr Cys Ala Ala Asp Leu Thr Arg Trp Tyr Ser Gly Gly Trp Arg
            100                 105                 110
Asp Pro Arg Gly Tyr Lys Tyr Trp Gly Gln Gly Thr Gln Val Thr Val
        115                 120                 125
Ser Ser
    130
```

<210> SEQ ID NO 341
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 341

| caggtccagc tccaggagtc tggcggtggc tcagtacaag ctgggggctc tctgcgtttg | 60 |
| tcctgtgtgg cgagcgggta cggatactgt gggtacgaca tgagttggta cagacaggcc | 120 |
| cctggcaagg aacgtgaatt tgtggccctc atcacttctg atcgctccat tagctacgag | 180 |
| gattctgtca agctcgcttt atcatttccc gcgacaacg ccgctaacac tggttatctg | 240 |
| gacatgacta gactgacccc cgatgacacg gccatttact attgcaagac cagtgcagcg | 300 |
| gcccgcgaat cttcctggtg tcgctctcgc taccgcgtgg catcatgggg ccagggtact | 360 |
| caggtcaccg tgtctagc | 378 |

<210> SEQ ID NO 342
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 342

| caagtccaac tccaggagtc tggtgggggc tctgttcaag ctggcgggtc cctgcgcctt | 60 |
| tcctgtaccg ccagcggcta cacgtactct agcgccttca tggcttggtt tcggcaggcc | 120 |
| cctggaaaag agagagaggg agtggcagct atctacactc gtgacggcgg aaccgtgtac | 180 |
| gctgatagtg tcaagggccg cttcaccatt tcccaggata tgccaagaa tatcctgtat | 240 |
| ctccagatga actcccttaa agccgaagac actgcgatgt actattgcgc agccaaaatc | 300 |
| ccgcagccag gccgggcttc tttgctggat agccaaacct acgactattg gggtcaaggc | 360 |

```
actcaggtta ccgtgtcttc c                                          381
```

```
<210> SEQ ID NO 343
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 343
caggtccagc ttcaggagag cggcggaggc tccgtgcagg ctgggggatc tttgagactc    60
agctgcgtgg ccagtggcta ctcttactgt gggtacgaca tgatgtggta tcgccaagcg   120
ccgggcaagg aacgtgagtt cgtggcgctc atcacttccg actactcaat tcgttacgag   180
gattccgttg agggccgctt cagcatttct cgtgacaacg cgaagaacac aggatacttg   240
ctgatgagta acctcacccc cgccgatacc gctatttatt actgcaagac aagtacagct   300
gccagggaga gcagttggtg tcggtctcgc tatcgtgtgg cctcctgggg acagggcacc   360
caagtaaccg tgtcatca                                                378
```

```
<210> SEQ ID NO 344
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 344
caggtgcagc tccaggaatc tggtgggggc agtgttcagg ctggtggcag cctgagactt    60
agctgcgtgg cttctggcta tggttactgt gggtacgaca tgagctggta tcggcagacc   120
cccggaaagg agcgggagtt cgtagcgctc atcacaagtg accgcatcgc ctcctatgaa   180
gactccgtta agggtcgctt tatcattagc cgggacaatg ccaagaacac aggttaccto   240
gatatgactc gggtcacacc tgacgatacc gctatctatt actgcaagac ttctgcggct   300
gcccgtgaaa acagctggtg ccgctcaaga taccgggtgg cctcctgggg acagggaact   360
caggtcaccg tctctagc                                                378
```

```
<210> SEQ ID NO 345
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 345
caggtgcagt tgcaggagag cggaggcgga tctgtgcagg ccggtggatt tctgcggctg    60
tcttgcgtgg cgagcggcta tggctattgc ggatacgaca tgagctggta tcgccaggtt   120
ccgggtaagg agcgtgagtt cgtcgctctg attacctctg atcgctctgt gtcctatgag   180
gactccgtta agggtagatt ctctatctct cgcgataatg ctaagaacac agcctacctg   240
gagatgaaca gactgacccc cgacgatacc gctgtctatt actgtaagac ctccacagcc   300
gctcgcgaga ataactggtg ccgctctcgc tatagaatcg cctattgggg tcagggtaca   360
caagttaccg tatcctcc                                                378
```

```
<210> SEQ ID NO 346
```

```
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 346
caggtgcagt tgcaggagag tggcgggggc tctgttcagg ctggtggatc attgcgtctg      60
agctgtgctg cctcccgcta cacctacact aataacttca tggcttggtt tagacaagct    120
cctggcaagg aacgcgaagg cgttgccgcg atttataccg gagacggtta cgcatattac    180
ttctattccg tgaagggccg cttcacaatc tcccaggata cgacgaaaa tatgctctac     240 ttgcagatga actccctcaa acctgaggac acggcaatgt actattgtgc ggctatggag    300
cgccgtatcg gaactcgccg tatgaccgaa aacgctgagt ataagtattg gggacaagga    360
acccaggtga ccgtatcctc c                                              381

<210> SEQ ID NO 347
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 347
caggtccagt tgcaggagtc tggtggcgga agcgtgcagg ctgggggcag cctcaggctg      60
tcctgtgctg tgtccgggta cgactactgc ggctacgacg tgcgctggta tcgccgtgcc    120
cccggcaagg agagggagtt cgtctccggg attgattccg atggctctac cagttacgca    180
gattccgtca aggtcgtttt taccattagt caggataacg ctgagaacac aagctatctg    240
cacatgttct cactgaagcc tgaggatacg gccatgtact attgcaagac tgagtccccc    300
gcaggtgaat ccgcctggtg tcgtaacttt cgcggcatgg actactgggg aaagggcacc    360
caggtcactg tgtcttct                                                  378

<210> SEQ ID NO 348
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 348
caggtgcagc tccaggaatc aggcggtggg tccgtgcagg caggagggag tctgcgcctg      60
tcctgtgtgg cctccggtta cagctactgc ggctacgata tgatgtggta taggcaagct    120
ccagggaagg agcgtgagtt cgtggcccct atcacatctg actattccat ccgctacgag    180
gactccgtgg agggaagatt ttcaatctcc agagacaacg caaagaacac cggataccto    240 ctgatgtcta acctgacccc agccgacacg gcaatctatt actgtaaaac ctccacagca    300
gcgagggagt ccagctggtg caggtccaga taccgtgttg cctcctgggg acagggcact    360
caggtgacgg tgagttct                                                  378

<210> SEQ ID NO 349
<211> LENGTH: 378
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 349

```
caggtgcagc tccaggagtc cggtggcggg agcgtgcagg ctggcggatc tctgcggctc    60
agttgcgtcg cctcagggta ttcctattgt ggctacgata tgatgtggta tcgtcaggcc   120
cccggcaagg agcgcgagtt cgtcgccctg attacaagcg attattcaat ccgttatgaa   180
gattccgtgg aggggcgctt ctccatcagt cgcgacaacg ccaaaaacac tggctacctt   240
ctgatgtcaa acctgactcc cgctgacacc gcgatctact attgtaaaac ctcaacggct   300
gcccgcgagt ccggctggtg ccggtctagg tatcgtgtgg ccagctgggg gcagggcact   360
caggtcaccg tgtcatcc                                                 378
```

<210> SEQ ID NO 350
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 350

```
caggtccagc tgcaagaatc cggtggaggc tctgtgcagg cgggtgggtc cctgcgcctg    60
tcttgcgccg tgtctggcta tgattattgc ggatatgacg tgcgctggta tcgccaggct   120
cccggcaagg aacgcgagtt tgtctctggg attgactcag acggcagcac tagctatgcc   180
gactccgtga aggtcgcttt caccatttcc aagacaacg ccgagaatac cagctatctg    240
cacatgttca gcctcaaacc tgaagatact gccatgtatt actgtaagac ggagagtccc   300
gcaggcgaat ccgcttggtg tcggaatttc aggggaatgg actactgggg caagggtact   360
caagtgaccg taagctct                                                 378
```

<210> SEQ ID NO 351
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 351

```
caggtgcagc tccaggagag cggcggaggc tccgtgcagg cgggcgggag cctgcgtctg    60
tcttgtgccg tatctggcta tgactattgc ggttacgacg ttcgctggta caggcaggct   120
ccgggcaagg agcgtgagtt tgtcagcggg attgacagtg acggctccac ctcttatgcg   180
gattccgtga agggacgctt cacaatttcc caggataacg cagagaacac ctcctacctc   240
cacatgttca gcctcaaacc cgaagatact gctatgtatt actgtaaaac agagagccca   300
gccggggagt ctgcttggtg tcgtaacttt cgcggcatgg actactgggg caagggaacc   360
caggtgaccg tctcttcc                                                 378
```

<210> SEQ ID NO 352
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 352

```
caggtgcaac tccaagagag cggaggcggg agtgttcagg ccgggggctc tctgcggctg    60
tcctgcaccg cctctggtta cacctactcc agcgccttca tggcctggtt ccggcaggca   120
cctggcaagg aacgcgaagg cgtagccgct atctatacgc gcgatggggg tacagtttat   180
gctgatagcg ttaaaggacg cttcactatc tcccaggaca cgccaaaaa cccctgtac    240 ttgcagatga actccctcaa acctgaagat acggcgatgt actattgtgc ggcaaagatg   300
cctcagcccg gacgcgcaag tctgcttgac tctcaaactt atgattactg gggccaaggg   360
actcaggtga ccgttagctc c                                              381
```

<210> SEQ ID NO 353
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 353

```
caggtgcagt tgcaggaaag cggcggtggc tcagtccagg ccgggggctt cttgcgcttg    60
agttgcgtgg cgagcggata tggctactgt ggctacgata tgagctggta tcgtcaggct   120
ccgggcaagg aacgtgagtt cgtcgcgctc atcactagcg aaagagtcat ctcctacgaa   180
gactccgtta agggccgctt ttccatttct cgcgacaacg ccgagaacac gggctacctt   240
gaaatgaata gactgactcc cgacgatact gccatctact attgcaagac aagcgccgct   300
gcacgcgagt cctcttggtg caggtctcgc taccgcgtgg cttcttgggg gcaggggacc   360
caggtgaccg tatcatcc                                                  378
```

<210> SEQ ID NO 354
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 354

```
caggttcaac tccaggagtc cggggggcggt tccgtgcagg ctgggggctc ccttagactt    60
agctgtgccg tgtctggata cgattactgt gggtatgacg tgcggtggta cagacgcgct   120
ccgggaaagg aacgcgagtt cgtgagcgga attgattccg atggcagcac ctcctatgcg   180
gattctgtga agggccgctt cactatctct caagacaacg ccgagaacac tagctacctg   240
cacatgttca gtctgaaacc ggaggatacc gcgatgtatt actgtaagac cgagtctcct   300
gctggagaga gcgcgtggtg cagaaacttc cgtggaatgg actattgggg taaaggaact   360
caggtgactg tgtccagt                                                  378
```

<210> SEQ ID NO 355
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355

```
caagtgcagc tccaggaatc tggaggcgga agcgtacagg ccggtggctc actccggctt    60
tcttgcgctg tgtcaggtta cgactattgt ggatatgatg tccggtggta taggcaagcg   120
```

```
ccgggaaagg agcgcgagtt cgtgagcggt atcaactctg acggctccac ctcctacgcc    180
gactctgtca agggccgctt tacaatttct caggacaacg cagagaacac ctcttacctg    240
cacatgttca gcttgaagcc ggaggacacc gcgatgtact attgtaagac tgagtccccc    300
gctggagagt ctgcatggtg ccgtaatttt cgcggcatgg actattgggg gaaaggtact    360
caggttaccg taagctca                                                   378
```

<210> SEQ ID NO 356
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 356

```
caggtacagc tccaggagag tggaggcggg tcagtgcagg ccggggggctc actgcgcttg    60 agctgcaccg cgagcggtta cacctacagc tccgcattca tggcttggtt caggcaagcc    120
ccaggcaagg agcgcgaggg cgtggctgcc atgtataccc gcgacggggg caccgtgtat    180
gccgattccg tgaagggccg tttcaccatc tcccaggata acgctaagaa cccctctac    240 ctccagatcc acactctcaa agccgaagac acggctatgt actattgcgc cgcgaagatc    300
cctcaacctg gcagggcaag ccttctggac tcccagacgt atgactattg gggccagggg    360
actcaggtta cagtgtccag c                                               381
```

<210> SEQ ID NO 357
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 357

```
caggtgcagc tccaggaatc cggcggtggg tctgtgcagg caggggggttt tctccgcttg    60 agctgtgtgg ctagtggata cggttattgt ggatacgaca tgagctggta tcgccaagta    120
ccgggcaagg agcgtgagtt tgtggccctc atcacctctg atcgctccgt gtcttatgag    180
gacagcgtga agggccgctt cagcatcagt cgcgacaacg ccaagaacac cgcttatctg    240
gaaatgaaca gactcacccc ggatgacaca gctatctact attgcaagac ctccacagcg    300
gccagagaga ataactggtg ccggtcccgc taccgcatcg cgtcctgggg ccagggcacc    360
caggtgactg tctcctct                                                   378
```

<210> SEQ ID NO 358
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 358

```
caggtgcagt tgcaggagtc tggagggggc agcgtgcagg ccggaggctc cctccgcctc    60
agctgcgcgg cctcccggta cacctacacc aataacttca tggcatggtt caggcaggcc    120
ccaggaaagg agcgtgaggg ggtcgccgca atctataccg gagacggcta cgcctattac    180
tttgactccg ttaaagggcg tttcaccatc agtcaagaca acgacaaaaa catgctctac    240
```

```
ctccagatga atagcttgaa gccggaggat accgcaatgt actattgtgc cgcgatggag    300
agacgctccg gtcggcgtcg catgactgaa aatgccgagt acaagtactg ggggcagggg    360
actcaggtga ccgtgagcag c                                              381
```

```
<210> SEQ ID NO 359
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 359
caagttcagc tccaggagag tggaggcggt tccgtacagg ctggcggaag tctgcgcctc    60
tcctgcgccg tctccggtta cgactattgt gggtacgacg tgcgctggta tagacaggct    120
cctggaaagg agcgtgagtt tgtgagtggc atcaactccg acggtagcac ctcctatgct    180
gattctgtga agggtcgctt tacaatctca caggacaacg ccgaaaacac ttcctatctg    240
cacatgttca gcctcaagcc cgaagacacc gcaatgtact attgtaagac tgaaggtcca    300
gctggcgaga gtgcatggtg caggaatttt aggggcatgg actactgggg caagggcacc    360
caggtcaccg tgtcttca                                                  378
```

```
<210> SEQ ID NO 360
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360
caggtgcagt tgcaggaatc aggaggcggt tctgtgcagg ccggaggcag cctgcgtctg    60
agctgcaccg cttctgggta cacctactca agtgccttca tggcctggtt tcggcaagcg    120
cccggcaagg aacgcgaggg agttgcggcc atctacacca gggacggcag tcccgtgtac    180
gctgactccc tgaagggccg tttcaccatc agccaggata acgcaaagaa caccctgcac    240
ctccagatga acagcctgaa acctgaggac acagctatgt attactgcgc ggccaaaatc    300
cctgagcctg gaagaatcag cctccttgac tcccagacct acgactactg gggtcacggc    360
actcaggtga ctgtgtcttc t                                              381
```

```
<210> SEQ ID NO 361
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 361
caggttcaac tccaagagtc tggaggcggg tccgtgcagg ctgggggctc cctcagactg    60
tcctgtactg cgtcagggta cacctacagc tccgctttca tggcttggtt ccggcaagct    120
ccgggcaagg agcgcgaggg cgtggccgcg atgtataccc gcgacggtgg caccgtgtac    180
gccgactctg ttaaaggccg cttcaccatc tcccaggata cgccaagaa cacccctgtac    240 ctccagatga actctttgaa gaccgaggat accgctatgt actattgcgc cgcaaaaatt    300
ccccagccgg gccgtgcttc ccttctggac agccaaacct atgattactg ggccagggc    360
```

```
acacaggtga ccgtgtcctc c                                               381

<210> SEQ ID NO 362
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 362
caggtgcaac ttcaggaatc tggcggtggc agcgtgcagg ctggtggctc cctgcgcctg    60
agctgtactg cttccggcta cacatactct agtgcgttca tggcctggtt caggcaagct   120
ccgggaaagg agcgcgaggg tgtggcggcc atttatacac gcgacggagg caccgtgtac   180
gctgactctg tcaagggccg cttcaccatc tcacaggaca atgcaaaaaa taccctctac   240
cttcagatga acagcctgaa ggcagaggac acagcaatgt attactgtgc agccaagatc   300
ccacaacccg gacgcgcgtc cctcctggat tcacagacct acgactactg gggccagggc   360
acgcaggtta ctgtatcaag c                                              381

<210> SEQ ID NO 363
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 363
caggtgcagc tccaggaaag cgggggaggt tccgtccagg ccgtggctc cctccgcctg     60 tcatgcacag cgagcggtta cacgtatagc tccgccttta tggcctggtt tagacaggcc   120
ccagggaaag aacgtgaggg agtggctgca atttacaccc gcgatggcgg gactgtttac   180
gccgatagcg tcaagggtcg ctttaccatc agccaggaca acgctaaaaa caccctctat   240
ctccagatga atagcctgaa ggccgaggac actgcgatgt attactgcgc cgctaagatc   300
cctcaacctg gccgcgccag cttgctggat agccagacat acgattactg gggtcaggga   360
acacaagtga cggtcagcag c                                              381

<210> SEQ ID NO 364
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 364
caggtgcagc tccaggagag cggcgggggc tccgtacagg ccgtggatc actccgcctg      60 agctgtgctg tgagcgggta cgactattgc ggatacgacg tgcgctggta tcgccaagct   120
ccagggaagg aaaggagtt cgtgagcgga attgattccg atggctccac cagttatgcc    180
gactccgtta aggaaggtt taccatctcc caagataacg ccgagaacac ctcctatctg    240
catatgtttt ccctgaaacc cgaggatacc gctatgtatt actgtaagac agagagccct   300
gccggagagt ccgcctggtg ccgcaacttt cggggcatgg actactgggg aaagggcacc   360
caggtgacag tgtctagc                                                  378
```

```
<210> SEQ ID NO 365
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 365
caggtgcagc tgcaagaatc aggaggtgga tctgtgcaag ctgggggctc tttgcgcctg     60
tcctgtgtcg cctccggcta tagctattgc ggctatgaca tgatgtggta caggcaagcc    120
ccaggtaagg agagggagtt tgtggctctc atcacctccg actacagcat tcgctatgaa    180
gatagtgtcg agggacgctt ctccatttct cgcgacaacg cgaagaacac tggctatttg    240
ctgatgagta acctcacccc cgccgacacc gcgatctact attgcaaaac atctaccgcc    300
gctcgggaaa gtagctggtg taggtcacgt tatagggtcg cttcctgggg tcagggcacg    360
caggtgaccg tctcatcc                                                  378

<210> SEQ ID NO 366
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 366
caggtgcagt tgcaggagag cggaggcgga tctgtgcagg caggcggaag cctccgcctg     60
tcttgcgccg cttcccggta cacctacaca aataacttta tggcatggtt ccgccaagcg    120
cccggcaagg agcgcgaggg tgtcgcggcc atttacacag gtgatggcta cgcctattac    180
ttcgactccg tgaaaggcag gttcacgatc tcccaggata cgacaagaa tatgttgtat     240 cttcagatga actctctgaa acctgaggac accgctatgt actattgtgc agctatggaa    300
cgcaggtcag gcaggcgcag gatgaccgag aacgccgagt acaagtactg gggccagggc    360
acccaggtga ccgtgtcttc a                                              381

<210> SEQ ID NO 367
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 367
caggtgcagc tccaggagtc tggaggcggt tccgtccagg ccggggaaac gctccggctt     60
agctgcaccg tctccggttt caccattgat gactccgaaa tgggttggta tcgccaagcg    120
cccggccatg agtgcgaact ggtggccagc ggaagttccg acgatgacac ctattacgtg    180
gactcagtga agggtcgctt tacgatctct ctggataacg ccaaaaacat ggtgtacctc    240
cagatgaact cactcaagcc agaggataca gcagtttatt actgtgccac tggacctaca    300
taccctccca aggatggtga ctgcgcacac tggggtcaag cacccaggt cactgtctcc     360 tcc                                                                  363

<210> SEQ ID NO 368
<211> LENGTH: 381
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 368

```
caagtccagc tccaggagtc tgggggaggc tcagtgcaag ctggtggatc tcttcgcctg    60
tcttgcaccg cttctgggta cacctatagc tctgccttca tggcctggtt taggcaagcg   120
cctggcaagg agcgggaggg cgtcgccgct atctacaccc gcgacggcag tccggtttat   180
gccgactccc tgaagggtag atttactatc tctcaggata atgcaaagaa tacgctgcac   240
ttgcagatga actccctcaa acccgaggac acggccatgt attactgtgc tgcaaaaatc   300
ccagagcctg gtcggatctc cctcctggat tcacagacct acgactactg gggccacggc   360
acccaggtga cagtctcttc c                                             381
```

<210> SEQ ID NO 369
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 369

```
caggtgcagc tccaggagtc cggtggcgga agcgtgcagg ccggtggctc cctgcggttg    60
agttgcgcgg tctcaggtta cgattattgt ggctacgacg tgcgctggta tagacgcgct   120
cctggcaagg agcgtgagtt cgtgtctggc atcgactccg atggctctac ttcatacgct   180
gattccgtca aaggccgttt caccatctct caggataacg ccgagaacac ctcctacctt   240
cacatgttct ctctgaagcc cgaggatact gcaatgtatt actgtaagac tgagtctcct   300
gccggagaat ccgcctggtg tcgtaacttt cgtggcatgg actactgggg taagggaacc   360
caggtgactg tatcttcc                                                 378
```

<210> SEQ ID NO 370
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 370

```
caggtccagt tgcaggagtc tggtggaggc tccgtccaag ctgggggctt tcttaggctg    60
tcatgtgtgg catccggcta tgggtattgt ggctatgata tgtcctggta tagacaagcg   120
cccggcaagg agcgcgagtt cgtggcgctg attaccagcg agcgcgttat cagctacgag   180
gactccgtca aaggcagatt ctccatctca cgcgacaacg ccgagaacac aggctatctg   240
gaaatgaatc gtttgacacc tgatgacacc gctatctact attgcaagac ctctgcggct   300
gcgcgtgagt ctagctggtg ccgttcccgc tatagagtgg cttcttgggg tcagggaacc   360
caggtgacag tctccagc                                                 378
```

<210> SEQ ID NO 371
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 371
caggtacagc tccaggagtc tggaggcggg agcgtgcagg caggcggttc cctgcgtctg        60
tcctgcgtcg cctctgggta tgggtactgc ggctacgata tgtcctggta tcgtcaggct       120
cccggcaaag aaagagagtt cgtagccctc atcacatctg accggagcat ttcctacgaa       180
gactccgtca aggcccgctt cattatctca cgggataacg cagccaacac cggatacctg       240
gacatgactc gcctgacccc cgatgacact gctatctatt actgcaagac gagcgcggca       300
gctcgcgaga gttcttggtg ccggtcccgg tacagggtgg cgtcctgggg ccaggggact       360
caggtcaccg tctcctcc                                                     378

<210> SEQ ID NO 372
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 372
caggtgcaac tccaggagag tggaggtggc tcagtacagg ccgggggaag cctccgtctg        60
agctgtgccg tgtccggcta cgattactgt ggttacgacg tgcggtggta tcgccaggcc       120
cctggtaagg aaagagagtt cgtgtccggc atcgacagcg atggtagcac atcttacgcc       180
gactccgtga agggccgctt cacaatctcc caggacaacg ccgaaaacac gtcttacctc       240
catatgtttt ccctgaaacc tgaagacacc gctatgtatt actgcaagac cgagtctccc       300
gctggcgagt cagcatggtg taggaacttt cgcggcatgg actattgggg taagggcacc       360
caggtgacgg tgagttct                                                     378

<210> SEQ ID NO 373
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 373
caggtgcagc tccaggaaag cggcggggga agcgtgcagg caggaggctc ccttcggttg        60
agctgcgtgg ccagcggcta cagctactgc ggctacgaca tgatgtggta tcgccaagct       120
ccggggaagg agcgcgagtt cgtcgccctc atcaccagtg attattctat ccgctacgaa       180
gactctgtgg aaggtaggtt ctccattagc agagacaacg caaagaacac tggatacctg       240
cttatgagca acctcacacc cgccgacact gccatctact attgtaagac ctctaccgcc       300
gctcgcgaaa gctcctggtg caggtcccgc tatcgcgtgg ccagttgggg tcagggaacc       360
caggtgacgg tatctagc                                                     378

<210> SEQ ID NO 374
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 374
caggttcagt tgcaggagtc tggaggtggc agtgtgcaag ctggaggctc cctccgcctg        60
```

```
agttgcgctg ccagcagata tacctatacg aataacttta tggcttggtt tagacaggcc    120
cccggtaaag agcgggaagg tgtggccgcg atttacaccg gcgatggcta cgcctattac    180
ttttacagcg tgaagggacg tttcaccatt tctcaggata acgatgaaaa catgctgtat    240
ctccaaatga actctctgaa gcctgaagac accgctatgt attactgcgc ggctatggag    300
cgcaggatcg gaacaagacg catgactgag aacgctgagt ataaatattg gggacaaggc    360
acacaggtga cagttagctc c                                              381
```

<210> SEQ ID NO 375
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 375

```
caggtccaac tccaggagtc cggggagggg tctgtgcagg cgggtggctc cctgcgcctg    60
agctgtgtcg cgtctggtta ctcctactgt ggatatgata tgatgtggta tagacaggcc    120
ccaggtaagg agcgcgagtt tgtggccctg attaccagcg actacagtat ccgctatgag    180
gattccgtgg agggccgctt ctctatctca cgcgacaacg ccaagaatac aggctacctc    240
ctgatgagca acctgacccc tgccgacaca gccatttatt actgcaagac ctccaccgcc    300
gcgcgtgaat ccggctggtg caggtcacgc tatcgtgtcg ccagctgggg tcagggggaca    360 caggtgacgg tgtcatct                                                  378
```

<210> SEQ ID NO 376
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376

```
caagtgcagt tgcaagaatc aggaggcggg tccgtgcagg cgggcggatc tctgcgtctg    60
tcttgtgctg tctccggtta tgactactgt ggttacgacg tgcgctggta tcgccaggcc    120
cctggtaagg aacgtgagtt cgtgagcggg atcaatagcg acggctccac ctcttatgcc    180
gacagtgtga agggtaggtt taccatcagt caagacaacg ccgagaacac atcctacctt    240
catatgttct ctctcaagcc tgaggatacc gcaatgtact attgcaagac ggagtccccca   300 gcaggtgagt ccgcttggtg cagaaacttt cgcggcatgg attattgggg aagggaacc    360 caggtcaccg tgtcttcc                                                  378
```

<210> SEQ ID NO 377
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 377

```
caggtgcaac ttcaggaatc cggtggcgga tctgttcagg ctggcggatt cctgcgcctg    60
tcttgcgtgg ccagtggcta cggctactgc ggctatgata tgtcatggta tcgccaagtg    120
cccggcaagg agcgcgagtt tgtagccctc atcacatctg atcgttctgt cagctacgaa    180
```

```
gacagtgtca agggccgctt ttccatcagc cgcgataatg cgaagaacac ggcctacctg      240
gagatgaaca gactgacacc ggatgacacc gctgtatatt actgtaagac ctcaacggct      300
gccagagaga ataattggtg ccgttctcgc taccgcatcg cttattgggg ccagggaaca      360
caggtcacag tctcctcc                                                    378

<210> SEQ ID NO 378
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 378
caggtgcaac tccaggagag cggggggaggt tccgttcagg ccgggggttc cctcagattg      60
tcttgtgccg tctccgggta cgattactgt ggctatgacg tgcgctggta tcggcaggct     120
cctgggaagg agcgggagtt cgtgagtggc attaactcag acgggtctac ctcctatgcc     180
gacagcgtta agggcaggtt tactatcagt caggacaatg cggagaatac cagttacctg     240
cacatgttca gcctcaagcc cgaggatacc gccatgtatt actgcaagac agagggtcca     300
gctggcgagt ccgcatggtg ccgcaacttc aggggtatgg actactgggg caagggtact     360
caggtgactg tgtcctct                                                    378

<210> SEQ ID NO 379
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 379
caggtgcagt tgcaggagtc aggcgggggc tctgtccagg ctgggggctc tctgagactg      60
tcttgtactg cgtctggtta cacgtacagt tctgccttta tggcctggtt tcggcaagcg     120
cccggaaagg agcgcgaggg tgttgctgcc atgtataccc gtgatggcgg aaccgtctac     180
gcagattctg ttaagggtcg tttcacaatc tcccaggaca atgcgaaaaa taccctctat     240
ctccagatcc acaccttgaa ggctgaggac accgcgatgt attactgtgc tgccaagatc     300
ccgcagcctg gccgcgcttc cctgctcgac agccagacat acgactactg gggtcagggc     360
acacaggtta ccgtgagtag t                                                381

<210> SEQ ID NO 380
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 380
caagtccaac tccaggaaag cggaggtggc agcgtccagg ccgggggctc tctgagactg      60
tcttgtaccg cttccggcta tacatattcc tctgccttta tggcatggtt ccgccaagcg     120
ccaggcaagg agcgcgaggg cgtcgccgct atgtatacca gagacggagg caccgtctac     180
gctgacagcg tcaagggacg cttcacaatc tcccaggaca acgccaagaa tactttgtat     240
ctccagatga atagcctcaa gacggaggac accgcaatgt attactgcgc tgcaaaaatc     300
```

```
cctcagccag gtcgcgcctc cctcctggac agtcagacct atgattattg gggccagggg      360
acccaggtga ctgtctcctc c                                                 381

<210> SEQ ID NO 381
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 381
caggtacagt tgcaggagtc cggcggaggc agcgttcagg ccggtggctt cctgaggctg       60
tcctgcgtcg ccagcggcta tggatattgc ggctacgata tgtcctggta cagacaggtc      120
cctgggaaag aacgcgagtt cgtggctctt atcacatccg acaggtccgt gtcctatgag      180
gactctgtca agggccgttt cagcatcagc cgtgacaacg caaaaaacac ggcttacttg      240
gagatgaacc ggcttacccc cgacgatacc gcgatttatt actgcaagac cagcacagca      300
gccagggaaa ataattggtg tcggagccgt tatcgtatcg cctcttgggg acagggaacc      360
caggtgactg tctcctca                                                    378

<210> SEQ ID NO 382
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 382
caggtgcagc tccaggagtc cggcggaggc tcagtacaag ctggcggttc actcaggttg       60
agttgtgtcg ccagtggcta cggctattgt ggctatgata tgtcttggta tcgccagacc      120
cccggcaagg agcgtgagtt cgtggcactc atcacgtccg accggatcgc tcttacgaa       180 gactctgtca agggccgttt tattatcagc cgcgacaacg caaaaaacac tggttatctc      240
gacatgactc gggtgacccc cgatgacact gccatctact attgcaaaac ctctgctgcg      300
gcccgcgaga actcctggtg ccgtagtcgc taccgcgtcg cctcctgggg acagggtaca      360
caggtgaccg ttagctcc                                                    378

<210> SEQ ID NO 383
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 383
caggtccaac tgcaagagtc tggcggtggc tccgtgcagg ctggcggtag tctgcgcctg       60
tcttgtgcag tcagcgggta cgactactgc ggttatgatg tcagatggta tcgccgtgct      120
cccggcaagg aacgcgagtt cgtctctggc attgactccg acggctctac ctcctatgcc      180
gatagcgtaa agggaaggtt caccatcagc caggacaacg ctgagaacac cagctacttg      240
cacatgttct cccttaaacc tgaggacaca gctatgtatt actgtaaaac tgagagcccg      300
gctggcgaga gcgcctggtg tcgcaacttt cgtggcatgg actactgggg taagggcacc      360
caggttactg tctctagt                                                    378
```

<210> SEQ ID NO 384
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 384
caggtgcaac ttcaggagag cggtggcggt tcagtgcagg ctgggggaag cctgcgcctg    60
tcttgcaccg cttccggcta cacctattcc agtgccttca tggcctggtt ccgccaggcc   120
cctggaaagg aacgcgaagg cgtggctgcc atttatacac gggatggggg aaccgtctac   180
gcggactccg tcaagggaag attcaccatt agccaggata atgctaagaa catcctgtac   240
ctccagatga actccctcaa agccgaggat actgctatgt actattgtgc cgctaagatt   300
ccgcagccag gccgggcatc cctcctggac agccagacct atgactactg gggacagggg   360
acccaggtga ccgtgtcttc c                                             381

<210> SEQ ID NO 385
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 385
caggtgcagc tccaggagtc cggcggtggc agtgtccagg caggaggcag tctgcgtctg    60
tcttgcactg cctcaggcta cacatactca agcgcattca tggcctggtt caggcaggcc   120
cctgggaagg agcgcgaggg tgtggcagct atctacaccc gcgatggcgg tactgtgtac   180
gccgatagtg tcaagggggcg ctttaccatt tctcaggaca acgcgaagaa caccctgtac   240
ttgcagatga acagcctgaa gccggaggat actgctatgt attactgcgc cgcaaaaatg   300
ccccagccgg gccgcgcgtc tttgctggat tcccagacat acgactactg ggggcagggc   360
acccaggtta cggttagctc c                                             381

<210> SEQ ID NO 386
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 386
caggtccagc tccaggaaag cggaggtgga tctgtgcagg ccggtggatc actgcggctg    60
agttgcgccg caagcggctt taccgtgaca agatattgca tggggtggtt gcgccaggca   120
cccggcaaac agcgtgaagg cgtggctatc attgagcgcg acgtcggac cggctatgcg    180 gatagcgtca agggcagatt caccatcagc aaggacaacg cgaaaaatac cctgtacctg   240
caaatgaact ccctcaagcc cgaggatacg gcgatgtact attgcggcgc gattgagggt   300
tcttgtcggc ctgatttcgg ttatcgcggg cagggaaccc aagtgaccgt ctcctct      357

<210> SEQ ID NO 387
<211> LENGTH: 357
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 387

```
caggtacagt tgcaggagag tggcggaggt agcgtccaag cgggcgggag cctgcgcctg    60
agttgtgctg ccagcggttt taccatctct cgctactgta tggatggct gcggcaagcg   120
cctggcaagc agagggaagg agtggccatt atcgagaggg atggccgcac cggatacgcc   180
gactccgtga agggacgctt cacgatctca aaggataacg ctaagaacac tctctacctc   240
cagatgaaca gtctgaagcc ggaggatact gctatgtatt actgtggggc cattgagggt   300
agctgtcggc ctgactttgg ttatcgcgga cagggaacgc aggtaaccgt gtcatcc      357
```

<210> SEQ ID NO 388
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 388

```
caggtgcagc tccaggagag cggcgggggt tccgttcagg ctggaggttc tctgcgcctt    60
agttgtactg ccagcggcct gactttcgac gatgtcgaga tggcatggta tcgccaaggt   120
cccggcgacg attacgatct ggtgtccagt atcaataccg atagcagggt ctattacgtc   180
gatagcgtca aggacagatt caccatcagc cgggacaacg ccaagaacac cctctacttg   240
cagatgaata acctgaagcc ggaggataca gctgtttatt actgtgccgc agacccttgg   300
ggtggcgacc tcaggggcta cccgaactat tggggccagg cacacaggt gaccgttagc    360
tct                                                                 363
```

<210> SEQ ID NO 389
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 389

```
caggtgcagt tgcaggagag cgggggaggt agcgtgcagg cgggcggttc cctgcgcttg    60
tcttgtgtcg cctccggttt taccatctcc cgttattgta tgggctggtt gcgccaggca   120
cccggcaagc agcgggaggg ggtggctatt atcgagcggg atggccgtac tggatatgcc   180
gactccgtga agggccgttt cacaatctcc aaagacaatg caaagaatac tctgtatctt   240
cagatgaact ccctgaagcc cggcgacact gctatgtact attgcggggc catcgagggt   300
tcctgtcggc ccgacttcgg ctaccgtggc cagggcaccc aggtcaccgt tagttcc      357
```

<210> SEQ ID NO 390
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 390

```
caggttcagc tccaggagtc tggcggaggc ctggttcagc ctggaggtag cctgaagctg    60
tcttgcgccg cttctggttt taccttctct acctacgcta tgtcttgggt gaggcaggca   120
```

```
cctggcaagg agcctgagtg gatcagccgt atctcttccg gcgggggcaa tacatattac    180
gctgacgctg ttaaggggcg cttcgccatc agtcgcgata atgccaagaa cactctgtat    240
ctccagctga acagcctgaa gacagaggac actgcaattt atgtatgtac tatggacgat    300
tactatgggg gctcctggca tcccatctcc agagggcatg ggacccaggt aaccgtgtcc    360
tct                                                                  363
```

<210> SEQ ID NO 391
<211> LENGTH: 372
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 391

```
caggtgcagc tccaggaaag cggcggtggg cttgtgcagg caggtggctc cctgaggctg    60
tcctgccagg ccagcgggta cacatacggc ttgttctgta tgggctggtt ccgtcaggtc    120
agcggtaaaa agcgcgaagg ggttgccgtc gtggatagcc caggaggccg ccacgtggcc    180
gacagcctga agggccgttt caccatctcc aaggacaacg ccaataacat cttgtatctg    240
gacatgacca atctgaagtc cgaggacacc gcaacctatt actgcgccgc tgaccctgag    300
aagtattgct ttctcttctc cgatgctggc tatcagtact ggggacaagg cacacaggtt    360
acagtatcct cc                                                        372
```

<210> SEQ ID NO 392
<211> LENGTH: 384
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 392

```
caagtacagc ttcaggaatc tgggggtggc tccgtccagg caggaggctc ccttagactg    60
tcctgtgcgg ccagcggggt cacctactcc agatattgta tggggtggtt ccggcaggcc    120
cctggactgg aacgcgaacg tgtggccact atctactcca gggcattat cacatattac     180 acagacagcg ttaagggaag gtttaccatt tcccaggaca gtgctaaaaa gaccgtctac    240
ttgcagatga actccttgaa gcctgaggac acggcaatgt actattgtgc cgcgactcgc    300
gagacttacg gtggatctgg cgactgtgac tacgagtctg tctacaacta ctgggctcaa    360
ggcacccagg tgacagtctc aagc                                           384
```

<210> SEQ ID NO 393
<211> LENGTH: 357
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 393

```
caggtgcaac tgcaagaatc tgggggcggt tccgttcagg ccggaggtag cctgcgcctg    60
agctgcgcgg cttcaggctt caccgtgagc agatactgta tgggctggtt gaggcaagct    120
cctggaaagc aacgcgaagg ggtcgccatt atcgagcgtg agggacgtac cggctacgcc    180
gatagcgtta agggacgttt taccatctct aaggacaacg ccaagaacac gctgtatttg    240
```

```
cagatgaaca gtctcaagcc cgaagataca gctatgtatt actgcggcgc aatcgaaggc    300
tcttgcaggc ccgactttgg atatcgcggc caaggtacac aggttactgt gtcttcc      357
```

<210> SEQ ID NO 394
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394

```
caggtgcagc tgcaagagtc aggtggcggg agcgtgcagg cgggaggcag ccttcgcctg    60
agttgcgcag cctccggctt caccatctca cgctactgta tgggttggct gcgccaagcg   120
cctggaaaac agcgcgaagg tgtggctatc attgaacgcg acggaaggac cggctacgca   180
gattcagtga agggccgctt caccatcagc aaggataacg ctaagaacac tctttatctc   240
cagatgaact ccttgaaacc agaggatact gcgatgtact tctgcggcgc tattgagggt   300
tcctgccgcc ccgatttttgg ctatcgcggg cagggcaccc aggtcaccgt gagcagt     357
```

<210> SEQ ID NO 395
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 395

```
caggtgcagc ttcaggagag cgggggaggc agcgtgcaag ctggtggctc cttgcgcttg    60
agctgtgcag cgtctggatt caccgttaca agatattgca tgggatggct ccgtcaagcg   120
cctggcaagc agcgcgaggg cgtggccatc attgagaggg acggaaggac aggttacgcc   180
gatagtgtga agggacggtt cactatcagc aaggataatg ccaagaatac gctttatctt   240
cagatgaact cccttaaacc agaggacacc gctatgtatt actgtggggc tatcgaaggc   300
agctgtaggc cggacttcgg atatcgcggc cagggaactc aggttaccgt aagctcc     357
```

<210> SEQ ID NO 396
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396

```
caagtgcagc ttcaggagtc tgggggcggt tccgtgcaag ccggaggcag cctgcgcctg    60
agctgcgccg caagcggatt tacagtgagc cgctattgta tggggtggct gcggcaggcc   120
ccaggaaagc agcgcgaggg ggtggccatc attgagagag atggaaggac cggctatgcc   180
gatagcgtca aaggccgttt taccatcagt aaagatgacg ccaagaacac actgtatctt   240
cagatgaact ccctcaagcc tgaggacacc gccatgtatt actgtggcgc aatcgaaggc   300
agctgtcgcc ccgatttttgg ttacagaggc cagggcactc aggtgaccgt cagcagc     357
```

<210> SEQ ID NO 397
<211> LENGTH: 384
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 397
caggtgcagc ttcaggagtc tgggggaggc tctgtccagg ctggaggctc cctgcgcctg      60
tcctgtgcag cctctggcgt gacctattcc cgctactgca tgggctggtt tcgtcaggcc     120
ccagggctgg agagagagcg ggtggccacg atctactctc gcgggattat cacctattac     180
actgactccg tgaagggcag attcaccatc tcccaggatt ccgcgaaaaa gaccgtgtac     240
cttcaaatga acatgctgaa gcccgaggat acagccatgt attactgcgc cgctacaagg     300
gagacctacg gcggaagcgg tgactgcgac tatgaaagcg tttacaacta ctgggctcag     360
ggcacgcagg tgaccgtaag ctct                                            384

<210> SEQ ID NO 398
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 398
caggtgcagc tccaagagtc tggaggcggg tccgtgcaag ccgggggctc actgcgcctg      60
tcctgcgctg cgagcggttt tactattagc aagtactgca tgggatggct ccgccaagca     120
ccgggcaaac agcgcgaagg cgtggcgatt atcgagagag atggccgtac cgggtacgcc     180
gactccgtca agggccgctt caccatcagc aaggacaatg ctaagaacac cctgtatttg     240
cagatgaaca gtctgaagcc ggaggacact gctatgtatt actgcggtgc cattgagggt     300
tcttgccgtc cagacttcgg ctatcgcgga cagggcacgc aagtcactgt ttctagt        357

<210> SEQ ID NO 399
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 399
caggtgcagc tgcaagaatc aggtggcggt tctgtgcagg ctggaggcag cctgaggctg      60
tcctgtgctg ccagtggtgt aacatactcc cgctactgta tgggttggtt cgccaggct     120 ccgggcctgg agagggagcg cgtcgcccat atctatagcc gtggcattat cacctattac     180
accgacagcg tgaagggtcg tttcaccatc agccaggact ctgctaagaa aaccgtgtat     240
ctccagatga acagcctgaa gcctgaggat accgccatgt attactgcgc agcgactaga     300
gagacctacg gtgggtccgg ggattgcgga tacgagagcg tctacaacta ctgggctcag     360
ggcacccaag tcaccgtgtc ctct                                            384

<210> SEQ ID NO 400
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 400
```

```
caggtgcagt tgcaggagtc cggcggtggc tctgtgcagg ccggggggctc ccttcgcctg    60 tcctgcgcag ccagtggttt caccatctcc cgttactgca tgggctggct gcgccaagcc   120
cccggcaagc agcgggaggg ggttgcaatt atcgagcgtg acggtaggac cggatacgct   180
gattccgtga aaggcaggtt tacaattagt aaagataatg ctaagaacac cctttacctc   240
cagatgaact cccttaaacc agaggatact gctatgtatt actgcggggc cattgagggt   300
agttgtcgcc ctgacctggg ctacagaggc cagggaactc aggtgaccgt gtccagt      357
```

<210> SEQ ID NO 401
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401

```
caggtgcagc ttcaggaatc cggtggcggg tctgtgcagg ccggtggcag cctgcggctg    60
tcctgcgctg cctctggcgt gacatactct cgttattgta tgggctggtt ccgccaggct   120
cccggcctgg agcgtgagag agttgcacac atttattcta gggcattat cacgtactat   180 accgattctg tgaagggacg cttcaccatt tcccaggaca gcgcgaaaaa gacggtttac   240
ctccagatga actcactgaa acctgaggat accgccatgt attactgcgc tgccacccgt   300
gagacctacg gtggctctgg tgattgtagc tacgagtctg tttacaacca ttgggcacag   360
ggaacccagg tgaccgtgtc aagc                                          384
```

<210> SEQ ID NO 402
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 402

```
caggttcagt tgcaggagtc aggagggggc tcagtgcagg cgggcggtag cttgcgtctg    60
agttgcgctg ccagtggatt gacgatttct cgctactgca tgggttggct tcgccaggcc   120
cctggtaaac aacgggaagg tgtagcaatt atcgagcgcg atggccggac ggggtacgcc   180
gatagcgtga agggccgctt cactattagc aaggacaacg ccaaaaacac cctgtacttg   240
cagatgaaca gcttgaagcc tgaggatact gccatgtatt actgcggagc tatcgagggc   300
tcctgccgcc cggatttcgg atacagggc caaggcactc aggtgacagt gagtagt       357
```

<210> SEQ ID NO 403
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 403

```
caggtccagc tccaggaatc tggcggaggc tcagtccaag ccggtggcag cttgcgcctg    60
tcttgctcag cctccggttt caccgtggat gactttgcta tgggatggta tcgccaggca   120
ccgggtaacg agtgtgagct ggtgtccact atctcctctg ggggcagcac ctattacgcg   180
gactctgtga agggaagatt tacaatttct caggattccg cgaagaacac cgtctatctt   240
```
cagatgaaca gcctgaagcc tgaagacaca gccgtgtact attgtgcgcc atcctctgta    300
gggtgtccat tggggtactg gggccagggt acacaagtca ctgtgtcaag c            351

<210> SEQ ID NO 404
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404
caggtgcagc ttcaggagag tggcggaggc agtgttcagg ctggtggatc attgcgcctg    60
tcctgtgcgg cttccggcta cacatattct aaccgccaca tgggctggtt taggcaggcc   120
cctggcaagg aacgcgaggg tgtggcggca atctacactg ggggtggctc cacatattac   180
gcggactccg tgaaggaccg cttcaccatt tcccaggata cgcgaagaa cacgttgtac    240 ttgcagatga acagtctgac tcccgaagac accgccatgt attactgcgc agccgatttg   300
acacgttggt atagtggtgg ctggcgcgat cccaggggtt acaaatactg ggccagggc    360 acgcaggtaa cggtgtca                                                  378

<210> SEQ ID NO 405
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405
caagttcagc ttcaggagag tggaggtggc agcgtgcagg ccggtgggtc cctgaggctg    60
tcctgtgctg ccagcggagt tacctacggc agctattaca tggcagcttg gtttaggcag   120
gccccaggta aggagcgcga aggcgtcgcc tccatctatg gcggtagcga ctccaccctat  180 tacgcagact ctgtcctggg ccgtttcacc atctctcagg acaatggaaa gaacacccct   240
tacttgcaga tgaactcact gaagccagat gacaccgcga tgtactattg tgctgccgct   300
cctccgggca gtggttcct gaagcgtctg gaaggccaca actacagtta ttggggtcag    360
ggcactcagg taaccgtgtc atct                                           384

<210> SEQ ID NO 406
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406
caggtccagc tccaggagag cggagggggc tctgttcagg tgggtggctc cctgcgcctg    60
tcttgtgccg cgtctggttt cacttatagc tcttcctgcc tgggctggtt ccggcaggct   120
cctgggaagg agcgtgaagg agtggccacc atctatcccg caggtggcaa catctttac    180 gccgacagtg tgaagggccg cttcaccatt tcccaggata cgctaagaa cactgtttac    240 ctccagatgg attctctgaa accggaggac accgcgatgt attactgcgc tgcacgggga   300
ggtcagacct gggggtccgg cggaaataga tgttctttgt ggctcccagc ttacaactat   360
tggggccagg gcacccaggt cactgtttcc tct                                 393

<210> SEQ ID NO 407
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 407

```
caggtccagc tccaggagtc cgggggtggc tctgtgcagg tcggtggcag cctgcggctg      60
tcttgcgccg ttagcggcaa gctgtacgga ggggcctggt tccggcaggc ccagggcaag     120
gggcgtgaag gagtggcggc aatctggatt ggcaccggaa caaccttcta cgccgacagt    180
gtgaagggac gcttcactat cagccgcgac aacgcgaaga acaccgtcta tctgcaaatg    240
gatgggctga agcccgagga caccgctctg tactattgtg ctgccgatga tcgcccaggt    300
tatcgggacc ctctggcccc cgtgtcttac aatcactggg gtcagggcac ccaggtgaca    360
gtgtctagt                                                             369
```

<210> SEQ ID NO 408
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 408

```
caggtgcagc ttcaggagag cggtgggggt agcgtgcagg caggcggaag tctgaggttg      60
tcttgtgccg ctagtggaat cacttatcgc ggggtctgga tgggatggtt ccggcaagcg    120
cccggtaagg aaagagaagg agtggcgact atctatacag gctccggtca tacatattac    180
gcagattctg ttaagggccg cttcaccatc tctcaagaca acgccaagaa cactgtctat    240
ctccagatga actccctgaa gcccgaggac acagctatgt attactcgcg cgctaggacc    300
gtcggggta cttttacac tctcgcggct gactcattta acacatgggg tcagggcacc    360
caagtgacag tgtccagt                                                  378
```

<210> SEQ ID NO 409
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 409

```
caggtccagt tgcaggagag cggtggaggt tccgttcagg caggtggaag cctccggctg      60
tcctgtgctg tgtctggcaa ggcctacgga ggtgcctggt tccgtcaggc tcaaggcaaa    120
ggccgggaag cgtcgctgc aatctggatt ggtactggaa ccacattcta tgcagactcc    180
gtgaagggca gatttaccat ttctcgtgac aacgcgaaaa acaccgttta cttgcagatg    240
gacgggctga agcctgagga taccgctgtc tattactgcg cggcagatga cagaccgggc    300
taccgcgacc ctctggcccc ggtgtcttat aaccattggg ggcaaggcac ccaggtgacc    360
gtttcttcc                                                             369
```

<210> SEQ ID NO 410
<211> LENGTH: 369
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 410

```
caggtccagc tccaggagtc cggcggggga agtgtccaag ctggtgggtc cctcaaactt    60
tcttgtgcgg tgtccggtaa cccttacggt ggagcctggt tccgccaggc ccagggcaag   120
tctcgcgaag gggtgctgc catttggctg ggaactggca ccactttta cgctgactcc    180
gtgaagggcc gcttcaccat ttccagagac aacgctaaga acaccgtgta tgtccagatc   240
gacgggttga aacctgagga taccgccatg tattactgcg ccgctgatga tcgccccggc   300
tatcgcgatc cgctcgctcc cgtcagttac aaccactggg gtcagggcac ccaggtgacc   360
gtttcctcc                                                           369
```

<210> SEQ ID NO 411
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 411

```
caagtgcagc ttcaggaaag tggaggcggg agcgtgcagg cgggcggttc cctgagactt    60
agctgtgtcg tgtctggcaa agcgtatggg ggtgcttggt tccgccaggc ccagggcaaa   120
tctagggagg gcgtgctgc catctggatc ggcaccggaa cgacctttta cgccgactcc    180
gtaaagggac gtttcaccat ctctcgggat aatgccaaga ataccgtcta ccttcagatg   240
gacgggctga agcctgagga taccgccatg tattactgtg ccgctgatga caggccagga   300
taccgcgatc ctctggctcc tgtctcttat aaccactggg gccaaggtac tcaagttacc   360
gtctcttcc                                                           369
```

<210> SEQ ID NO 412
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 412

```
caggtgcagt tgcaggagag cggcggaggc tctgttcagg ctggcgggag cctcacactg    60
tcctgcgttg tgtccggcaa ggcctttggt ggcgcttggt ttcgtcaggc gcagggtaag   120
ggacgcgagg gcgtcgcggc tatctggatc ggcaccggaa ccacatttta tgccgacagt   180
gtgaaaggcc gtttcacgat cagccgcgac aacgcaaaga ataccgtgta tctgcaaatg   240
gacggtctga agccggatga cactgcaatg tactattgcg ctgccgacga taggccgggc   300
tatagagacc cccttgcccc agtgagctac aaccactggg gacagggcac tcaggtaact   360
gtctctagt                                                           369
```

<210> SEQ ID NO 413
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 413

```
caggttcagc tccaggagag tggtggcggg agtgtgcagg ctggtggcag tctgaggctg      60
tcatgcgccg cttccggtta cacgttcagt aatcatcaca tggggtggtt cggcaggcc     120
cctggtaagg agcgtgaggg tgtggcggcc atctacaccg cgctggcaa catctattac     180
gcggacagtg tgaaagatcg gtttactatc tccaaggaca ccgcgaagaa caccctgtac     240
cttcagatga actctctcac ccctgaggat accggcatgt actattgcgc agccgatctc     300
actcgctggt actccggtgg gtggcgtgac ccgaggggct acaaatactg gggtcagggg     360
acgcaggtaa cagtctcttc a                                                381
```

<210> SEQ ID NO 414
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414

```
caggtgcagc tccaggagag cggggtggc ccagtccagg cggaggttc ccttcggctg       60
tcctgcgcgg cttcaggcta cacgtttagc aatcatcaca tgggctggtt cgtcaagca     120
ccaggaaagg agcgtgaggg tgtggcagct atttataccg cgctgggaa catctattac     180
gccgactccg tgaaggatcg gttcaccatc tccaagaca ccgccaagaa caccctgtat     240
ctccagatga actcactgac acccgaggac acaggtatgt attactgcgc tgccgatctg     300
acccgttggt acagcggggg ttggagagac cctcgcggtt ataaatattg gggccagggc     360
acccaggtga ccgtctccag c                                                381
```

<210> SEQ ID NO 415
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415

```
caggtgcagt tgcaggagtc cggggggcggg gtcgtgcaac ctggggggctc cctcagactg    60
agctgtgctg ccagcgggta tactttctcc aaccatcaca tgggatggtt caggcaggcc    120
cctggtaagg aacgggaagg cgtcgctgcc atctacactg gtgctggtaa catctattac    180
gcagacagcg tcaaagatcg ctttactatc agcaaggaca cagccaagaa taccctgtat    240
ctgcaaatga actctctgac cccagaggac acgggtatgt attactgtgc cgcagacctg    300
actcggtggt atagcggggg ctggagagac ccacgggggct acaaatactg gggtcagggc    360
acccaggtta ctgtgagcag c                                                381
```

<210> SEQ ID NO 416
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416

```
caagtgcaac tccaggagtc cggtggaggc agcgttcagg cgggcggtag cctgcgtctg      60
```

```
tcttgcgccg tgagcggcta tacctttagc aaccatcaca tgggatggtt ccgccaggct    120
cccggaaagg agagagaggg ggttgctgcc atctacaccg gagccggtaa catctactat    180
gccgacagcg tcaaggaccg tttcactatt tctaaggaca ccgctaagaa tactctctat    240
ctgcaaatga actctcttac tcccgaggac accggcatgt attactgcgc tgccgacctc    300
acccgctggt attcaggggg ctggcgcgac ccgcgcgggt acaagtattg gggacaggga    360
actcaagtga cagtctccag c                                              381
```

<210> SEQ ID NO 417
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 417

```
caagtgcagc tccaggaaag cgggggcggt agtgtgcagg ctggtggcag cctgagactg     60
agctgcgccg cttctggggc cactaattcc aacagacaca tgggatggtt ccgtcaggct    120
cccggtaagg agcgcgaagg cgtggcggct atttacaccg gatacactgg tgggggcaac    180
acatattacg cagacagcgt tcgggatcgg ttcaccatta gccaggataa cgctaaaaac    240
acactgtatc tccagatgaa tagcctgacc cccgaggaca ccgctatgta ttactgtgcc    300
gcagacctca cacgttggta ctctggaggc tggcgcgacc ctcgtggcta caagtattgg    360
ggacagggca cacaagtgac tgtaagctcc                                     390
```

<210> SEQ ID NO 418
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 418

```
caggtccagc tccaggagtc tggcggtggc agcgtacagg acgggggatc actgcgcctg     60
tcctgcgctg ccagcggcga catttacgcg aggaactgta tgggatggtt ccgccaggcc    120
cccggcaaag agcgcgaaaa gattgcggtc gccgacacag gcgggcgttc tccctattac    180
gctgactccg tgaagggacg ctttaccatc agtagggaca atgccaagaa caccgtggac    240
ctgcaaatga actccctcaa gcccgaggac accgccgtgt attactgcgc cgctggccca    300
ctggtgcctg tggtcaatac agctgcccgc tgcgtgtacg agtattgggg ccagggaacc    360
caggtgacag tctcctcc                                                  378
```

<210> SEQ ID NO 419
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 419

```
caggtgcagc tccaagagtc cggtggaggc agtgtgcagg ccggggggcag tctgaggctt     60 agctgtgcag cgtccggtgc caccaactcc aataggcaca tggttggtt ccggcaggct    120 ccggggaagg agcgcgaggg cgtcgccgca atctacaccg gctacaccgg cggtgggaat    180
```

```
acatattacg ccgattctgt gaaggacagg ttcacaatct cccaggacaa cgccaagaac    240
actctgtatc tccagatgaa ctccttgacc cccgaggata ctgcgatgta ttactgcgcc    300
gctgacctga ccagatggta ctctggcgga tggcgtgacc ctcgcggata taaatactgg    360
gggcagggca cccaggtcac cgtctctagc                                     390
```

```
<210> SEQ ID NO 420
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 420

His His His His His His
1               5

<210> SEQ ID NO 421
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 421

His His His His His His His His
1               5

<210> SEQ ID NO 422
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
```

```
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
```

```
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This sequence may encompass 1-20
      "(Gly)m(Ser)o" repeating units,
      wherein m = 1 to 20, o = 1 to 20
<220> FEATURE:
<223> OTHER INFORMATION: See specification as filed for detailed
      description of substitutions and preferred embodiments

<400> SEQUENCE: 422

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser
            20                  25                  30

Ser Ser Ser Ser Ser Ser Ser Gly Gly Gly Gly Gly Gly Gly
        35                  40                  45

Gly Gly Gly Gly Gly Gly Gly Gly Gly Gly Gly Ser Ser Ser
    50                  55                  60

Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly
                85                  90                  95

Gly Gly Gly Gly Ser Ser Ser Ser Ser Ser Ser Ser Ser Ser Ser
            100                 105                 110
```

```
Ser Ser Ser Ser Ser Ser Ser Gly Gly Gly Gly Gly Gly Gly
        115                 120                 125

Gly Gly Gly Gly Gly Gly Gly Gly Gly Gly Ser Ser Ser Ser
        130                 135                 140

Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly
                165                 170                 175

Gly Gly Gly Gly Ser Ser Ser Ser Ser Ser Ser Ser Ser Ser
        180                 185                 190

Ser Ser Ser Ser Ser Ser Ser Gly Gly Gly Gly Gly Gly Gly
        195                 200                 205

Gly Gly Gly Gly Gly Gly Gly Gly Gly Gly Ser Ser Ser Ser
        210                 215                 220

Ser Ser Ser Ser Ser Ser Ser Ser Ser Ser Ser Ser Ser Ser
225                 230                 235                 240

Gly Gly Gly Gly Gly Gly Gly Gly Gly Gly Gly Gly Gly Gly
                245                 250                 255

Gly Gly Gly Gly Ser Ser Ser Ser Ser Ser Ser Ser Ser Ser
        260                 265                 270

Ser Ser Ser Ser Ser Ser Ser Gly Gly Gly Gly Gly Gly Gly
        275                 280                 285

Gly Gly Gly Gly Gly Gly Gly Gly Gly Gly Ser Ser Ser Ser
        290                 295                 300

Ser Ser Ser Ser Ser Ser Ser Ser Ser Ser Ser Ser Ser Ser
305                 310                 315                 320

Gly Gly Gly Gly Gly Gly Gly Gly Gly Gly Gly Gly Gly Gly
                325                 330                 335

Gly Gly Gly Gly Ser Ser Ser Ser Ser Ser Ser Ser Ser Ser
        340                 345                 350

Ser Ser Ser Ser Ser Ser Ser Gly Gly Gly Gly Gly Gly Gly
        355                 360                 365

Gly Gly Gly Gly Gly Gly Gly Gly Gly Gly Ser Ser Ser Ser
        370                 375                 380

Ser Ser Ser Ser Ser Ser Ser Ser Ser Ser Ser Ser Ser Ser
385                 390                 395                 400

Gly Gly Gly Gly Gly Gly Gly Gly Gly Gly Gly Gly Gly Gly
                405                 410                 415

Gly Gly Gly Gly Ser Ser Ser Ser Ser Ser Ser Ser Ser Ser
        420                 425                 430

Ser Ser Ser Ser Ser Ser Ser Gly Gly Gly Gly Gly Gly Gly
        435                 440                 445

Gly Gly Gly Gly Gly Gly Gly Gly Gly Gly Ser Ser Ser Ser
        450                 455                 460

Ser Ser Ser Ser Ser Ser Ser Ser Ser Ser Ser Ser Ser Ser
465                 470                 475                 480

Gly Gly Gly Gly Gly Gly Gly Gly Gly Gly Gly Gly Gly Gly
                485                 490                 495

Gly Gly Gly Gly Ser Ser Ser Ser Ser Ser Ser Ser Ser Ser
        500                 505                 510

Ser Ser Ser Ser Ser Ser Ser Ser Gly Gly Gly Gly Gly Gly Gly
        515                 520                 525
```

```
Gly Gly Gly Gly Gly Gly Gly Gly Gly Gly Ser Ser Ser
            530                 535                 540

Ser Ser Ser Ser Ser Ser Ser Ser Ser Ser Ser Ser Ser Ser Ser
545                 550                 555                 560

Gly Gly Gly Gly Gly Gly Gly Gly Gly Gly Gly Gly Gly Gly Gly
            565                 570                 575

Gly Gly Gly Gly Ser Ser Ser Ser Ser Ser Ser Ser Ser Ser Ser
            580                 585                 590

Ser Ser Ser Ser Ser Ser Gly Gly Gly Gly Gly Gly Gly Gly Gly
            595                 600                 605

Gly Gly Gly Gly Gly Gly Gly Gly Gly Gly Ser Ser Ser Ser
            610                 615                 620

Ser Ser Ser Ser Ser Ser Ser Ser Ser Ser Ser Ser Ser Ser Ser
625                 630                 635                 640

Gly Gly Gly Gly Gly Gly Gly Gly Gly Gly Gly Gly Gly Gly Gly
            645                 650                 655

Gly Gly Gly Gly Ser Ser Ser Ser Ser Ser Ser Ser Ser Ser Ser
            660                 665                 670

Ser Ser Ser Ser Ser Ser Ser Gly Gly Gly Gly Gly Gly Gly
            675                 680                 685

Gly Gly Gly Gly Gly Gly Gly Gly Gly Gly Ser Ser Ser Ser
            690                 695                 700

Ser Ser Ser Ser Ser Ser Ser Ser Ser Ser Ser Ser Ser Ser Ser
705                 710                 715                 720

Gly Gly Gly Gly Gly Gly Gly Gly Gly Gly Gly Gly Gly Gly Gly
            725                 730                 735

Gly Gly Gly Gly Ser Ser Ser Ser Ser Ser Ser Ser Ser Ser Ser
            740                 745                 750

Ser Ser Ser Ser Ser Ser Ser Gly Gly Gly Gly Gly Gly Gly
            755                 760                 765

Gly Gly Gly Gly Gly Gly Gly Gly Gly Gly Ser Ser Ser Ser
            770                 775                 780

Ser Ser Ser Ser Ser Ser Ser Ser Ser Ser Ser Ser Ser Ser Ser
785                 790                 795                 800

<210> SEQ ID NO 423
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(100)
<223> OTHER INFORMATION: This sequence may encompass 1-20
      "Gly Ser Gly Gly Ser" repeating units
<220> FEATURE:
<223> OTHER INFORMATION: See specification as filed for detailed
      description of substitutions and preferred embodiments

<400> SEQUENCE: 423

Gly Ser Gly Gly Ser Gly Ser Gly Gly Ser Gly Ser Gly Gly Ser
1               5                   10                  15

Ser Gly Gly Ser Gly Ser Gly Gly Ser Gly Ser Gly Gly Ser
            20                  25                  30

Gly Gly Ser Gly Ser Gly Gly Ser Gly Ser Gly Gly Ser Gly
            35                  40                  45
```

Gly Ser Gly Ser Gly Ser Gly Ser Gly Ser Gly Ser Gly Gly
            50                  55                  60

Ser Gly Ser Gly Gly Ser Gly Ser Gly Ser Gly Ser Gly Gly Ser
65                  70                  75                  80

Gly Ser Gly Gly Ser Gly Ser Gly Gly Ser Gly Ser Gly Gly Gly
                85                  90                  95

Ser Gly Gly Ser
            100

```
<210> SEQ ID NO 424
<211> LENGTH: 1200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
```

```
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
```

```
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (801)..(820)
<223> OTHER INFORMATION: This region may encompass 1-20 residues
<220> FEATURE:
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
<223> OTHER INFORMATION: This region may encompass 1-20 residues
<220> FEATURE:
<221> NAME/KEY: SITE
<222> LOCATION: (1001)..(1020)
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
<221> NAME/KEY: SITE
<222> LOCATION: (1061)..(1080)
<223> OTHER INFORMATION: This region may encompass 1-20 residues
<220> FEATURE:
```

```
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1)..(1200)
<223> OTHER INFORMATION: This sequence may encompass 1-20
      "(Gly)m(Ser)o(Gly)m" repeating units,
      wherein m = 1 to 20, o = 1 to 20
<220> FEATURE:
<223> OTHER INFORMATION: See specification as filed for detailed
      description of substitutions and preferred embodiments

<400> SEQUENCE: 424

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser
                20                  25                  30

Ser Ser Ser Ser Ser Ser Ser Gly Gly Gly Gly Gly Gly Gly Gly
                35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Ser Ser Ser Ser Ser Ser Ser Ser Ser Ser Ser Ser Ser Ser Ser
                85                  90                  95

Ser Ser Ser Ser Gly Gly Gly Gly Gly Gly Gly Gly Gly Gly Gly
                100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Ser Ser Ser Ser
    130                 135                 140

Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Ser Ser Ser Ser Ser Ser Ser Ser
        195                 200                 205

Ser Ser Ser Ser Ser Ser Ser Ser Ser Ser Ser Gly Gly Gly Gly
    210                 215                 220

Gly Gly Gly Gly Gly Gly Gly Gly Gly Gly Gly Gly Gly Gly Gly
225                 230                 235                 240
```

-continued

```
Gly Gly Gly Gly Gly Gly Gly Gly Gly Gly Gly Gly Gly
            245                 250                 255
Gly Gly Gly Gly Ser Ser Ser Ser Ser Ser Ser Ser Ser
            260                 265                 270
Ser Ser Ser Ser Ser Ser Ser Gly Gly Gly Gly Gly Gly
            275                 280                 285
Gly Gly Gly Gly Gly Gly Gly Gly Gly Gly Gly Gly Gly
            290                 295                 300
Gly Gly Gly Gly Gly Gly Gly Gly Gly Gly Gly Gly Gly
305                 310                 315                 320
Ser Ser Ser Ser Ser Ser Ser Ser Ser Ser Ser Ser Ser
            325                 330                 335
Ser Ser Ser Ser Gly Gly Gly Gly Gly Gly Gly Gly Gly
            340                 345                 350
Gly Gly Gly Gly Gly Gly Gly Gly Gly Gly Gly Gly Gly
            355                 360                 365
Gly Gly Gly Gly Gly Gly Gly Gly Gly Gly Ser Ser Ser
            370                 375                 380
Ser Ser Ser Ser Ser Ser Ser Ser Ser Ser Ser Ser Ser
385                 390                 395                 400
Gly Gly Gly Gly Gly Gly Gly Gly Gly Gly Gly Gly Gly
            405                 410                 415
Gly Gly Gly Gly Gly Gly Gly Gly Gly Gly Gly Gly Gly
            420                 425                 430
Gly Gly Gly Gly Gly Gly Gly Ser Ser Ser Ser Ser Ser
            435                 440                 445
Ser Ser Ser Ser Ser Ser Ser Ser Ser Gly Gly Gly Gly
            450                 455                 460
Gly Gly Gly Gly Gly Gly Gly Gly Gly Gly Gly Gly Gly
465                 470                 475                 480
Gly Gly Gly Gly Gly Gly Gly Gly Gly Gly Gly Gly Gly
            485                 490                 495
Gly Gly Gly Gly Ser Ser Ser Ser Ser Ser Ser Ser Ser
            500                 505                 510
Ser Ser Ser Ser Ser Ser Ser Gly Gly Gly Gly Gly Gly
            515                 520                 525
Gly Gly Gly Gly Gly Gly Gly Gly Gly Gly Gly Gly Gly
            530                 535                 540
Gly Gly Gly Gly Gly Gly Gly Gly Gly Gly Gly Gly Gly
545                 550                 555                 560
Ser Ser Ser Ser Ser Ser Ser Ser Ser Ser Ser Ser Ser
            565                 570                 575
Ser Ser Ser Ser Gly Gly Gly Gly Gly Gly Gly Gly Gly
            580                 585                 590
Gly Gly Gly Gly Gly Gly Gly Gly Gly Gly Gly Gly Gly
            595                 600                 605
Gly Gly Gly Gly Gly Gly Gly Gly Gly Gly Ser Ser Ser
            610                 615                 620
Ser Ser Ser Ser Ser Ser Ser Ser Ser Ser Ser Ser Ser
625                 630                 635                 640
Gly Gly Gly Gly Gly Gly Gly Gly Gly Gly Gly Gly Gly
            645                 650                 655
```

Gly Gly Gly Gly Gly Gly Gly Gly Gly Gly Gly Gly Gly
        660                 665                 670

Gly Gly Gly Gly Gly Gly Gly Ser Ser Ser Ser Ser Ser Ser
        675                 680                 685

Ser Ser Ser Ser Ser Ser Ser Ser Ser Ser Ser Gly Gly Gly Gly
        690                 695                 700

Gly Gly Gly Gly Gly Gly Gly Gly Gly Gly Gly Gly Gly Gly
705                 710                 715                 720

Gly Gly Gly Gly Gly Gly Gly Gly Gly Gly Gly Gly Gly Gly
                725                 730                 735

Gly Gly Gly Gly Ser Ser Ser Ser Ser Ser Ser Ser Ser Ser
        740                 745                 750

Ser Ser Ser Ser Ser Ser Ser Gly Gly Gly Gly Gly Gly Gly
            755                 760                 765

Gly Gly Gly Gly Gly Gly Gly Gly Gly Gly Gly Gly Gly Gly
        770                 775                 780

Gly Gly Gly Gly Gly Gly Gly Gly Gly Gly Gly Gly Gly Gly
785                 790                 795                 800

Ser Ser Ser Ser Ser Ser Ser Ser Ser Ser Ser Ser Ser Ser
                805                 810                 815

Ser Ser Ser Ser Gly Gly Gly Gly Gly Gly Gly Gly Gly Gly
        820                 825                 830

Gly Gly Gly Gly Gly Gly Gly Gly Gly Gly Gly Gly Gly Gly
        835                 840                 845

Gly Gly Gly Gly Gly Gly Gly Gly Gly Gly Ser Ser Ser Ser
850                 855                 860

Ser Ser Ser Ser Ser Ser Ser Ser Ser Ser Ser Ser Ser Ser
865                 870                 875                 880

Gly Gly Gly Gly Gly Gly Gly Gly Gly Gly Gly Gly Gly Gly
                885                 890                 895

Gly Gly Gly Gly Gly Gly Gly Gly Gly Gly Gly Gly Gly Gly
        900                 905                 910

Gly Gly Gly Gly Gly Gly Gly Gly Ser Ser Ser Ser Ser Ser
        915                 920                 925

Ser Ser Ser Ser Ser Ser Ser Ser Ser Gly Gly Gly Gly
930                 935                 940

Gly Gly Gly Gly Gly Gly Gly Gly Gly Gly Gly Gly Gly Gly
945                 950                 955                 960

Gly Gly Gly Gly Gly Gly Gly Gly Gly Gly Gly Gly Gly Gly
                965                 970                 975

Gly Gly Gly Gly Ser Ser Ser Ser Ser Ser Ser Ser Ser Ser
        980                 985                 990

Ser Ser Ser Ser Ser Ser Ser  Gly Gly Gly Gly Gly  Gly Gly Gly
        995                 1000                1005

Gly Gly  Gly Gly Gly Gly Gly  Gly Gly Gly Gly Gly  Gly Gly Gly
    1010                1015                1020

Gly Gly  Gly Gly Gly Gly Gly  Gly Gly Gly Gly Gly  Gly Gly Gly
    1025                1030                1035

Gly Gly  Ser Ser Ser Ser Ser  Ser Ser Ser Ser Ser  Ser Ser Ser
    1040                1045                1050

Ser Ser  Ser Ser Ser Ser Ser  Gly Gly Gly Gly Gly  Gly Gly Gly
    1055                1060                1065

Gly Gly  Gly Gly Gly Gly Gly  Gly Gly Gly Gly Gly  Gly Gly Gly

```
                    1070                1075                1080

Gly  Gly  Gly  Gly  Gly  Gly  Gly  Gly  Gly  Gly  Gly  Gly  Gly  Gly
         1085                1090                1095

Gly  Gly  Ser  Ser  Ser  Ser  Ser  Ser  Ser  Ser  Ser  Ser  Ser  Ser
         1100                1105                1110

Ser  Ser  Ser  Ser  Ser  Ser  Ser  Gly  Gly  Gly  Gly  Gly  Gly  Gly
         1115                1120                1125

Gly  Gly  Gly  Gly  Gly  Gly  Gly  Gly  Gly  Gly  Gly  Gly  Gly  Gly
         1130                1135                1140

Gly  Gly  Gly  Gly  Gly  Gly  Gly  Gly  Gly  Gly  Gly  Gly  Gly  Gly
         1145                1150                1155

Gly  Gly  Ser  Ser  Ser  Ser  Ser  Ser  Ser  Ser  Ser  Ser  Ser  Ser
         1160                1165                1170

Ser  Ser  Ser  Ser  Ser  Ser  Ser  Gly  Gly  Gly  Gly  Gly  Gly  Gly
         1175                1180                1185

Gly  Gly  Gly  Gly  Gly  Gly  Gly  Gly  Gly  Gly  Gly  Gly
         1190                1195                1200

<210> SEQ ID NO 425
<211> LENGTH: 2000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
```

```
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
```

```
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (801)..(820)
<223> OTHER INFORMATION: This region may encompass 1-20 residues
<220> FEATURE:
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
<223> OTHER INFORMATION: This region may encompass 1-20 residues
<220> FEATURE:
<221> NAME/KEY: SITE
<222> LOCATION: (1001)..(1020)
```

```
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
<221> NAME/KEY: SITE
<222> LOCATION: (1061)..(1080)
<223> OTHER INFORMATION: This region may encompass 1-20 residues
<220> FEATURE:
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1201)..(1220)
<223> OTHER INFORMATION: This region may encompass 1-20 residues
<220> FEATURE:
<221> NAME/KEY: SITE
<222> LOCATION: (1221)..(1240)
<223> OTHER INFORMATION: This region may encompass 1-20 residues
<220> FEATURE:
<221> NAME/KEY: SITE
<222> LOCATION: (1241)..(1260)
<223> OTHER INFORMATION: This region may encompass 1-20 residues
<220> FEATURE:
<221> NAME/KEY: SITE
<222> LOCATION: (1261)..(1280)
<223> OTHER INFORMATION: This region may encompass 1-20 residues
<220> FEATURE:
<221> NAME/KEY: SITE
<222> LOCATION: (1281)..(1300)
<223> OTHER INFORMATION: This region may encompass 1-20 residues
<220> FEATURE:
<221> NAME/KEY: SITE
<222> LOCATION: (1301)..(1320)
<223> OTHER INFORMATION: This region may encompass 1-20 residues
<220> FEATURE:
<221> NAME/KEY: SITE
<222> LOCATION: (1321)..(1340)
<223> OTHER INFORMATION: This region may encompass 1-20 residues
<220> FEATURE:
<221> NAME/KEY: SITE
<222> LOCATION: (1341)..(1360)
<223> OTHER INFORMATION: This region may encompass 1-20 residues
<220> FEATURE:
<221> NAME/KEY: SITE
<222> LOCATION: (1361)..(1380)
<223> OTHER INFORMATION: This region may encompass 1-20 residues
<220> FEATURE:
<221> NAME/KEY: SITE
<222> LOCATION: (1381)..(1400)
<223> OTHER INFORMATION: This region may encompass 1-20 residues
<220> FEATURE:
<221> NAME/KEY: SITE
```

```
<222> LOCATION: (1401)..(1420)
<223> OTHER INFORMATION: This region may encompass 1-20 residues
<220> FEATURE:
<221> NAME/KEY: SITE
<222> LOCATION: (1421)..(1440)
<223> OTHER INFORMATION: This region may encompass 1-20 residues
<220> FEATURE:
<221> NAME/KEY: SITE
<222> LOCATION: (1441)..(1460)
<223> OTHER INFORMATION: This region may encompass 1-20 residues
<220> FEATURE:
<221> NAME/KEY: SITE
<222> LOCATION: (1461)..(1480)
<223> OTHER INFORMATION: This region may encompass 1-20 residues
<220> FEATURE:
<221> NAME/KEY: SITE
<222> LOCATION: (1481)..(1500)
<223> OTHER INFORMATION: This region may encompass 1-20 residues
<220> FEATURE:
<221> NAME/KEY: SITE
<222> LOCATION: (1501)..(1520)
<223> OTHER INFORMATION: This region may encompass 1-20 residues
<220> FEATURE:
<221> NAME/KEY: SITE
<222> LOCATION: (1521)..(1540)
<223> OTHER INFORMATION: This region may encompass 1-20 residues
<220> FEATURE:
<221> NAME/KEY: SITE
<222> LOCATION: (1541)..(1560)
<223> OTHER INFORMATION: This region may encompass 1-20 residues
<220> FEATURE:
<221> NAME/KEY: SITE
<222> LOCATION: (1561)..(1580)
<223> OTHER INFORMATION: This region may encompass 1-20 residues
<220> FEATURE:
<221> NAME/KEY: SITE
<222> LOCATION: (1581)..(1600)
<223> OTHER INFORMATION: This region may encompass 1-20 residues
<220> FEATURE:
<221> NAME/KEY: SITE
<222> LOCATION: (1601)..(1620)
<223> OTHER INFORMATION: This region may encompass 1-20 residues
<220> FEATURE:
<221> NAME/KEY: SITE
<222> LOCATION: (1621)..(1640)
<223> OTHER INFORMATION: This region may encompass 1-20 residues
<220> FEATURE:
<221> NAME/KEY: SITE
<222> LOCATION: (1641)..(1660)
<223> OTHER INFORMATION: This region may encompass 1-20 residues
<220> FEATURE:
<221> NAME/KEY: SITE
<222> LOCATION: (1661)..(1680)
<223> OTHER INFORMATION: This region may encompass 1-20 residues
<220> FEATURE:
<221> NAME/KEY: SITE
<222> LOCATION: (1681)..(1700)
<223> OTHER INFORMATION: This region may encompass 1-20 residues
<220> FEATURE:
<221> NAME/KEY: SITE
<222> LOCATION: (1701)..(1720)
<223> OTHER INFORMATION: This region may encompass 1-20 residues
<220> FEATURE:
<221> NAME/KEY: SITE
<222> LOCATION: (1721)..(1740)
<223> OTHER INFORMATION: This region may encompass 1-20 residues
<220> FEATURE:
<221> NAME/KEY: SITE
<222> LOCATION: (1741)..(1760)
<223> OTHER INFORMATION: This region may encompass 1-20 residues
<220> FEATURE:
<221> NAME/KEY: SITE
<222> LOCATION: (1761)..(1780)
<223> OTHER INFORMATION: This region may encompass 1-20 residues
<220> FEATURE:
<221> NAME/KEY: SITE
<222> LOCATION: (1781)..(1800)
<223> OTHER INFORMATION: This region may encompass 1-20 residues
<220> FEATURE:
```

```
<221> NAME/KEY: SITE
<222> LOCATION: (1801)..(1820)
<223> OTHER INFORMATION: This region may encompass 1-20 residues
<220> FEATURE:
<221> NAME/KEY: SITE
<222> LOCATION: (1821)..(1840)
<223> OTHER INFORMATION: This region may encompass 1-20 residues
<220> FEATURE:
<221> NAME/KEY: SITE
<222> LOCATION: (1841)..(1860)
<223> OTHER INFORMATION: This region may encompass 1-20 residues
<220> FEATURE:
<221> NAME/KEY: SITE
<222> LOCATION: (1861)..(1880)
<223> OTHER INFORMATION: This region may encompass 1-20 residues
<220> FEATURE:
<221> NAME/KEY: SITE
<222> LOCATION: (1881)..(1900)
<223> OTHER INFORMATION: This region may encompass 1-20 residues
<220> FEATURE:
<221> NAME/KEY: SITE
<222> LOCATION: (1901)..(1920)
<223> OTHER INFORMATION: This region may encompass 1-20 residues
<220> FEATURE:
<221> NAME/KEY: SITE
<222> LOCATION: (1921)..(1940)
<223> OTHER INFORMATION: This region may encompass 1-20 residues
<220> FEATURE:
<221> NAME/KEY: SITE
<222> LOCATION: (1941)..(1960)
<223> OTHER INFORMATION: This region may encompass 1-20 residues
<220> FEATURE:
<221> NAME/KEY: SITE
<222> LOCATION: (1961)..(1980)
<223> OTHER INFORMATION: This region may encompass 1-20 residues
<220> FEATURE:
<221> NAME/KEY: SITE
<222> LOCATION: (1981)..(2000)
<223> OTHER INFORMATION: This region may encompass 1-20 residues
<220> FEATURE:
<221> NAME/KEY: SITE
<222> LOCATION: (1)..(2000)
<223> OTHER INFORMATION: This sequence may encompass 1-20
      "(Gly)m(Ser)o(Gly)m(Ser)o(Gly)m" repeating units,
      wherein m = 1 to 20, o = 1 to 20
<220> FEATURE:
<223> OTHER INFORMATION: See specification as filed for detailed
      description of substitutions and preferred embodiments

<400> SEQUENCE: 425

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser
            20                  25                  30

Ser Ser Ser Ser Ser Ser Ser Ser Gly Gly Gly Gly Gly Gly Gly
        35                  40                  45

Gly Gly Gly Gly Gly Gly Gly Gly Gly Gly Gly Ser Ser Ser Ser
    50                  55                  60

Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Ser Ser Ser Ser Ser Ser Ser Ser
        115                 120                 125

Ser Ser Ser Ser Ser Ser Ser Ser Ser Ser Ser Gly Gly Gly Gly
    130                 135                 140

Gly Gly Gly Gly Gly Gly Gly Gly Gly Gly Gly Gly Gly Gly Gly
```

```
            145                 150                 155                 160
Ser Ser Ser Ser Ser Ser Ser Ser Ser Ser Ser Ser Ser
                165                 170                 175

Ser Ser Ser Gly Gly Gly Gly Gly Gly Gly Gly Gly Gly
            180                 185                 190

Gly Gly Gly Gly Gly Gly Gly Gly Gly Gly Gly Gly Gly
                195                 200                 205

Gly Gly Gly Gly Gly Gly Gly Gly Gly Gly Ser Ser Ser
            210                 215                 220

Ser Ser Ser Ser Ser Ser Ser Ser Ser Ser Ser Ser Ser
225                 230                 235                 240

Gly Gly Gly Gly Gly Gly Gly Gly Gly Gly Gly Gly Gly
                245                 250                 255

Gly Gly Gly Gly Ser Ser Ser Ser Ser Ser Ser Ser Ser
            260                 265                 270

Ser Ser Ser Ser Ser Ser Ser Gly Gly Gly Gly Gly Gly
                275                 280                 285

Gly Gly Gly Gly Gly Gly Gly Gly Gly Gly Gly Gly Gly
            290                 295                 300

Gly Gly Gly Gly Gly Gly Gly Gly Gly Gly Gly Gly Gly
305                 310                 315                 320

Ser Ser Ser Ser Ser Ser Ser Ser Ser Ser Ser Ser Ser
                325                 330                 335

Ser Ser Ser Ser Gly Gly Gly Gly Gly Gly Gly Gly Gly
            340                 345                 350

Gly Gly Gly Gly Gly Gly Gly Ser Ser Ser Ser Ser Ser
                355                 360                 365

Ser Ser Ser Ser Ser Ser Ser Ser Ser Gly Gly Gly Gly
            370                 375                 380

Gly Gly Gly Gly Gly Gly Gly Gly Gly Gly Gly Gly Gly
385                 390                 395                 400

Gly Gly Gly Gly Gly Gly Gly Gly Gly Gly Gly Gly Gly
                405                 410                 415

Gly Gly Gly Gly Ser Ser Ser Ser Ser Ser Ser Ser Ser
            420                 425                 430

Ser Ser Ser Ser Ser Ser Ser Gly Gly Gly Gly Gly Gly
                435                 440                 445

Gly Gly Gly Gly Gly Gly Gly Gly Gly Gly Ser Ser Ser
            450                 455                 460

Ser Ser Ser Ser Ser Ser Ser Ser Ser Ser Ser Ser Ser
465                 470                 475                 480

Gly Gly Gly Gly Gly Gly Gly Gly Gly Gly Gly Gly Gly
                485                 490                 495

Gly Gly Gly Gly Gly Gly Gly Gly Gly Gly Gly Gly Gly
            500                 505                 510

Gly Gly Gly Gly Gly Gly Gly Ser Ser Ser Ser Ser Ser
                515                 520                 525

Ser Ser Ser Ser Ser Ser Ser Ser Ser Ser Gly Gly Gly Gly
            530                 535                 540

Gly Gly Gly Gly Gly Gly Gly Gly Gly Gly Gly Gly Gly
545                 550                 555                 560

Ser Ser Ser Ser Ser Ser Ser Ser Ser Ser Ser Ser Ser Ser
                565                 570                 575
```

-continued

Ser Ser Ser Ser Gly Gly Gly Gly Gly Gly Gly Gly Gly
        580             585             590

Gly Gly Gly Gly Gly Gly Gly Gly Gly Gly Gly Gly Gly
    595             600             605

Gly Gly Gly Gly Gly Gly Gly Gly Gly Gly Ser Ser Ser Ser
    610             615             620

Ser Ser Ser Ser Ser Ser Ser Ser Ser Ser Ser Ser Ser
625             630             635             640

Gly Gly Gly Gly Gly Gly Gly Gly Gly Gly Gly Gly Gly
        645             650             655

Gly Gly Gly Gly Ser Ser Ser Ser Ser Ser Ser Ser Ser
        660             665             670

Ser Ser Ser Ser Ser Ser Ser Gly Gly Gly Gly Gly Gly Gly
        675             680             685

Gly Gly Gly Gly Gly Gly Gly Gly Gly Gly Gly Gly Gly
    690             695             700

Gly Gly Gly Gly Gly Gly Gly Gly Gly Gly Gly Gly Gly
705             710             715             720

Ser Ser Ser Ser Ser Ser Ser Ser Ser Ser Ser Ser Ser
        725             730             735

Ser Ser Ser Ser Gly Gly Gly Gly Gly Gly Gly Gly Gly
        740             745             750

Gly Gly Gly Gly Gly Gly Gly Ser Ser Ser Ser Ser Ser
        755             760             765

Ser Ser Ser Ser Ser Ser Ser Ser Ser Ser Gly Gly Gly Gly
        770             775             780

Gly Gly Gly Gly Gly Gly Gly Gly Gly Gly Gly Gly Gly
785             790             795             800

Gly Gly Gly Gly Gly Gly Gly Gly Gly Gly Gly Gly Gly
        805             810             815

Gly Gly Gly Gly Ser Ser Ser Ser Ser Ser Ser Ser Ser Ser
        820             825             830

Ser Ser Ser Ser Ser Ser Ser Gly Gly Gly Gly Gly Gly Gly
        835             840             845

Gly Gly Gly Gly Gly Gly Gly Gly Gly Gly Ser Ser Ser Ser
        850             855             860

Ser Ser Ser Ser Ser Ser Ser Ser Ser Ser Ser Ser Ser
865             870             875             880

Gly Gly Gly Gly Gly Gly Gly Gly Gly Gly Gly Gly Gly
        885             890             895

Gly Gly Gly Gly Gly Gly Gly Gly Gly Gly Gly Gly Gly
        900             905             910

Gly Gly Gly Gly Gly Gly Gly Ser Ser Ser Ser Ser Ser
        915             920             925

Ser Ser Ser Ser Ser Ser Ser Ser Ser Gly Gly Gly Gly
        930             935             940

Gly Gly Gly Gly Gly Gly Gly Gly Gly Gly Gly Gly Gly
945             950             955             960

Ser Ser Ser Ser Ser Ser Ser Ser Ser Ser Ser Ser Ser
        965             970             975

Ser Ser Ser Ser Gly Gly Gly Gly Gly Gly Gly Gly Gly Gly
        980             985             990

-continued

Gly Gly Gly Gly Gly Gly Gly Gly Gly Gly Gly Gly Gly Gly Gly
        995                 1000                1005

Gly Gly Gly Gly Gly Gly Gly Gly Gly Gly Gly Ser Ser Ser
        1010                1015                1020

Ser Ser Ser Ser Ser Ser Ser Ser Ser Ser Ser Ser Ser Ser
        1025                1030                1035

Ser Ser Gly Gly Gly Gly Gly Gly Gly Gly Gly Gly Gly Gly
        1040                1045                1050

Gly Gly Gly Gly Gly Gly Ser Ser Ser Ser Ser Ser Ser Ser
        1055                1060                1065

Ser Ser Ser Ser Ser Ser Ser Ser Ser Ser Ser Gly Gly Gly
        1070                1075                1080

Gly Gly Gly Gly Gly Gly Gly Gly Gly Gly Gly Gly Gly Gly
        1085                1090                1095

Gly Gly Gly Gly Gly Gly Gly Gly Gly Gly Gly Gly Gly Gly
        1100                1105                1110

Gly Gly Gly Gly Gly Gly Gly Ser Ser Ser Ser Ser Ser Ser
        1115                1120                1125

Ser Ser Ser Ser Ser Ser Ser Ser Ser Ser Ser Gly Gly Gly
        1130                1135                1140

Gly Gly Gly Gly Gly Gly Gly Gly Gly Gly Gly Gly Gly Gly
        1145                1150                1155

Gly Gly Ser Ser Ser Ser Ser Ser Ser Ser Ser Ser Ser Ser
        1160                1165                1170

Ser Ser Ser Ser Ser Ser Ser Gly Gly Gly Gly Gly Gly Gly
        1175                1180                1185

Gly Gly Gly Gly Gly Gly Gly Gly Gly Gly Gly Gly Gly Gly
        1190                1195                1200

Gly Gly Gly Gly Gly Gly Gly Gly Gly Gly Gly Gly Gly Gly
        1205                1210                1215

Gly Gly Ser Ser Ser Ser Ser Ser Ser Ser Ser Ser Ser Ser
        1220                1225                1230

Ser Ser Ser Ser Ser Ser Ser Gly Gly Gly Gly Gly Gly Gly
        1235                1240                1245

Gly Gly Gly Gly Gly Gly Gly Gly Gly Gly Gly Ser Ser Ser
        1250                1255                1260

Ser Ser Ser Ser Ser Ser Ser Ser Ser Ser Ser Ser Ser Ser
        1265                1270                1275

Ser Ser Gly Gly Gly Gly Gly Gly Gly Gly Gly Gly Gly Gly
        1280                1285                1290

Gly Gly Gly Gly Gly Gly Gly Gly Gly Gly Gly Gly Gly Gly
        1295                1300                1305

Gly Gly Gly Gly Gly Gly Gly Gly Gly Gly Gly Ser Ser Ser
        1310                1315                1320

Ser Ser Ser Ser Ser Ser Ser Ser Ser Ser Ser Ser Ser Ser
        1325                1330                1335

Ser Ser Gly Gly Gly Gly Gly Gly Gly Gly Gly Gly Gly Gly
        1340                1345                1350

Gly Gly Gly Gly Gly Gly Gly Ser Ser Ser Ser Ser Ser Ser
        1355                1360                1365

Ser Ser Ser Ser Ser Ser Ser Ser Ser Ser Ser Gly Gly Gly
        1370                1375                1380

Gly Gly Gly Gly Gly Gly Gly Gly Gly Gly Gly Gly Gly Gly

-continued

Gly Gly Gly Gly Gly Gly Gly Gly Gly Gly Gly Gly Gly Gly
1385        1390            1395
Gly Gly Gly Gly Gly Gly Gly Gly Gly Gly Gly Gly Gly Gly
1400        1405            1410
Gly Gly Gly Gly Gly Gly Gly Ser Ser Ser Ser Ser Ser Ser
1415        1420            1425
Ser Ser Ser Ser Ser Ser Ser Ser Ser Ser Ser Gly Gly Gly
1430        1435            1440
Gly Gly Gly Gly Gly Gly Gly Gly Gly Gly Gly Gly Gly Gly
1445        1450            1455
Gly Gly Ser Ser Ser Ser Ser Ser Ser Ser Ser Ser Ser Ser
1460        1465            1470
Ser Ser Ser Ser Ser Ser Ser Gly Gly Gly Gly Gly Gly Gly
1475        1480            1485
Gly Gly Gly Gly Gly Gly Gly Gly Gly Gly Gly Gly Gly Gly
1490        1495            1500
Gly Gly Gly Gly Gly Gly Gly Gly Gly Gly Gly Gly Gly Gly
1505        1510            1515
Gly Gly Ser Ser Ser Ser Ser Ser Ser Ser Ser Ser Ser Ser
1520        1525            1530
Ser Ser Ser Ser Ser Ser Ser Gly Gly Gly Gly Gly Gly Gly
1535        1540            1545
Gly Gly Gly Gly Gly Gly Gly Gly Gly Gly Gly Ser Ser Ser
1550        1555            1560
Ser Ser Ser Ser Ser Ser Ser Ser Ser Ser Ser Ser Ser Ser
1565        1570            1575
Ser Ser Gly Gly Gly Gly Gly Gly Gly Gly Gly Gly Gly Gly
1580        1585            1590
Gly Gly Gly Gly Gly Gly Gly Gly Gly Gly Gly Gly Gly Gly
1595        1600            1605
Gly Gly Gly Gly Gly Gly Gly Gly Gly Gly Gly Ser Ser Ser
1610        1615            1620
Ser Ser Ser Ser Ser Ser Ser Ser Ser Ser Ser Ser Ser Ser
1625        1630            1635
Ser Ser Gly Gly Gly Gly Gly Gly Gly Gly Gly Gly Gly Gly
1640        1645            1650
Gly Gly Gly Gly Gly Gly Gly Ser Ser Ser Ser Ser Ser Ser
1655        1660            1665
Ser Ser Ser Ser Ser Ser Ser Ser Ser Ser Ser Gly Gly Gly
1670        1675            1680
Gly Gly Gly Gly Gly Gly Gly Gly Gly Gly Gly Gly Gly Gly
1685        1690            1695
Gly Gly Gly Gly Gly Gly Gly Gly Gly Gly Gly Gly Gly Gly
1700        1705            1710
Gly Gly Gly Gly Gly Gly Gly Ser Ser Ser Ser Ser Ser Ser
1715        1720            1725
Ser Ser Ser Ser Ser Ser Ser Ser Ser Ser Ser Gly Gly Gly
1730        1735            1740
Gly Gly Gly Gly Gly Gly Gly Gly Gly Gly Gly Gly Gly Gly
1745        1750            1755
Gly Gly Ser Ser Ser Ser Ser Ser Ser Ser Ser Ser Ser Ser
1760        1765            1770
Ser Ser Ser Ser Ser Ser Ser Gly Gly Gly Gly Gly Gly Gly
1775        1780            1785

Gly Gly Gly Gly Gly Gly Gly  Gly Gly Gly Gly  Gly Gly Gly
    1790                1795                1800

Gly Gly Gly Gly Gly Gly Gly  Gly Gly Gly Gly  Gly Gly Gly
    1805                1810                1815

Gly Gly Ser Ser Ser Ser Ser  Ser Ser Ser Ser  Ser Ser Ser
    1820                1825                1830

Ser Ser Ser Ser Ser Ser Ser  Gly Gly Gly Gly  Gly Gly Gly
    1835                1840                1845

Gly Gly Gly Gly Gly Gly Gly  Gly Gly Gly Gly  Ser Ser Ser
    1850                1855                1860

Ser Ser Ser Ser Ser Ser Ser  Ser Ser Ser Ser  Ser Ser Ser
    1865                1870                1875

Ser Ser Gly Gly Gly Gly Gly  Gly Gly Gly Gly  Gly Gly Gly
    1880                1885                1890

Gly Gly Gly Gly Gly Gly Gly  Gly Gly Gly Gly  Gly Gly Gly
    1895                1900                1905

Gly Gly Gly Gly Gly Gly Gly  Gly Gly Gly Gly  Ser Ser Ser
    1910                1915                1920

Ser Ser Ser Ser Ser Ser Ser  Ser Ser Ser Ser  Ser Ser Ser
    1925                1930                1935

Ser Ser Gly Gly Gly Gly Gly  Gly Gly Gly Gly  Gly Gly Gly
    1940                1945                1950

Gly Gly Gly Gly Gly Gly Gly  Ser Ser Ser Ser  Ser Ser Ser
    1955                1960                1965

Ser Ser Ser Ser Ser Ser Ser  Ser Ser Ser Ser  Gly Gly Gly
    1970                1975                1980

Gly Gly Gly Gly Gly Gly Gly  Gly Gly Gly Gly  Gly Gly Gly
    1985                1990                1995

Gly Gly
    2000

<210> SEQ ID NO 426
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (5)..(24)
<223> OTHER INFORMATION: This region may encompass 1-20 residues
<220> FEATURE:
<221> NAME/KEY: SITE
<222> LOCATION: (29)..(48)
<223> OTHER INFORMATION: This region may encompass 1-20 residues
<220> FEATURE:
<221> NAME/KEY: SITE
<222> LOCATION: (53)..(72)
<223> OTHER INFORMATION: This region may encompass 1-20 residues
<220> FEATURE:
<221> NAME/KEY: SITE
<222> LOCATION: (77)..(96)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (125)..(144)
<223> OTHER INFORMATION: This region may encompass 1-20 residues
<220> FEATURE:

```
<221> NAME/KEY: SITE
<222> LOCATION: (149)..(168)
<223> OTHER INFORMATION: This region may encompass 1-20 residues
<220> FEATURE:
<221> NAME/KEY: SITE
<222> LOCATION: (173)..(192)
<223> OTHER INFORMATION: This region may encompass 1-20 residues
<220> FEATURE:
<221> NAME/KEY: SITE
<222> LOCATION: (197)..(216)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (245)..(264)
<223> OTHER INFORMATION: This region may encompass 1-20 residues
<220> FEATURE:
<221> NAME/KEY: SITE
<222> LOCATION: (269)..(288)
<223> OTHER INFORMATION: This region may encompass 1-20 residues
<220> FEATURE:
<221> NAME/KEY: SITE
<222> LOCATION: (293)..(312)
<223> OTHER INFORMATION: This region may encompass 1-20 residues
<220> FEATURE:
<221> NAME/KEY: SITE
<222> LOCATION: (317)..(336)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (365)..(384)
<223> OTHER INFORMATION: This region may encompass 1-20 residues
<220> FEATURE:
<221> NAME/KEY: SITE
<222> LOCATION: (389)..(408)
<223> OTHER INFORMATION: This region may encompass 1-20 residues
<220> FEATURE:
<221> NAME/KEY: SITE
<222> LOCATION: (413)..(432)
<223> OTHER INFORMATION: This region may encompass 1-20 residues
<220> FEATURE:
<221> NAME/KEY: SITE
<222> LOCATION: (437)..(456)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (1)..(480)
<223> OTHER INFORMATION: This sequence may encompass 1-20
      "(Gly)(Ser)(Gly)(Gly)(Ser)m" repeating units,
      wherein m = 1 to 20
<220> FEATURE:
<223> OTHER INFORMATION: See specification as filed for detailed
      description of substitutions and preferred embodiments

<400> SEQUENCE: 426

Gly Ser Gly Gly Ser Ser Ser Ser Ser Ser Ser Ser Ser Ser Ser
1               5                   10                  15

Ser Ser Ser Ser Ser Ser Ser Gly Ser Gly Gly Ser Ser Ser Ser
            20                  25                  30

Ser Ser Ser Ser Ser Ser Ser Ser Ser Ser Ser Ser Ser Ser Ser
        35                  40                  45

Gly Ser Gly Gly Ser Ser Ser Ser Ser Ser Ser Ser Ser Ser Ser
    50                  55                  60
```

```
Ser Ser Ser Ser Ser Ser Ser Gly Ser Gly Gly Ser Ser Ser
 65                  70                  75                  80

Ser Ser Ser Ser Ser Ser Ser Ser Ser Ser Ser Ser Ser
                 85                  90                  95

Gly Ser Gly Gly Ser Ser Ser Ser Ser Ser Ser Ser Ser
            100                 105                 110

Ser Ser Ser Ser Ser Ser Gly Ser Gly Gly Ser Ser Ser
            115                 120                 125

Ser Ser Ser Ser Ser Ser Ser Ser Ser Ser Ser Ser Ser
        130                 135                 140

Gly Ser Gly Gly Ser Ser Ser Ser Ser Ser Ser Ser Ser
145                 150                 155                 160

Ser Ser Ser Ser Ser Ser Gly Ser Gly Gly Ser Ser Ser
            165                 170                 175

Ser Ser Ser Ser Ser Ser Ser Ser Ser Ser Ser Ser Ser
            180                 185                 190

Gly Ser Gly Gly Ser Ser Ser Ser Ser Ser Ser Ser Ser
            195                 200                 205

Ser Ser Ser Ser Ser Ser Gly Ser Gly Gly Ser Ser Ser
210                 215                 220

Ser Ser Ser Ser Ser Ser Ser Ser Ser Ser Ser Ser Ser
225                 230                 235                 240

Gly Ser Gly Gly Ser Ser Ser Ser Ser Ser Ser Ser Ser
            245                 250                 255

Ser Ser Ser Ser Ser Ser Gly Ser Gly Gly Ser Ser Ser
            260                 265                 270

Ser Ser Ser Ser Ser Ser Ser Ser Ser Ser Ser Ser Ser
            275                 280                 285

Gly Ser Gly Gly Ser Ser Ser Ser Ser Ser Ser Ser Ser
            290                 295                 300

Ser Ser Ser Ser Ser Ser Ser Gly Ser Gly Gly Ser Ser Ser
305                 310                 315                 320

Ser Ser Ser Ser Ser Ser Ser Ser Ser Ser Ser Ser Ser Ser
            325                 330                 335

Gly Ser Gly Gly Ser Ser Ser Ser Ser Ser Ser Ser Ser Ser
            340                 345                 350

Ser Ser Ser Ser Ser Ser Gly Ser Gly Gly Ser Ser Ser
            355                 360                 365

Ser Ser Ser Ser Ser Ser Ser Ser Ser Ser Ser Ser Ser
            370                 375                 380

Gly Ser Gly Gly Ser Ser Ser Ser Ser Ser Ser Ser Ser Ser
385                 390                 395                 400

Ser Ser Ser Ser Ser Ser Gly Ser Gly Gly Ser Ser Ser
            405                 410                 415

Ser Ser Ser Ser Ser Ser Ser Ser Ser Ser Ser Ser Ser
            420                 425                 430

Gly Ser Gly Gly Ser Ser Ser Ser Ser Ser Ser Ser Ser
            435                 440                 445

Ser Ser Ser Ser Ser Ser Gly Ser Gly Gly Ser Ser Ser
            450                 455                 460

Ser Ser Ser Ser Ser Ser Ser Ser Ser Ser Ser Ser Ser Ser
465                 470                 475                 480
```

```
<210> SEQ ID NO 427
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (4)..(23)
<223> OTHER INFORMATION: This region may encompass 1-20 residues
<220> FEATURE:
<221> NAME/KEY: SITE
<222> LOCATION: (28)..(47)
<223> OTHER INFORMATION: This region may encompass 1-20 residues
<220> FEATURE:
<221> NAME/KEY: SITE
<222> LOCATION: (52)..(71)
<223> OTHER INFORMATION: This region may encompass 1-20 residues
<220> FEATURE:
<221> NAME/KEY: SITE
<222> LOCATION: (76)..(95)
<223> OTHER INFORMATION: This region may encompass 1-20 residues
<220> FEATURE:
<221> NAME/KEY: SITE
<222> LOCATION: (100)..(119)
<223> OTHER INFORMATION: This region may encompass 1-20 residues
<220> FEATURE:
<221> NAME/KEY: SITE
<222> LOCATION: (124)..(143)
<223> OTHER INFORMATION: This region may encompass 1-20 residues
<220> FEATURE:
<221> NAME/KEY: SITE
<222> LOCATION: (148)..(167)
<223> OTHER INFORMATION: This region may encompass 1-20 residues
<220> FEATURE:
<221> NAME/KEY: SITE
<222> LOCATION: (172)..(191)
<223> OTHER INFORMATION: This region may encompass 1-20 residues
<220> FEATURE:
<221> NAME/KEY: SITE
<222> LOCATION: (196)..(215)
<223> OTHER INFORMATION: This region may encompass 1-20 residues
<220> FEATURE:
<221> NAME/KEY: SITE
<222> LOCATION: (220)..(239)
<223> OTHER INFORMATION: This region may encompass 1-20 residues
<220> FEATURE:
<221> NAME/KEY: SITE
<222> LOCATION: (244)..(263)
<223> OTHER INFORMATION: This region may encompass 1-20 residues
<220> FEATURE:
<221> NAME/KEY: SITE
<222> LOCATION: (268)..(287)
<223> OTHER INFORMATION: This region may encompass 1-20 residues
<220> FEATURE:
<221> NAME/KEY: SITE
<222> LOCATION: (292)..(311)
<223> OTHER INFORMATION: This region may encompass 1-20 residues
<220> FEATURE:
<221> NAME/KEY: SITE
<222> LOCATION: (316)..(335)
<223> OTHER INFORMATION: This region may encompass 1-20 residues
<220> FEATURE:
<221> NAME/KEY: SITE
<222> LOCATION: (340)..(359)
<223> OTHER INFORMATION: This region may encompass 1-20 residues
<220> FEATURE:
<221> NAME/KEY: SITE
<222> LOCATION: (364)..(383)
<223> OTHER INFORMATION: This region may encompass 1-20 residues
<220> FEATURE:
<221> NAME/KEY: SITE
<222> LOCATION: (388)..(407)
<223> OTHER INFORMATION: This region may encompass 1-20 residues
<220> FEATURE:
<221> NAME/KEY: SITE
<222> LOCATION: (412)..(431)
<223> OTHER INFORMATION: This region may encompass 1-20 residues
```

```
<220> FEATURE:
<221> NAME/KEY: SITE
<222> LOCATION: (436)..(455)
<223> OTHER INFORMATION: This region may encompass 1-20 residues
<220> FEATURE:
<221> NAME/KEY: SITE
<222> LOCATION: (460)..(479)
<223> OTHER INFORMATION: This region may encompass 1-20 residues
<220> FEATURE:
<221> NAME/KEY: SITE
<222> LOCATION: (1)..(480)
<223> OTHER INFORMATION: This sequence may encompass 1-20
      "(Gly)(Ser)(Gly)(Ser)m(Gly)" repeating units,
      wherein m = 1 to 20
<220> FEATURE:
<223> OTHER INFORMATION: See specification as filed for detailed
      description of substitutions and preferred embodiments

<400> SEQUENCE: 427

Gly Ser Gly Ser Ser Ser Ser Ser Ser Ser Ser Ser Ser Ser Ser
1               5                   10                  15

Ser Ser Ser Ser Ser Ser Ser Gly Gly Ser Gly Ser Ser Ser Ser
                20                  25                  30

Ser Ser Ser Ser Ser Ser Ser Ser Ser Ser Ser Ser Ser Ser Gly
            35                  40                  45

Gly Ser Gly Ser Ser Ser Ser Ser Ser Ser Ser Ser Ser Ser Ser
    50                  55                  60

Ser Ser Ser Ser Ser Ser Gly Gly Ser Gly Ser Ser Ser Ser Ser
65                  70                  75                  80

Ser Ser Ser Ser Ser Ser Ser Ser Ser Ser Ser Ser Ser Ser Gly
                85                  90                  95

Gly Ser Gly Ser Ser Ser Ser Ser Ser Ser Ser Ser Ser Ser Ser
            100                 105                 110

Ser Ser Ser Ser Ser Gly Gly Ser Gly Ser Ser Ser Ser Ser Ser
        115                 120                 125

Ser Ser Ser Ser Ser Ser Ser Ser Ser Ser Ser Ser Ser Ser Gly
        130                 135                 140

Gly Ser Gly Ser Ser Ser Ser Ser Ser Ser Ser Ser Ser Ser Ser
145                 150                 155                 160

Ser Ser Ser Ser Ser Ser Gly Gly Ser Gly Ser Ser Ser Ser Ser
                165                 170                 175

Ser Ser Ser Ser Ser Ser Ser Ser Ser Ser Ser Ser Ser Ser Gly
            180                 185                 190

Gly Ser Gly Ser Ser Ser Ser Ser Ser Ser Ser Ser Ser Ser Ser
        195                 200                 205

Ser Ser Ser Ser Ser Ser Gly Gly Ser Gly Ser Ser Ser Ser Ser
        210                 215                 220

Ser Ser Ser Ser Ser Ser Ser Ser Ser Ser Ser Ser Ser Ser Gly
225                 230                 235                 240

Gly Ser Gly Ser Ser Ser Ser Ser Ser Ser Ser Ser Ser Ser Ser
                245                 250                 255

Ser Ser Ser Ser Ser Ser Gly Gly Ser Gly Ser Ser Ser Ser Ser
            260                 265                 270

Ser Ser Ser Ser Ser Ser Ser Ser Ser Ser Ser Ser Ser Ser Gly
        275                 280                 285

Gly Ser Gly Ser Ser Ser Ser Ser Ser Ser Ser Ser Ser Ser Ser
    290                 295                 300

Ser Ser Ser Ser Ser Ser Gly Gly Ser Gly Ser Ser Ser Ser Ser
305                 310                 315                 320
```

```
Ser Ser Ser Ser Ser Ser Ser Ser Ser Ser Ser Ser Ser Gly
                325                 330                 335

Gly Ser Gly Ser Ser Ser Ser Ser Ser Ser Ser Ser Ser Ser
        340                 345                 350

Ser Ser Ser Ser Ser Ser Ser Gly Gly Ser Gly Ser Ser Ser Ser
            355                 360                 365

Ser Ser Ser Ser Ser Ser Ser Ser Ser Ser Ser Ser Gly
    370                 375                 380

Gly Ser Gly Ser Ser Ser Ser Ser Ser Ser Ser Ser Ser Ser
385             390                 395                 400

Ser Ser Ser Ser Ser Ser Gly Gly Ser Gly Ser Ser Ser Ser
            405                 410                 415

Ser Ser Ser Ser Ser Ser Ser Ser Ser Ser Ser Ser Gly
        420                 425                 430

Gly Ser Gly Ser Ser Ser Ser Ser Ser Ser Ser Ser Ser Ser
            435                 440                 445

Ser Ser Ser Ser Ser Ser Gly Gly Ser Gly Ser Ser Ser Ser
    450                 455                 460

Ser Ser Ser Ser Ser Ser Ser Ser Ser Ser Ser Ser Ser Gly
465                 470                 475                 480

<210> SEQ ID NO 428
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (4)..(23)
<223> OTHER INFORMATION: This region may encompass 1-20 residues
<220> FEATURE:
<221> NAME/KEY: SITE
<222> LOCATION: (27)..(46)
<223> OTHER INFORMATION: This region may encompass 1-20 residues
<220> FEATURE:
<221> NAME/KEY: SITE
<222> LOCATION: (50)..(69)
<223> OTHER INFORMATION: This region may encompass 1-20 residues
<220> FEATURE:
<221> NAME/KEY: SITE
<222> LOCATION: (73)..(92)
<223> OTHER INFORMATION: This region may encompass 1-20 residues
<220> FEATURE:
<221> NAME/KEY: SITE
<222> LOCATION: (96)..(115)
<223> OTHER INFORMATION: This region may encompass 1-20 residues
<220> FEATURE:
<221> NAME/KEY: SITE
<222> LOCATION: (119)..(138)
<223> OTHER INFORMATION: This region may encompass 1-20 residues
<220> FEATURE:
<221> NAME/KEY: SITE
<222> LOCATION: (142)..(161)
<223> OTHER INFORMATION: This region may encompass 1-20 residues
<220> FEATURE:
<221> NAME/KEY: SITE
<222> LOCATION: (165)..(184)
<223> OTHER INFORMATION: This region may encompass 1-20 residues
<220> FEATURE:
<221> NAME/KEY: SITE
<222> LOCATION: (188)..(207)
<223> OTHER INFORMATION: This region may encompass 1-20 residues
<220> FEATURE:
<221> NAME/KEY: SITE
<222> LOCATION: (211)..(230)
<223> OTHER INFORMATION: This region may encompass 1-20 residues
```

```
<220> FEATURE:
<221> NAME/KEY: SITE
<222> LOCATION: (234)..(253)
<223> OTHER INFORMATION: This region may encompass 1-20 residues
<220> FEATURE:
<221> NAME/KEY: SITE
<222> LOCATION: (257)..(276)
<223> OTHER INFORMATION: This region may encompass 1-20 residues
<220> FEATURE:
<221> NAME/KEY: SITE
<222> LOCATION: (280)..(299)
<223> OTHER INFORMATION: This region may encompass 1-20 residues
<220> FEATURE:
<221> NAME/KEY: SITE
<222> LOCATION: (303)..(322)
<223> OTHER INFORMATION: This region may encompass 1-20 residues
<220> FEATURE:
<221> NAME/KEY: SITE
<222> LOCATION: (326)..(345)
<223> OTHER INFORMATION: This region may encompass 1-20 residues
<220> FEATURE:
<221> NAME/KEY: SITE
<222> LOCATION: (349)..(368)
<223> OTHER INFORMATION: This region may encompass 1-20 residues
<220> FEATURE:
<221> NAME/KEY: SITE
<222> LOCATION: (372)..(391)
<223> OTHER INFORMATION: This region may encompass 1-20 residues
<220> FEATURE:
<221> NAME/KEY: SITE
<222> LOCATION: (395)..(414)
<223> OTHER INFORMATION: This region may encompass 1-20 residues
<220> FEATURE:
<221> NAME/KEY: SITE
<222> LOCATION: (418)..(437)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (1)..(460)
<223> OTHER INFORMATION: This sequence may encompass 1-20
      "(Gly)(Gly)(Gly)(Ser)m" repeating units,
      wherein m = 1 to 20
<220> FEATURE:
<223> OTHER INFORMATION: See specification as filed for detailed
      description of substitutions and preferred embodiments

<400> SEQUENCE: 428

Gly Gly Gly Ser Ser Ser Ser Ser Ser Ser Ser Ser Ser Ser Ser
1               5                   10                  15

Ser Ser Ser Ser Ser Ser Ser Gly Gly Gly Ser Ser Ser Ser Ser
                20                  25                  30

Ser Ser Ser Ser Ser Ser Ser Ser Ser Ser Ser Ser Ser Gly Gly
            35                  40                  45

Gly Ser Ser Ser Ser Ser Ser Ser Ser Ser Ser Ser Ser Ser Ser
    50                  55                  60

Ser Ser Ser Ser Ser Gly Gly Gly Ser Ser Ser Ser Ser Ser Ser
65                  70                  75                  80

Ser Ser Ser Ser Ser Ser Ser Ser Ser Ser Ser Gly Gly Gly Ser
                85                  90                  95

Ser Ser Ser Ser Ser Ser Ser Ser Ser Ser Ser Ser Ser Ser Ser
            100                 105                 110

Ser Ser Ser Gly Gly Gly Ser Ser Ser Ser Ser Ser Ser Ser Ser
        115                 120                 125

Ser Ser Ser Ser Ser Ser Ser Ser Ser Gly Gly Gly Ser Ser Ser
    130                 135                 140
```

```
Ser Ser Ser Ser Ser Ser Ser Ser Ser Ser Ser Ser Ser Ser Ser Ser
145                 150                 155                 160
Ser Gly Gly Gly Ser Ser Ser Ser Ser Ser Ser Ser Ser Ser Ser
                165                 170                 175
Ser Ser Ser Ser Ser Ser Ser Gly Gly Gly Ser Ser Ser Ser Ser
            180                 185                 190
Ser Ser Ser Ser Ser Ser Ser Ser Ser Ser Ser Ser Ser Ser Gly
        195                 200                 205
Gly Gly Ser Ser Ser Ser Ser Ser Ser Ser Ser Ser Ser Ser Ser
    210                 215                 220
Ser Ser Ser Ser Ser Gly Gly Gly Ser Ser Ser Ser Ser Ser Ser
225                 230                 235                 240
Ser Ser Ser Ser Ser Ser Ser Ser Ser Ser Ser Gly Gly Gly
                245                 250                 255
Ser Ser Ser Ser Ser Ser Ser Ser Ser Ser Ser Ser Ser Ser Ser
                260                 265                 270
Ser Ser Ser Ser Gly Gly Gly Ser Ser Ser Ser Ser Ser Ser Ser
            275                 280                 285
Ser Ser Ser Ser Ser Ser Ser Ser Ser Gly Gly Gly Ser
290                 295                 300
Ser Ser Ser Ser Ser Ser Ser Ser Ser Ser Ser Ser Ser Ser Ser
305                 310                 315                 320
Ser Ser Gly Gly Gly Ser Ser Ser Ser Ser Ser Ser Ser Ser Ser
            325                 330                 335
Ser Ser Ser Ser Ser Ser Ser Ser Gly Gly Gly Ser Ser Ser Ser
            340                 345                 350
Ser Ser Ser Ser Ser Ser Ser Ser Ser Ser Ser Ser Ser Ser Ser
        355                 360                 365
Gly Gly Gly Ser Ser Ser Ser Ser Ser Ser Ser Ser Ser Ser Ser
    370                 375                 380
Ser Ser Ser Ser Ser Ser Gly Gly Gly Ser Ser Ser Ser Ser Ser
385                 390                 395                 400
Ser Ser Ser Ser Ser Ser Ser Ser Ser Ser Ser Ser Ser Gly Gly
                405                 410                 415
Gly Ser Ser Ser Ser Ser Ser Ser Ser Ser Ser Ser Ser Ser Ser
        420                 425                 430
Ser Ser Ser Ser Ser Gly Gly Gly Ser Ser Ser Ser Ser Ser Ser
            435                 440                 445
Ser Ser Ser Ser Ser Ser Ser Ser Ser Ser Ser
        450                 455                 460
```

<210> SEQ ID NO 429
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(60)
<223> OTHER INFORMATION: This sequence may encompass 1-20
      "Gly Gly Ser" repeating units
<220> FEATURE:
<223> OTHER INFORMATION: See specification as filed for detailed
      description of substitutions and preferred embodiments

<400> SEQUENCE: 429

-continued

```
Gly Gly Ser Gly Gly Ser Gly Gly Ser Gly Gly Ser Gly
1               5                   10                  15

Gly Ser Gly Gly Ser Gly Gly Ser Gly Gly Ser Gly Gly
            20                  25                  30

Ser Gly Gly Ser Gly Gly Ser Gly Gly Ser Gly Gly Ser
            35                  40                  45

Gly Gly Ser Gly Gly Ser Gly Gly Ser Gly Gly Ser Gly
    50                  55                  60

<210> SEQ ID NO 430
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Ala Ser His His His His His His
1               5

<210> SEQ ID NO 431
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Gly Ser His His His His His His His His
1               5                   10

<210> SEQ ID NO 432
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 432

His His His His His His
1               5
```

IL12 RECEPTOR SYNTHETIC CYTOKINES AND METHODS OF USE

CROSS-REFERENCES TO RELATED APPLICATIONS

This application is a U.S. National Phase International Application No. PCT/US2021/044855, filed Aug. 5, 2021, which claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 20, 2023, is named 106249-1361740_SEQ_LST.txt and is 350,258 bytes in size.

BACKGROUND OF THE DISCLOSURE

Cytokine and growth-factor ligands typically signal through multimerization of cell surface receptors subunits. In some instance, cytokines act as multispecific (e.g., bispecific or trispecific) ligands which facilitate the association of such receptor subunits, bringing their intracellular domains into proximity such that intracellular signaling may occur. The nature of the cytokine determines which receptor subunits are associated to form the cytokine receptor complex. Cytokines thus act to bridge the individual receptor subunits into a receptor complex that results in intracellular signaling.

The intracellular domains of cytokine receptor subunits possess proline rich JAK binding domains which are typically located in the box1/box region of the intracellular domain of the cytokine receptor subunit near the interior surface of the cell membrane. Intracellular JAK kinases associate with JAK binding domains. When the intracellular domains receptor subunits are brought into proximity, typically by the binding of the cognate ligand for the receptor to the extracellular domains of the receptor subunits, the JAKs phosphorylate each other. Four Janus kinases have been identified in mammalian cells: JAK1, JAK2, JAK3 and TYK2. Ihle, et al. (1995) Nature 377(6550):591-4, 1995; O'Shea and Plenge (2012) Immunity 36(4):542-50. The phosphorylation of the JAK induces a conformational change in the JAK providing the ability to further phosphorylate other intracellular proteins which initiates a cascade that results in activation of multiple intracellular factors which transduce the intracellular signal associated with the receptor resulting intracellular responses such as gene transcription, frequently referred to as downstream signaling. In many instances, the proteins which are phosphorylated by the JAKs are members of the signal transducer and activator of transcription (STAT) protein family. Seven members of the mammalian STAT family have been identified to date: STAT1, STAT2, STAT3, STAT4, STAT5a STAT5b, and STAT6. Delgoffe, et al., (2011) Curr Opin Immunol. 23(5): 632-8; Levy and Darnell (2002) Nat Rev Mol Cell Biol. 3(9):651-62 and Murray, (2007) J Immunol. 178(5):2623-9. The selective interplay of activated JAK and STAT proteins, collectively referred to a the JAK/STAT pathway, provide for a wide variety of intracellular responses observed in response to cytokine binding.

The human genome encodes for approximately forty different JAK/STAT cytokine receptors. In principle, approximately 1600 unique homodimeric and heterodimeric cytokine receptor pairs could be generated with the potential to signal through different JAK/TYK/STAT combinations (Bazan, Proc Natl Acad Sci USA. 87(18):6934-8, 1990; Huising et al., J Endocrinol. 189(1):1-25, 2006). However, as of the present knowledge, the human genome encodes for less than fifty different cytokine ligands (Bazan, Proc Natl Acad Sci USA. 87(18):6934-8, 1990; Huising et al., J Endocrinol. 189(1):1-25, 2006), limiting the scope of cytokine receptor complexes to those that can be assembled by the natural ligands. Given that interaction of the a cytokine ligand with the extracellular domains of the cytokine receptor subunits determines the composition of receptor subunits in a receptor complex and the intracellular JAK/TYK and RTK enzymes are degenerate, the number of cytokine and growth factor receptor dimer pairings that occur in nature represents only a fraction of the total number of signaling-competent receptor pairings theoretically allowed by the system.

Naturally occurring cytokine ligands mediate a wide variety of cellular response. In some instances, a heteromultimeric cytokine receptor is composed of one or more receptor subunits that is unique to the receptor complex, referred to as "proprietary" subunits, which interact with other receptor subunits that are shared by multiple cytokine receptors, frequently referred to as "common" receptor subunits. For example, the IL7 receptor is a heterodimeric receptor complex of the IL7Ra proprietary subunit and a CD132 subunit which is also referred to as the "common gamma" subunit as it is a shared receptor subunit of multiple cytokine receptor complexes including IL2, IL4, IL19, IL15 and IL21. The relative affinity and kinetic of the interaction of the cytokine for the ECDs of the receptor subunits and the stability of the complex formed in response to cytokine binding mediates the nature and intensity of the intracellular signaling. In some instances, the binding of the cytokine to a the proprietary subunit enhances the formation of the complete receptor where the affinity of the cytokine for the common subunit may be significantly lower when not associated with the proprietary subunit.

The nuances of the interplay between the cytokine ligand and the receptor subunits is a matter of significant scientific investigation. For example, many properties of naturally occurring cytokines suggest their potential utility in the treatment of human disease but such naturally occurring cytokines may also trigger adverse and undesirable effects. In many instances, the disease is associated with a particular cell type which expresses the receptor for the potentially therapeutic cytokine. However, the cytokine receptor is also expressed on other cell types not desired to be targeted for therapeutic intervention. The administration of the native ligand activates both cell types resulting result in undesirable side effects.

To attempt to generate cytokine analogs which provide selective activation of the desired cell types, a variety of engineered cytokine ligands (or components thereof) have been generated so as to selectively modulate their affinity for the extracellular domains of receptor subunits. These efforts have generated cytokine variants been shown to provide partial activity which results in uncoupling of the beneficial properties of the ligand from the undesired effects. See, e.g, Mendoza, et al. (2019) 567:56-60. However, the engineering of such selective cytokines ligand is based on selective modulation of individual amino acid residues at the interface of the ligand and the receptor. This protein engineering approach to modulation of cytokine receptor affinity requires a three dimensional, usually x-ray crystallographic, map of the interation of the receptor and the cytokine to identify the residues of the cytokine that interface with the receptor subunit. Additionally the effects of amino acid substitutions at these interface residues can be highly variable often requiring a significant amount of time consuming trial-and-error to identify the particular amino acid substitutions required to produce the desired activity profile. However, even once the engineered cytokine with the desired signaling profile is achieved, many proteins are highly sensitive to amino acid substitutions result in significant issues for recombinant expression, both in mammalian expression systems and procaryotic systems where such amino acid substitutions can affect protein refolding when expressed in inclusion bodies.

IL12 is a heterodimeric cytokine comprise of the p35 and p40 subunits produced by dendritic cells, macrophages and neutrophils. The IL12 heterodimer is also referred to as p70. IL12 is typically identified as a T cell stimulating factor which can stimulate the proliferation and activity of T cells. IL12 stimulates the production of IFNgamma and TNFalpha and modulates the cytotoxic activity of NK and CD8+ cytotoxic T cells. IL12 is also involved in the immune cell differentiation in particular the differentiation of naïve T cells into Th1 (CD4+) cells. IL12 is also reported to provide anti-antiogenic activity. IL12 has been proposed for use in the treatment of a variety of neoplastic diseases, viral and bacterial infections.

IL12 binds to the IL12 receptor, a heterodimeric complex of IL12 receptor subunit beta-1 (IL12Rβ1 or IL12RB1) and IL12 receptor subunit beta-2 (IL12Rβ2 or IL12RB2). IL12Rβ1 and IL12Rβ2 are members of the class I cytokine receptor family and have homology to gp130. The expression of IL12Rβ1 and IL12Rβ2 are upregulated in response to IL2 with the majority of IL12Rβ2 is found on activated T cells.

IL12Rβ1 (also known as CD212) is a constitutively expressed type I transmembrane protein that belongs to the hemopoietin receptor superfamily. IL12Rβ1 binds with low affinity to IL12. IL12Rβ1 is required for high-affinity binding to the IL12p40 subunit and it is associated with the Janus kinase (Jak) family member Tyk-2. The binding IL12p40 and IL12p35 to IL12Rβ1 and IL12Rβ2, respectively results in the activation of the Tyk-2 and Jak-2 Janus kinases occurs. The phosphorylated intracellular signaling domain of IL12Rβ2 provides a binding site for STAT4, which are phosphorylated and translocate to the nucleus regulating IFNgamma gene transcription.

In addition to forming one of the components of the IL12 receptor, IL12Rβ1 is also a component of the IL23 receptor. The IL23 receptor is a heterodimer of IL23R and IL12Rβ1. IL23 binds IL23R with an affinity of 44 nM but binds to IL12Rβ1 with a significantly lower affinity of 2 μM. There is no apparent direct binding of IL23R to IL12Rβ1, the completion of the IL23:IL23R:IL12Rβ1 complex mediated by the initial formation of the IL23:IL23R complex which in turn binds to IL12Rβ1.

The p40 subunit of the IL23 and IL12 cytokines provides the majority of binding sites for IL12Rβ1. In addition to forming a subunit of IL12 and IL23, p40 alone has significant bioactivity. P40 is reported to exist as both a monomer and a disulfide linked homodimer and which has a chemo attractant role for macrophages mediated by IL12Rβ1 alone. Gillesssen, et al (1995) European J. Immuno 25(1):200-206. The p40 homodimer is reported as a IL12 antagonist and its binding to IL12Rb1 is postulated to sequester the IL12Rb1 on the cell surface and suppressing the internalization or endocytosis of IL12Rβ1. Kundu, et al. (2017) PNASUSA 114(43):1148211487. Neutralization of p40 has been identified as reducing acute and chronic GVHD through reducing Th1 and Th17 differentiation. This is in contrast to reports that IL12 can both exacerbate and suppress GVHD in various contexts but that targeting p40 has been p40 can be efficacious in reducing GVHD severity in experimental and clinical settings. In short, the activity of IL12 is a function of the competitive interaction of the IL12, p40 monomer and p40 homodimer with the IL12 receptor, in particular IL12Rβ1. Consequently, molecules which interfere in the association of p40 with IL12Rβ1 may be useful in the modulation of IL12 activity.

Although monoclonal antibodies are the most widely used reagents for the detection and quantification of proteins, monoclonal antibodies are large molecules of about 150 kDa and it sometimes limits their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicunas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents that selectively bind cell surface exposed proteins.

SUMMARY OF THE DISCLOSURE

The present disclosure provides compositions useful in the pairing of cellular receptors to generate desirable effects useful in treatment of disease in mammalian subjects.

The present disclosure relates to synthetic mimetics of the naturally occurring IL12 which are agonists of the IL12R. The IL12R is a heterodimeric protein complex of IL12Rb1 and IL12Rb2. The binding of the IL12 results in dimerization IL12Rb1 and IL12Rb2 and intracellular signaling in cells expressing IL12Rb1 and IL12Rb2 characteristic of the binding of the naturally occurring IL12 for the IL12R. In some embodiments, the IL12R is the human IL12R and the IL12 is the human IL12. In some embodiments the IL12R is the murine IL12R and the IL12 is the murine IL12

The present disclosure provides binding molecules that comprise a first domain that binds to IL12Rb1 of the IL12R receptor and a second domain that binds to IL12Rb2 the IL12R receptor, such that upon contacting with a cell expressing IL12Rb1 the IL12R receptor and IL12Rb2 the IL12R receptor, the IL12R binding molecule causes the functional association of IL12Rb1 and IL12Rb2, thereby resulting in functional dimerization of the receptors and downstream signaling.

In some embodiments, the disclosure provides an IL12 receptor binding molecule that specifically binds to IL12Rb1 and IL12Rb2, wherein the binding molecule causes the multimerization of IL12Rb1 and IL12Rb2 when bound to IL12Rb1 and IL12Rb2, and wherein the binding molecule comprises a single-domain antibody (sdAb) that specifically binds to IL12Rb1 and a sdAb that specifically binds to IL12Rb2.

In some embodiments, the anti-IL12Rb1 sdAb is a $V_HH$ antibody and/or the anti-IL12Rb2 sdAb is a $V_HH$ antibody.

In some embodiments, the anti-IL12Rb1 sdAb and the anti-IL12Rb2 sdAb are joined by a peptide linker. In some embodiments, the peptide linker comprises between 1 and 50 amino acids. In some embodiments, the peptide linker comprises a sequence of GGGS (SEQ ID NO:13).

In some embodiments, the anti-IL12Rb1 sdAb comprises one or more CDRs in a row of Table 2 or Table 3 wherein each CDR independently comprises 0, 1, 2, or 3 amino acid changes relative to the sequence of Table 2 or Table 3.

In some embodiments, the anti-IL12Rb2 sdAb comprises one or more CDRs in a row of Table 4 or Table 5 wherein each CDR independently comprises 0, 1, 2, or 3 amino acid changes relative to the sequence of Table 4 or Table 5.

In some embodiments, the IL12 receptor binding molecule comprises an anti-IL12Rb1 sdAb comprising a CDR1, a CDR2, and a CDR3 in a row of Table 2 or Table 3 and an anti-IL12Rb2 sdAb a CDR1, a CDR2, and a CDR3 in a row of Table 4 or Table 5.

In some embodiments, the binding molecule comprises an anti-IL12Rb1 sdAb linked to the N-terminus of a linker and an anti-IL12Rb2 sdAb linked to the C-terminus of the linker.

In some embodiments, the binding molecule comprises an anti-IL12Rb2 sdAb linked to the N-terminus of a linker and an anti-IL12Rb1 sdAb linked to the C-terminus of the linker.

In some embodiments, the anti-IL12Rb1 sdAb comprises a sequence having at least 90% sequence identity to a sequence of Table 6 or Table 7.

In some embodiments, the anti-IL12Rb1 sdAb comprises a sequence of Table 6 or Table 7.

In some embodiments, wherein the anti-IL12Rb2 sdAb comprises a sequence having at least 90% sequence identity to a sequence of Table 8 or Table 9.

In some embodiments, the anti-IL12Rb1 sdAb comprises a sequence having at least 90% sequence identity to a sequence of Table 6 or Table 7 and the anti-IL12Rb2 sdAb comprises a sequence having at least 90% sequence identity to a sequence of Table 8 or Table 9.

In some embodiments, the anti-IL12Rb1 sdAb comprises a sequence having at least 90% sequence identity to a sequence of Table 6 and the anti-IL12Rb2 sdAb comprises a sequence having at least 90% sequence identity to a sequence of Table 8.

In some embodiments, the anti-IL12Rb1 sdAb comprises a sequence of Table 6 or Table 7 and the anti-IL12Rb2 sdAb comprises a sequence of Table 8 or Table 9.

In some embodiments, the disclosure provides an isolated nucleic acid encoding an IL12 receptor binding molecule of the disclosure. In some embodiments, the isolated nucleic acid comprises a sequence having at least 90% sequence identity to a sequence of Table 10 or Table 11 and the anti-IL12Rb2 sdAb comprises a sequence having at least 90% sequence identity to a sequence of Table 12 or Table 13.

In some embodiments, the disclosure provides an expression vector comprising a nucleic acid encoding an IL12 receptor binding molecule of the disclosure.

In some embodiments, the disclosure provides an isolated host cell comprising a vector comprising a nucleic acid encoding an IL12 receptor binding molecule of the disclosure.

In some embodiments, the disclosure provides a pharmaceutical composition comprising an IL12 receptor binding molecule of the disclosure and a pharmaceutically acceptable carrier.

Several advantages flow from the binding molecules described herein. The natural ligand of the IL12R, IL12, causes IL12Rb1 and IL12Rb2 to come into proximity (i.e., by their simultaneous binding of IL12). However, when IL12 is used as a therapeutic in mammalian, particularly human, subjects, it may also trigger a number of adverse and undesirable effects by a variety of mechanisms including the presence of IL12Rb1 and IL12Rb2 on other cell types and the binding to IL12Rb1 and IL12Rb2 on the other cell types may result in undesirable effects and/or undesired signaling on cells expressing IL12Rb1 and IL12Rb2. The present disclosure is directed to methods and compositions that modulate the multiple effects of IL12Rb1 and IL12Rb2 binding so that desired therapeutic signaling occurs, particularly in a desired cellular or tissue subtype, while minimizing undesired activity and/or intracellular signaling.

In some embodiments, the IL12R binding molecules described herein are partial agonists of the IL12 receptor. In some embodiments, the binding molecules described herein are designed such that the binding molecules are full agonists. In some embodiments, the binding molecules described herein are designed such that the binding molecules are super agonists.

In some embodiments, the binding molecules provide the maximal desired IL12 intracellular signaling from binding to IL12Rb1 and IL12Rb2 on the desired cell types, while providing significantly less IL12 signaling on other undesired cell types. This can be achieved, for example, by selection of binding molecules having differing affinities or causing different $E_{max}$ for IL12Rb1 and IL12Rb2 as compared to the affinity of IL12 for IL12Rb1 and IL12Rb2. Because different cell types respond to the binding of ligands to its cognate receptor with different sensitivity, by modulating the affinity of the dimeric ligand (or its individual binding moieties) for the IL12 receptor relative to wild-type IL12 binding facilitates the stimulation of desired activities while reducing undesired activities on non-target cells.

The present disclosure provides disclosure provides bivalent binding molecules that are agonists of the IL12R receptor, the bivalent binding molecule comprising:
  a first single domain antibody (sdAb) that specifically binds to the extracellular domain of IL12Rb1 of the IL12R (an "anti-IL12Rb1 sdAb"), and
  a second single domain antibody that specifically binds to extracellular domain IL12Rb2 of the IL12R ((an "anti-IL12Rb2 sdAb"),
wherein the anti-IL12Rb1 sdAb and anti-IL12Rb2 sdAb are STABLY ASSOCIATED and first wherein contacting a cell expressing IL12Rb1 and IL12Rb2 with an effective amount of the bivalent binding molecule results the dimerization of IL12Rb1 and IL12Rb2 and results in intracelluar signaling characteristic of the IL12R receptor when activated by its natural cognate IL12. In some embodiments, one or both of the sdAbs is a an scFv. In some embodiments, one or both of the sdAbs is a VHH.

In some embodiments, one sdAb of the bivalent binding molecule is an scFv and the other sdAb is a VHH.

In some embodiments, the first and second sdAbs are covalently bound via a chemical linkage.

In some embodiments, the first and second sdAbs are provided as single continuous polypeptide.

In some embodiments, the first and second sdAbs are provided as single continuous polypeptide optionally comprising an intervening polypeptide linker between the amino acid sequences of the first and second sdAbs.

In some embodiments the bivalent binding molecule optionally comprising a linker, is optionally expressed as a fusion protein with an additional amino acid sequence. In some embodiments, the additional amino acid sequence is a purification handle such as a chelating peptide or an additional protein such as a subunit of an Fc molecule.

The disclosure also provides an expression vector comprising a nucleic acid encoding the bispecific binding molecule operably linked to one or more expression control sequences.

The disclosure also provides an isolated host cell comprising the expression vector expression vector comprising a nucleic acid encoding the bispecific binding molecule operably linked to one or more expression control sequences functional in the host cell.

In another aspect, the disclosure provides a pharmaceutical composition comprising the IL12R binding molecule described herein and a pharmaceutically acceptable carrier.

In another aspect, the disclosure provides a method of treating an autoimmune or inflammatory disease, disorder, or condition or a viral infection in a subject in need thereof, comprising administering to the subject a therapeutically effective amount of an IL12R binding molecule described herein or a pharmaceutical composition described herein.

BRIEF DESCRIPTION OF THE FIGURES

FIG. 4, Panel B provides a schematic representations of a binding molecule the binding domains are single domain antibodies associated via transition metal coordinate covalent complex. As illustrated, the binding molecules comprises two polypeptide subunits: the first subunit comprising a first single domain antibody (1) is attached via a first linker (15) to a first chelating peptide (17) and second subunit comprising a second single domain antibody (3) is attached via a second linker (16) to a second chelating peptide (18), wherein the first chelating peptide (17) and second chelating peptide (18) form a coordinate covalent complex with a single transition metal ion ("M"). The transition metal ion may be in a kinetically labile or kinetically inert oxidation state.

DETAILED DESCRIPTION OF THE INVENTION

Figure 1:
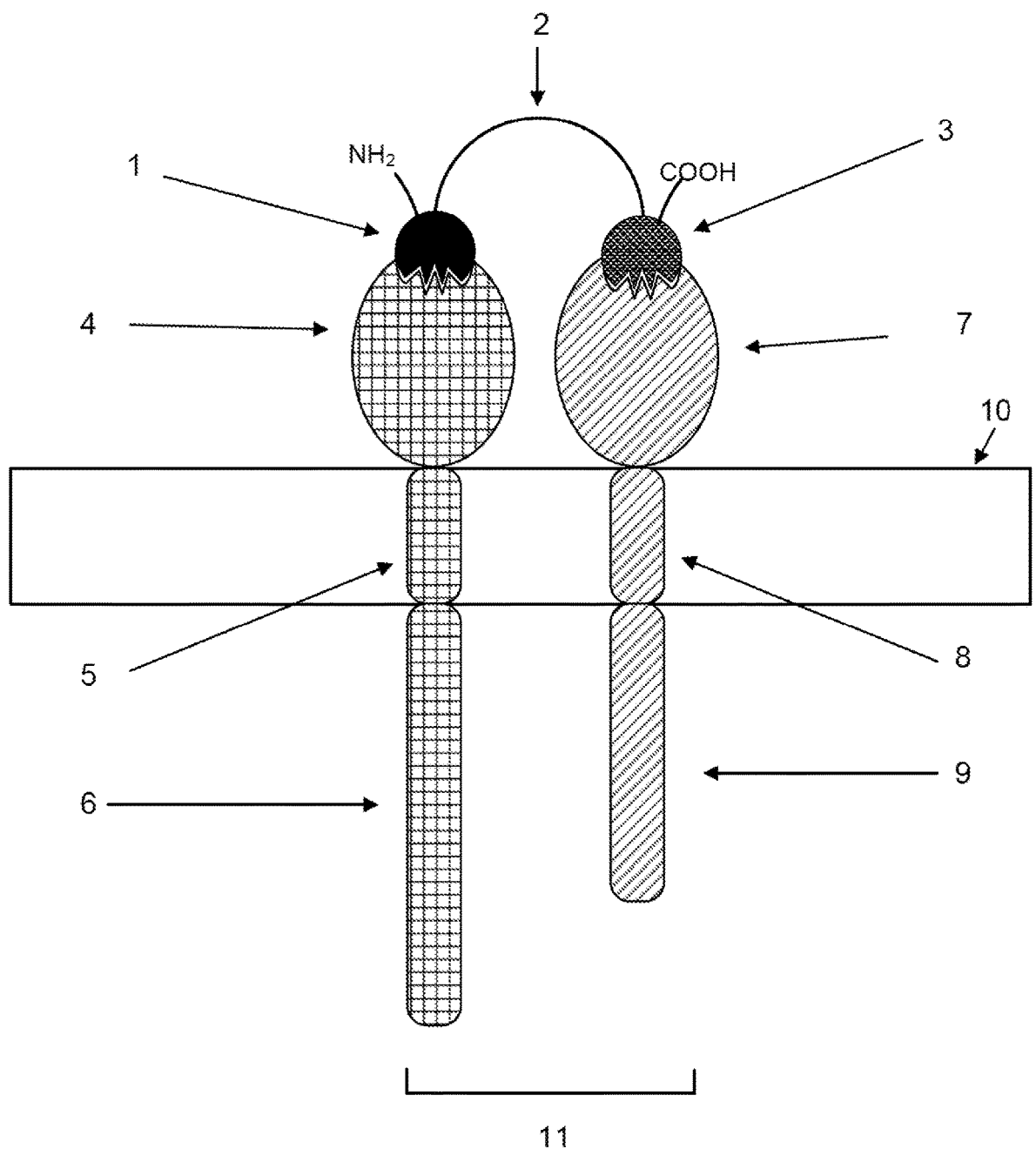
FIG. 1 of the attached drawings provides a schematic representation of one embodiment of the bivalent binding molecule of the present disclosure comprising a first single domain antibody (1) and a second single domain antibody (3) and a linker (2) depicted as interacting with a cell membrane (10) associated heterodimeric receptor comprising a first receptor subunit comprising an extracellular domain (4), and transmembrane domain (5) and an intracellular domain (6) interaction of a bivalent binding molecule and a second first receptor subunit comprising an extracellular domain (7), and transmembrane domain (8) and an intracellular domain (9) wherein the intracellular domain of the first receptor (6) and the intracellular domain of the second receptor (9) on of a bivalent binding molecule are within a proximal distance (11).

To facilitate the understanding of present disclosure, certain terms and phrases are defined below as well as throughout the specification. The definitions provided herein are non-limiting and should be read in view of the knowledge of one of skill in the art would know.

Before the present methods and compositions are described, it is to be understood that this invention is not limited to a particular method or composition described, as such may, of course, vary. It is also to be understood that the terminology used herein is for the purpose of describing embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); AA or aa=amino acid(s); kb=kilobase(s); nt=nucleotide(s); pg=picogram; ng=nanogram; g=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=once weekly; QM=once monthly; HPLC=high performance liquid chromatography; BW=body weight; U=unit; ns=not statistically significant; PBS=phosphate-buffered saline; PCR=polymerase chain reaction; HSA=human serum albumin; MSA=mouse serum albumin; DMEM=Dulbeco's Modification of Eagle's Medium; EDTA=ethylenediaminetetraacetic acid.

It will be appreciated that throughout this disclosure reference is made to amino acids according to the single letter or three letter codes. For the reader's convenience, the single and three letter amino acid codes are provided in Table 1 below:

TABLE 1

| Amino Acid Abbreviations | | |
| --- | --- | --- |
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g. an assay) or biological or chemical property (e.g. the degree of binding of the molecule to another molecule) or of a physical property of a material or cell (e.g. modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc. As used herein, the term "proliferative activity" refers to an activity that promotes cell proliferation and replication.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g. an ortholog, an IL2 ortholog, an engineered cell expressing an orthogonal receptor, an engineered cell expressing an orthogonal IL2 receptor, a CAR-T cell expressing an orthogonal IL2 receptor, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, inhalation and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant (KD), a ratio of the dissociation rate constant between the molecule and its target (Koff) and the association rate constant between the molecule and its target (Kon).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state, resulting in a biological response. The response mimics the effect of the endogenous activator of the receptor. The term "agonist" includes partial agonists, full agonists and superagonists. An agonist may be described as a "full agonist" when such agonist which leads to a substantially full biological response (i.e., the response associated with the naturally occurring ligand/receptor binding interaction) induced by receptor under study, or a partial agonist. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist. A "superagonist" is a type of agonist that is capable of producing a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway, or cell.

Antibody: As used herein, the term "antibody" refers collectively to: (a) glycosylated and non-glycosylated immunoglobulins (including but not limited to mammalian immunoglobulin classes IgG1, IgG2, IgG3 and IgG4) that specifically binds to target molecule and (b) immunoglobulin derivatives including but not limited to IgG(1-4)del-ta$C_H2$, F(ab')$_2$, Fab, ScFv, $V_H$, $V_L$, tetrabodies, triabodies, diabodies, dsFv, F(ab')$_3$, scFv-Fc and (scFv)$_2$ that competes with the immunoglobulin from which it was derived for binding to the target molecule. The term antibody is not restricted to immunoglobulins derived from any particular mammalian species and includes murine, human, equine, and camelids antibodies (e.g., human antibodies). The term "antibody" encompasses antibodies isolatable from natural sources or from animals following immunization with an antigen and as well as engineered antibodies including monoclonal antibodies, bispecific antibodies, trispecific, chimeric antibodies, humanized antibodies, human antibodies, CDR-grafted, veneered, or deimmunized (e.g., to remove T-cell epitopes) antibodies. The term "human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries.

Binding molecule: As used herein, the term "binding molecule" refers to a bivalent molecule that can bind to the extracellular domain of two cell surface receptors. In some embodiments, a binding molecule specifically binds to two different receptors (or domains or subunits thereof) such that the receptors (or domains or subunits) are maintained in proximity to each other such that the receptors (or domains or subunits), including domains thereof (e.g., intracellular domains) interact with each other and result in downstream signaling.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., J. Biol. Chem. 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

Clonotype: As used herein, a clonotype refers to a collection of binding molecules that originate from the same B-cell progenitor cell. The term "clonotype" is used to refer to a collection of antigen binding molecules that belong to the same germline family, have the same CDR3 lengths, and have 70% or greater homology in CDR3 sequence.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Effective Concentration (EC): As used herein, the terms "effective concentration" or its abbreviation "EC" are used interchangeably to refer to the concentration of an agent (e.g., an hIL2 mutein) in an amount sufficient to effect a change in a given parameter in a test system.

The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect. The EC of a particular effective concentration of a test agent may be abbreviated with respect to the with respect to particular parameter and test system.

Extracellular Domain: As used herein the term "extracellular domain" or its abbreviation "ECD" refers to the portion of a cell surface protein (e.g. a cell surface receptor) which is outside of the plasma membrane of a cell. The term "ECD" may include the extra-cytoplasmic portion of a transmembrane protein or the extra-cytoplasmic portion of a cell surface (or membrane associated protein).

Identity: As used herein, the term "percent (%) sequence identity" or "substantially identical" used in the context of nucleic acids or polypeptides, refers to a sequence that has at least 50% sequence identity with a reference sequence. Alternatively, percent sequence identity can be any integer from 50% to 100%. In some embodiments, a sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined with BLAST using standard parameters, as described below. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned. Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)). The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference sequence if the smallest sum probability in a comparison of the test amino acid sequence to the reference amino acid sequence is less than about 0.01, more preferably less than about $10^{-5}$, and most preferably less than about $10^{-20}$.

Intracellular Signaling: As used herein, the terms "intracellular signaling" and "downstream signaling" are used interchangeably to refer to the to the cellular signaling process that is caused by the interaction of the intracellular domains (ICDs) of two or more cell surface receptors that are in proximity of each other. In receptor complexes via the JAK/STAT pathway, the association of the ICDS of the receptor subunits brings the JAK domains of the ICDs into proximit which initiates a phosphorylation cascade in which STAT molecules are phosphorylated and translocate to the nucleus associating with particular nucleic acid sequences resulting in the activation and expression of particular genes in the cell. The binding molecules of the present disclosure provide intracellular signaling characteristic of the IL12R receptor when activated by its natural cognate IL12. To measure downstream signaling activity, a number of methods are available. For example, in some embodiments, one can measure JAK/STAT signaling by the presence of phosphorylated receptors and/or phosphorylated STATs. In other embodiments, the expression of one or more downstream genes, whose expression levels can be affected by the level of downstream signaling caused by the binding molecule, can also be measured.

Ligand: As used herein, the term "ligand" refers to a molecule that exhibits specific binding to a receptor and results in a change in the biological activity of the receptor so as to effect a change in the activity of the receptor to which it binds. In one embodiment, the term "ligand" refers to a molecule, or complex thereof, that can act as an agonist or antagonist of a receptor. As used herein, the term "ligand" encompasses natural and synthetic ligands. "Ligand" also encompasses small molecules, e.g., peptide mimetics of cytokines and peptide mimetics of antibodies. The complex of a ligand and receptor is termed a "ligand-receptor complex."

As used herein, the term "linker" refers to a linkage between two elements, e.g., protein domains. A linker can be a covalent bond or a peptide linker. The term "bond" refers to a chemical bond, e.g., an amide bond or a disulfide bond, or any kind of bond created from a chemical reaction, e.g., chemical conjugation. The term "peptide linker" refers to an amino acid or polypeptide that may be employed to link two protein domains to provide space and/or flexibility between the two protein domains.

Modulate: As used herein, the terms "modulate", "modulation" and the like refer to the ability of a test agent to affect a response, either positive or negative or directly or indirectly, in a system, including a biological system or biochemical pathway.

Multimerization: As used herein, the term "multimerization" refers to two or more cell surface receptors, or domains or subunits thereof, being brought in close proximity to each other such that the receptors, or domains or subunits thereof, can interact with each other and cause intracellular signaling.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. The terms "immediately N-terminal" or "immediately C-terminal" are used to refers to a position of a first amino acid residue relative to a second amino acid residue where the first and second amino acid residues are covalently bound to provide a contiguous amino acid sequence.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between nucleic acid sequences encoding differing functions when combined into a single nucleic acid sequence that, when introduced into a cell, provides a nucleic acid which is capable of effecting the transcription and/or translation of a particular nucleic acid sequence in a cell. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, certain genetic elements such as enhancers need not be contiguous with respect to the sequence to which they provide their effect.

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Clinically, partial agonists can be used to activate receptors to give a desired submaximal response when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. A In some embodiments, the IL12R binding molecule has a reduced $E_{max}$ compared to the $E_{max}$ caused by IL12. $E_{max}$ reflects the maximum response level in a cell type that can be obtained by a ligand (e.g., a binding molecule described herein or the native cytokine (e.g., IL12)). In some embodiments, the IL12R binding molecule described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by IL12. In other embodiments, the $E_{max}$ of the IL12R binding molecule described herein is greater (e.g., at least 1%, 5%, 10%, 15%, 20%, 25%, 30%, 35%, 40%, 45%, or 50% greater) than the $E_{max}$ of the natural ligand, IL12. In some embodiments, by varying the linker length of the IL12R binding molecule, the $E_{max}$ of the IL12R binding molecule can be changed. The IL12R binding molecule can cause $E_{max}$ in the most desired cell types, and a reduced $E_{max}$ in other cell types.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; fusion proteins of immunologically active proteins (e.g. antigenic diphtheria or tetanus toxin fragments) and the like.

As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Proximity: As used herein, the term "proximity" refers to the spatial proximity or physical distance between two cell surface receptors, or domains or subunits thereof, after a binding molecule described herein binds to the two cell surface receptors, or domains or subunits thereof. In some embodiments, after the binding molecule binds to the cell surface receptors, or domains or subunits thereof, the spatial proximity between the cell surface receptors, or domains or subunits thereof, can be, e.g., less than about 500 angstroms, such as e.g., a distance of about 5 angstroms to about 500 angstroms. In some embodiments, the spatial proximity amounts to less than about 5 angstroms, less than about 20 angstroms, less than about 50 angstroms, less than about 75 angstroms, less than about 100 angstroms, less than about 150 angstroms, less than about 250 angstroms, less than about 300 angstroms, less than about 350 angstroms, less than about 400 angstroms, less than about 450 angstroms, or less than about 500 angstroms. In some embodiments, the spatial proximity amounts to less than about 100 angstroms. In some embodiments, the spatial proximity amounts to less than about 50 angstroms. In some embodiments, the spatial proximity amounts to less than about 20 angstroms. In some embodiments, the spatial proximity amounts to less than about 10 angstroms. In some embodiments, the spatial proximity ranges from about 10 to 100 angstroms, from about 50 to 150 angstroms, from about 100 to 200 angstroms, from about 150 to 250 angstroms, from about 200 to 300 angstroms, from about 250 to 350 angstroms, from about 300 to 400 angstroms, from about 350 to 450 angstroms, or about 400 to 500 angstroms. In some embodiments, the spatial proximity amounts to less than about 250 angstroms, alternatively less than about 200 angstroms, alternatively less than about 150 angstroms, alternatively less than about 120 angstroms, alternatively less than about 100 angstroms, alternatively less than about 80 angstroms, alternatively less than about 70 angstroms, or alternatively less than about 50 angstroms.

Receptor: As used herein, the term "receptor" refers to a polypeptide having a domain that specifically binds a ligand that binding of the ligand results in a change to at least one biological property of the polypeptide. In some embodiments, the receptor is a "soluble" receptor that is not associated with a cell surface. In some embodiments, the receptor is a cell surface receptor that comprises an extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of the ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface molecule having not associated with any intracellular signaling alone but upon ligand binding facilitates the formation of a multimeric complex that results in intracellular signaling.

Recombinant: As used herein, the term "recombinant" is used as an adjective to refer to the method by a polypeptide, nucleic acid, or cell that was modified using recombinant DNA technology. A recombinant protein is a protein produced using recombinant DNA technology and may be designated as such using the abbreviation of a lower case "r" (e.g., rhIL2) to denote the method by which the protein was produced. Similarly, a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors. In contrast, the terms "inhibition", "down-regulation" and the like refer to the opposite effects.

Single Domain Antibody (sdAb): The term "single-domain antibody" or "sdAbs," refers to an antibody having a single (only one) monomeric variable antibody domain. A sdAb is able to bind selectively to a specific antigen. A $V_HH$ antibody, further defined below, is an example of a sdAb.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant ($K_D$) between antibody and the antigen is lesser than about $10^{-6}$ M, alternatively lesser than about $10^{-8}$ M, alternatively lesser than about $10^{-10}$ M, alternatively lesser than about $10^{-11}$ M, lesser than about $10^{-12}$ M as determined by, e.g., Scatchard analysis (Munsen, et al. (1980) Analyt. Biochem. 107:220-239). In one embodiment where the ligand is an ILR binding sdAb and the receptor comprises an ILR, the ILR binding sdAb specifically binds if the equilibrium dissociation constant ($K_D$) of the ILR binding sdAb/ILR ECD is lesser than about $10^{-5}$M, alternatively lesser than about $10^{-6}$ M, alternatively lesser than about $10^{-7}$M, alternatively lesser than about $10^{-8}$M, alternatively lesser than about $10^{-9}$ M, alternatively lesser than about $10^{-10}$ M, or alternatively lesser than about $10^{-11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore S200, Biacore T200 (GE Healthcare Bio-Sciences, 100 Results Way, Marlborough MA 01752). In some embodiments, the present disclosure provides molecules (e.g., ILR binding sdAbs) that specifically bind to the hILR. As used herein, the binding affinity of an ILR binding molecule for the ILR, the binding affinity may be determined and/or quantified by surface plasmon resonance ("SPR"). In evaluating binding affinity of an ILR binding molecule for the ILR, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CM5 chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 420) or 8×His (SEQ ID NO: 421)) for retention on a chip conjugated with NTA. In some embodiments, the ILR binding molecule may be immobilized on the chip and ILR (or ECD fragment thereof) be provided in the mobile phase. Alternatively, the ILR (or ECD fragment thereof) may be immobilized on the chip and the ILR binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of ILR binding molecule for ILR using SPR, the ILR binding molecule may be derivatized by the C-terminal addition of a poly-His sequence (e.g., 6×His (SEQ ID NO: 420) or 8×His (SEQ ID NO: 421)) and immobilized on the NTA derivatized sensor chip and the ILR receptor subunit for which the ILR VHH's binding affinity is being evaluated is provided in the mobile phase. The means for incorporation of a poly-His sequence into the C-terminus of the ILR binding molecule produced by recombinant DNA technology is well known to those of skill in the relevant art of biotechnology. In some embodiments, the binding affinity of ILR binding molecule for an ILR comprises using SPR substantially in accordance with the teaching of the Examples.

Stably Associated: As used herein, the term "stably associated" or "in stable association with" are used to refer to the various means by which one molecule (e.g., a polypeptide) may be associated with another molecule over an extended period of time. The stable association of one molecule to another may be effected by a variety of means, including covalent bonding and non-covalent interactions. In some embodiments, stable association of two molecules may be effected by covalent bonds such as peptide bonds. In other embodiments, stable association of two molecules may be effected b non-covalent interactions. Examples of non-covalent interactions which may provide a stable association between two molecules include electrostatic interactions (e.g., hydrogen bonding, ionic bonding, halogen binding, dipole-dipole interactions, Van der Waals forces and π-effects including cation-π interactions, anion-π interactions and π-π interactions) and hydrophobic/hydrophilic interactions. In some embodiments, the stable association of sdAbs of the bivalent binding molecules of the present disclosure may be effected by non-covalent interactions. In one embodiment, the non-covalent stable association of the sdAbs of the bivalent binding molecules may be achieved by conjugation of the sdAbs to "knob-into-hole" modified Fc monomers. An Fc "knob" monomer stably associates non-covalently with an Fc "hole" monomer. Conjugation of a first sdAb which specifically binds to the extracellular domain of a first subunit of a heterodimeric receptor to an "Fc knob" monomer and conjugation of an second sdAb which specifically binds to the extracellular domain of a second subunit of a heterodimeric receptor to an "Fc hole" monomer provides stable association of the first and second sdAbs.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially: As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher of a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g., blood count), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

Therapeutically Effective Amount: As used herein, the term The phrase "therapeutically effective amount" is used in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, modification of biomarker levels, increase in duration of survival, extended duration of progression free survival, extension of the time to progression, increased time to treatment failure, extended duration of event free survival, extension of time to next treatment, improvement objective response rate, improvement in the duration of response, and the like that that are relied upon by clinicians in the field for the assessment of an improvement in the condition of the subject in response to administration of an agent.

Treat: The terms "treat", "treating", treatment" and the like refer to a course of action (such as administering a binding molecule described herein, or a pharmaceutical composition comprising same) initiated with respect to a subject after a disease, disorder or condition, or a symptom thereof, has been diagnosed, observed, or the like in the subject so as to eliminate, reduce, suppress, mitigate, or ameliorate, either temporarily or permanently, at least one of the underlying causes of such disease, disorder, or condition afflicting a subject, or at least one of the symptoms associated with such disease, disorder, or condition. The treatment includes a course of action taken with respect to a subject suffering from a disease where the course of action results in the inhibition (e.g., arrests the development of the disease, disorder or condition or ameliorates one or more symptoms associated therewith) of the disease in the subject.

VHH: As used herein, the term "$V_HH$" is a type of sdAb that has a single monomeric heavy chain variable antibody domain. Such antibodies can be found in or produced from Camelid mammals (e.g., camels, llamas) which are naturally devoid of light chains $V_HH$s can be obtained from immunization of camelids (including camels, llamas, and alpacas (see, e.g., Hamers-Casterman, et al. (1993) Nature 363:446-448) or by screening libraries (e.g., phage libraries) constructed in $V_HH$ frameworks. Antibodies having a given specificity may also be derived from non-mammalian sources such as $V_HH$s obtained from immunization of cartilaginous fishes including, but not limited to, sharks. In a particular embodiment, a $V_HH$ in a bispecific $V_HH^2$ binding molecule described herein binds to a receptor (e.g., the first receptor or the second receptor of the natural or non-natural receptor pairs) if the equilibrium dissociation constant between the $V_HH$ and the receptor is lesser than about $10^{-6}$ M, alternatively lesser than about $10^{-8}$ M, alternatively lesser than about $10^{-10}$ M, alternatively lesser than about $10^{-11}$ M, alternatively lesser than about $10^{-10}$ M, lesser than about $10^{-12}$ M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in *Methods in Molecular Biology*, Walker, J. editor (Humana Press, Totowa NJ). Specific binding may be assessed using techniques known in the art including but not limited to competition ELISA, BIACORE® assays and/or KINEXA® assays. In some embodiments, a $V_HH$ described herein can be humanized to contain human framework regions. Examples of human germlines that could be used to create humanized $V_HH$s include, but are not limited to, VH3-23 (e.g., UniProt ID: P01764), VH3-74 (e.g., UniProt ID: AOAOB4J1X5), VH3-66 (e.g., UniProt ID: AOAOC4DH42), VH3-30 (e.g., UniProt ID: P01768), VH3-11 (e.g., UniProt ID: P01762), and VH3-9 (e.g., UniProt ID: P01782).

$V_HH^2$: As used herein, the term "$V_HH^2$" and "bispecific $V_HH^2$" and "VHH dimer" refers to are used interchangeably to refer to a subtype of the binding molecules of the present disclosure wherein the first and second sdAbs are both $V_HH$s and first $V_HH$ binding to a first receptor, or domain or subunit thereof, and a second $V_HH$ binding to a second receptor, or domain or subunit thereof.

Wild Type: As used herein, the term "wild type" or "WT" or "native" is used to refer to an amino acid sequence or a nucleotide sequence that is found in nature and that has not been altered by the hand of man.

Cytokine Receptor Binding Molecules

General Description

The present disclosure provides disclosure provides cytokine receptor binding molecules that are ligands for a cytokine receptor, the cytokine receptor binding molecule comprising:
  (a) a first single domain antibody (sdAb) that specifically binds to the extracellular domain a first subunit of a cytokine receptor; and
  (b) a second single domain antibody that specifically binds to extracellular domain of a second subunit of cytokine receptor subunit;
wherein:
  the first sdAb and second sdAb are in stable association;
  the first and second subunits of the cytokine receptor are dimerized in response to contact with the cognate ligand for the cytokine receptor; and
  contacting a cell expressing the first and the second subunits of the cytokine receptor with an effective amount of the cytokine receptor binding molecule results in the intracellular domains of the first and second subunits of the cytokine receptors being brought into proximity and results in intracelluar signaling.

Single Domain Antibody

The cytokine receptor binding molecules of the present disclosure comprise two or more single domain antibodies. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. In some embodiments, one or both of the sdAbs of the cytokine receptor binding molecule is a an scFv. In some embodiments, one or both of the sdAbs is a VHH. In some embodiments, one or both of the sdAbs is a scFv.

Single Domain Antibody Is A VHH

In some embodiments, one or more of the sdAb of the cytokine receptor binding molecules of the present disclosure is a VHH. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks. A VHH is a type of single-domain antibody (sdAb) containing a single monomeric variable antibody domain. Like a full-length antibody, it is able to bind selectively to a specific antigen. The complementary determining regions (CDRs) of VHHs are within a single-domain polypeptide. VHHs can be engineered from heavy-chain antibodies found in camelids. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains. Descriptions of sdAbs and VHHS can be found in, e.g., De Greve et al., *Curr Opin Biotechnol.* 61:96-101, 2019; Ciccarese, et al., *Front Genet.* 10:997, 2019; Chanier and Chames, *Antibodies (Basel)* 8(1), 2019; and De Vlieger et al., *Antibodies (Basel)* 8(1), 2018.

Engineered sdAbs.

The term single domain antibody includes engineered sdAbs including but not limited to chimeric sdAbs, CDR grafted sdAbs and humanized sdAbs.

In some embodiments, the one or more of the sdAbs for incorporation into the bivalent binding molecules of the present disclosure are CDR grafted. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. Any framework region can be used with the CDRs as described herein.

In some embodiments, one or more of the sdAbs for incorporation into the bivalent binding molecules is a chimeric sdAb, in which the CDRs are derived from one species (e.g., camel) and the framework and/or constant regions are derived from another species (e.g., human or mouse). In specific embodiments, the framework regions are human or humanized sequences. Thus, bivalent binding molecules comprising one or more humanized sdAbs are considered within the scope of the present disclosure. The techniques for humanization of camelid single domain antibodies are well known in the art. See, e.g., Vincke, et al. (2009) General Strategy to Humanize a Camelid Single-domain Antibody and Identification of a Universal Humanized Nanobody Scaffold J. Biol. Chem. 284(5)3273-3284.

In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProtID: AOAOB4J1X5), VH3-66 (e.g., UniProt ID: AOAOC4DH42), VH3-30 (e.g., UniProt ID: P01768), VH3-11 (e.g., UniProt ID: P01762), and VH3-9 (e.g., UniProt ID: P01782).

Stably Associated:

The present disclosure provides a synthetic cytokine receptor ligand comprising at least two binding domains, the synthetic ligand comprising a first binding domain that specifically binds to the extracellular domain of a first cytokine receptor subunit in stable association with a second binding domain that specifically binds to the extracellular domain of a second cytokine receptor subunit. As used herein, the term "stably associated" or "in stable association with" are used to refer to the various means by which one molecule (e.g., a polypeptide) may be thermodynamically and/or kinetically associated with another molecule. The stable association of one molecule to another may be achieved by a variety of means, including covalent bonding and non-covalent interactions.

Covalent Bonding

In some embodiments, stable association of two molecules may be effected by covalent bonds such as peptide bonds. In some embodiments, the covalent linkage between the first and second binding domains is a covalent bond between the C-terminus of the first binding domain and the N-terminus of the second binding domain.

In some embodiments, the first binding domain that specifically binds to the extracellular domain of a first cytokine receptor subunit in stable association with a second binding domain that specifically binds to the extracellular domain of a second cytokine receptor subunit are covalent bonded via a linker. In some embodiments, a linker joins the C-terminus of the first sdAb which binds to the ECD of the first receptor subunit of the cytokine receptor of the binding molecule to the N-terminus of the second sdAb which binds to the ECD of the second receptor subunit of the cytokine receptor. In some embodiments, a linker joins the C-terminus of the second sdAb which binds to the ECD of the second receptor subunit of the cytokine receptor of the binding molecule to the N-terminus of the first sdAb which binds to the ECD of the first receptor subunit of the cytokine receptor. Linkers may be selected from selected from the group including but not limited to peptide linkers or chemical linkers.

Peptide Linkers

In some embodiments, the stable association of the first and second domains may be achieved by covalent linkage of the C-terminus of the first binding domain and the N-terminus of the second binding domain via a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids). Examples of flexible peptide linkers include glycine polymers (G)n, glycine-alanine polymers, alanine-serine polymers, glycine-serine polymers (for example, (GmSo)n (SEQ ID NO: 422), (GSGGS)n (SEQ ID NO: 423), (GmSoGm)n (SEQ ID NO: 424), (GmSoGm-SoGm)n (SEQ ID NO: 425), (GSGGSm)n (SEQ ID NO: 426), (GSGSmG)n (SEQ ID NO: 427) and (GGGSm)n (SEQ ID NO: 428), and combinations thereof, where m, n, and o are each independently selected from an integer of at least 1 to 20, e.g., 1-18, 216, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Exemplary flexible linkers include the linkers of but are not limited to the linkers provided in Table 16 as SEQ ID NOS; 462-484.

Chemical Linkers

In some embodiments, the covalent linkage of the first and second domains may be achieved by a chemical linker. Examples of chemical linkers include aryl acetylene, ethylene glycol oligomers containing 2-10 monomer units, diamines, diacids, amino acids, polymers such as PEG or combinations thereof.

Non-Covalent Bonding

In some embodiments, stable association of the first and second binding domains of the binding molecules may be effected by non-covalent interactions. Examples of non-covalent interactions which may provide a stable association between two molecules include electrostatic interactions (e.g., hydrogen bonding, ionic bonding, halogen binding, dipole-dipole interactions, Van der Waals forces and p-effects including cation-p interactions, anion-p interactions and p-p interactions) and hydrophobic/hydrophilic interactions. In some embodiments, the stable association of sdAbs of the binding molecules of the present disclosure may be effected by non-covalent interactions. In one embodiment, the non-covalent stable association of a receptor binding molecules to a subunit of an Fc, domain optionally incorporating a linker between the receptor binding molecule and the Fc such as the IgG4 hinge comain. Alternatively, the receptor binding molecule or individual sdAbs of the binding molecules may be achieved by conjugation to a domain (or both domains) of the sdAbs to "knob-into-hole" modified Fc monomers.

Figure 4:
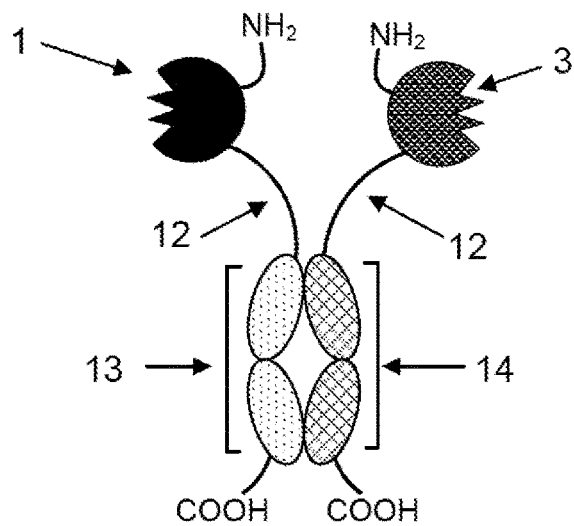
FIG. 4, Panel A provides alternative schematic representations of configurations of the bivalent binding molecules of the present disclosure where one single domain antibody is attached to each subunit of a knob-into-hole Fc domain comprising two polypeptides, the first polypeptide comprising from amino to carboxy, a first single domain antibody (1), an IgG hinge sequence (12) and a Fc knob subunit (13), the second polypeptide comprising from amino to carboxy, a second single domain antibody (3), an IgG hinge sequence (12) and a Fc hole subunit (13), wherein the first and second single domain antibodies are in stable associate via the interaction of the knob-into-hole Fc domain.
Figure 4:
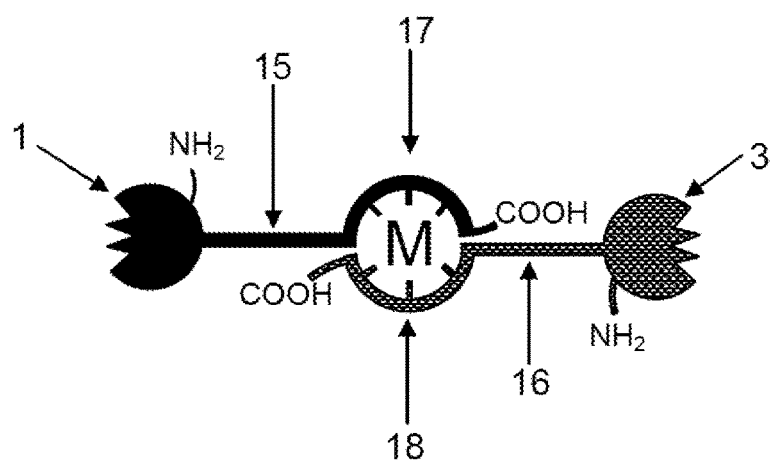

In one embodiment, the non-covalent stable association of the sdAbs of the binding molecules may be achieved by conjugation of the sdAbs to "knob-into-hole" modified Fc monomers. An Fc "knob" monomer stably associates non-covalently with an Fc "hole" monomer. Conjugation of a first sdAb which specifically binds to the extracellular domain of a first subunit of a heterodimeric receptor to an "Fc knob" monomer and conjugation of an second sdAb which specifically binds to the extracellular domain of a second subunit of a heterodimeric receptor to an "Fc hole" monomer provides stable association of the first and second sdAbs. The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 on one chain and Y349 on the second chain which results in a stabilizing disulfide bridge between the two antibody heavy chains in the Foe region (Carter, et al. (2001) Immunol Methods 248, 7-15). The knob-into-hole format is used to facilitate the expression of a first polypeptide (e.g., an IL27Ra binding sdAb) on a first Fc monomer with a "knob" modification and a second polypeptide on the second Fc monomer possessing a "hole" modification to facilitate the expression of heterodimeric polypeptide conjugates. A schematic illustration of this wherein each binding domain is be provided on separate subunits of a knob-into-hole Fc dimer such that the first and second binding domains are non-covalently linked via the non-covalent linkage of the knob and hole as illustrated in FIG. 4, Panel A of the attached drawings.

Coordinate Covalent Bonding

In some embodiments, stable association of the first and second binding domains of the binding molecules may be effected by a coordinate covalent linkage. The present disclosure provides examples of single domain antibodies comprising a chelating peptide. The chelating peptide results in a coordinate covalent linkage to a transition metal ion. In some embodiments, a transition metal ion is capable of forming a coordinate covalent linkage with two or more chelating peptides. Consequently, the first and second binding domains may each comprise a chelating peptide and a stable association of the binding domains by each subunit forming a coordinate covalent complex with a transition metal ion. In some embodiments, the transition metal ion is selected from vanadium, manganese, iron, iridium, osmium, rhenium platinum, palladium, cobalt, chromium or ruthenium. A schematic illustration of this configuration is provided in FIG. 4, Panel B of the attached drawings. It should be noted that in each of the configurations illustrated in FIG. 4, Panels A and B, the N-terminal domain of the single domain antibody is presented to the environment enabling facilitating enhanced exposure of the CDRs of the sdAb to the target cytokine receptor ECD. The formation of the coordinate covalent linkage between the is favored when the transition metal ion is in a kinetically labile oxidation state, for example Co(II), Cr(II), or Ru(III). Following complexation, the oxidation state of the transition metal may be changed (oxidized or reduced) to a kinetically inert oxidation state, for example Co(III), Cr(III), or Ru(II), provide a kinetically inert coordinate covalent complex. The formation of kinetically inert and kinetically labile coordinate covalent complexes between proteins comprising chelating peptides via a transition metal are described in more detail in Anderon, et al. U.S. Pat. No. 5,439,928 issued Aug. 8, 1995.

Modulation of Activity of Receptor Binding Molecules

In some embodiments, such as to achieve partial agonism or selective activation of particular cell types, the design of the cytokine receptor binding molecules of the present disclosure may be modulated by structural variations in the design of the receptor binding molecule. This variation in activity may be employed to modulate the binding and activity of the receptor binding molecule, for example to variations in achieving partial agonism, selective cell type activation or increased or decreased activity relative to the cognate ligand for the receptor. Examples of the means by which the modulation of the activity and/or specificity of the receptor binding molecule of the present disclosure include but are not limited to altering the sequential orientation of the sdAb, independently varying the binding affinity of the sdAbs with respect to each target, and modulating the distance between the sdAbs such as by employing linkers or varying lengths.

In some embodiments, the cytokine receptor binding protein has a reduced $E_{max}$ compared to the $E_{max}$ caused by the cognate ligand. $E_{max}$ reflects the maximum response level in a cell type that can be obtained by a ligand (e.g., a binding protein described herein or the cognate ligand (e.g., IFNG). In some embodiments, the IL12R binding protein described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by hIFNG.

Modulation of Activity By Varying the Distance Between the sdAbs

In some embodiments, by modulating the distance between the sdAbs of receptor binding protein (e.g. by varying the linker length between the sdAbs), the $E_{max}$ of the binding protein can be modulated. The variations in receptor binding protein geometry can exploited to increase activity in the most desired cell types (e.g., $CD8^+$ T cells), while reducing activity in other cell types (e.g., macrophages). With respect to the IL12R binding molecules, in some embodiments, the $E_{max}$ of the IL12R binding protein on macrophages is between 1% and 100% (e.g., between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ the IL12R binding protein on T cells (e.g., $CD8^+$ T cells). In other embodiments, the $E_{max}$ of the IL12R binding protein described herein is greater (e.g., at least 1%, 5%, 10%, 15%, 20%, 25%, 30%, 35%, 40%, 45%, or 50% greater) than the $E_{max}$ of the natural ligand, IFNG.

Sequential Orientation of sdAbs

When the cytokine receptor binding molecule of the present disclosure is expressed as a single polypeptide chain, the binding activity and/or specificity of the receptor binding molecule may be modulated by the order (N-terminal versus C-terminal) arrangements of the sdAbs in the polypeptide. In some embodiments, the cytokine receptor binding molecule is a polypeptide IL12R binding molecule and the activity and/or specificity of the IL12R binding is modulated by the sequential arrangement of the IL12RB1 and IL12RB2 sdAbs in the polypeptide.

"Forward Orientation"

In some embodiments, the cytokine receptor binding molecule (e.g., an IL12R binding molecule) comprises a polypeptide of the structure:

$$H_2N\text{-[First Receptor Subunit sdAb]-}[L]_x\text{-[Second Receptor Subunit sdAb]-}[CP]_y\text{—COOH}$$

wherein and L is a polypeptide linker of 1-50 amino acids and x=0 or 1, and CP is a chelating peptide or a subunit of an Fc domain and y=0 or 1.

In one embodiment, the present disclosure provides a IL12R binding molecule comprises a polypeptide of the structure:

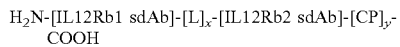
H₂N-[IL12Rb1 sdAb]-[L]ₓ-[IL12Rb2 sdAb]-[CP]ᵧ-COOH wherein and L is a polypeptide linker of 1-50 amino acids and x=0 or 1, and CP is a chelating peptide or a subunit of an Fc domain and y=0 or 1. This is referred to herein as the "forward orientation" of the IL12R sdAbs of the IL12R binding molecule "Reverse Orientation"

In some embodiments, the cytokine receptor binding molecule (e.g., an IL12R binding molecule) comprises a polypeptide of the structure:

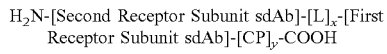
H₂N-[Second Receptor Subunit sdAb]-[L]ₓ-[First Receptor Subunit sdAb]-[CP]ᵧ-COOH wherein and L is a polypeptide linker of 1-50 amino acids and x=0 or 1, and CP is a chelating peptide or a subunit of an Fc domain and y=0 or 1.

In some embodiments, the bivalent IL12R binding molecule comprises a polypeptide of the structure:

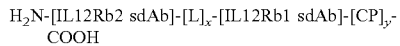
H₂N-[IL12Rb2 sdAb]-[L]ₓ-[IL12Rb1 sdAb]-[CP]ᵧ-COOH wherein and L is a polypeptide linker of 1-50 amino acids and x=0 or 1, and CP is a chelating peptide or a subunit of an Fc domain, and y=0 or 1.

Modulation of Activity Variation of the Binding Affinities of sdAbs

In some embodiments, the activity and/or specificity of the bivalent receptor binding molecule of the present disclosure may be modulated by independently varying the respective binding affinities of the first and second sdAbs for their respective receptor subunits.

It will be appreciated by one of skill in the art that the binding of the first sdAb of the bivalent binding molecule to the first receptor subunit ECD on the cell surface will enhance the probability of a binding interaction between the second sdAb of the bivalent binding molecule with the ECD of the second receptor subunit. This cooperative binding effect may result in a bivalent receptor binding molecule which has a very high affinity for the receptor and a very slow "off rate" from the receptor. Typical VHH single domain antibodies have an affinity for their targets of from about $10^{-5}$M to about $10^{-10}$M. In those instances such slow off-rate kinetics are desirable in the bivalent IL12R binding molecules, the selection of sdAbs having high affinities (about $10^{-7}$M to about $10^{-10}$M) for incorporation into the bivalent IL12R binding molecule are favored.

Naturally occurring cytokine ligands for typically do not exhibit a similar affinity for each subunit of a heterodimeric receptor. Consequently, in designing a bivalent cytokine receptor binding molecule which is a mimetic of the cognate cytokine ligand as contemplated by some embodiments of the present disclosure, selection of sdAbs for the first and second receptor subunit have an affinity similar to (e.g., having an affinity about 10 fold, alternatively about 20 fold, or alternatively about 50 fold higher or lower than) the cognate IFNG for the respective receptor subunit may be used.

In some embodiments, the bivalent receptor binding molecules of the present disclosure are partial agonists. As such, the activity of the binding molecule may be modulated by selecting sdAb which have greater or lesser affinity for either one or both of the receptor subunits relative to the cognate ligand. As some heterodimeric cytokine receptors are comprised of a "proprietary subunit" (i.e., a subunit which is not naturally a subunit of another multimeric receptor) and a second "common" subunit which is a shared component of multiple cytokine receptors, selectivity for the formation of such receptor may be enhanced by employing first sdAb which has a higher affinity for the proprietary receptor subunit and second sdAb which exhibits a lower affinity for the common receptor subunit. Additionally, the common receptor subunit may be expressed on a wider variety of cell types than the proprietary receptor subunit. In some embodiments wherein the receptor is a heterodimeric receptor comprising a proprietary subunit and a common subunit, the first sdAb of the bivalent IL12R binding molecule exhibits a significantly greater (more than 10 times greater, alternatively more than 100 times greater, alternatively more than 1000 times greater) affinity for the proprietary receptor than the second sdAb of the bivalent IL12R binding molecule for the common receptor subunit. In one embodiment, the present disclosure provides a bivalent IL12R binding molecule wherein the affinity of the IL12Rb1 sdAb has an affinity of more than 10 times greater, alternatively more than 100 times greater, alternatively more than 1000 times greater than the affinity for the IL12Rb2 sdAb common receptor subunit.

With respect to the IL12R binding molecules of the present disclosure, in some embodiments, the affinity of the IL12Rb1 sdAb of the IL12R binding molecule for the IL12R1 ECD is at least about 2 fold, alternatively at least about 5 fold, alternatively at least about 5 fold, alternatively at least about 10 fold, alternatively at least about 50 fold, alternatively at least about 100 fold, alternatively at least about 200 fold, alternatively at least about 500 fold, or alternatively at least about 1000 fold greater than the binding affinity of IL12R2 sdAb of the IL12R binding molecule for the IL12Rb2 ECD. In some embodiments, the affinity of the IL12Rb2 sdAb of the IL12R binding molecule for the IL12Rb2 ECD is at least about 2 fold, alternatively at least about 5 fold, alternatively at least about 5 fold, alternatively at least about 10 fold, alternatively at least about 50 fold, alternatively at least about 100 fold, alternatively at least about 200 fold, alternatively at least about 500 fold, or alternatively at least about 1000 fold greater than the binding affinity of IL12Rb1 sdAb of the IL12R binding molecule for the IL12Rb1 ECD.

Cross Reactivity:

In some instances, due to sequence or structural similarities between the extracellular domains of IL12Rb2 receptors from various mammalian species, immunization with an antigen derived from a IL12Rb2 of a first mammalian species (e.g., the hIL12Rb2-ECD) may provide antibodies which specifically bind to IL12Rb2 receptors of one or more additional mammalian species. Such antibodies are termed "cross reactive." For example, immunization of a camelid with a human derived antigen (e.g., the hIL12Rb2-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL12Rb2 VHH" or "hIL12Rb2 VHH" merely denotes that the species of the IL12Rb2 antigen used for immunization of the camelid from which the VHH was derived was the human IL12Rb2 (e.g., the hIL12Rb2 ECD, SEQ ID NO:6) but should not be understood as limiting with respect to the specific binding affinity of the VHH for IL12Rb2 molecules of other mammalian species. Similarly, the use of the term "mouse IL12Rb2 VHH" or "mIL12Rb2 VHH" merely denotes that the species of the IL12Rb2 antigen used for immunization of the camelid from which the VHH was derived was the murine IL12Rb2 (e.g., the mIL12Rb2 ECD, SEQ ID NO:8) but should not be understood as limiting with respect to the specific binding affinity of the VHH for IL12Rb2 molecules of other mammalian species.

The mIL12Rb2 VHHs of Table 6 were evaluated for cross-reactivity with the hIL12Rb2 by ELISA and were found to bind both the extracellular domain of hIL12Rb2 (SEQ ID NO. 6) and the extracellular domain of mIL12Rb2 (SEQ ID NO. 8). Consequently, the VHHs provided in Table 6 may be used in both murine and human applications avoiding the necessity of a surrogate anti-mIL12Rb2 for anti-hIL12Rb2 for in vivo models of efficacy, such as a mouse model of a human disease state.

I. IL12 Receptor Binding Molecules

In one embodiment, the present disclosure provides an IL12 receptor binding molecule that is a ligand for IL12, the IL12 receptor binding molecule comprising:
 a first single domain antibody (sdAb) that specifically binds to the extracellular domain of IL12Rb1 subunit of the IL12R (an "anti-IL12Rb1 sdAb"), and
 a second single domain antibody that specifically binds to extracellular domain IL12Rb2 subunit of the IL12R (an "anti-IL12Rb2 sdAb"),
wherein:
 the first sdAb and second sdAb are in stable association;
 the L12Rb1 and IL12Rb2 subunits of the IL12R are dimerized in response to contact with the IFNGR binding molecule; and
 contacting a cell expressing the L12Rb1 and IL12Rb2 with an effective amount of the IL12R binding molecule results in the intracellular domains of L12Rb1 and IL12Rb2 being brought into proximity and intracellular signaling.

In some embodiments, one or both of the sdAbs is a an scFv. In some embodiments, one or both of the sdAbs is a VHH.

As used herein, the term "IL12 receptor" or "IL12R" refers to a heterodimeric receptor formed by subunits IL12Rb1 and IL12Rb2 when associated with the cognate IL12R.

Provided herein is an IL12R binding molecule that specifically binds to IL12Rb1 and IL12Rb2. In some embodiments, the IL12R binding molecule binds to a mammalian cell expressing both IL12Rb1 and IL12Rb2. In some embodiments, the IFNGR binding molecule can be a bispecific $V_HH^2$ as described below.

IL12: the Cognate Ligand for the IL12Receptor

The cognate ligand for the IL12 receptor is the cytokine IL12. IL12 is a heterodimeric polypeptide which is an agonist of the IL12R. Human IL12R is a non-covalently linked heterodimeric protein comprising two different subunits. The canonical amino acid sequence of the human IL12A subunit ("IL12A" also called IL12 subunit p35) is provided below (UniProt Reference No: P29459).

```
                                          (SEQ ID NO: 9)
MCPARSLLLVATLVLLDHLSLARNLPVATPDPGMF

PCLHHSQNLLRAVSNMLQKARQTLEFYPCTSEEID

HEDITKDKTSTVEACLPLELTKNESCLNSRETSFI

TNGSCLASRKTSFMMALCLSSIYEDLKMYQVEFKT

MNAKLLMDPKRQIFLDQNMLAVIDELMQALNFNSE

TVPQKSSLEEPDFYKTKIKLCILLHAFRIRAVTID

RVMSYLNAS
```

The canonical amino acid sequence of the murine IL12A subunit is provided below (UniProt Reference No: P43431).

```
                                          (SEQ ID NO: 10)
MCQSRYLLFLATLALLNHLSLARVIPVSGPARCLS

QSRNLLKTTDDMVKTAREKLKHYSCTAEDIDHEDI

TRDQTSTLKTCLPLELHKNESCLATRETSSTTRGS

CLPPQKTSLMMTLCLGSIYEDLKMYQTEFQAINAA

LQNHNHQQIILDKGMLVAIDELMQSLNHNGETLRQ

KPPVGEADPYRVKMKLCILLHAFSTRVVTINRVMG

YLSSA
```

The canonical amino acid sequence of the human IL12B subunit is provided below (UniProt Reference No: P29460).

```
                                          (SEQ ID NO: 11)
MCHQQLVISWFSLVFLASPLVAIWELKKDVYVVEL

DWYPDAPGEMVVLTCDTPEEDGITWTLDQSSEVLG

SGKTLTIQVKEFGDAGQYTCHKGGEVLSHSLLLLH

KKEDGIWSTDILKDQKEPKNKTFLRCEAKNYSGRF

TCWWLTTISTDLTFSVKSSRGSSDPQGVTCGAATL

SAERVRGDNKEYEYSVECQEDSACPAAEESLPIEV

MVDAVHKLKYENYTSSFFIRDIIKPDPPKNLQLKP

LKNSRQVEVSWEYPDTWSTPHSYFSLTFCVQVQGK

SKREKKDRVFTDKTSATVICRKNASISVRAQDRYY

SSSWSEWASVPCS
```

The canonical amino acid sequence of the murine IL12B subunit is provided below (UniProt Reference No: P43432).

```
                                          (SEQ ID NO: 12)
MCPQKLTISWFAIVLLVSPLMAMWELEKDVYVVEV

DWTPDAPGETVNLTCDTPEEDDITWTSDQRHGVIG

SGKTLTITVKEFLDAGQYTCHKGGETLSHSHLLLH

KKENGIWSTEILKNFKNKTFLKCEAPNYSGRFTCS

WLVQRNMDLKFNIKSSSSSPDSRAVTCGMASLSAE

KVTLDQRDYEKYSVSCQEDVTCPTAEETLPIELAL

EARQQNKYENYSTSFFIRDIIKPDPPKNLQMKPLK

NSQVEVSWEYPDSWSTPHSYFSLKFFVRIQRKKEK
```

-continued

MKETEEGCNQKGAFLVEKTSTEVQCKGGNVCVQAQ

DRYYNSSCSKWACVPCRVRS

II. Bispecific Binding Molecules

The present disclosure provides bivalent binding molecules that are agonists of the IL12R receptor, the bivalent binding molecule comprising:
  a first single domain antibody (sdAb) that specifically binds to the extracellular domain of IL12Rb1 of the IL12R (an "anti-IL12Rb1 sdAb"), and
  a second single domain antibody that specifically binds to extracellular domain IL12Rb2 of the IL12R ((an "anti-IL12Rb2 sdAb"),
wherein the anti-IL12Rb1 sdAb and anti-IL12Rb2 sdAb are STABLY ASSOCIATED and first wherein contacting a cell expressing IL12Rb1 and IL12Rb2 with an effective amount of the bivalent binding molecule results the dimerization of IL12Rb1 and IL12Rb2 and results in intracelluar signaling characteristic of the IL12R receptor when activated by its natural cognate IL12. In some embodiments, one or both of the sdAbs is a an scFv. In some embodiments, one or both of the sdAbs is a VHH.

In one aspect, provided herein is an IL12 receptor (IL12R) binding protein that specifically binds to IL12Rβ1 and IL12Rβ2, wherein the binding protein causes the multimerization of IL12Rβ1 and IL12Rβ2 and the multimerization results in the association of intracellular domains of IL12Rβ1 and IL12Rβ2 and intracelluar signaling, and wherein the binding protein comprises a single-domain antibody (sdAb) that specifically binds to IL12Rβ1 (an anti-IL12Rβ1 sdAb) and a sdAb that specifically binds to IL12Rβ2 (an anti-IL12Rβ2 sdAb).

In some embodiments, the anti-IL12Rβ1 sdAb is a $V_HH$ antibody (an anti IL12Rβ1 $V_HH$ antibody) and/or the anti-IL12Rβ2 sdAb is a $V_HH$ antibody (an anti IL12Rβ2 $V_HH$ antibody). In some embodiments, the anti-IL12Rβ1 sdAb and the anti-IL12Rβ2 sdAb are joined directly or via a peptide linker. In some embodiments, the peptide linker comprises between 1 and 50 amino acids. In some embodiments, the IL12R binding protein has a reduced $E_{max}$ compared to IL12. In some embodiments, the IL12R binding protein has an increased $E_{max}$ compared to IL12. In some embodiments, the IL12R binding protein has a similar potency compared to that of IL12.

In some embodiments, the IL12R binding protein binds to a mammalian cell expressing both IL12Rβ1 and IL12Rβ2. In some embodiments, the IL12R binding protein can be a bispecific $V_HH^2$ as described below. In other embodiments, the IL12R binding protein can include a first domain that is a $V_HH$ and a second domain which can be a fragment of IL12 or, for example, a scFv.

The IL12R binding protein can be a bispecific $V_HH^2$ that has a first $V_HH$ binding to IL12Rβ1 (an anti-IL12Rβ1 $V_HH$ antibody) and a second $V_HH$ binding to IL12Rβ2 (an anti-IL12Rβ2 $V_HH$ antibody) and causes the dimerization of the two receptor subunits and downstream signaling when bound to a cell expressing IL12Rβ1 and IL12Rβ2, e.g., a natural killer or a T cell (e.g., a CD4$^+$ T cells, and/or a CD8$^+$ T cell).

A linker can be used to join the anti-IL12Rβ1 $V_HH$ antibody and the anti-IL12Rβ2 $V_HH$ antibody. For example, a linker can simply be a covalent bond or a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids). A peptide linker joining the anti-IL12Rβ1 $V_HH$ antibody and the anti-IL12Rβ2 $V_HH$ antibody can be a flexible glycine-serine linker. A linker can also be a chemical linker, such as a synthetic polymer, e.g., a polyethylene glycol (PEG) polymer.

The anti-IL12Rβ1 $V_HH$ antibody can have a sequence having at least 90% (e.g., 91%, 92%, 93%, 94%, 95%, 96%, 97%, 98%, 99%, or 100%) sequence identity to the sequence of any one of the sequences in Table 6 or Table 7.

The anti-IL12Rβ2 $V_HH$ antibody can have a sequence having at least 90% (e.g., 91%, 92%, 93%, 94%, 95%, 96%, 97%, 98%, 99%, or 100%) sequence identity to the sequence of any one of the sequences in Table 8 or Table 9.

In some embodiments, the IL12R binding protein has a reduced $E_{max}$ compared to the $E_{max}$ caused by IL12. $E_{max}$ reflects the maximum response level in a cell type that can be obtained by a ligand (e.g., a binding protein described herein or the native cytokine (e.g., IL12)). In some embodiments, the IL12R binding protein described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by IL12. In some embodiments, by varying the linker length of the IL12R binding protein, the $E_{max}$ of the IL12R binding protein can be changed. The IL12R binding protein can cause $E_{max}$ in the most desired cell types (e.g., CD8$^+$ T cells), and a reduced $E_{max}$ in other cell types (e.g., natural killer cells). In some embodiments, the $E_{max}$ in natural killer cells caused by an IL12R binding protein described herein is between 1% and 100% (e.g., between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ in T cells (e.g., CD8$^+$ T cells) caused by the IL12R binding protein. In other embodiments, the $E_{max}$ of the IL12R binding protein described herein is greater (e.g., at least 1%, 5%, 10%, 15%, 20%, 25%, 30%, 35%, 40%, 45%, or 50% greater) than the $E_{max}$ of the natural ligand, IL12.

An IL12R binding protein described herein are useful in the treatment of neoplastic diseases, such as cancer (e.g., a solid tumor cancer; e.g., non-small-cell lung carcinoma (NSCLC), renal cell carcinoma (RCC), or melanoma) in a subject in need thereof. The IL12R binding protein binds to and activates natural killer, CD4$^+$ T cells, and/or CD8$^+$ T cells. The IL12R binding protein can trigger different levels of downstream signaling in different cell types. For example, by varying the length of the linker between the anti-IL12Rβ1 $V_HH$ antibody and the anti-IL12Rβ2 $V_HH$ antibody in the IL12R binding protein, the IL12R binding protein can cause a higher level of downstream signaling in desired cell types compared to undesired cell types. In some embodiments, by varying the linker length, an IL12R binding protein can cause a higher level of downstream signaling in T cells (e.g., CD8⁺ T cells) compared to the level of downstream signaling in natural killer cells, a cell type that expresses both IL12Rβ1 and IL12Rβ2 receptors but when activated too potently can give rise to toxicities. In other embodiments, different anti-IL12Rβ1 $V_HH$ antibodies with different binding affinities and different anti-IL12Rβ2 $V_HH$ antibodies with different binding affinities can be combined to make different IL12R binding proteins. Further, the orientation of the two antibodies in the binding protein can also be changed to make a different binding protein (i.e., anti-IL12Rβ1 $V_HH$ antibody-linker-anti-IL12Rβ2 $V_HH$ antibody, or anti-IL12Rβ2 $V_HH$ antibody-linker-anti-IL12Rβ1 $V_HH$ antibody). Different IL12R binding proteins can be screened to find the ideal binding protein that causes a higher level of downstream signaling in desired cell types compared to undesired cell types. In some embodiments, IL12R binding proteins can be partial agonists that have different activities on different cell types, e.g., T cells versus natural killer cells. For example, the selective activation of T cells over natural killer cells is desirable to avoid the toxicity associated with IL12 activated natural killer cells. In some embodiments IL12R binding protein is a partial agonist, where the partial agonist activates T cells selectively over NK cells. In some embodiments, the level of downstream signaling in T cells (e.g., CD8⁺ T cells) is at least 1.1, 1.5, 2, 3, 5, or 10 times of the level of downstream signaling in natural killer cells.

IL12RB1

The IL12RB1 binding molecules of the present disclosure specifically bind to the extracellular domain of the IL12RB1.

Human IL12RB1

In one embodiment, the IL12RB1 binding molecules of the present disclosure specifically bind to the extracellular domain of the human IL12RB1 receptor subunit (hIL12RB1). hIL12RB1 is expressed as a 662 amino acid precursor comprising a 23 amino acid N-terminal signal sequence which is post-translationally cleaved to provide an 639 amino acid mature protein. The canonical full-length acid hIL12RB1 precursor (including the signal peptide) is a 662 amino acid polypeptide having the amino acid sequence:

```
                                            (SEQ ID NO: 1)
MEPLVTWVVPLLFLFLLSRQGAACRTSECCFQDPP

YPDADSGSASGPRDLRCYRISSDRYECSWQYEGPT

AGVSHFLRCCLSSGRCCYFAAGSATRLQFSDQAGV

SVLYTVTLWVESWARNQTEKSPEVTLQLYNSVKYE

PPLGDIKVSKLAGQLRMEWETPDNQVGAEVQFRHR

TPSSPWKLGDCGPQDDDTESCLCPLEMNVAQEFQL

RRRQLGSQGSSWSKWSSPVCVPPENPPQPQVRFSV

EQLGQDGRRRLTLKEQPTQLELPEGCQGLAPGTEV

TYRLQLHMLSCPCKAKATRTLHLGKMPYLSGAAYN

VAVISSNQFGPGLNQTWHIPADTHTEPVALNISVG

TNGTTMYWPARAQSMTYCIEWQPVGQDGGLATCSL

TAPQDPDPAGMATYSWSRESGAMGQEKCYYITIFA
```

```
                                            -continued
SAHPEKLTLWSTVLSTYHFGGNASAAGTPHHVSVK

NHSLDSVSVDWAPSLLSTCPGVLKEYVVRCRDEDS

KQVSEHPVQPTETQVTLSGLRAGVAYTVQVRADTA

WLRGVWSQPQRFSIEVQVSDWLIFFASLGSFLSIL

LVGVLGYLGLNRAARHLCPPLPTPCASSAIEFPGG

KETWQWINPVDFQEEASLQEALVVEMSWDKGERTE

PLEKTELPEGAPELALDTELSLEDGDRCKAKM.
```

For purposes of the present disclosure, the numbering of amino acid residues of the hIL12RB1polypeptides as described herein is made in accordance with the numbering of this canonical sequence (UniProt Reference No P42701, SEQ ID NO:1). Amino acids 1-23 of SEQ ID NO:1 are identified as the signal peptide of hIL12RB1, amino acids 24-545 of SEQ ID NO:1 are identified as the extracellular domain, amino acids 546-570 of SEQ ID NO:1 are identified as the transmembrane domain, and amino acids 571-662 of SEQ ID NO:1 are identified as the intracellular domain.

For the purposes of generating antibodies that bind to the ECD of IL12RB1, immunization may be performed with the extracellular domain of the hTL12RB1. The extracellular domain of hIL12RB1 is a 522 amino acid polypeptide of the sequence:

```
                                            (SEQ ID NO: 2)
CRTSECCFQDPPYPDADSGSASGPRDLRCYRISSD

RYECSWQYEGPTAGVSHFLRCCLSSGRCCYFAAGS

ATRLQFSDQAGVSVLYTVTLWVESWARNQTEKSPE

VTLQLYNSVKYEPPLGDIKVSKLAGQLRMEWETPD

NQVGAEVQFRHRTPSSPWKLGDCGPQDDDTESCLC

PLEMNVAQEFQLRRRQLGSQGSSWSKWSSPVCVPP

ENPPQPQVRFSVEQLGQDGRRRLTLKEQPTQLELP

EGCQGLAPGTEVTYRLQLHMLSCPCKAKATRTLHL

GKMPYLSGAAYNVAVISSNQFGPGLNQTWHIPADT

HTEPVALNISVGTNGTTMYWPARAQSMTYCIEWQP

VGQDGGLATCSLTAPQDPDPAGMATYSWSRESGAM

GQEKCYYITIFASAHPEKLTLWSTVLSTYHFGGNA

SAAGTPHHVSVKNHSLDSVSVDWAPSLLSTCPGVL

KEYVVRCRDEDSKQVSEHPVQPTETQVTLSGLRAG

VAYTVQVRADTAWLRGVWSQPQRFSIEVQVSD.
```

Mouse IL12RB1

In one embodiment, the IL12RB1 binding molecules of the present disclosure specifically bind to the extracellular domain of the mouse or murine IL12RB1 receptor subunit (mIL12RB1). mIL12RB1 is expressed as a 738 amino acid precursor comprising a 19 amino acid N-terminal signal sequence which is post-translationally cleaved to provide a 719 amino acid mature protein. The canonical full-length acid mIL12RB1 precursor (including the 24 amino acid signal peptide) is a 738 amino acid polypeptide having the amino acid sequence:

(SEQ ID NO: 3)
MDMMGLAGTSKHITFLLLCQLGASGPGDGCCVEKT

SFPEGASGSPLGPRNLSCYRVSKTDYECSWQYDGP

EDNVSHVLWCCFVPPNHTHTGQERCRYFSSGPDRT

VQFWEQDGIPVLSKVNFWVESRLGNRTMKSQKISQ

YLYNWTKTTPPLGHIKVSQSHRQLRMDWNVSEEAG

AEVQFRRRMPTTNWTLGDCGPQVNSGSGVLGDIRG

SMSESCLCPSENMAQEIQIRRRRRLSSGAPGGPWS

DWSMPVCVPPEVLPQAKIKFLVEPLNQGGRRRLTM

QGQSPQLAVPEGCRGRPGAQVKKHLVLVRMLSCRC

QAQTSKTVPLGKKLNLSGATYDLNVLAKTRFGRST

IQKWHLPAQELTETRALNVSVGGNMTSMQWAAQAP

GTTYCLEWQPWFQHRNHTHCTLIVPEEEDPAKMVT

HSWSSKPTLEQEECYRITVFASKNPKNPMLWATVL

SSYYFGGNASRAGTPRHVSVRNQTGDSVSVEWTAS

QLSTCPGVLTQYVVRCEAEDGAWESEWLVPPTKTQ

VTLDGLRSRVMYKVQVRADTARLPGAWSHPQRFSF

EVQISRLSIIFASLGSFASVLLVGSLGYIGLNRAA

WHLCPPLPTPCGSTAVEFPGSQGKQAWQWCNPEDF

PEVLYPRDALVVEMPGDRGDGTESPQAAPECALDT

RRPLETQRQRQVQALSEARRLGLAREDCPRGDLAH

VTLPLLLGGVTQGASVLDDLWRTHKTAEPGPPTLG

QEA

For purposes of the present disclosure, the numbering of amino acid residues of the mIL12RB1 polypeptides as described herein is made in accordance with the numbering of this canonical sequence (UniProt Reference No. Q60837, SEQ ID NO:3). Amino acids 1-19 of SEQ ID NO:3 are identified as the signal peptide of mIL12RB1, amino acids 20-565 of SEQ ID NO:3 are identified as the extracellular domain, amino acids 566-591 of SEQ ID NO:3 are identified as the transmembrane domain, and amino acids 592-738 of SEQ ID NO:3 are identified as the intracellular domain.

For the purposes of generating antibodies that bind to the ECD of IL12RB1, immunization may be performed with the extracellular domain of the mIL12RB1. The extracellular domain of the mIL12RB1 receptor is a 546 amino acid polypeptide of the sequence:

(SEQ ID NO: 4)
QLGASGPGDGCCVEKTSFPEGASGSPLGPRNLSCY

RVSKTDYECSWQYDGPEDNVSHVLWCCFVPPNHTH

TGQERCRYFSSGPDRTVQFWEQDGIPVLSKVNFWV

ESRLGNRTMKSQKISQYLYNWTKTTPPLGHIKVSQ

SHRQLRMDWNVSEEAGAEVQFRRRMPTTNWTLGDC

GPQVNSGSGVLGDIRGSMSESCLCPSENMAQEIQI

RRRRRLSSGAPGGPWSDWSMPVCVPPEVLPQAKIK

-continued
FLVEPLNQGGRRRLTMQGQSPQLAVPEGCRGRPGA

QVKKHLVLVRMLSCRCQAQTSKTVPLGKKLNLSGA

TYDLNVLAKTRFGRSTIQKWHLPAQELTETRALNV

SVGGNMTSMQWAAQAPGTTYCLEWQPWFQHRNHTH

CTLIVPEEEDPAKMVTHSWSSKPTLEQEECYRITV

FASKNPKNPMLWATVLSSYYFGGNASRAGTPRHVS

VRNQTGDSVSVEWTASQLSTCPGVLTQYVVRCEAE

DGAWESEWLVPPTKTQVTLDGLRSRVMYKVQVRAD

TARLPGAWSHPQRFSFEVQIS.

Cross Reactivity:

In some instances, due to sequence or structural similarities between the extracellular domains of IL12RB1 receptors from various mammalian species, immunization with an antigen derived from a IL12RB1 of a first mammalian species (e.g., the hIL12RB1-ECD) may provide antibodies which specifically bind to IL12RB1 receptors of one or more additional mammalian species. Such antibodies are termed "cross reactive." For example, immunization of a camelid with a human derived antigen (e.g., the hIL12RB1-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL12RB1 VHH" or "hIL12RB1 VHH" merely denotes that the species of the IL12RB1 antigen used for immunization of the camelid from which the VHH was derived was the human IL12RB1 (e.g., the hIL12RB1 ECD) but should not be understood as limiting with respect to the specific binding affinity of the VHH for IL12RB1 molecules of other mammalian species. Similarly, the use of the term "mouse IL12RB1 VHH" or "mIL12RB1 VHH" merely denotes that the species of the IL12RB1 antigen used for immunization of the camelid from which the VHH was derived was the murine IL12RB1 (e.g., the mIL12RB1 ECD) but should not be understood as limiting with respect to the specific binding affinity of the VHH for IL12RB1 molecules of other mammalian species.

IL12Rb2

The IL12Rb2 binding molecules of the present disclosure specifically bind to the extracellular domain of the IL12Rb2.

Human IL12Rb2

In one embodiment, the IL12Rb2 binding molecules of the present disclosure specifically bind to the extracellular domain of the human IL12Rb2 receptor subunit (hIL12Rb2). hIL12Rb2 is expressed as an 862 amino acid precursor comprising a 23 amino acid N-terminal signal sequence which is post-translationally cleaved to provide an 839 amino acid mature protein. The canonical full-length acid hIL12Rb2 precursor (including the signal peptide) is an 862 amino acid polypeptide having the amino acid sequence:

(SEQ ID NO: 5)
MAHTFRGCSLAFMFIITWLLIKAKIDACKRGDVTV

KPSHVILLGSTVNITCSLKPRQGCFHYSRRNKLIL

YKFDRRINFHHGHSLNSQVTGLPLGTTLFVCKLAC

INSDEIQICGAEIFVGVAPEQPQNLSCIQKGEQGT

VACTWERGRDTHLYTEYTLQLSGPKNLTWQKQCKD

IYCDYLDFGINLTPESPESNFTAKVTAVNSLGSSS

SLPSTFTFLDIVRPLPPWDIRIKFQKASVSRCTLY

WRDEGLVLLNRLRYRPSNSRLWNMVNVTKAKGRHD

LLDLKPFTEYEFQISSKLHLYKGSWSDWSESLRAQ

TPEEEPTGMLDVWYMKRHIDYSRQQISLFWKNLSV

SEARGKILHYQVTLQELTGGKAMTQNITGHTSWTT

VIPRTGNWAVAVSAANSKGSSLPTRINIMNLCEAG

LLAPRQVSANSEGMDNILVTWQPPRKDPSAVQEYV

VEWRELHPGGDTQVPLNWLRSRPYNVSALISENIK

SYICYEIRVYALSGDQGGCSSILGNSKHKAPLSGP

HINAITEEKGSILISWNSIPVQEQMGCLLHYRIYW

KERDSNSQPQLCEIPYRVSQNSHPINSLQPRVTYV

LWMTALTAAGESSHGNEREFCLQGKANWMAFVAPS

ICIAIIMVGIFSTHYFQQKVFVLLAALRPQWCSRE

IPDPANSTCAKKYPIAEEKTQLPLDRLLIDWPTPE

DPEPLVISEVLHQVTPVFRHPPCSNWPQREKGIQG

HQASEKDMMHSASSPPPPRALQAESRQLVDLYKVL

ESRGSDPKPENPACPWTVLPAGDLPTHDGYLPSNI

DDLPSHEAPLADSLEELEPQHISLSVFPSSSLHPL

TFSCGDKLTLDQLKMRCDSLML

For purposes of the present disclosure, the numbering of amino acid residues of the human IL12Rb2polypeptides as described herein is made in accordance with the numbering of this canonical sequence (UniProt Reference No Q99665, SEQ ID NO:5). Amino acids 1-23 of SEQ ID NO:5 are identified as the signal peptide of hIL12Rb2, amino acids 24-622 of SEQ ID NO:5 are identified as the extracellular domain, amino acids 623-643 of SEQ ID NO:5 are identified as the transmembrane domain, and amino acids 644-862 of SEQ ID NO:5 are identified as the intracellular domain.

For the purposes of generating antibodies that bind to the ECD of IL12Rb2, immunization may be performed with the extracellular domain of the hIL12Rb2. The extracellular domain of hIL12Rb2 is a 599 amino acid polypeptide of the sequence:

(SEQ ID NO: 6)
KIDACKRGDVTVKPSHVILLGSTVNITCSLKPRQG

CFHYSRRNKLILYKFDRRINFHHGHSLNSQVTGLP

LGTTLFVCKLACINSDEIQICGAEIFVGVAPEQPQ

NLSCIQKGEQGTVACTWERGRDTHLYTEYTLQLSG

PKNLTWQKQCKDIYCDYLDFGINLTPESPESNFTA

KVTAVNSLGSSSSLPSTFTFLDIVRPLPPWDIRIK

FQKASVSRCTLYWRDEGLVLLNRLRYRPSNSRLWN

MVNVTKAKGRHDLLDLKPFTEYEFQISSKLHLYKG

SWSDWSESLRAQTPEEEPTGMLDVWYMKRHIDYSR

QQISLFWKNLSVSEARGKILHYQVTLQELTGGKAM

TQNITGHTSWTTVIPRTGNWAVAVSAANSKGSSLP

TRINIMNLCEAGLLAPRQVSANSEGMDNILVTWQP

PRKDPSAVQEYVVEWRELHPGGDTQVPLNWLRSRP

YNVSALISENIKSYICYEIRVYALSGDQGGCSSIL

GNSKHKAPLSGPHINAITEEKGSILISWNSIPVQE

QMGCLLHYRIYWKERDSNSQPQLCEIPYRVSQNSH

PINSLQPRVTYVLWMTALTAAGESSHGNEREFCLQ

GKAN.

Mouse IL12Rb2

In one embodiment, the IL12Rb2 binding molecules of the present disclosure specifically bind to the extracellular domain of the mouse or murine IL12Rb2 receptor subunit (mIL12Rb2). mIL12Rb2 is expressed as an 874 amino acid precursor comprising a 23 amino acid N-terminal signal sequence which is post-translationally cleaved to provide a 851 amino acid mature protein. The canonical full-length acid mIL12Rb2 precursor (including the 23 amino acid signal peptide) is an 874 amino acid polypeptide having the amino acid sequence:

(SEQ ID NO: 7)
MAQTVRECSLALLFLFMWLLIKANIDVCKLGTVTV

QPAPVIPLGSAANISCSLNPKQGCSHYPSSNELIL

LKFVNDVLVENLHGKKVHDHTGHSSTFQVTNLSLG

MTLFVCKLNCSNSQKKPPVPVCGVEISVGVAPEPP

QNISCVQEGENGTVACSWNSGKVTYLKTNYTLQLS

GPNNLTCQKQCFSDNRQNCNRLDLGINLSPDLAES

RFIVRVTAINDLGNSSSLPHTFTFLDIVIPLPPWD

IRINFLNASGSRGTLQWEDEGQVVLNQLRYQPLNS

TSWNMVNATNAKGKYDLRDLRPFTEYEFQISSKLH

LSGGGSWSNWSESLRTRTPEEEPVGILDIWYMKQDI

DYDRQQISLFWKSLNPSEARGKILHYQVTLQEVTK

KTTLQNTTRHTSWTRVIPRTGAWTASVSAANSKGA

SAPTHINIVDLCGTGLLAPHQVSAKSENMDNILVT

WQPPKKADSAVREYIVEWRALQPGSITKFPPHWLR

IPPDNMSALISENIKPYICYEIRVHALSESQGGCS

SIRGDSKHKAPVSGPHITAITEKKERLFISWTHIP

FPEQRGCILHYRIYWKERDSTAQPELCEIQYRRSQ

NSHPISSLQPRVTYVLWMTAVTAAGESPQGNEREF

CPQGKANWKAFVISSICIAIITVGTFSIRYFRQKA

FTLLSTLKPQWYSRTIPDPANSTWVKKYPILEEKI

```
QLPTDNLLMAWPTPEEPEPLIIHEVLYHMIPVVRQ

PYYFKRGQGFQGYSTSKQDAMYIANPQATGTLTAE

TRQLVNLYKVLESRDPDSKLANLTSPLTVTPVNYL

PSHEGYLPSNIEDLSPHEADPTDSFDLEHQHISLS

IFASSSLRPLIFGGERLTLDRLKMGYDSLMSNEA.
```

For purposes of the present disclosure, the numbering of amino acid residues of the mIL12Rb2 polypeptides as described herein is made in accordance with the numbering of this canonical sequence (UniProt Reference No. P97378, SEQ ID NO: 7). Amino acids 1-23 of SEQ ID NO: 7 are identified as the signal peptide of mgp130, amino acids 23-510 of SEQ ID NO: 7 are identified as the extracellular domain, amino acids 511-531 of SEQ ID NO: 7 are identified as the transmembrane domain, and amino acids 532-623 of SEQ ID NO: 7 are identified as the intracellular domain.

For the purposes of generating antibodies that bind to the ECD of IL12Rb2, immunization may be performed with the extracellular domain of the mIL12Rb2. The extracellular domain of the mIL12Rb2 receptor is a 614 amino acid polypeptide of the sequence:

```
                                        (SEQ ID NO: 8)
NIDVCKLGTVTVQPAPVIPLGSAANISCSLNPKQG

CSHYPSSNELILLKFVNDVLVENLHGKKVHDHTGH

SSTFQVTNLSLGMTLFVCKLNCSNSQKKPPVPVCG

VEISVGVAPEPPQNISCVQEGENGTVACSWNSGKV

TYLKTNYTLQLSGPNNLTCQKQCFSDNRQNCNRLD

LGINLSPDLAESRFIVRVTAINDLGNSSSLPHTFT

FLDIVIPLPPWDIRINFLNASGSRGTLQWEDEGQV

VLNQLRYQPLNSTSWNMVNATNAKGKYDLRDLRPF

TEYEFQISSKLHLSGGSWSNWSESLRTRTPEEEPV

GILDIWYMKQDIDYDRQQISLFWKSLNPSEARGKI

LHYQVTLQEVTKKTTLQNTTRHTSWTRVIPRTGAW

TASVSAANSKGASAPTHINIVDLCGTGLLAPHQVS

AKSENMDNILVTWQPPKKADSAVREYIVEWRALQP

GSITKFPPHWLRIPPDNMSALISENIKPYICYEIR

VHALSESQGGCSSIRGDSKHKAPVSGPHITAITEK

KERLFISWTHIPFPEQRGCILHYRIYWKERDSTAQ

PELCEIQYRRSQNSHPISSLQPRVTYVLWMTAVTA

AGESPQGNEREFCPQGKAN.
```

Cross Reactivity:

In some instances, due to sequence or structural similarities between the extracellular domains of IL12Rb2 receptors from various mammalian species, immunization with an antigen derived from a IL12Rb2 of a first mammalian species (e.g., the hIL12Rb2-ECD) may provide antibodies which specifically bind to IL12Rb2 receptors of one or more additional mammalian species. Such antibodies are termed "cross reactive." For example, immunization of a camelid with a human derived antigen (e.g., the hIL12Rb2-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL12Rb2 VHH" or "hIL12Rb2 VHH" merely denotes that the species of the IL12Rb2 antigen used for immunization of the camelid from which the VHH was derived was the human IL12Rb2 (e.g., the hIL12Rb2 ECD) but should not be understood as limiting with respect to the specific binding affinity of the VHH for IL12Rb2 molecules of other mammalian species. Similarly, the use of the term "mouse IL12Rb2 VHH" or "mIL12Rb2 VHH" merely denotes that the species of the IL12Rb2 antigen used for immunization of the camelid from which the VHH was derived was the murine IL12Rb2 (e.g., the mIL12Rb2 ECD) but should not be understood as limiting with respect to the specific binding affinity of the VHH for IL12Rb2 molecules of other mammalian species.

Single Domain Antibody is a VHH

In some embodiments, the single domain antibody is a VHH. A $V_HH$ is a type of single-domain antibody (sdAb) containing a single monomeric variable antibody domain. Like a full-length antibody, it is able to bind selectively to a specific antigen. The complementary determining regions (CDRs) of $V_H$Hs are within a single-domain polypeptide. $V_H$Hs can be engineered from heavy-chain antibodies found in camelids. An exemplary $V_H$H has a molecular weight of approximately 12-15 kDa which is much smaller than traditional mammalian antibodies (150-160 kDa) composed of two heavy chains and two light chains. $V_H$Hs can be found in or produced from Camelidae mammals (e.g., camels, llamas, dromedary, alpaca, and guanaco) which are naturally devoid of light chains. Descriptions of sdAbs and $V_H$HS can be found in, e.g., De Greve et al., Curr Opin Biotechnol. 61:96-101, 2019; Ciccarese, et al., Front Genet. 10:997, 2019; Chanier and Chames, Antibodies (Basel) 8(1), 2019; and De Vlieger et al., Antibodies (Basel) 8(1), 2018.

Exemplary Anti IL12Rb1 Single Domain Antibodies

Tables 2 and 3 provide CDRs useful in the preparation of anti-IL12Rb1 sdAbs for incorporation into the bivalent binding molecules of the present disclosure. In some embodiments, the anti-IL12Rb1 sdAbs is a single domain antibody comprising, with reference to the CDRs provided in Table 2 or 3: a CDR1 having 0, 1, 2, or 3 amino acid changes relative to the sequence of any one of the CDR1s in Table 2 or 3; a CDR2 having 0, 1, 2, or 3 amino acid changes relative to the sequence of any one of the CDR2s in Table 2 or 3; and a CDR3 having 0, 1, 2, or 3 amino acid changes relative to the sequence of any one of the CDR3s in Table 2 or 3. Optionally, the CDRs can comprise conservative amino acid changes relative to CDRs in Table 2 or 3.

In some embodiments, the anti-IL12Rb1 sdAb comprises a VHH sequence having at least 90% (e.g., 91%, 92%, 93%, 94%, 95%, 96%, 97%, 98%, 99%, or 100%) sequence identity to a sequence of any one the of anti-IL12Rb1 sdAbs provided in Table 6 or 7. In certain embodiments, the binding molecule comprises a VHH sequence that is substantially identical to a sequence of any one of the sequences listed in a row of Table 6 or 7.

In another aspect, the disclosure provides an isolated nucleic acid encoding anti-IL12Rb1 sdAb described herein. Tables 10 and 11 provide DNA sequences encoding the anti-IL12Rb1 sdAbs of Tables 6 and 7, respectively. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence listed in a row Table 6 or 7.

Exemplary Anti IL12Rb2 Single Domain Antibodies

Tables 4 and 5 provides CDRs useful in the preparation of anti-IL12Rb2 sdAbs. In some embodiments, the anti-IL12Rb2 sdAbs is a single domain antibody comprising, with reference to the CDRs provided in Table 4 or 5: a CDR1 having 0, 1, 2, or 3 amino acid changes relative to the sequence of any one of the CDR1s in Table 4 or 5; a CDR2 having 0, 1, 2, or 3 amino acid changes relative to the sequence of any one of the CDR2s in Table 4 or 5; and a CDR3 having 0, 1, 2, or 3 amino acid changes relative to the sequence of any one of the CDR3s in Table 4 or 5. Optionally, the CDRs can comprise conservative amino acid changes relative to CDRs in Table 4 or 5.

In some embodiments, the anti-IL12Rb2 sdAb comprises a VHH sequence having at least 90% (e.g., 91%, 92%, 93%, 94%, 95%, 96%, 97%, 98%, 99%, or 100%) sequence identity to a sequence of any one the of anti-IL12Rb2 sdAbs provided in Table 8 or 9. In certain embodiments, the binding molecule comprises a VHH sequence that is substantially identical to a sequence of any one of the sequences listed in a row of Table 8 or 9.

In another aspect, the disclosure provides an isolated nucleic acid encoding anti-IL12Rb2 sdAb described herein. Tables 12 and 13 provide DNA encoding the anti-IL12Rb1 sdAbs of Tables 8 and 9, respectively. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence listed in a row of Table 12 or 13.

Anti IL12R VHH Dimer Bispecific Binding Molecules

A. "Forward Orientation"

In some embodiments, the bivalent IL12R binding molecule comprises a polypeptide of the structure:

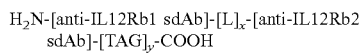

wherein and L is a polypeptide linker of 1-50 amino acids and x=0 or 1, and TAG is a chelating peptide or a subunit of an Fc domain and y=0 or 1.

In some embodiments, a bivalent IL12R binding molecule of the foregoing structure comprises a polypeptide from amino to carboxy terminus:

(a) an anti-IL12Rb1 sdAb comprising:
  a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Tables 2 or 3.
  a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Tables 2 or 3; and
  a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR3s in Tables 2 or 3;

(b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and (c) an anti-IL12Rb2 sdAb comprising:
  a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Tables 4 or 5;
  a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Tables 4 or 5; and
  a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR3s in Tables 4 or 5.

In some embodiments, the bivalent IL12R binding molecule comprises an anti-IL12Rb1 sdAb comprising a CDR1, a CDR2, and a CDR3 as listed in a row Tables 2 or 3 and an anti-IL12Rb2 sdAb comprising a CDR1, a CDR2, and a CDR3 as listed in a row of Tables 4 and 5.

In some embodiments, the anti-IL12Rb1 sdAb of the bivalent IL12R binding molecule comprises a VHH sequence having at least 90% (e.g., 91%, 92%, 93%, 94%, 95%, 96%, 97%, 98%, 99%, or 100%) sequence identity to a sequence of any one the of anti-IL12Rb1 sdAbs provided in Table 6 or 7. In some embodiments, the anti-IL12Rb2 sdAb the bivalent IL12R binding molecule comprises a sequence having at least 90% (e.g., 91%, 92%, 93%, 94%, 95%, 96%, 97%, 98%, 99%, or 100%) sequence identity to a sequence of any one the of anti-IL12Rb2 sdAbs provided in Table 6 or 7.

B. "Reverse Orientation"

In some embodiments, the bivalent IL12R binding molecule comprises a polypeptide of the structure:

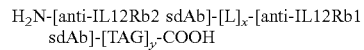

wherein and L is a polypeptide linker of 1-50 amino acids and x=0 or 1, and TAG is a chelating peptide or a subunit of an Fc domain and y=0 or 1.

In some embodiments, a bivalent IL12R binding molecule of the foregoing structure comprises a polypeptide from amino to carboxy terminus:

(a) an anti-IL12Rb2 sdAb comprising:
  a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Tables 4 or 5;
  a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Tables 4 or 5; and
  a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR3s in Tables 4 or 5;
(b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
(c) an anti-IL12Rb1 sdAb comprising:
a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Tables 2 or 3;
a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Tables 2 or 3; and
a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR3s in Tables 2 or 3.

In some embodiments, the binding molecule comprises an anti-IL12Rb2 sdAb comprising a CDR1, a CDR2, and a CDR3 as listed in a row of Tables 5 or 6 and an anti-IL12Rb1 sdAb comprising a CDR1, a CDR2, and a as listed in a row of Tables 2 and 3.

In some embodiments, the anti-IL12Rb1 sdAb comprises a VHH sequence having at least 90% (e.g., 91%, 92%, 93%, 94%, 95%, 96%, 97%, 98%, 99%, or 100%) sequence identity to a sequence listed in a row of Table 6 or 7. In certain embodiments, the anti-IL12Rb1 sdAb comprises a VHH sequence having at least 90% sequence identity to a sequence listed in a row of Table 6 or 7.

III. Linkers

A linker can be used to join the anti-IL12Rb1 sdAb and the anti-IL12Rb1 sdAb antibody. A linker is a linkage between two linker is a linkage between the two sdAbs in the binding molecule, e.g., protein domains. For example, a linker can simply be a covalent bond or a peptide linker. In some embodiments, the sdAbs in a binding molecule are joined directly (i.e., via a covalent bond). In a bispecific $V_HH^2$ binding molecule described herein, a linker is a linkage between the two $V_H$Hs in the binding molecule. A In some embodiments, the linker is a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids).

Examples of flexible linkers include glycine polymers (G)n, glycine-alanine polymers, alanine-serine polymers, glycine-serine polymers (for example, (GmSo)n (SEQ ID NO: 422), (GGS)nG (SEQ ID NO: 429), (GSGGS)n (SEQ ID NO: 423), (GmSoGm)n (SEQ ID NO: 424), (GmSoGm-SoGm)n (SEQ ID NO: 425), (GSGGSm)n (SEQ ID NO: 426), (GSGSmG)n (SEQ ID NO: 427) and (GGGSm)n (SEQ ID NO: 428), and combinations thereof, where m, n, and o are each independently selected from an integer of at least 1 to 20, e.g., 1-18, 216, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between component-sExemplary flexible linkers include, but are not limited to GGGS (SEQ ID NO:13), GGGGS (SEQ ID NO: 14), GGSG (SEQ ID NO: 15), GGSGG (SEQ ID NO: 16), GSGSG (SEQ ID NO: 17), GSGGG (SEQ ID NO: 18), GGGSG (SEQ ID NO: 19) and GSSSG (SEQ ID NO: 20). In yet other embodiments, a peptide linker can contain 4 to 20 amino acids including motifs of GGSG (SEQ ID NO:15), e.g., GGSGGGSG (SEQ ID NO:21), GGSGGGSGGGSG (SEQ ID NO:22), GGSGGGSGGGSGGGSG (SEQ ID NO:23), or GGSGGGSGGGSGGGSGGGSG (SEQ ID NO:24). In other embodiments, a peptide linker can contain motifs of GGSG (SEQ ID NO:15), e.g., GGSGGGSG (SEQ ID NO:21), GGSGGGSGGGSG (SEQ ID NO:22), GGSGGGSGGGSGGGSG (SEQ ID NO:23), or GGSGGGSGGGSGGGSGGGSG (SEQ ID NO:24)

A linker can also be a chemical linker, such as a synthetic polymer, e.g., a polyethylene glycol (PEG) polymer.

The length of the linker between two sdAb in a binding molecule can be used to modulate the proximity of the two sdAb of the binding molecule. By varying the length of the linker, the overall size and length of the binding molecule can be tailored to bind to specific cell receptors or domains or subunits thereof. For example, if the binding molecule is designed to bind to two receptors or domains or subunits thereof that are located close to each other on the same cell, then a short linker can be used. In another example, if the binding molecule is designed to bind to two receptors or domains or subunits there of that are located on two different cells, then a long linker can be used.

In some embodiments, a linker joins the C-terminus of the anti-IL12Rb1 sdAb in the binding molecule to the N-terminus of the anti-IL12Rb2 sdAb in the binding molecule. In other embodiments, a linker joins the C-terminus of the anti-IL12Rb2 sdAb in the binding molecule to the N-terminus of the anti-IL12Rb1 sdAb in the binding molecule.

Modulation of sdAb Binding Affinity:

In some embodiments, the activity and/or specificity of the bivalent IL12R binding molecule of the present disclosure may be modulated by the respective binding affinities of the sdAbs for their respective receptor subunits.

It will be appreciated by one of skill in the art that the binding of the first sdAb of the bivalent IL12R binding molecule to the first receptor subunit ECD on the cell surface will enhance the probability of a binding interaction between the second sdAb of the bivalent IL12R binding molecule with the ECD of the second receptor subunit. This cooperative binding effect may result in a bivalent IL12R binding molecule which has a very high affinity for the receptor and a very slow "off rate" from the receptor. Typical VHH single domain antibodies have an affinity for their targets of from about $10^{-5}$ M to about $10^{-10}$ M. In those instances such slow off-rate kinetics are desirable in the bivalent IL12R binding molecule, the selection of sdAbs having high affinities (about $10^{-7}$M to about $10^{-10}$M) for incorporation into the bivalent IL12R binding molecule are favored.

Naturally occurring cytokine ligands for typically do not exhibit a similar affinity for each subunit of a heterodimeric receptor. Consequently, in designing a bivalent IL12R binding molecule which is a mimetic of the cognate cytokine IL12 as contemplated by some embodiments of the present disclosure, selection of sdAbs for the first and second IL12R receptor subunit have an affinity similar to (e.g., having an affinity about 10 fold, alternatively about 20 fold, or alternatively about 50 fold higher or lower than) the cognate IL12 for the respective receptor subunit may be used.

In some embodiments, the bivalent IL12R binding molecules of the present disclosure are partial agonists of the IL12R. As such, the activity of the bivalent binding molecule may be modulated by selecting sdAb which have greater or lesser affinity for either one or both of the IL12R receptor subunits. As some heterodimeric cytokine receptors are comprised of a "proprietary subunit" (i.e., a subunit which is not naturally a subunit of another multimeric receptor) and a second "common" subunit (such as CD132) which is a shared component of multiple cytokine receptors), selectivity for the formation of such receptor may be enhanced by employing first sdAb which has a higher affinity for the proprietary receptor subunit and second sdAB which exhibits a lower affinity for the common receptor subunit. Additionally, the common receptor subunit may be expressed on a wider variety of cell types than the proprietary receptor subunit. In some embodiments wherein the receptor is a heterodimeric receptor comprising a proprietary subunit and a common subunit, the first sdAb of the bivalent IL12R binding molecule exhibits a significantly greater (more than 10 times greater, alternatively more than 100 times greater, alternatively more than 1000 times greater) affinity for the proprietary receptor than the second sdAb of the bivalent IL12R binding molecule for the common receptor subunit. In one embodiment, the present disclosure provides a bivalent IL12R binding molecule wherein the affinity of the anti-IL12Rb1 sdAb of has an affinity of more than 10 times greater, alternatively more than 100 times greater, alternatively more than 1000 times greater) affinity anti-IL12Rb2 sdAb common receptor subunit.

III. Modifications to Extend Duration of Action In Vivo

The IL12R bivalent binding molecule described herein can be modified to provide for an extended lifetime in vivo and/or extended duration of action in a subject. In some embodiments, the binding molecule can be conjugated to carrier molecules to provide desired pharmacological properties such as an extended half-life. In some embodiments, the binding molecule can be covalently linked to the Fc domain of IgG, albumin, or other molecules to extend its half-life, e.g., by pegylation, glycosylation, and the like as known in the art. In some embodiments, the IL12R bivalent binding molecule modified to provide an extended duration of action in a mammalian subject has a half-life in a mammalian of greater than 4 hours, alternatively greater than 5 hours, alternatively greater than 6 hours, alternatively greater than 7 hours, alternatively greater than 8 hours, alternatively greater than 9 hours, alternatively greater than 10 hours, alternatively greater than 12 hours, alternatively greater than 18 hours, alternatively greater than 24 hours, alternatively greater than 2 days, alternatively greater than 3 days, alternatively greater than 4 days, alternatively greater than 5 days, alternatively greater than 6 days, alternatively greater than 7 days, alternatively greater than 10 days, alternatively greater than 14 days, alternatively greater than 21 days, or alternatively greater than 30 days.

Modifications of the IL12R bivalent binding molecule to provide an extended duration of action in a mammalian subject include (but are not limited to);

conjugation of the IL12R bivalent binding molecule to one or more carrier molecules, conjugation IL12R bivalent binding molecule to protein carriers molecules, optionally in the form of a fusion protein with additional polypeptide sequences (e.g., IL12R bivalent binding molecule-Fc fusions) and conjugation to polymers, (e.g. water soluble polymers to provide a PEGylated IL12R bivalent binding molecule).

It should be noted that the more than one type of modification that provides for an extended duration of action in a mammalian subject may be employed with respect to a given IL12R bivalent binding molecule. For example, IL12R bivalent binding molecule of the present disclosure may comprise both amino acid substitutions that provide for an extended duration of action as well as conjugation to a carrier molecule such as a polyethylene glycol (PEG) molecule.

Protein Carrier Molecules:

Examples of protein carrier molecules which may be covalently attached to the IL12R bivalent binding molecule to provide an extended duration of action in vivo include, but are not limited to, albumins, antibodies and antibody fragments such and Fc domains of IgG molecules Fc Fusions:

In some embodiments, the IL12R bivalent binding molecule is conjugated to a functional domain of an Fc-fusion chimeric polypeptide molecule. Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fc region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The binding molecule described herein can be conjugated to the entire Fc region, or a smaller portion that retains the ability to extend the circulating half-life of a chimeric polypeptide of which it is a part. In addition, full-length or fragmented Fc regions can be variants of the wild-type molecule. In a typical presentation, each monomer of the dimeric Fc can carry a heterologous polypeptide, the heterologous polypeptides being the same or different.

Illustrative examples of Fc formats useful for IL12R bivalent binding molecules of the present disclosure are provided schematically in FIGS. 1-4 of the attached drawings.

Linkage of Bivalent Binding Molecule to Fc

As indicated, the linkage of the IL12R bivalent binding molecule to the Fc subunit may incorporate a linker molecule as described below between the bivalent sdAb and Fc subunit. In some embodiments, the IL12R bivalent binding molecule is expressed as a fusion protein with the Fc domain incorporating an amino acid sequence of a hinge region of an IgG antibody. The Fc domains engineered in accordance with the foregoing may be derived from IgG1, IgG2, IgG3 and IgG4 mammalian IgG species. In some embodiments, the Fc domains may be derived from human IgG1, IgG2, IgG3 and IgG4 IgG species. In some embodiments, the hinge region is the hinge region of an IgG1. In one particular embodiment, the IL12R bivalent binding is linked to an Fc domain using an human IgG1 hinge domain.

Knob-into-Hole Fc Format

In some embodiments, when the IL12R bivalent binding molecule described herein is to be administered in the format of an Fc fusion, particularly in those situations when the polypeptide chains conjugated to each subunit of the Fc dimer are different, the Fc fusion may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob"), and ii) in the CH3 domain of a second heavy chain, an amino acid residue is replaced with an amino acid residue having a smaller side chain (e.g., alanine or threonine), thereby generating a cavity ("hole") at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fc region (Carter, et al. (2001) Immunol Methods 248, 7-15).

Figure 2:
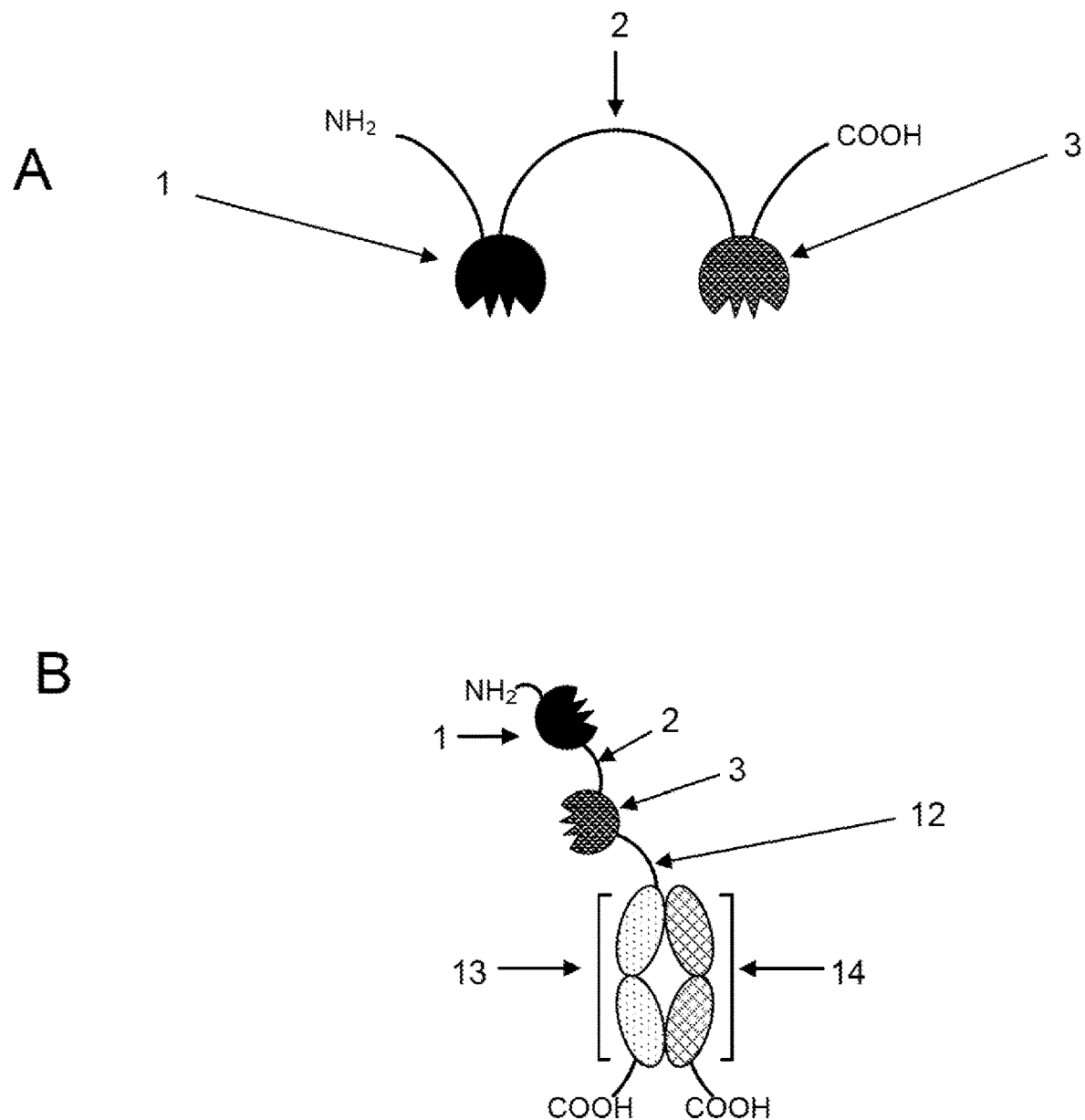
FIG. 2 of the attached drawings provides a schematic representation of two illustrative configurations of bivalent binding molecules of the present disclosure. Panel A provides a schematic representation of an illustrative single polypeptide chain bivalent binding molecule comprising, from amino to carboxy, a first single domain antibody (1) and a second single domain antibody (3) and a linker (2). Panel B provides a schematic representation of a bivalent binding molecule comprising a first single domain antibody (1) and a second single domain antibody (3) and a linker (2) and a knob-into-hole Fc domain, the Fc domain comprising a first subunit which is a Fc knob (13) and a second subunit which is a Fc hole (14) wherein the bivalent binding molecule is covalently linked to an Fc domain subunit via a IgG hinge sequence (12).
Figure 3:
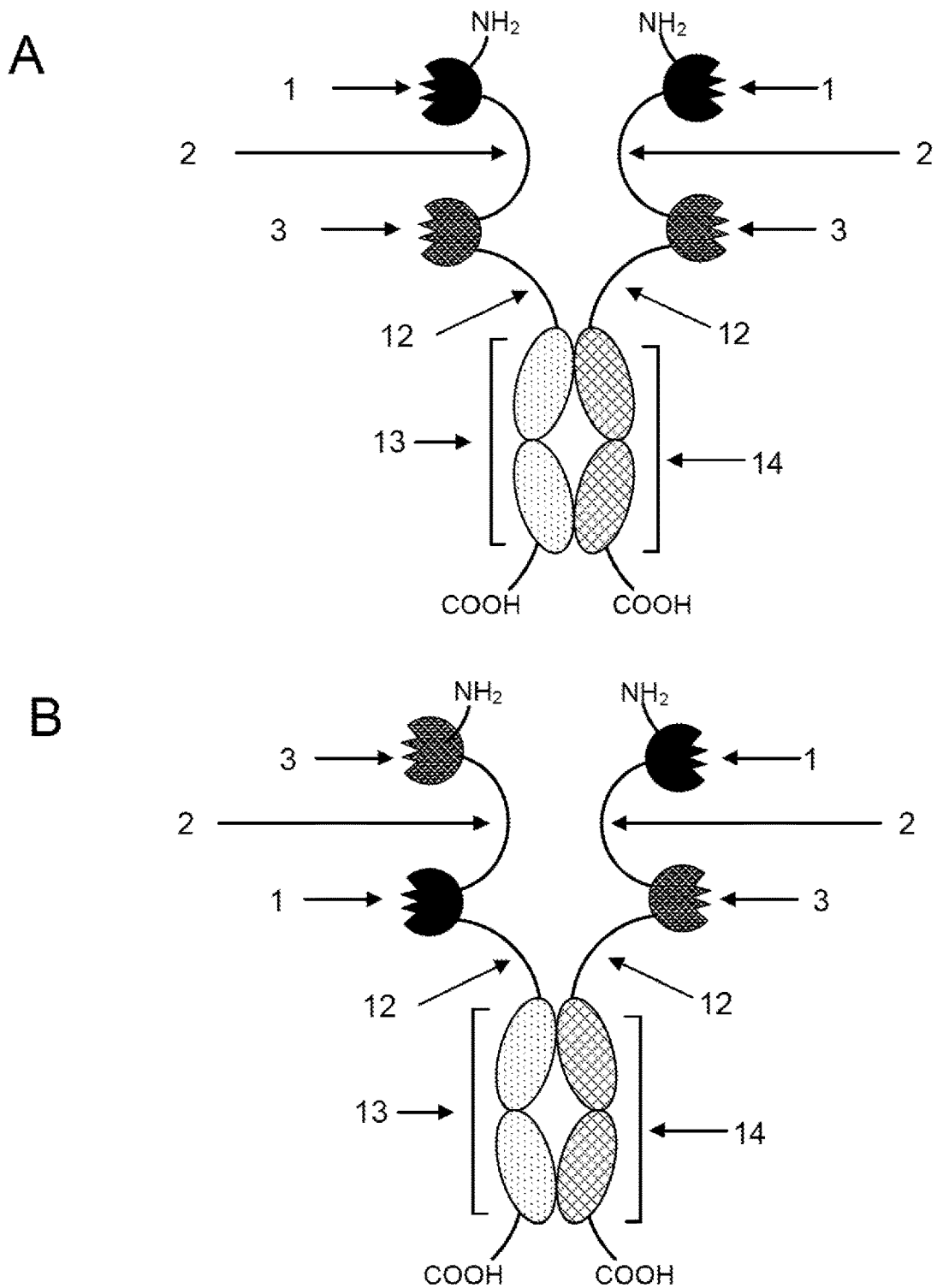
FIG. 3 of the attached drawings provides a schematic representations of two illustrative configurations of bivalent binding molecules of the present disclosure. Panel A provides a schematic representation of an illustrative bivalent binding molecule construct comprising two bivalent binding molecules each attached to a subunit of a knob-into-hole Fc domain, the construct comprising two polypeptide chains, the first polypeptide chain comprising, from amino to carboxy, a first single domain antibody (1), a linker (2) and a second single domain antibody (3), a IgG hinge sequence (12) and a Fc knob subunit (13) and a second polypeptide chain comprising, from amino to carboxy, a first single domain antibody (1), a linker (2) and a second single domain antibody (3), a IgG hinge sequence (12) and a Fc hole subunit (14) wherein the first and second polypeptides are in stable associate via the interaction of the knob-into-hole Fc domain. Panel B provides schematic representation of a an alternative arrangement of a bivalent binding molecule construct comprising two polypeptides a first polypeptide chain comprising, from amino to carboxy, a first single domain antibody (1), a linker (2) and a second single domain antibody (3), an IgG hinge sequence (12) and a Fc knob subunit (13) and a second polypeptide chain comprising, from amino to carboxy, a first second domain antibody (3), a linker (2) and a first single domain antibody (1), a IgG hinge sequence (12) and a Fc hole subunit (14), wherein the first and second polypeptides are in stable association via the interaction of the knob-into-hole Fc domain.

The knob-into-hole format is used to facilitate the expression of a first polypeptide on a first Fc monomer with a "knob" modification and a second polypeptide on the second Fc monomer possessing a "hole" modification to facilitate the expression of heterodimeric polypeptide conjugates. In some embodiments, the IL12R bivalent binding molecule covalently linked to a single subunit of the Fc as illustrated in FIG. 2, a IL12R bivalent binding molecule is provided on each of the subunits of the Fc as illustrated in FIG. 3.

Albumin Carrier Molecules

In some embodiments, the IL12R bivalent binding molecule conjugated to an is albumin molecule (e.g., human serum albumin) which is known in the art to facilitate extended exposure in vivo. In one embodiment of the invention, the IL12R bivalent binding molecule is conjugated to albumin via chemical linkage or expressed as a fusion protein with an albumin molecule referred to herein as an IL12R bivalent binding molecule albumin fusion." The term "albumin" as used in the context αβhIL2 mutein albumin fusions include albumins such as human serum albumin (HSA), cyno serum albumin, and bovine serum albumin (BSA). In some embodiments, the HSA the HSA comprises a C34S or K573P amino acid substitution relative to the wild-type HSA sequence According to the present disclosure, albumin can be conjugated to a IL12R bivalent binding molecule at the carboxyl terminus, the amino terminus, both the carboxyl and amino termini, and internally (see, e.g., U.S. Pat. Nos. 5,876,969 and 7,056,701). In the HAS IL12R bivalent binding molecule contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a IL12R bivalent binding molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. As an alternative to chemical linkage between the IL12R bivalent binding molecule and the albumin molecule the IL12R bivalent binding molecule—albumin complex may be provided as a fusion protein comprising an albumin polypeptide sequence and an IL12R bivalent binding molecule recombinantly expressed in a host cell as a single polypeptide chain, optionally comprising a linker molecule between the albumin and IL12R bivalent binding molecule. Such fusion proteins may be readily prepared through recombinant technology to those of ordinary skill in the art. Nucleic acid sequences encoding such fusion proteins may be ordered from any of a variety of commercial sources. The nucleic acid sequence encoding the fusion protein is incorporated into an expression vector operably linked to one or more expression control elements, the vector introduced into a suitable host cell and the fusion protein isolated from the host cell culture by techniques well known in the art.

Polymeric Carriers

In some embodiments, extended in vivo duration of action of the IL12R bivalent binding molecule may be achieved by conjugation to one or more polymeric carrier molecules such as XTEN polymers or water soluble polymers.

XTEN Conjugates

The IL12R bivalent binding molecule may further comprise an XTEN polymer. The XTEN polymer may be is conjugated (either chemically or as a fusion protein) the αβhIL2 mutein provides extended duration of akin to PEGylation and may be produced as a recombinant fusion protein in E. coli. XTEN polymers suitable for use in conjunction with the IL12R bivalent binding molecule of the present disclosure are provided in Podust, et al. (2016) "Extension of in vivo half-life of biologically active molecules by XTEN protein polymers", J Controlled Release 240:52-66 and Haeckel et al. (2016) "XTEN as Biological Alternative to PEGylation Allows Complete Expression of a Protease-Activatable Killin-Based Cytostatic" PLOS ONE|DOI: 10.1371/journal.pone.0157193 Jun. 13, 2016. The XTEN polymer may fusion protein may incorporate a protease sensitive cleavage site between the XTEN polypeptide and the hIL2 mutein such as an MMP-2 cleavage site.

Water Soluble Polymers

In some embodiments, the IL12R bivalent binding molecule can be conjugated to one or more water-soluble polymers. Examples of water soluble polymers useful in the practice of the present disclosure include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol), polysaccharides), poly-alpha-hydroxy acid), polyvinyl alcohol (PVA), polyphosphazene, polyoxazolines (POZ), poly(N-acryloylmorpholine), or a combination thereof.

In some embodiments, IL12R bivalent binding molecule can be conjugated to one or more polyethylene glycol molecules or "PEGylated." Although the method or site of PEG attachment to the binding molecule may vary, in certain embodiments the PEGylation does not alter, or only minimally alters, the activity of the binding molecule.

PEGs suitable for conjugation to a polypeptide sequence are generally soluble in water at room temperature, and have the general formula

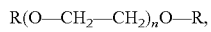

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

In some embodiments, selective PEGylation of the IL12R bivalent binding molecule, for example, by the incorporation of non-natural amino acids having side chains to facilitate selective PEG conjugation, may be employed. Specific PEGylation sites can be chosen such that PEGylation of the binding molecule does not affect its binding to the target receptors.

In some instances, the sequences of IL12R bivalent binding molecules provided in Tables 6-9 of the present disclosure possess an N-terminal glutamine ("1Q") residue. N-terminal glutamine residues have been observed to spontaneously cyclize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL12R binding molecules of the present disclosure, particularly when aldehyde chemistry is to be employed, the IL12R binding molecules possessing an amino acid at position 1 (e.g., 1Q) are substituted at position 1 with an alternative amino acid or are deleted at position 1 (e.g., des-1Q). In some embodiments, the IL12R binding molecules of the present disclosure comprise an amino acid substitution selected from the group Q1E and Q1D.

In certain embodiments, the increase in half-life is greater than any decrease in biological activity. PEGs suitable for conjugation to a polypeptide sequence are generally soluble in water at room temperature, and have the general formula R(O—CH$_2$—CH$_2$)$_n$O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa, or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula R(O—CH$_2$—CH$_2$)$_n$O—R, where R is hydrogen or a protective group such as an alkyl or an alkanol group, and where n is an integer from 1 to 1000. When R is a protective group, it generally has from 1 to 8 carbonst Two widely used first generation activated monomethoxy PEGs (mPEGs) are succinimdyl carbonate PEG (SC-PEG; see, e.g., Zalipsky, et al. (1992) *Biotehnol. Appl. Biochem* 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation most frequently occurs at the a-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General PEGylation strategies known in the art can be applied herein.

The PEG can be bound to a binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the binding molecules is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin et al., PCT International Application No. PCT/US2018/045257 filed Aug. 3, 2018 and published Feb. 7, 2019 as International Publication Number WO 2019/028419A1.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF), a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

In some embodiments, a linker can used to join the IL12R bivalent binding molecule and the PEG molecule. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers are described in Section IV. Further, a multimer (e.g., 1, 2, 3, 4, 5, 6, 7, 8, 9, 10, 10-20, 20-30, or 30-50) of these linker sequences may be linked together to provide flexible linkers that may be used to conjugate two molecules. Alternative to a polypeptide linker, the linker can be a chemical linker, e.g., a PEG-aldehyde linker. In some embodiments, the binding molecule is acetylated at the N-terminus by enzymatic reaction with N-terminal acetyltransferase and, for example, acetyl CoA. Alternatively, or in addition to N-terminal acetylation, the binding molecule can be acetylated at one or more lysine residues, e.g., by enzymatic reaction with a lysine acetyltransferase. See, for example Choudhary et al. (2009) Science 325 (5942):834-840.

Fatty Acid Carriers

In some embodiments an IL12R bivalent binding molecule having an extended duration of action in a mammalian subject and useful in the practice of the present disclosure is achieved by covalent attachment of the IL12R bivalent binding molecule to a fatty acid molecule as described in Resh (2016) Progress in Lipid Research 63: 120-131. Examples of fatty acids that may be conjugated include myristate, palmitate and palmitoleic acid. Myristoylate is typically linked to an N-terminal glycine but lysines may also be myristoylated. Palmitoylation is typically achieved by enzymatic modification of free cysteine —SH groups such as DHHC proteins catalyze S-palmitoylation. Palmitoleylation of serine and threonine residues is typically achieved enzymatically using PORCN enzymes. In some embodiments, the IL12R bivalent binding molecule is acetylated at the N-terminus by enzymatic reaction with N-terminal acetyltransferase and, for example, acetyl CoA. Alternatively, or in addition to N-terminal acetylation, the IL12R bivalent binding molecule is acetylated at one or more lysine residues, e.g., by enzymatic reaction with a lysine acetyltransferase. See, for example Choudhary et al. (2009) Science 325 (5942):834L2 ortho840.

Modifications to Provide Additional Functions

In some embodiments, embodiment, the IL12R bivalent binding molecule may comprise a functional domain of a chimeric polypeptide. IL12R bivalent binding molecule fusion proteins of the present disclosure may be readily produced by recombinant DNA methodology by techniques known in the art by constructing a recombinant vector comprising a nucleic acid sequence comprising a nucleic acid sequence encoding the IL12R bivalent binding molecule in frame with a nucleic acid sequence encoding the fusion partner either at the N-terminus or C-terminus of the IL12R bivalent binding molecule, the sequence optionally further comprising a nucleic acid sequence in frame encoding a linker or spacer polypeptide.

FLAG Tags

In other embodiments, the IL12R bivalent binding molecule can be modified to include an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the binding molecule further comprises a C-terminal c-myc epitope tag.

Chelating Peptides

In some embodiments, the IL12R bivalent binding molecule (including fusion proteins of the IL12R bivalent binding molecule) of the present disclosure are may be covalently bonded via a peptide bond to one or more transition metal chelating polypeptide sequences. The association of the IL12R bivalent binding molecule with chelating peptide provides multiple utilities including: the purification of the IL12R bivalent binding molecule using immobilized metal affinity chromatography (IMAC) as described in Smith, et al. U.S. Pat. No. 4,569,794 issued Feb. 11, 1986; immobilization of the IL12R bivalent binding molecule on nitrilotriacetic acid (NTA) modified surface plasmon resonance sensor chips (e.g., Sensor Chip NTA available from Cytiva Global Life Science Solutions USA LLC, Marlborough MA as catalog number BR100407) as described in Nieba, et al. (1997) Analytical Biochemistry 252(2):217-228, or to form kinetically inert or kinetically labile complexes between the IL12R bivalent binding molecule and a transition metal ion as described in Anderson, et al. (U.S. Pat. No. 5,439,829 issued Aug. 8, 1995 and Hale, J. E (1996) Analytical Biochemistry 231(1):46-49. Examples of transition metal chelating polypeptides useful in the practice of the present disclosure are described in Smith, et al. supra and Dobeli, et al. U.S. Pat. No. 5,320,663 issued May 10, 1995 the entire teachings of which are hereby incorporated by reference. Particular transition metal chelating polypeptides useful in the practice of the present disclosure are peptides comprising 3-6 contiguous histidine residues (SEQ ID NO: 432) such as a six-histidine peptide $(His)_6$ (SEQ ID NO: 420) and are frequently referred to in the art as "His-tags." In some embodiments, a purification handle is a polypeptide having the sequence Ala-Ser-His- His-His-His-His-His ("ASH6") (SEQ ID NO: 430) or Gly-Ser-His-His-His-His-His-His-His-His ("GSH8") (SEQ ID NO: 431).

Targeting Moieties:

In some embodiments, IL12R bivalent binding molecule is conjugated to molecule which provides ("targeting domain") to facilitate selective binding to particular cell type or tissue expressing a cell surface molecule that specifically binds to such targeting domain, optionally incorporating a linker molecule of from 1-40 (alternatively 2-20, alternatively 5-20, alternatively 10-20) amino acids between IL12R bivalent binding molecule sequence and the sequence of the targeting domain of the fusion protein.

In other embodiments, a chimeric polypeptide including a IL12R bivalent binding molecule and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the targeting moiety is an antibody that specifically binds to at least one cell surface molecule associated with a tumor cell (i.e. at least one tumor antigen) wherein the cell surface molecule associated with a tumor cell is selected from the group consisting of GD2, BCMA, CD19, CD33, CD38, CD70, GD2, IL3Ra2, CD19, mesothelin, Her2, EpCam, Mucd, ROR1, CD133, CEA, EGR-FRVIII, PSCA, GPC3, Pan-ErbB and FAP Recombinant Production Alternatively, the IL12R binding molecules of the present disclosure are produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide.

Construction of Nucleic Acid Sequences Encoding the IL12R binding molecule

In some embodiments, the IL12R binding molecule is produced by recombinant methods using a nucleic acid sequence encoding the IL12R binding molecule (or fusion protein comprising the IL12R binding molecule). The nucleic acid sequence encoding the desired αβhIL12R binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the IL12R binding molecule (and fusions thereof) may contain naturally occurring sequences or sequences that differ from those that occur naturally, but, due to the degeneracy of the genetic code, encode the same polypeptide.

These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the IL12R binding molecule may be obtained from various commercial sources that provide custom made nucleic acid sequences. Amino acid sequence variants of the IL12R binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Methods for constructing a DNA sequence encoding a IL12R binding molecule and expressing those sequences in a suitably transformed host include, but are not limited to, using a PCR-assisted mutagenesis technique. Mutations that consist of deletions or additions of amino acid residues to a IL12R binding molecule can also be made with standard recombinant techniques. In the event of a deletion or addition, the nucleic acid molecule encoding a IL12R binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A IL12R binding molecule of the present disclosure may be produced recombinantly not only directly, but also as a fusion polypeptide with a heterologous polypeptide, e.g. a signal sequence or other polypeptide having a specific cleavage site at the N-terminus or C-terminus of the mature IL12R binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. The inclusion of a signal sequence depends on whether it is desired to secrete the IL12R binding molecule from the recombinant cells in which it is made. If the chosen cells are prokaryotic, it generally is preferred that the DNA sequence not encode a signal sequence. When the recombinant host cell is a yeast cell such as *Saccharomyces cerevisiae*, the alpha mating factor secretion signal sequence may be employed to achieve extracellular secretion of the IL12R binding molecule into the culture medium as described in Singh, U.S. Pat. No. 7,198,919 B1 issued Apr. 3, 2007.

In the event the IL12R binding molecule to be expressed is to be expressed as a chimera (e.g., a fusion protein comprising a IL12R binding molecule and a heterologous polypeptide sequence), the chimeric protein can be encoded by a hybrid nucleic acid molecule comprising a first sequence that encodes all or part of the IL12R binding molecule and a second sequence that encodes all or part of the heterologous polypeptide. For example, subject IL12R binding molecules described herein may be fused to a hexa-/octa-histidine (SEQ ID NOS 420 and 421, respectively) tag to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the IL12R binding molecule. For example, the N-terminus may be linked to a targeting domain and the C-terminus linked to a hexa-histidine tag (SEQ ID NO: 420) purification handle.

The complete amino acid sequence of the polypeptide (or fusion/chimera) to be expressed can be used to construct a back-translated gene. A DNA oligomer containing a nucleotide sequence coding a IL12R binding molecule can be synthesized. For example, several small oligonucleotides coding for portions of the desired polypeptide can be synthesized and then ligated. The individual oligonucleotides typically contain 5' or 3' overhangs for complementary assembly.

Codon Optimization:

In some embodiments, the nucleic acid sequence encoding the IL12R binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g. Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors:

Once assembled (by synthesis, site-directed mutagenesis or another method), the nucleic acid sequence encoding an a IL12R binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors.

To facilitate efficient expression of the recombinant polypeptide, the nucleic acid sequence encoding the polypeptide sequence to be expressed is operably linked to transcriptional and translational regulatory control sequences that are functional in the chosen expression host.

Selectable Marker:

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Regulatory Control Sequences:

Expression vectors for a IL12R binding molecules of the present disclosure contain a regulatory sequence that is recognized by the host organism and is operably linked to nucleic acid sequence encoding the IL12R binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject a IL12R binding molecule, particularly as regards potential secondary structures.

Promoters:

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Enhancers:

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context.

Proper assembly of the expression vector can be confirmed by nucleotide sequencing, restriction mapping, and expression of a biologically active polypeptide in a suitable host.

Host Cells:

The present disclosure further provides prokaryotic or eukaryotic cells that contain and express a nucleic acid molecule that encodes a IL12R binding molecule. A cell of the present disclosure is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this invention, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant IL12R binding molecule can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast S. cerenvisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The IL12R binding molecule may be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, a IL12R binding molecule obtained will be glycosylated or unglycosylated depending on the host organism used to produce the mutein. If bacteria are chosen as the host then the a IL12R binding molecule produced will be unglycosylated. Eukaryotic cells, on the other hand, will typically result in glycosylation of the IL12R binding molecule.

In some embodiments, it is possible that an amino acid sequence (particularly a CDR sequence) of an sdAb to be incorporated into a bivalent IL12R binding molecule may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the N-linked glycosylation motif is disrupted by the incorporation of conservative amino acid substitution of the Asn (N) residue of the N-linked glycosylation motif.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection:

The expression constructs of the can be introduced into host cells to thereby produce a IL12R binding molecule disclosed herein. The expression vector comprising a nucleic acid sequence encoding IL12R binding molecule is introduced into the prokaryotic or eukaryotic host cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals. To facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture:

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins:

Recombinantly produced IL12R binding molecule polypeptides can be recovered from the culture medium as a secreted polypeptide if a secretion leader sequence is employed.

Alternatively, the IL12R binding molecule polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

A recombinantly IL12R binding molecule by the transformed host can be purified according to any suitable method. Recombinant IL12R binding molecules can be isolated from inclusion bodies generated in E. coli, or from conditioned medium from either mammalian or yeast cultures producing a given mutein using cation exchange, gel filtration, and or reverse phase liquid chromatography. The substantially purified forms of the recombinant a IL12R binding molecule can be purified from the expression system using routine biochemical procedures, and can be used, e.g., as therapeutic agents, as described herein.

In some embodiments, where the IL12R binding molecule is expressed with a purification tag as discussed above, this purification handle may be used for isolation of the IL12R binding molecule from the cell lysate or cell medium. Where the purification tag is a chelating peptide, methods for the isolation of such molecules using immobilized metal affinity chromatography are well known in the art. See, e.g., Smith, et al. U.S. Pat. No. 4,569,794.

The biological activity of the IL12R binding molecules recovered can be assayed for activating by any suitable method known in the art and may be evaluated as substantially purified forms or as part of the cell lysate or cell medium when secretion leader sequences are employed for expression.

Pharmaceutical Formulations

In some embodiments, the subject IL12R binding molecule (and/or nucleic acids encoding the IL12R binding molecule or recombinant cells incorporating a nucleic acid sequence and modified to express the IL12R binding molecule) can be incorporated into compositions, including pharmaceutical compositions. Such compositions typically include the polypeptide or nucleic acid molecule and a pharmaceutically acceptable carrier. A pharmaceutical composition is formulated to be compatible with its intended route of administration and is compatible with the therapeutic use for which the IL12R binding molecule is to be administered to the subject in need of treatment or prophylaxis.

Carriers:

Carriers include a sterile diluent such as water for injection, saline solution, fixed oils, polyethylene glycols, glycerine, propylene glycol or other synthetic solvents. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. For intravenous administration, suitable carriers include physiological saline, bacteriostatic water, Cremophor EL™ (BASF, Parsippany, N.J.) or phosphate buffered saline (PBS).

Buffers:

The term buffers includes buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5).

Dispersions:

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Preservatives:

The pharmaceutical formulations for parenteral administration to a subject should be sterile and should be fluid to facilitate easy syringability. It should be stable under the conditions of manufacture and storage and are preserved against the contamination. Prevention of the action of microorganisms can be achieved by various antibacterial and antifungal agents, for example, agents such as benzyl alcohol or methyl parabens; antioxidants such as ascorbic acid or sodium bisulfite; chelating agents such as ethylenediaminetetraacetic acid, parabens, chlorobutanol, phenol, ascorbic acid, thimerosal, and the like. Sterile solutions can be prepared by incorporating the active compound in the required amount in an appropriate solvent with one or a combination of ingredients enumerated above, as required, followed by filtered sterilization.

Tonicity Agents:

In many cases, it will be preferable to include isotonic agents, for example, sugars, polyalcohols such as mannitol, sorbitol, sodium chloride in the composition.

Routes of Administration

In some embodiments of the therapeutic methods of the present disclosure involve the administration of a pharmaceutical formulation comprising a IL12R binding molecule (and/or nucleic acids encoding the IL12R binding molecule or recombinantly modified host cells expressing the IL12R binding molecule) to a subject in need of treatment. The pharmaceutical formulation comprising a IL12R binding molecules of the present disclosure may be administered to a subject in need of treatment or prophylaxis by a variety of routes of administration, including parenteral administration, oral, topical, or inhalation routes.

Parenteral Administration:

In some embodiments, the methods of the present disclosure involve the parenteral administration of a pharmaceutical formulation comprising a IL12R binding molecule (and/or nucleic acids encoding the IL12R binding molecule or recombinantly modified host cells expressing the IL12R binding molecule) to a subject in need of treatment. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion. The parenteral preparation can be enclosed in ampoules, disposable syringes or multiple dose vials made of glass or plastic. In one embodiment, the formulation is provided in a prefilled syringe for parenteral administration.

Oral Administration:

In some embodiments, the methods of the present disclosure involve the oral administration of a pharmaceutical formulation comprising a IL12R binding molecule (and/or nucleic acids encoding the IL12R binding molecule or recombinantly modified host cells expressing the IL12R binding molecule) to a subject in need of treatment. Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

Inhalation Formulations:

In some embodiments, the methods of the present disclosure involve the inhaled administration of a pharmaceutical formulation comprising a IL12R binding molecule (and/or nucleic acids encoding the IL12R binding molecule or recombinantly modified host cells expressing the IL12R binding molecule) to a subject in need of treatment. In the event of administration by inhalation, subject IL12R binding molecules, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Mucosal and Transdermal Formulations:

In some embodiments, the methods of the present disclosure involve the mucosal or transdermal administration of a pharmaceutical formulation comprising a IL12R binding molecule (and/or nucleic acids encoding the IL12R binding molecule or recombinantly modified host cells expressing the IL12R binding molecule) to a subject in need of treatment. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

Extended Release and Depot Formulations:

In some embodiments of the method of the present disclosure, the IL12R binding molecule is administered to a subject in need of treatment in a formulation to provide extended release of the IL12R binding molecule agent. Examples of extended release formulations of the injectable compositions can be brought about by including in the composition an agent which delays absorption, for example, aluminum monostearate and gelatin. In one embodiment, the subject IL12R binding molecules or nucleic acids are prepared with carriers that will protect the IL12R binding molecules against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Administration of Nucleic Acids Encoding the IL12R Binding Molecule:

In some embodiments of the method of the present disclosure, delivery of the IL12R binding molecule to a subject in need of treatment is achieved by the administration of a nucleic acid encoding the IL12R binding molecule. Methods for the administration nucleic acid encoding the IL12R binding molecule to a subject is achieved by transfection or infection using methods known in the art, including but not limited to the methods described in McCaffrey et al. (Nature (2002) 418:6893), Xia et al. (Nature Biotechnol. (2002) 20:1006-1010), or Putnam (Am. J. Health Syst. Pharm. (1996) 53: 151-160 erratum at Am. J. Health Syst. Pharm. (1996) 53:325). In some embodiments, the IL12R binding molecule is administered to a subject by the administration of a pharmaceutically acceptable formulation of recombinant expression vector comprising a nucleic acid sequence encoding the IL12R binding molecule operably linked to one or more expression control sequences operable in a mammalian subject. In some embodiments, the expression control sequence may be selected that is operable in a limited range of cell types (or single cell type) to facilitate the selective expression of the IL12R binding molecule in a particular target cell type. In one embodiment, the recombinant expression vector is a viral vector. In some embodiments, the recombinant vector is a recombinant viral vector. In some embodiments the recombinant viral vector is a recombinant adenoassociated virus (rAAV) or recombinant adenovirus (rAd), in particular a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways in a human cell. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in the target cell type.

In some embodiments, particularly for administration of IL12R binding molecules to the subject, particular for treatment of diseases of the intestinal tract or bacterial infections in a subject, the nucleic acid encoding the IL12R binding molecule may be delivered to the subject by the administration of a recombinantly modified bacteriophage vector encoding the IL12R binding molecule. As used herein, the terms 'procaryotic virus," "bacteriophage" and "phage" are used interchangeably hereinto describe any of a variety of bacterial viruses that infect and replicate within a bacterium. Bacteriophage selectively infect procaryotic cells, restricting the expression of the IL12R binding molecule to procaryotic cells in the subject while avoiding expression in mammalian cells. A wide variety of bacteriophages capable of selection a broad range of bacterial cells have been identified and characterized extensively in the scientific literature. In some embodiments, the phage is modified to remove adjacent motifs (PAM). Elimination of the of Cas9 sequences from the phage genome reduces ability of the Cas9 endonuclease of the target procaryotic cell to neutralize the invading phage encoding the IL12R binding molecule.

Administration of Recombinantly Modified Cells Expressing the IL12R Binding Molecule:

In some embodiments of the method of the present disclosure, delivery of the IL12R binding molecule to a subject in need of treatment is achieved by the administration of recombinant host cells modified to express the IL12R binding molecule may be administered in the therapeutic and prophylactic applications described herein. In some embodiments, the recombinant host cells are mammalian cells, e.g., human cells.

In some embodiments, the nucleic acid sequence encoding the IL12R binding molecule (or vectors comprising same) may be maintained extrachromosomally in the recombinantly modified host cell for administration. In other embodiments, the nucleic acid sequence encoding the IL12R binding molecule may be incorporated into the genome of the host cell to be administered using at least one endonuclease to facilitate incorporate insertion of a nucleic acid sequence into the genomic sequence of the cell. As used herein, the term "endonuclease" is used to refer to a wild-type or variant enzyme capable of catalyzing the cleavage of bonds between nucleic acids within a DNA or RNA molecule, preferably a DNA molecule. Endonucleases are referred to as "rare-cutting" endonucleases when such endonucleases have a polynucleotide recognition site greater than about 12 base pairs (bp) in length, more preferably of 14-55 bp. Rare-cutting endonucleases can be used for inactivating genes at a locus or to integrate transgenes by homologous recombination (HR) i.e. by inducing DNA double-strand breaks (DSBs) at a locus and insertion of exogenous DNA at this locus by gene repair mechanism. Examples of rare-cutting endonucleases include homing endonucleases (Grizot, et al (2009) Nucleic Acids Research 37(16):5405-5419), chimeric Zinc-Finger nucleases (ZFN) resulting from the fusion of engineered zinc-finger domains (Porteus M and Carroll D., Gene targeting using zinc finger nucleases (2005) Nature Biotechnology 23(3):967-973, a TALEN-nuclease, a Cas9 endonuclease from CRISPR system as or a modified restriction endonuclease to extended sequence specificity (Eisenschmidt, et al. 2005; 33(22): 7039-7047).

In some embodiments, particularly for administration of IL12R binding molecules to the intestinal tract, the IL12R binding molecule may be delivered to the subject by a recombinantly modified procaryotic cell (e.g., *Lactobacillus lacti*). The use of engineered procaryotic cells for the delivery of recombinant proteins to the intestinal tract are known in the art. See, e.g. Lin, et al. (2017) Microb Cell Fact 16:148. In some embodiments, the engineered bacterial cell expressing the IL12R binding molecule may be administered orally, typically in aqueous suspension, or rectally (e.g. enema).

Therapeutic Applications

The present disclosure further provides methods of treating a subject suffering from a disease disorder or condition by the administration of a therapeutically effective amount of an IL12R binding molecule (or nucleic acid encoding an IL12R binding molecule including recombinant viruses encoding the IL12R binding molecule) of the present disclosure.

Use in Combination with Supplementary Agents:

In some embodiments of the therapeutic uses of the compositions of the present disclosure, the administration of a therapeutically effective amount of an IL12R binding molecule (or nucleic acid encoding an IL12R binding molecule including recombinant viruses encoding the IL12R binding molecule) are administered in combination with one or more additional active agents ("supplementary agents").

As used herein, the term "in combination with" when used in reference to the administration of multiple agents to a subject refers to the administration of a first agent at least one additional (i.e., second, third, fourth, fifth, etc.) agent to a subject. For purposes of the present invention, one agent (e.g., IL12R binding molecule) is considered to be administered in combination with a second agent (e.g. a therapeutic autoimmune antibody such as Humira®) if the biological effect resulting from the administration of the first agent persists in the subject at the time of administration of the second agent such that the therapeutic effects of the first agent and second agent overlap. For example, the therapeutic antibodies are sometimes administered by IV infusion every two weeks while the IL12R binding molecules of the present disclosure may be administered more frequently, e.g. daily, BID, or weekly. However, the administration of the first agent (e.g. entaercept) provides a therapeutic effect over an extended time and the administration of the second agent (e.g. an IL12R binding molecule) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL12R binding molecule and the supplementary agent(s) are administered or applied sequentially, e.g., where one agent is administered prior to one or more other agents. In other embodiments, the IL12R binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Supplementary agents may administered or introduced separately, for example, formulated separately for separate administration (e.g., as may be provided in a kit) and/or therapies that can be administered or introduced in combination with the IL12R binding molecules.

Kits: The present disclosure also contemplates kits comprising pharmaceutical compositions IL12R binding molecules and a pharmaceutical composition thereof. The kits are generally in the form of a physical structure housing various components, as described below, and can be utilized, for example, in practicing the methods described above. A kit may comprise a IL12R binding molecule in the form of a pharmaceutical composition suitable for administration to a subject that is ready for use or in a form or requiring preparation for example, thawing, reconstitution or dilution prior to administration. When the IL12R binding molecule is in a form that needs to be reconstituted by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL12R binding molecule or kit comprising) in compliance with governmental regulations (e.g., HIPAA) are provided.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this dis Prophylactic Applications In some embodiments where the IL12R binding molecule is used in prophylaxis of disease, the supplementary agent may be a vaccine. The IL12R binding molecule of the present invention may be administered to a subject in combination with vaccines as an adjuvant to enhance the immune response to the vaccine in accordance with the teaching of Doyle, et al U.S. Pat. No. 5,800,819 issued Sep. 1, 1998. Examples of vaccines that may be combined with the IL12R binding molecule of the present invention include are HSV vaccines, Bordetella pertussis, Escherichia coli vaccines, pneumococcal vaccines including multivalent pneumococcal vaccines such as Prevnar® 13, diptheria, tetanus and pertussis vaccines (including combination vaccines such as Pediatrix®) and Pentacel®), varicella vaccines, Haemophilus influenzae type B vaccines, human papilloma virus vaccines such as Garasil®, polio vaccines, Leptospirosis vaccines, combination respiratory vaccine, Moraxella vaccines, and attenuated live or killed virus vaccine products such as bovine respiratory disease vaccine (RSV), multivalent human influenza vaccines such as Fluzone® and Quadravlent Fluzone®), feline leukemia vaccine, transmissible gastroenteritis vaccine, COVID-19 vaccine, and rabies vaccine.

EXAMPLES

Example 1—$V_HH$ Generation

Camels were acclimated at research facility for at least 7 days before immunization. Antigen was diluted with 1×PBS (antigen total about 1 mg). The quality of the antigen was assessed by SDS-PAGE to ensure purity (e.g., >80%). For the first time, 10 mL CFA (then followed 6 times using IFA) was added into mortar, then 10 mL antigen in 1×PBS was slowly added into the mortar with the pestle grinding. The antigen and CFA/IFA were ground until the component showed milky white color and appeared hard to disperse. Camels were injected with antigen emulsified in CFA subcutaneously at at least six sites on the body, injecting about 2 mL at each site (total of 10 mL per camel). A stronger immune response was generated by injecting more sites and in larger volumes. The immunization was conducted every week (7 days), for 7 times. The needle was inserted into the subcutaneous space for 10 to 15 seconds after each injection to avoid leakage of the emulsion. Alternatively, a light pull on the syringe plunger also prevented leakage. The blood sample was collected three days later after 7th immunization.

After immunization, the library was constructed. Briefly, RNA was extracted from blood and transcribed to cDNA. The VHH regions were obtained via two-step PCR, which fragment about 400 bp. The PCR outcomes and the vector of pMECS phagemid were digested with Pst I and Not I, subsequently, ligated to pMECS/Nb recombinant. After ligation, the products were transformed into Escherichia coli (E. coli) TG1 cells by electroporation. Then, the transformants were enriched in growth medium and planted on plates. Finally, the library size was estimated by counting the number of colonies.

Bio-panning of the phage library was conducted to identify VHHs that bind IL12Rb. A 96-well plate was coated with IL12Rb and the phage library was incubated in each well to allow phage-expressing IL12Rb reactive VHH to bind to the IL12Rb on the plate. Non-specifically bound phage were washed off and the specifically bound phage isolated. After the selection, the enriched phage library expressing IL12Rb reactive VHH were amplified in TG1 cells. The aforementioned bio-panning process was repeated for 2-3 rounds to enrich the library for VHH selective for IL12Rb. Once biopanning was complete, three 96-well plates of individual phage clones were isolated in order to perform periplasmic extract ELISA PE-ELISA) on antigen coated plates to identify positive VHH binders. Briefly, A 96-well plate was coated with antigen and PBS under the same conditions. Next, wells were blocked at 37° C. for 1 h. Then, 100 μl of extracted antibodies was added to each well and incubated for 1 h. Subsequently, 100 μl of anti-tag polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader and antibodies with absorbance of the antigen-coated well at least threefold greater than PBS-coated control were considered positive binding molecules and subjected to sequence analysis.

Example 2—Recombinant Production and Purification

Codon optimized DNA inserts were cloned into modified pcDNA3.4 (Genscript) for small scale expression in HEK293 cells in 24 well plates. The binding molecules were purified in substantial accordance with the following procedure. Using a Hamilton Star automated system, 96×4 mL of supernatants in 4×24-well blocks were re-arrayed into 4×96-well, 1 mL blocks. PhyNexus micropipette tips (Biotage, San Jose CA) holding 80 μL of Ni-Excel IMAC resin (Cytiva) are equilibrated wash buffer: PBS pH 7.4, 30 mM imidazole. PhyNexus tips were dipped and cycled through 14 cycles of 1 mL pipetting across all 4×96-well blocks. PhyNexus tips were washed in 2×1 mL blocks holding wash buffer. PhyNexus tips were eluted in 3×0.36 mL blocks holding elution buffer: PBS pH 7.4, 400 mM imidazole. PhyNexus tips were regenerated in 3×1 mL blocks of 0.5 M sodium hydroxide.

The purified protein eluates were quantified using a Biacore® T200 as in substantial accordance with the following procedure. 10 uL of the first 96×0.36 mL eluates were transferred to a Biacore® 96-well microplate and diluted to 60 uL in HBS-EP+ buffer (10 mM Hepes pH 7.4, 150 mM NaCl, 1 mM EDTA, 0.05% Tween 20). Each of the 96 samples was injected on a CM5 series S chip previously functionalized with anti-histidine capture antibody (Cytiva): injection is performed for 18 seconds at 5 μL/min. Capture levels were recorded 60 seconds after buffer wash. A standard curve of known VHH concentrations (270, 90, 30, 10, 3.3, 1.1 μg/mL) was acquired in each of the 4 Biacore chip flow cells to eliminate cell-to-cell surface variability. The 96 captures were interpolated against the standard curve using a non-linear model including specific and unspecific, one-site binding. Concentrations in the first elution block varied from 12 to 452 μg/mL corresponding to a 4-149 μg. SDS-PAGE analysis of 5 randomly picked samples was performed to ensure molecular weight of eluates corresponded to expected values (~30 kDa).

The concentration of the proteins was normalized using the Hamilton Star automated system in substantial accordance with the following procedure. Concentration values are imported in an Excel spreadsheet where pipetting volumes were calculated to perform dilution to 50 μg/mL in 0.22 mL. The spreadsheet was imported in a Hamilton Star method dedicated to performing dilution pipetting using the first elution block and elution buffer as diluent. The final, normalized plate was sterile filtered using 0.22 µm filter plates (Corning).

Example 3—Binding of VHH Proteins to IL12 Receptors

Figure 5:
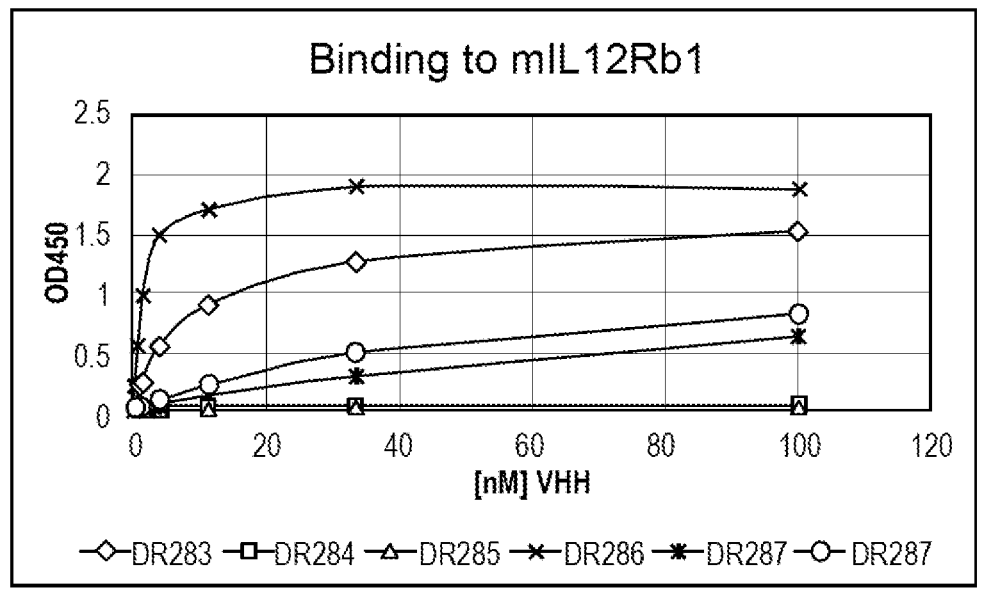
FIG. 5 shows binding data of the VHH dimers to mIL12Rb1.
Figure 6:
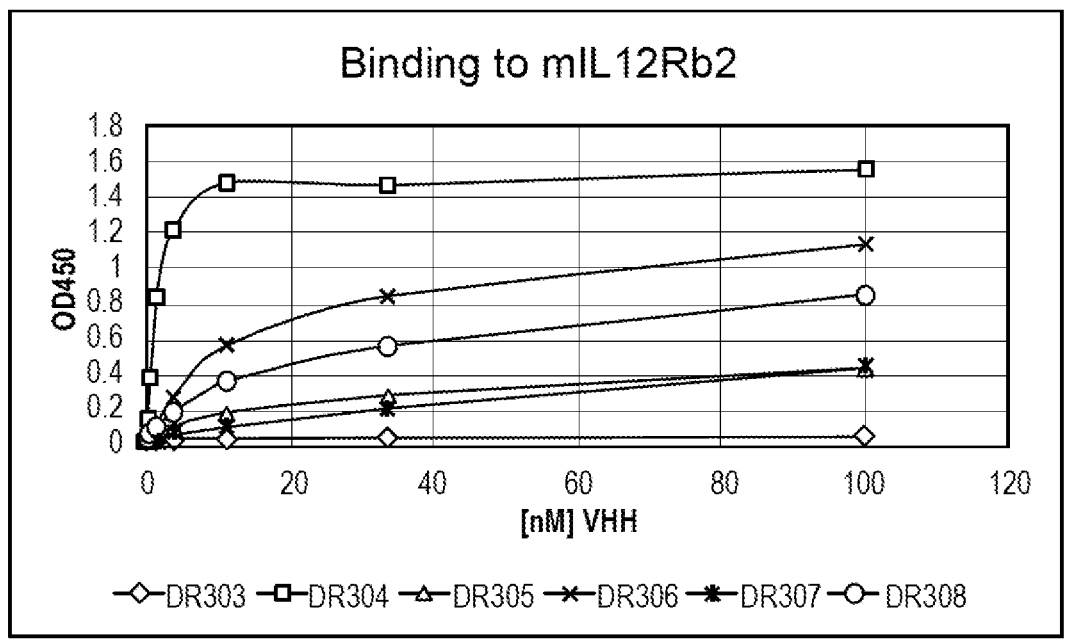
FIG. 6 shows binding data of the VHH dimers to mIL12Rb2.

Binding of VHH dimers to mIL12Rb1 was determined by ELISA assays. The data is shown in FIGS. 5 and 6. Briefly, a 96-well high binding plate was coated with antigen for 1 hour at 37° C. Next, wells were blocked at 37° C. for 1 h. Then, serial dilutions of sdAb were added to each well and incubated for 1 h. Subsequently, 100 µl of anti-VHH polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader. Binding was confirmed by the increasing absorbance values at 450 nm with increasing concentrations of sdAb.

The following Table provides correspondence between the constructs in the Figures and the VHH sequences in Tables 7 and 9.

DR283 mIL12Rb1_VHH1
DR284 mIL12Rb1_VHH2
DR285 mIL12Rb1_VHH3
DR286 mIL12Rb1_VHH4
DR287 mIL12Rb1_VHH5
DR288 mIL12Rb1_VHH6
DR289 mIL12Rb1_VHH7
DR303 mIL12Rb2_VHH1
DR304 mIL12Rb2_VHH2
DR305 mIL12Rb2_VHH3
DR306 mIL12Rb2_VHH4
DR307 mIL12Rb2_VHH5

It is understood that the embodiments described herein are for illustrative purposes only and that various modifications or changes in light thereof will be suggested to persons skilled in the art and are to be included within the spirit and purview of this application and scope of the appended claims. All publications, patents, patent applications, and the sequences of the sequence accession numbers cited herein are hereby incorporated by reference.

Tables

TABLE 2 anti-hIL12Rb1 sdAb VHH CDRs Human

| Name | CDR1 | SEQ ID NO: | CDR2 | SEQ ID NO: | CDR3 | SEQ ID NO: |
|---|---|---|---|---|---|---|
| hIL12Rb1_VHH1 | YGYCGYDMS | 25 | LITSDRSISYEDSVKA | 47. | SAAARESSWCRSRYRVAS | 69. |
| hIL12Rb1_VHH2 | YTYSSAFMA | 26 | AIYTRDGGTVYADSVKG | 48. | KIPQPGRASLLDSQTYDY | 70. |
| hIL12Rb1_VHH3 | YSYCGYDMM | 27 | LITSDYSIRYEDSVEG | 49. | STAARESSWCRSRYRVAS | 71. |
| hIL12Rb1_VHH4 | YGYCGYDMS | 28 | LITSDRIASYEDSVKG | 50. | SAAARENSWCRSRYRVAS | 72. |
| hIL12Rb1_VHH5 | YGYCGYDMS | 29 | LITSDRSVSYEDSVKG | 51. | STAARENNWCRSRYRIAY | 73. |
| hIL12Rb1_VHH6 | YTYTNNFMA | 30 | AIYTGDGYAYYFYSVKG | 52. | MERRIGTRRMTENAEYKY | 74. |
| hIL12Rb1_VHH7 | YDYCGYDVR | 31 | GIDSDGSTSYADSVKG | 53. | ESPAGESAWCRNFRGMDY | 75. |
| hIL12Rb1_VHH8 | YSYCGYDMM | 32 | LITSDYSIRYEDSVEG | 54. | STAARESSWCRSRYRVAS | 76. |
| hIL12Rb1_VHH9 | YSYCGYDMM | 33 | LITSDYSTRYEDSVEG | 55. | STAARESGWCRSRYRVAS | 77. |
| hIL12Rb1_VHH10 | YDYCGYDVR | 34 | GIDSDGSTSYADSVKG | 56. | ESPAGESAWCRNFRGMDY | 78. |
| hIL12Rb1_VHH11 | YDYCGYDVR | 35 | GIDSDGSTSYADSVKG | 57. | ESPAGESAWCRNFRGMDY | 79. |
| hIL12Rb1_VHH12 | YTYSSAFMA | 36 | AIYTRDGGTVYADSVKG | 58. | KMPQPGRASLLDSQTYDY | 80. |
| hIL12Rb1_VHH13 | YGYCGYDMS | 37 | LITSERVISYEDSVKG | 59. | SAAARESSWCRSRYRVAS | 81. |
| hIL12Rb1_VHH14 | YDYCGYDVR | 38 | GIDSDGSTSYADSVKG | 60. | ESPAGESAWCRNFRGMDY | 82. |
| hIL12Rb1_VHH15 | YDYCGYDVR | 39 | GINSDGSTSYADSVKG | 61. | ESPAGESAWCRNFRGMDY | 83. |
| hIL12Rb1_VHH16 | YTYSSAFMA | 40 | AMYTRDGGTVYADSVKG | 62. | KIPQPGRASLLDSQTYDY | 84. |
| hIL12Rb1_VHH17 | YGYCGYDMS | 41 | LITSDRSVSYEDSVKG | 63. | STAARENNWCRSRYRIAS | 85. |
| hIL12Rb1_VHH18 | YTYTNNFMA | 42 | AIYTGDGYAYYFDSVKG | 64. | MERRSGRRRMTENAEYKY | 86. |
| hIL12Rb1_VHH19 | YDYCGYDVR | 43 | GINSDGSTSYADSVKG | 65. | EGPAGESAWCRNFRGMDY | 87. |

TABLE 2-continued anti-hIL12Rb1 sdAb VHH CDRs Human

| Name | CDR1 | SEQ ID NO: | CDR2 | SEQ ID NO: | CDR3 | SEQ ID NO: |
|---|---|---|---|---|---|---|
| hIL12Rb1_VHH20 | YTYSSAFMA | 44 | AIYTRDGSPVYADSLKG | 66 | KIPEPGRISLLDSQTYDY | 88 |
| hIL12Rb1_VHH21 | YTYSSAFMA | 45 | AMYTRDGGTVYADSVKG | 67 | KIPQPGRASLLDSQTYDY | 89 |
| hIL12Rb1_VHH22 | YTYSSAFMA | 46 | AIYTRDGGTVYADSVKG | 68 | KIPQPGRASLLDSQTYDY | 90 |

TABLE 3 anti-mIL12Rb1 sdAb CDRs MOUSE

| Name | CDR1 (AA Seq) | SEQ ID NO | CDR2 (AA Seq) | SEQ ID NO | CDR3 (AA Seq) | SEQ ID NO |
|---|---|---|---|---|---|---|
| mIL12Rb1_VHH1 | YTYSSAFMA | 91 | AIYTRDGGTVYADSVKG | 114 | KIPQPGRASLLDSQTYDY | 137 |
| mIL12Rb1_VHH2 | YDYCGYDVR | 92 | GIDSDGSTSYADSVKG | 115 | ESPAGESAWCRNFRGMDY | 138 |
| mIL12Rb1_VHH3 | YSYCGYDMM | 93 | LITSDYSIRYEDSVEG | 116 | STAARESSWCRSRYRVAS | 139 |
| mIL12Rb1_VHH4 | YTYTNNFMA | 94 | AIYTGDGYAYYFDSVKG | 117 | MERRSGRRRMTENAEYKY | 140 |
| mIL12Rb1_VHH5 | FTIDDSEMG | 95 | SGSSDDDTYYVDSVKG | 118 | GPTYPPKDGDCAH | 141 |
| mIL12Rb1_VHH6 | YTYSSAFMA | 96 | AIYTRDGSPVYADSLKG | 119 | KIPEPGRISLLDSQTYDY | 142 |
| mIL12Rb1_VHH7 | YDYCGYDVR | 97 | GIDSDGSTSYADSVKG | 120 | ESPAGESAWCRNFRGMDY | 143 |
| mIL12Rb1_VHH8 | YGYCGYDMS | 98 | LITSERVISYEDSVKG | 121 | SAAARESSWCRSRYRVAS | 144 |
| mIL12Rb1_VHH9 | YGYCGYDMS | 99 | LITSDRSISYEDSVKA | 122 | SAAARESSWCRSRYRVAS | 145 |
| mIL12Rb1_VHH10 | YDYCGYDVR | 100 | GIDSDGSTSYADSVKG | 123 | ESPAGESAWCRNFRGMDY | 146 |
| mIL12Rb1_VHH11 | YSYCGYDMM | 101 | LITSDYSIRYEDSVEG | 124 | STAARESSWCRSRYRVAS | 147 |
| mIL12Rb1_VHH12 | YTYTNNFMA | 102 | AIYTGDGYAYYFYSVKG | 125 | MERRIGTRRMTENAEYKY | 148 |
| mIL12Rb1_VHH13 | YSYCGYDMM | 103 | LITSDYSIRYEDSVEG | 126 | STAARESGWCRSRYRVAS | 149 |
| mIL12Rb1_VHH14 | YDYCGYDVR | 104 | GINSDGSTSYADSVKG | 127 | ESPAGESAWCRNFRGMDY | 150 |
| mIL12Rb1_VHH15 | YGYCGYDMS | 105 | LITSDRSVSYEDSVKG | 128 | STAARENNWCRSRYRIAY | 151 |
| mIL12Rb1_VHH16 | YDYCGYDVR | 106 | GINSDGSTSYADSVKG | 129 | EGPAGESAWCRNFRGMDY | 152 |
| mIL12Rb1_VHH17 | YTYSSAFMA | 107 | AMYTRDGGTVYADSVKG | 130 | KIPQPGRASLLDSQTYDY | 153 |
| mIL12Rb1_VHH18 | YTYSSAFMA | 108 | AMYTRDGGTVYADSVKG | 131 | KIPQPGRASLLDSQTYDY | 154 |

TABLE 3-continued anti-mIL12Rb1 sdAb CDRs MOUSE

| Name | CDR1 (AA Seq) | SEQ ID NO | CDR2 (AA Seq) | SEQ ID NO | CDR3 (AA Seq) | SEQ ID NO |
|---|---|---|---|---|---|---|
| mIL12Rb1_VHH19 | YGYCGYDMS | 109. | LITSDRSVSYEDSVKG | 132. | STAARENNWCRSRYRIAS | 155. |
| mIL12Rb1_VHH20 | YGYCGYDMS | 110. | LITSDRIASYEDSVKG | 133. | SAAARENSWCRSRYRVAS | 156. |
| mIL12Rb1_VHH21 | YDYCGYDVR | 111. | GIDSDGSTSYADSVKG | 134. | ESPAGESAWCRNFRGMDY | 157. |
| mIL12Rb1_VHH22 | YTYSSAFMA | 112. | AIYTRDGGTVYADSVKG | 135. | KIPQPGRASLLDSQTYDY | 158. |
| mIL12Rb1_VHH23 | YTYSSAFMA | 113. | AIYTRDGGTVYADSVKG | 136. | KMPQPGRASLLDSQTYDY | 159. |

TABLE 4 anti-IL12Rb2 sdAb CDRs HUMAN

| Name | CDR1 | SEQ ID NO: | CDR2 | SEQ ID NO: | CDR3 | SEQ ID NO: |
|---|---|---|---|---|---|---|
| hIL12Rb2_VHH1 | FTVTRYCMG | 160. | IIERDGRTGYADSVKG | 178. | IEGSCRPDFGY | 196. |
| hIL12Rb2_VHH2 | FTISRYCMG | 161. | IIERDGRTGYADSVKG | 179. | IEGSCRPDFGY | 197. |
| hIL12Rb2_VHH3 | LTFDDVEMA | 162. | SINTDSRVYYVDSVKD | 180. | DPWGGDLRGYPNY | 198. |
| hIL12Rb2_VHH4 | FTISRYCMG | 163. | IIERDGRTGYADSVKG | 181. | IEGSCRPDFGY | 199. |
| hIL12Rb2_VHH5 | FTFSTYAMS | 164. | RISSGGGNTYYADAVKG | 182. | DDYYGGSWHPIS | 200. |
| hIL12Rb2_VHH6 | YTYGLFCMG | 165. | VVDSPGGRHVADSLKG | 183. | DPEKYCFLFSDAGYQY | 201. |
| hIL12Rb2_VHH7 | VTYSRYCMG | 166. | TIYSRGIITYYTDSVKG | 184. | TRETYGGSGDCDYESVYNY | 202. |
| hIL12Rb2_VHH8 | FTVSRYCMG | 167. | IIEREGRTGYADSVKG | 185. | IEGSCRPDFGY | 203. |
| hIL12Rb2_VHH9 | FTISRYCMG | 168. | IIERDGRTGYADSVKG | 186. | IEGSCRPDFGY | 204. |
| hIL12Rb2_VHH10 | FTVTRYCMG | 169. | IIERDGRTGYADSVKG | 187. | IEGSCRPDFGY | 205. |
| hIL12Rb2_VHH11 | FTVSRYCMG | 170. | IIERDGRTGYADSVKG | 188. | IEGSCRPDFGY | 206. |
| hIL12Rb2_VHH12 | VTYSRYCMG | 171. | TIYSRGIITYYTDSVKG | 189. | TRETYGGSGDCDYESVYNY | 207. |
| hIL12Rb2_VHH13 | FTISKYCMG | 172. | IIERDGRTGYADSVKG | 190. | IEGSCRPDFGY | 208. |
| hIL12Rb2_VHH14 | VTYSRYCMG | 173. | HIYSRGIITYYTDSVKG | 191. | TRETYGGSGDCGYESVYNY | 209. |
| hIL12Rb2_VHH15 | FTISRYCMG | 174. | IIERDGRTGYADSVKG | 192. | IEGSCRPDLGY | 210. |
| hIL12Rb2_VHH16 | VTYSRYCMG | 175. | HIYSRGIITYYTDSVKG | 193. | TRETYGGSGDCSYESVYNH | 211. |
| hIL12Rb2_VHH17 | LTISRYCMG | 176. | IIERDGRTGYADSVKG | 194. | IEGSCRPDFGY | 212. |
| hIL12Rb2_VHH18 | FTVDDFAMG | 177. | TISSGGSTYYADSVKG | 195. | SSVGCPLGY | 213. |

TABLE 5 anti-mIL12Rb2 sdAb CDRs MOUSE

| Name | CDR1 AA Seq | CDR1 SEQ ID | CDR2 AA Seq | CDR2 SEQ ID | CDR3 AA Seq | CDR3 SEQ ID |
|---|---|---|---|---|---|---|
| mIL12Rb2 VHH1 | YTYSNRHMG | 214. | AIYTGGSTYYADSVKD | 230. | DLTRWYSGGWRDPRGYKY | 246. |
| mIL12Rb2 VHH2 | VTYGSYYMAA | 215. | SIYGGSDSTYYADSVLG | 231. | APPGKWFLKRLEGHNYSY | 247. |
| mIL12Rb2 VHH3 | FTYSSSCLG | 216. | TIYPAGGNIFYADSVKG | 232. | RGGQTWGSGGNRCSLWLPAYNY | 248. |
| mIL12Rb2 VHH4 | KLYGGA | 217. | AIWIGTGTTFYADSVKG | 233. | DDRPGYRDPLAPVSYNH | 249. |
| mIL12Rb2 VHH5 | ITYRGVWMG | 218. | TIYTGSGHTYYADSVKG | 234. | RTVGGTFYTLAADSFNT | 250. |
| mIL12Rb2 VHH6 | KAYGGA | 219. | AIWIGTGTTFYADSVKG | 235. | DDRPGYRDPLAPVSYNH | 251. |
| mIL12Rb2 VHH7 | NPYGGA | 220. | AIWLGTGTTFYADSVKG | 236. | DDRPGYRDPLAPVSYNH | 252. |
| mIL12Rb2 VHH8 | KAYGGA | 221. | AIWIGTGTTFYADSVKG | 237. | DDRPGYRDPLAPVSYNH | 253. |
| mIL12Rb2 VHH9 | KAFGGA | 222. | AIWIGTGTTFYADSVKG | 238. | DDRPGYRDPLAPVSYNH | 254. |
| mIL12Rb2 VHH10 | YTFSNHHMG | 223. | AIYTGAGNIYYADSVKD | 239. | DLTRWYSGGWRDPRGYKY | 255. |
| mIL12Rb2 VHH11 | YTFSNHHMG | 224. | AIYTGAGNIYYADSVKD | 240. | DLTRWYSGGWRDPRGYKY | 256. |
| mIL12Rb2 VHH12 | YTFSNHHMG | 225. | AIYTGAGNIYYADSVKD | 241. | DLTRWYSGGWRDPRGYKY | 257. |
| mIL12Rb2 VHH13 | YTFSNHHMG | 226. | AIYTGAGNIYYADSVKD | 242. | DLTRWYSGGWRDPRGYKY | 258. |
| mIL12Rb2 VHH14 | ATNSNRHMG | 227. | AIYTGYTGGGNTYYADSVRD | 243. | DLTRWYSGGWRDPRGYKY | 259. |
| mIL12Rb2 VHH15 | DIYARNCMG | 228. | VADTGGRSPYYADSVKG | 244. | GPLVPVVNTAARCVYEY | 260. |
| mIL12Rb2 VHH16 | ATNSNRHMG | 229. | AIYTGYTGGGNTYYADSVKD | 245. | DLTRWYSGGWRDPRGYKY | 261. |

TABLE 6 anti-IL12Rb1 sdAb VHH AMINO ACID SEQUENCE HUMAN

| Name | Sequence | SEQ ID NO: |
|---|---|---|
| hIL12Rb1_VHH1 | QVQLQESGGGSVQAGGSLRLSCVASGYGYCGYDMSWYRQAPGKEREFVALITSDRSISYEDSVKARFIISRDNAANTGYLDMTRLTPDDTAIYYCKTSAAARESSWCRSRYRVASWGQGTQVTVSS | 262. |
| hIL12Rb1_VHH2 | QVQLQESGGGSVQAGGSLRLSCTASGYTYSSAFMAWFRQAPGKEREGVAAIYTRDGGTVYADSVKGRFTISQDNAKNILYLQMNSLKAEDTAMYYCAAKIPQPGRASLLDSQTYDYWGQGTQVTVSS | 263. |
| hIL12Rb1_VHH3 | QVQLQESGGGSVQAGGSLRLSCVASGYSYCGYDMMWYRQAPGKEREFVALITSDYSIRYEDSVEGRFSISRDNAKNTGYLLMSNLTPADTAIYYCKTSTAARESSWCRSRYRVASWGQGTQVTVSS | 264. |
| hIL12Rb1_VHH4 | QVQLQESGGGSVQAGGSLRLSCVASGYGYCGYDMSWYRQTPGKEREFVALITSDRIASYEDSVKGRFIISRDNAKNTGYLDMTRVTPDDTAIYYCKTSAAARENSWCRSRYRVASWGQGTQVTVSS | 265. |

TABLE 6-continued anti-IL12Rb1 sdAb VHH AMINO ACID SEQUENCE HUMAN

| Name | Sequence | SEQ ID NO: |
|---|---|---|
| hIL12Rb1_VHH5 | QVQLQESGGGSVQAGGFLRLSCVASGYGYCGYDMSWYRQVPGKEREFVALITSDRSVSYEDSVKGRFSISRDNAKNTAYLEMNRLTPDDTAVYYCKTSTAARENNWCRSRYRIAYWGQGTQVTVSS | 266. |
| hIL12Rb1_VHH6 | QVQLQESGGGSVQAGGSLRLSCAASRYTYTNNFMAWFRQAPGKEREGVAAIYTGDGYAYYFYSVKGRFTISQDNDENMLYLQMNSLKPEDTAMYYCAAMERRIGTRRMTENAEYKYWGQGTQVTVSS | 267. |
| hIL12Rb1_VHH7 | QVQLQESGGGSVQAGGSLRLSCAVSGYDYCGYDVRWYRRAPGKEREFVSGIDSDGSTSYADSVKGRFTISQDNAENTSYLHMFSLKPEDTAMYYCKTESPAGESAWCRNFRGMDYWGKGTQVTVSS | 268. |
| hIL12Rb1_VHH8 | QVQLQESGGGSVQAGGSLRLSCVASGYSYCGYDMMWYRQAPGKEREFVALITSDYSIRYEDSVEGRFSISRDNAKNTGYLLMSNLTPADTAIYYCKTSTAARESSWCRSRYRVASWGQGTQVTVSS | 269. |
| hIL12Rb1_VHH9 | QVQLQESGGGSVQAGGSLRLSCVASGYSYCGYDMMWYRQAPGKEREFVALITSDYSIRYEDSVEGRFSISRDNAKNTGYLLMSNLTPADTAIYYCKTSTAARESGWCRSRYRVASWGQGTQVTVSS | 270. |
| hIL12Rb1_VHH10 | QVQLQESGGGSVQAGGSLRLSCAVSGYDYCGYDVRWYRQAPGKEREFVSGIDSDGSTSYADSVKGRFTISQDNAENTSYLHMFSLKPEDTAMYYCKTESPAGESAWCRNFRGMDYWGKGTQVTVSS | 271. |
| hIL12Rb1_VHH11 | QVQLQESGGGSVQAGGSLRLSCAVSGYDYCGYDVRWYRQAPGKEREFVSGIDSDGSTSYADSVKGRFTISQDNAENTSYLHMFSLKPEDTAMYYCKTESPAGESAWCRNFRGMDYWGKGTQVTVSS | 272. |
| hIL12Rb1_VHH12 | QVQLQESGGGSVQAGGSLRLSCTASGYTYSSAFMAWFRQAPGKEREGVAAIYTRDGGTVYADSVKGRFTISQDNAKNTLYLQMNSLKPEDTAMYYCAAKMPQPGRASLLDSQTYDYWGQGTQVTVSS | 273. |
| hIL12Rb1_VHH13 | QVQLQESGGGSVQAGGFLRLSCVASGYGYCGYDMSWYRQAPGKEREFVALITSERVISYEDSVKGRFSISRDNAENTGYLEMNRLTPDDTAIYYCKTSAAARESSWCRSRYRVASWGQGTQVTVSS | 274. |
| hIL12Rb1_VHH14 | QVQLQESGGGSVQAGGSLRLSCAVSGYDYCGYDVRWYRRAPGKEREFVSGIDSDGSTSYADSVKGRFTISQDNAENTSYLHMFSLKPEDTAMYYCKTESPAGESAWCRNFRGMDYWGKGTQVTVSS | 275. |
| hIL12Rb1_VHH15 | QVQLQESGGGSVQAGGSLRLSCAVSGYDYCGYDVRWYRQAPGKEREFVSGINSDGSTSYADSVKGRFTISQDNAENTSYLHMFSLKPEDTAMYYCKTESPAGESAWCRNFRGMDYWGKGTQVTVSS | 276. |
| hIL12Rb1_VHH16 | QVQLQESGGGSVQAGGSLRLSCTASGYTYSSAFMAWFRQAPGKEREGVAAMYTRDGGTVYADSVKGRFTISQDNAKNTLYLQIHTLKAEDTAMYYCAAKIPQPGRASLLDSQTYDYWGQGTQVTVSS | 277. |
| hIL12Rb1_VHH17 | QVQLQESGGGSVQAGGFLRLSCVASGYGYCGYDMSWYRQVPGKEREFVALITSDRSVSYEDSVKGRFSISRDNAKNTAYLEMNRLTPDDTAIYYCKTSTAARENNWCRSRYRIASWGQGTQVTVSS | 278. |
| hIL12Rb1_VHH18 | QVQLQESGGGSVQAGGSLRLSCAASRYTYTNNFMAWFRQAPGKEREGVAAIYTGDGYAYYFDSVKGRFTISQDNDKNMLYLQMNSLKPEDTAMYYCAAMERRSGRRRMTENAEYKYWGQGTQVTVSS | 279. |
| hIL12Rb1_VHH19 | QVQLQESGGGSVQAGGSLRLSCAVSGYDYCGYDVRWYRQAPGKEREFVSGINSDGSTSYADSVKGRFTISQDNAENTSYLHMFSLKPEDTAMYYCKTEGPAGESAWCRNFRGMDYWGKGTQVTVSS | 280. |
| hIL12Rb1_VHH20 | QVQLQESGGGSVQAGGSLRLSCTASGYTYSSAFMAWFRQAPGKEREGVAAIYTRDGSPVYADSLKGRFTISQDNAKNTLHLQMNSLKPEDTAMYYCAAKIPEPGRISLLDSQTYDYWGHGTQVTVSS | 281. |
| hIL12Rb1_VHH21 | QVQLQESGGGSVQAGGSLRLSCTASGYTYSSAFMAWFRQAPGKEREGVAAMYTRDGGTVYADSVKGRFTISQDNAKNTLYLQMNSLKTEDTAMYYCAAKIPQPGRASLLDSQTYDYWGQGTQVTVSS | 282. |
| hIL12Rb1_VHH22 | QVQLQESGGGSVQAGGSLRLSCTASGYTYSSAFMAWFRQAPGKEREGVAAIYTRDGGTVYADSVKGRFTISQDNAKNTLYLQMNSLKAEDTAMYYCAAKIPQPGRASLLDSQTYDYWGQGTQVTVSS | 283. |

TABLE 7 anti-mIL 12RB1 sdAb VHH AMINO ACID SEQUENCE MOUSE
mIL12RB1 ECD Generated VHHs

| Name | VHH Amino Acid Sequence (CDRs underlined) | SEQ ID NO |
|---|---|---|
| mIL12Rb1_VHH1 | QVQLQESGGGSVQAGGSLRLSCTASGYTYSSAFMAWFRQAPGKE REGVAAIYTRDGGTVYADSVKGRFTISQDNAKNTLYLQMNSLKA EDTAMYYCAAKIPQPGRASLLDSQTYDYWGQGTQVTVSS | 284. |
| mIL12Rb1_VHH2 | QVQLQESGGGSVQAGGSLRLSCAVSGYDYCGYDVRWYRQAPGK EREFVSGIDSDGSTSYADSVKGRFTISQDNAENTSYLHMFSLKPED TAMYYCKTESPAGESAWCRNFRGMDYWGKGTQVTVSS | 285. |
| mIL12Rb1_VHH3 | QVQLQESGGGSVQAGGSLRLSCVASGYSYCGYDMMWYRQAPG KEREFVALITSDYSIRYEDSVEGRFSISRDNAKNTGYLLMSNLTPA DTAIYYCKTSTAARESSWCRSRYRVASWGQGTQVTVSS | 286. |
| mIL12Rb1_VHH4 | QVQLQESGGGSVQAGGSLRLSCAASRYTYTNNFMAWFRQAPGK EREGVAAIYTGDGYAYYFDSVKGRFTISQDNDKNMLYLQMNSLK PEDTAMYYCAAMERRSGRRRMTENAEYKYWGQGTQVTVSS | 287. |
| mIL12Rb1_VHH5 | QVQLQESGGGSVQAGETLRLSCTVSGFTIDDSEMGWYRQAPGHE CELVASGSSDDDTYYVDSVKGRFTISLDNAKNMVYLQMNSLKPE DTAVYYCATGPTYPPKDGDCAHWGQGTQVTVSS | 288. |
| mIL12Rb1_VHH6 | QVQLQESGGGSVQAGGSLRLSCTASGYTYSSAFMAWFRQAPGKE REGVAAIYTRDGSPVYADSLKGRFTISQDNAKNTLHLQMNSLKPE DTAMYYCAAKIPEPGRISLLDSQTYDYWGHGTQVTVSS | 289. |
| mIL12Rb1_VHH7 | QVQLQESGGGSVQAGGSLRLSCAVSGYDYCGYDVRWYRRAPGK EREFVSGIDSDGSTSYADSVKGRFTISQDNAENTSYLHMFSLKPED TAMYYCKTESPAGESAWCRNFRGMDYWGKGTQVTVSS | 290. |
| mIL12Rb1_VHH8 | QVQLQESGGGSVQAGGFLRLSCVASGYGYCGYDMSWYRQAPGK EREFVALITSERVISYEDSVKGRFSISRDNAENTGYLEMNRLTPDD TAIYYCKTSAAARESSWCRSRYRVASWGQGTQVTVSS | 291. |
| mIL12Rb1_VHH9 | QVQLQESGGGSVQAGGSLRLSCVASGYGYCGYDMSWYRQAPGK EREFVALITSDRSISYEDSVKARFIISRDNAANTGYLDMTRLTPDD TAIYYCKTSAAARESSWCRSRYRVASWGQGTQVTVSS | 292. |
| mIL12Rb1_VHH10 | QVQLQESGGGSVQAGGSLRLSCVASGYDYCGYDVRWYRQAPGK EREFVSGIDSDGSTSYADSVKGRFTISQDNAENTSYLHMFSLKPED TAMYYCKTESPAGESAWCRNFRGMDYWGKGTQVTVSS | 293. |
| mIL12Rb1_VHH11 | QVQLQESGGGSVQAGGSLRLSCVASGYSYCGYDMMWYRQAPG KEREFVALITSDYSIRYEDSVEGRFSISRDNAKNTGYLLMSNLTPA DTAIYYCKTSTAARESSWCRSRYRVASWGQGTQVTVSS | 294. |
| mIL12Rb1_VHH12 | QVQLQESGGGSVQAGGSLRLSCAASRYTYTNNFMAWFRQAPGK EREGVAAIYTGDGYAYYFYSVKGRFTISQDNDENMLYLQMNSLK PEDTAMYYCAAMERRIGTRRMTENAEYKYWGQGTQVTVSS | 295. |
| mIL12Rb1_VHH13 | QVQLQESGGGSVQAGGSLRLSCVASGYSYCGYDMMWYRQAPG KEREFVALITSDYSIRYEDSVEGRFSISRDNAKNTGYLLMSNLTPA DTAIYYCKTSTAARESGWCRSRYRVASWGQGTQVTVSS | 296. |
| mIL12Rb1_VHH14 | QVQLQESGGGSVQAGGSLRLSCAVSGYDYCGYDVRWYRQAPGK EREFVSGINSDGSTSYADSVKGRFTISQDNAENTSYLHMFSLKPED TAMYYCKTESPAGESAWCRNFRGMDYWGKGTQVTVSS | 297. |
| mIL12Rb1_VHH15 | QVQLQESGGGSVQAGGFLRLSCVASGYGYCGYDMSWYRQVPGK EREFVALITSDRSVSYEDSVKGRFSISRDNAKNTAYLEMNRLTPD DTAVYYCKTSTAARENNWCRSRYRIAYWGQGTQVTVSS | 298. |
| mIL12Rb1_VHH16 | QVQLQESGGGSVQAGGSLRLSCAVSGYDYCGYDVRWYRQAPGK EREFVSGINSDGSTSYADSVKGRFTISQDNAENTSYLHMFSLKPED TAMYYCKTEGPAGESAWCRNFRGMDYWGKGTQVTVSS | 299. |
| mIL12Rb1_VHH17 | QVQLQESGGGSVQAGGSLRLSCTASGYTYSSAFMAWFRQAPGKE REGVAAMYTRDGGTVYADSVKGRFTISQDNAKNTLYLQIHTLKA EDTAMYYCAAKIPQPGRASLLDSQTYDYWGQGTQVTVSS | 300. |
| mIL12Rb1_VHH18 | QVQLQESGGGSVQAGGSLRLSCTASGYTYSSAFMAWFRQAPGKE REGVAAMYTRDGGTVYADSVKGRFTISQDNAKNTLYLQMNSLK TEDTAMYYCAAKIPQPGRASLLDSQTYDYWGQGTQVTVSS | 301. |
| mIL12Rb1_VHH19 | QVQLQESGGGSVQAGGFLRLSCVASGYGYCGYDMSWYRQVPGK EREFVALITSDRSVSYEDSVKGRFSISRDNAKNTAYLEMNRLTPD DTAIYYCKTSTAARENNWCRSRYRIASWGQGTQVTVSS | 302. |

TABLE 7-continued anti-mIL12RB1 sdAb VHH AMINO ACID SEQUENCE MOUSE
mIL12RB1 ECD Generated VHHs

| Name | VHH Amino Acid Sequence (CDRs underlined) | SEQ ID NO |
|---|---|---|
| mIL12Rb1_VHH20 | QVQLQESGGGSVQAGGSLRLSCVASGYGYCGYDMSWYRQTPGK EREFVALITSDRIASYEDSVKGRFIISRDNAKNTGYLDMTRVTPDD TAIYYCKTSAAARENSWCRSRYRVASWGQGTQVTVSS | 303. |
| mIL12Rb1_VHH21 | QVQLQESGGGSVQAGGSLRLSCAVSGYDYCGYDVRWYRRAPGK EREFVSGIDSDGSTSYADSVKGRFTISQDNAENTSYLHMFSLKPED TAMYYCKTESPAGESAWCRNFRGMDYWGKGTQVTVSS | 304. |
| mIL12Rb1_VHH22 | QVQLQESGGGSVQAGGSLRLSCTASGYTYSSAFMAWFRQAPGKE REGVAAIYTRDGGTVYADSVKGRFTISQDNAKNILYLQMNSLKA EDTAMYYCAAKIPQPGRASLLDSQTYDYWGQGTQVTVSS | 305. |
| mIL12Rb1_VHH23 | QVQLQESGGGSVQAGGSLRLSCTASGYTYSSAFMAWFRQAPGKE REGVAAIYTRDGGTVYADSVKGRFTISQDNAKNTLYLQMNSLKP EDTAMYYCAAKMPQPGRASLLDSQTYDYWGQGTQVTVSS | 306. |

TABLE 8 anti-hIL12Rb2 sdAb VHH AMINO ACID SEQUENCE

| Name | Sequence | SEQ ID NO: |
|---|---|---|
| hIL12Rb2_VHH1 | QVQLQESGGGSVQAGGSLRLSCAASGFTVTRYCMGWLRQAPGKQREGVAIIER DGRTGYADSVKGRFTISKDNAKNTLYLQMNSLKPEDTAMYYCGAIEGSCRPDF GYRGQGTQVTVSS | 307. |
| hIL12Rb2_VHH2 | QVQLQESGGGSVQAGGSLRLSCAASGFTISRYCMGWLRQAPGKQREGVAIIER DGRTGYADSVKGRFTISKDNAKNTLYLQMNSLKPEDTAMYYCGAIEGSCRPDF GYRGQGTQVTVSS | 308. |
| hIL12Rb2_VHH3 | QVQLQESGGGSVQAGGSLRLSCTASGLTFDDVEMAWYRQGPGDDYDLVSSINT DSRVYYVDSVKDRFTISRDNAKNTLYLQMNNLKPEDTAVYYCAADPWGGDLRG YPNYWGQGTQVTVSS | 309. |
| hIL12Rb2_VHH4 | QVQLQESGGGSVQAGGSLRLSCVASGFTISRYCMGWLRQAPGKQREGVAIIER DGRTGYADSVKGRFTISKDNAKNTLYLQMNSLKPGDTAMYYCGAIEGSCRPDF GYRGQGTQVTVSS | 310. |
| hIL12Rb2_VHH5 | QVQLQESGGGLVQPGGSLKLSCAASGFTFSTYAMSWVRQAPGKEPEWISRISS GGGNTYYADAVKGRFAISRDNAKNTLYLQLNSLKTEDTAIYVCTMDDYYGGSW HPISRGHGTQVTVSS | 311. |
| hIL12Rb2_VHH6 | QVQLQESGGGLVQAGGSLRLSCQASGYTYGLFCMGWFRQVSGKKREGVAVVDS PGGRHVADSLKGRFTISKDNANNILYLDMTNLKSEDTATYYCAADPEKYCFLF SDAGYQYWGQGTQVTVSS | 312. |
| hIL12Rb2_VHH7 | QVQLQESGGGSVQAGGSLRLSCAASGVTYSRYCMGWFRQAPGLERERVATIYS RGIITYYTDSVKGRFTISQDSAKKTVYLQMNSLKPEDTAMYYCAATRETYGGS GDCDYESVYNYWAQGTQVTVSS | 313. |
| hIL12Rb2_VHH8 | QVQLQESGGGSVQAGGSLRLSCAASGFTVSRYCMGWLRQAPGKQREGVAIIER EGRTGYADSVKGRFTISKDNAKNTLYLQMNSLKPEDTAMYYCGAIEGSCRPDF GYRGQGTQVTVSS | 314. |
| hIL12Rb2_VHH9 | QVQLQESGGGSVQAGGSLRLSCAASGFTISRYCMGWLRQAPGKQREGVAIIER DGRTGYADSVKGRFTISKDNAKNTLYLQMNSLKPEDTAMYFCGAIEGSCRPDF GYRGQGTQVTVSS | 315. |
| hIL12Rb2_VHH10 | QVQLQESGGGSVQAGGSLRLSCAASGFTVTRYCMGWLRQAPGKQREGVAIIER DGRTGYADSVKGRFTISKDNAKNTLYLQMNSLKPEDTAMYYCGAIEGSCRPDF GYRGQGTQVTVSS | 316. |
| hIL12Rb2_VHH11 | QVQLQESGGGSVQAGGSLRLSCAASGFTVSRYCMGWLRQAPGKQREGVAIIER DGRTGYADSVKGRFTISKDDAKNTLYLQMNSLKPEDTAMYYCGAIEGSCRPDF GYRGQGTQVTVSS | 317. |
| hIL12Rb2_VHH12 | QVQLQESGGGSVQAGGSLRLSCAASGVTYSRYCMGWFRQAPGLERERVATIYS RGIITYYTDSVKGRFTISQDSAKKTVYLQMNMLKPEDTAMYYCAATRETYGGS GDCDYESVYNYWAQGTQVTVSS | 318. |

TABLE 8-continued anti-hIL12Rb2 sdAb VHH AMINO ACID SEQUENCE

| Name | Sequence | SEQ ID NO: |
|---|---|---|
| hIL12Rb2_VHH13 | QVQLQESGGGSVQAGGSLRLSCAASGFTISKYCMGWLRQAPGKQREGVAIIER DGRTGYADSVKGRFTISKDNAKNTLYLQMNSLKPEDTAMYYCGAIEGSCRPDF GYRGQGTQVTVSS | 319. |
| hIL12Rb2_VHH14 | QVQLQESGGGSVQAGGSLRLSCAASGVTYSRYCMGWFRQAPGLERERVAHIYS RGIITYYTDSVKGRFTISQDSAKKTVYLQMNSLKPEDTAMYYCAATRETYGGS GDCGYESVYNYWAQGTQVTVSS | 320. |
| hIL12Rb2_VHH15 | QVQLQESGGGSVQAGGSLRLSCAASGFTISRYCMGWLRQAPGKQREGVAIIER DGRTGYADSVKGRFTISKDNAKNTLYLQMNSLKPEDTAMYYCGAIEGSCRPDL GYRGQGTQVTVSS | 321. |
| hIL12Rb2_VHH16 | QVQLQESGGGSVQAGGSLRLSCAASGVTYSRYCMGWFRQAPGLERERVAHIYS RGIITYYTDSVKGRFTISQDSAKKTVYLQMNSLKPEDTAMYYCAATRETYGGS GDCSYESVYNHWAQGTQVTVSS | 322. |
| hIL12Rb2_VHH17 | QVQLQESGGGSVQAGGSLRLSCAASGLTISRYCMGWLRQAPGKQREGVAIIER DGRTGYADSVKGRFTISKDNAKNTLYLQMNSLKPEDTAMYYCGAIEGSCRPDF GYRGQGTQVTVSS | 323. |
| hIL12Rb2_VHH18 | VQVQLQESGGGSVQAGGSLRLSCSASGFTVDDFAMGWYRQAPGNECELVSTISS GGSTYYADSVKGRFTISQDSAKNTVYLQMNSLKPEDTAVYYCAPSSVGCPLGY WGQGTQVTVSS | 324. |

TABLE 9 anti-mIL12Rb2 VHH AMINO ACID SEQUENCE

| Name | VHH AA Sequence (CDRs Underlined) | VHH SEQ ID |
|---|---|---|
| mIL12Rb2_VHH1 | QVQLQESGGGSVQAGGSLRLSCAASGYTYSNRHMGWFRQAPGKEREGVAAIYT GGGSTYYADSVKDRFTISQDNAKNTLYLQMNSLTPEDTAMYYCAADLTRWYSG GWRDPRGYKYWGQGTQVTVS | 325. |
| mIL12Rb2_VHH2 | QVQLQESGGGSVQAGGSLRLSCAASGVTYGSYYMAAWFRQAPGKEREGVASIY GGSDSTYYADSVLGRFTISQDNGKNTLYLQMNSLKPDDTAMYYCAAAPPGKWF LKRLEGHNYSYWGQGTQVTVSS | 326. |
| mIL12Rb2_VHH3 | QVQLQESGGGSVQVGGSLRLSCAASGFTYSSSCLGWFRQAPGKEREGVATIYP AGGNIFYADSVKGRFTISQDNAKNTVYLQMDSLKPEDTAMYYCAARGGQTWGS GGNRCSLWLPAYNYWGQGTQVTVSS | 327. |
| mIL12Rb2_VHH4 | QVQLQESGGGSVQVGGSLRLSCAVSGKLYGGAWFRQAQGKGREGVAAIWIGTG TTFYADSVKGRFTISRDNAKNTVYLQMDGLKPEDTALYYCAADDRPGYRDPLA PVSYNHWGQGTQVTVSS | 328. |
| mIL12Rb2_VHH5 | QVQLQESGGGSVQAGGSLRLSCAASGITYRGVWMGWFRQAPGKEREGVATIYT GSGHTYYADSVKGRFTISQDNAKNTVYLQMNSLKPEDTAMYYCAARTVGGTFY TLAADSFNTWGQGTQVTVSS | 329. |
| mIL12Rb2_VHH6 | QVQLQESGGGSVQAGGSLRLSCAVSGKAYGGAWFRQAQGKGREGVAAIWIGTG TTFYADSVKGRFTISRDNAKNTVYLQMDGLKPEDTAVYYCAADDRPGYRDPLA PVSYNHWGQGTQVTVSS | 330. |
| mIL12Rb2_VHH7 | QVQLQESGGGSVQAGGSLKLSCAVSGNPYGGAWFRQAQGKSREGVAAIWLGTG TTFYADSVKGRFTISRDNAKNTVYVQIDGLKPEDTAMYYCAADDRPGYRDPLA PVSYNHWGQGTQVTVSS | 331. |
| mIL12Rb2_VHH8 | QVQLQESGGGSVQAGGSLRLSCVVSGKAYGGAWFRQAQGKSREGVAAIWIGTG TTFYADSVKGRFTISRDNAKNTVYLQMDGLKPEDTAMYYCAADDRPGYRDPLA PVSYNHWGQGTQVTVSS | 332. |
| mIL12Rb2_VHH9 | QVQLQESGGGSVQAGGSLTLSCVVSGKAFGGAWFRQAQGKGREGVAAIWIGTG TTFYADSVKGRFTISRDNAKNTVYLQMDGLKPDDTAMYYCAADDRPGYRDPLA PVSYNHWGQGTQVTVSS | 333. |
| mIL12Rb2_VHH10 | QVQLQESGGGSVQAGGSLRLSCAASGYTFSNHHMGWFRQAPGKEREGVAAIYT GAGNIYYADSVKDRFTISKDTAKNTLYLQMNSLTPEDTGMYYCAADLTRWYSG GWRDPRGYKYWGQGTQVTVSS | 334. |

TABLE 9-continued anti-mIL12Rb2 VHH AMINO ACID SEQUENCE

| Name | VHH AA Sequence (CDRs Underlined) | VHH SEQ ID |
|---|---|---|
| mIL12Rb2_VHH11 | QVQLQESGGGPVQAGGSLRLSCAASGYTFSNHHMGWFRQAPGKEREGVAAIYT GAGNIYYADSVKDRFTISKDTAKNTLYLQMNSLTPEDTGMYYCAADLTRWYSG GWRDPRGYKYWGQGTQVTVSS | 335. |
| mIL12Rb2_VHH12 | QVQLQESGGGVVQPGGSLRLSCAASGYTFSNHHMGWFRQAPGKEREGVAAIYT GAGNIYYADSVKDRFTISKDTAKNTLYLQMNSLTPEDTGMYYCAADLTRWYSG GWRDPRGYKYWGQGTQVTVSS | 336. |
| mIL12Rb2_VHH13 | QVQLQESGGGSVQAGGSLRLSCAVSGYTFSNHHMGWFRQAPGKEREGVAAIYT GAGNIYYADSVKDRFTISKDTAKNTLYLQMNSLTPEDTGMYYCAADLTRWYSG GWRDPRGYKYWGQGTQVTVSS | 337. |
| mIL12Rb2_VHH14 | QVQLQESGGGSVQAGGSLRLSCAASGATNSNRHMGWFRQAPGKEREGVAAIYT GYTGGGNTYYADSVRDRFTISQDNAKNTLYLQMNSLTPEDTAMYYCAADLTRW YSGGWRDPRGYKYWGQGTQVTVSS | 338. |
| mIL12Rb2_VHH15 | QVQLQESGGGSVQDGGSLRLSCAASGDIYARNCMGWFRQAPGKEREKIAVADT GGRSPYYADSVKGRFTISRDNAKNTVDLQMNSLKPEDTAVYYCAAGPLVPVVN TAARCVYEYWGQGTQVTVSS | 339. |
| mIL12Rb2_VHH16 | QVQLQESGGGSVQAGGSLRLSCAASGATNSNRHMGWFRQAPGKEREGVAAIYT GYTGGGNTYYADSVKDRFTISQDNAKNTLYLQMNSLTPEDTAMYYCAADLTRW YSGGWRDPRGYKYWGQGTQVTVSS | 340. |

TABLE 10 anti-IL12Rb1 sdAb VHH DNA SEQUENCE HUMAN

| Name | Sequence | SEQ ID NO: |
|---|---|---|
| hIL12Rb1_VHH1 | CAGGTCCAGCTCCAGGAGTCTGGCGGTGGCTCAGTACAAGCTGGGGGCTCTCT GCGTTTGTCCTGTGTGGCGAGCGGGTACGGATACTGTGGGTACGACATGAGTT GGTACAGACAGGCCCCCTGGCAAGGAACGTGAATTTGTGGCCCTCATCACTTTC GATCGCTCCATTAGCTACGAGGATTCTGTCAAAGCTCGCTTTATCATTTCCCG CGACAACGCCGCTAACACTGGTTATCTGGACATGACTAGACTGACCCCCGATG ACACGGCCATTTACTATTGCAAGACCAGTGCAGCGGCCCGCGAATCTTCCTGG TGTCGCTCTCGCTACCGCGTGGCATCATGGGGCCAGGGTACTCAGGTCACCGT GTCTAGC | 341. |
| hIL12Rb1_VHH2 | CAAGTCCAACTCCAGGAGTCTGGTGGGGGCTCTGTTCAAGCTGGCGGGTCCCT GCGCCTTTCCTGTACCGCCAGCGGCTACACGTACTCTAGCGCCCTTCATGGCTT GGTTTCGGCAGGCCCCTGGAAAAGAGAGAGAGGGAGTGGCAGCTATCTACACT CGTGACGGCGGAACCGTGTACGCTGATAGTGTCAAGGGCCGCTTCACCATTTC CCAGGATAATGCCAAGAATATCCTGTATCTCCAGATGAACTCCCTTAAAGCCG AAGCACTGCGATGTACTATTGCGCAGCCAAAATCCCGCAGCCAGGCCGGGCT TCTTTGCTGGATAGCCAAACCTACGACTATTGGGGTCAAGGCACTCAGGTTAC CGTGTCTTCC | 342. |
| hIL12Rb1_VHH3 | CAGGTCCAGCTTCAGGAGAGCGGCGGAGGCTCCGTGCAGGCTGGGGGATCTTT GAGACTCAGCTGCGTGGCCAGTGGCTACTCTTACTGTGGGTACGACATGATGT GGTATCGCCAAGCGCCGGGCAAGGAACGTGAGTTCGTGGCGCTCATCACTTCC GACTACTCAATTCGTTACGAGGATTCCGTTGAGGGCCGCTTCAGCATTTCTCG TGACAACGCGAAGAACACAGGATACTTGCTGATGAGTAACCTCACCCCCGCCG ATACCGCTATTTATTACTGCAAGACAAGTACAGCTGCCAGGGAGAGCAGTTGG TGTCGGTCTCGCTATCGTGTGGCCTCCTGGGGACAGGGCACCCAAGTAACCGT GTCATCA | 343. |
| hIL12Rb1_VHH4 | CAGGTGCAGCTCCAGGAATCTGGTGGGGGCAGTGTTCAGGCTGGTGGCAGCCT GAGACTTAGCTGCGTGGCTTCTGGCTATGGTTACTGTGGGTACGACATGAGCT GGTATCGGCAGACCCCCGGAAAGGAGCGGGAGTTCGTAGCGCTCATCACAAGT GACCGCATCGCCTCCTATGAAGACTCCGTTAAGGGTCGCTTTATCATTAGCCG GGACAATGCCAAGAACACAGGTTACCTCGATATGACTCGGGTCACACCTGACG ATACCGCTATCTATTACTGCAAGACTTCTGCGGCTGCCCGTGAAAACAGCTGG TGCCGCTCAAGATACCGGGTGGCCTCCTGGGGACAGGGAACTCAGGTCACCGT CTCTAGC | 344. |
| hIL12Rb1_VHH5 | CAGGTGCAGTTGCAGGAGAGCGGAGGCGGATCTGTGCAGGCCGGTGGATTTCT GCGGCTGTCTTGCGTGGCGAGCGGCTATGGCTATTGCGGATACGACATGAGCT GGTATCGCCAGGTTCCGGGTAAGGAGCGTGAGTTCGTCGCTCTGATTACCTCT GATCGCTCTGTGTCCTATGAGGACTCCGTTAAGGGTAGATTCTCTATCTCTCG CGATAATGCTAAGAACACAGCCTACCTGGAGATGAACAGACTGACCCCCGACG | 345. |

TABLE 10-continued anti-IL12Rb1 sdAb VHH DNA SEQUENCE HUMAN

| Name | Sequence | SEQ ID NO: |
|---|---|---|
| | ATACCGCTGTCTATTACTGTAAGACCTCCACAGCCGCTCGCGAGAATAACTGG TGCCGCTCTCGCTATAGAATCGCCTATTGGGGTCAGGGTACACAAGTTACCGT ATCCTCC | |
| hIL12Rb1_ VHH6 | CAGGTGCAGTTGCAGGAGAGTGGCGGGGGCTCTGTTCAGGCTGGTGGATCATT GCGTCTGAGCTGTGCTGCCTCCCGCTACACCTACACTAATAACTTCATGGCTT GGTTTAGACAAGCTCCTGGCAAGGAACGCGAAGGCGTTGCCGCGATTTATACC GGAGACGGTTACGCATATTACTTCTATTCCGTGAAGGGCCGCTTCACAATCTC CCAGGATAACGACGAAAATATGCTCTACTTGCAGATGAACTCCCTCAAACCTG AGGACACGGCAATGTACTATTGTGCGGCTATGGAGCGCCGTATCGGAACTCGC CGTATGACCGAAAACGCTGAGTATAAGTATTGGGACAAGGAACCCAGGTGAC CGTATCCTCC | 346. |
| hIL12Rb1_ VHH7 | CAGGTCCAGTTGCAGGAGTCTGGTGGCGGAAGCGTGCAGGCTGGGGGCAGCCT CAGGCTGTCCTGTGCTGTGTCCGGGTACGACTACTGCGGCTACGACGTGCGCT GGTATCGCCGTGCCCCCGGCAAGGAGAGGGAGTTCGTCTCCGGGATTGATTCC GATGGCTCTACCAGTTACGCAGATTCCGTCAAGGGTCGTTTTACCATTAGTCA GGATAACGCTGAGAACACAAGCTATCGCACATGTTCTCACTGAAGCCTGAGG ATACCGGCCATGTACTATTGCAAGACTGAGTCCCCCGCAGGTGAATCCGCCTGG TGTCGTAACTTTCGCGGCATGGACTACTGGGGAAAGGGCACCCAGGTCACTGT GTCTTCT | 347. |
| hIL12Rb1_ VHH8 | CAGGTGCAGCTCCAGGAATCAGGCGGTGGGTCCGTGCAGGCAGGAGGGAGTCT GCGCCTGTCCTGTGTGGCCTCCGGTTACAGCTACTGCGGCTACGATATGATGT GGTATAGGCAAGCTCCAGGGAAGGAGCGTGAGTTCGTGGCCCTTATCACATCT GACTATTCCATCCGCTACGAGGACTCCGTGGAGGGAAGATTTTCAATCTCCAG AGACAACGCAAAGAACACCGGATACCTCCTGATGTCTAACCTGACCCCAGCCG ACACGGCAATCTATTACTGTAAAACCTCCACAGCAGCGAGGGAGTCCAGCTGG TGCAGGTCCAGATACCGTGTTGCCTCCTGGGGACAGGGCACTCAGGTGACGGT GAGTTCT | 348. |
| hIL12Rb1_ VHH9 | CAGGTGCAGCTCCAGGAGTCCGGTGGCGGGAGCGTGCAGGCTGGCGGATCTCT GCGGCTCAGTTGCGTCGCCTCAGGGTATTCCTATTGTGGCTACGATATGATGT GGTATCGTCAGGCCCCCGGCAAGGAGCGCGAGTTCGTCGCCCTGATTACAAGC GATTATTCAATCCGTTATGAAGATTCCGTGGAGGGGCGCTTCTCCATCAGTCG CGACAACGCCAAAAACACTGGCTACCTTCTGATGTCAAACCTGACTCCCGCTG ACACCGCGATCTACTATTGTAAAACCTCAACGGCTGCCCGCGAGTCCGGCTGG TGCCGGTCTAGGTATCGTGTGGCCAGCTGGGGCAGGGCACTCAGGTCACCGT GTCATCC | 349. |
| hIL12Rb1_ VHH10 | CAGGTCCAGCTGCAAGAATCCGGTGGAGGCTCTGTGCAGGCGGGTGGGTCCCT GCGCCTGTCTTGCGCCGTGTCTGGCTATGATTATTGCGGATATGACGTGCGCT GGTATCGCCAGGCTCCCGGCAAGGAACGCGAGTTTGTCTCTGGGATTGACTCA GACGGCAGCACTAGCTATGCCGACTCCGTGAAAGGTCGCTTCACCATTTCCCA AGACAACGCCGAGAATACCAGCTATCTGCACATGTTCAGCCTCAAACCTGAAG ATACTGCCATGTATTACTGTAAGACGGAGAGTCCCGCAGGCGAATCCGCTTGG TGTCGGAATTTCAGGGGAATGGACTACTGGGGCAAGGGTACTCAAGTGACCGT AAGCTCT | 350. |
| hIL12Rb1_ VHH11 | CAGGTGCAGCTCCAGGAGAGCGGCGGAGGCTCCGTGCAGGCGGGCGGGAGCCT GCGTCTGTCTTGTGCCGTATCTGGCTATGACTATTGCGGTTACGACGTTCGCT GGTACAGGCAGGCTCCGGGCAAGGAGCGTGAGTTTGTCAGCGGGATTGACAGT GACGGCTCCACCTCTTATGCGGATTCCGTGAAGGGACGCTTCACAATTTCCCA GGATAACGCAGAGAACACCTCCTACCTCCACATGTTCAGCCTCAAACCCGAAG ATACTGCTATGTATTACTGTAAAACAGAGAGCCCAGCCGGGGAGTCTGCTTGG TGTCGTAACTTTCGCGGCATGGACTACTGGGGCAAGGGAACCCAGGTGACCGT CTCTTCC | 351. |
| hIL12Rb1_ VHH12 | CAGGTGCAACTCCAAGAGAGCGGAGGCGGAGTGTTCAGGCCGGGGCTCTCT GCGGCTGTCCTGCACCGCCTCTGGTTACACCTACTCCAGCGCCTTCATGGCCT GGTTCCGGCAGGCACCTGGCAAGGAACGCGAAGGCGTAGCCGCTATCTATACG CGCGATGGGGGTACAGTTTATGCTGATAGCGTTAAAGGACGCTTCACTATCTC CCAGGACAACGCCAAAAACACCCTGTACTTGCAGATGAACTCCCTCAAACCTG AAGATACGGCGATGTACTATTGTGCGGCAAAGATGCCTCAGCCCGGACGCGCA AGTCTGCTTGACTCTCAAACTTATGATTACTGGGGCAAGGGACTCAGGTGAC CGTTAGCTCC | 352. |
| hIL12Rb1_ VHH13 | CAGGTGCAGTTGCAGGAAAGCGGCGGTGGCTCAGTCCAGGCCGGGGGCTTCTT GCGCTTGAGTTGCGTGGCGAGCGGATATGGCTACTGTGGCTACGATATGAGCT GGTATCGTCAGGCTCCGGGCAAGGAACGTGAGTTCGTCGCGCTCATCACTAGC GAAAGAGTCATCTCCTACGAAGACTCCGTTAAGGGCCGCTTTTCCATTTCTCG CGACAACGCCGAGAACACGGGCTACCTTGAAATGAATAGACTGACTCCCGACG ATACTGCCATCTACTATTGCAAGACAAGCGCCGCTGCACGCGAGTCCTCTTGG TGCAGGTCTCGCTACCGCGTGGCTTCTTGGGGGCAGGGGACCCAGGTGACCGT ATCATCC | 353. |

TABLE 10-continued anti-IL12Rb1 sdAb VHH DNA SEQUENCE HUMAN

| Name | Sequence | SEQ ID NO: |
|---|---|---|
| hIL12Rb1_VHH14 | CAGGTTCAACTCCAGGAGTCCGGGGGCGGTTCCGTGCAGGCTGGGGGCTCCCTTAGACTTAGCTGTGCCGTGTCTGGATACGATTACTGTGGGTATGACGTGCGGTGGTACAGACGCGCTCCGGGAAAGGAACGCGAGTTCGTGAGCGGAATTGATTCCGATGGCAGCACCTCCTATGCGGATTCTGTGAAGGGCCGCTTCACTATCTCTCAAGACAACGCCGAGAACACTAGCTACCTGCACATGTTCAGTCTGAAACCGGAGGATACCGCGATGTATTACTGTAAGACCGAGTCTCCTGCTGGAGAGAGCGCGTGGTGCAGAAACTTCCGTGGAATGGACTATTGGGGTAAAGGAACTCAGGTGACTGTGTCCAGT | 354. |
| hIL12Rb1_VHH15 | CAAGTGCAGCTCCAGGAATCTGGAGGCGGAAGCGTACAGGCCGGTGGCTCACTCCGGCTTTCTTGCGCTGTGTCAGGTTACGACTATTGTGGATATGATGTCCGGTGGTATAGGCAAGCGCCGGGAAGGAGCGCGAGTTCGTGAGCGGTATCAACTCTGACGGCTCCACCTCCTACGCCGACTCTGTCAAGGGCCGCTTTACAATTTCTCAGGACAACGCAGAGAACACCTCTTACCTGCACATGTTCAGCTTGAAGCCGGAGACACCGCGATGTACTATTGTAAGACTGAGTCCCCCGCTGGAGAGTCTGCATGGTGCCGTAATTTTCGCGGCATGGACTATTGGGGAAAGGTACTCAGGTTACCGTAAGCTCA | 355. |
| hIL12Rb1_VHH16 | CAGGTACAGCTCCAGGAGAGTGGAGGCGGGTCAGTGCAGGCCGGGGGCTCACTGCGCTTGAGCTGCACCGCGAGCGGTTACACCTACAGCTCCGCATTCATGGCTTGGTTCAGGCAAGCCCCAGGCAAGGAGCGCGAGGGCGTGGCTGCCATGTATACCCGCGACGGGGGCACCGTGTATGCCGATTCCGTGAAGGGCCGTTTCACCATCTCCCAGGATAACGCTAAGAACACCCTCTACCTCCAGATCCACACTCTCAAAGCCGAAGACACGGCTATGTACTATTGCGCCGCGAAGATCCCTCAACCTGGCAGGGCAAGCCTTCTGGACTCCCAGACGTATGACTATTGGGGCCAGGGGACTCAGGTTACAGTGTCCAGC | 356. |
| hIL12Rb1_VHH17 | CAGGTGCAGCTCCAGGAATCCGGCGGTGGGTCTGTGCAGGCAGGGGTTTTCTCCGCTTGAGCTGTGTGGCTAGTGGATACGGTTATTGTGGATACGACATGAGCTGGTATCGCCAAGTACCGGGCAAGGAGCGTGAGTTTGTGGCCCTCATCACCTCTGATCGCTCCGTGTCTTATGAGGACAGCGTGAAGGGCCGCTTCAGCATCAGTCGCGACAACGCCAAGAACACCGCTTATCTGGAAATGAACAGACTCACCCCCGGATGACACAGCTATCTACTATTGCAAGACCTCCACAGCGGCCAGAGAGAATAACTGGTGCCGGTCCCGCTACCGCATCGCGTCCTGGGGCCAGGGCACCCAGGTGACTGTCTCCTCT | 357. |
| hIL12Rb1_VHH18 | CAGGTGCAGTTGCAGGAGTCTGGAGGGGGCAGCGTGCAGGCCGGAGGCTCCCTCCGCCTCAGCTGCGCGGCCTCCCGGTACACCTACACCAATAACTTCATGGCATGGTTCAGGCAGGCCCCAGGAAAGGAGCGTGAGGGGGTCGCCGCAATCTATACCGGAGACGGCTACGCCTATTACTTTGACTCCGTTAAAGGGCGTTTCACCATCAGTCAAGCAACGACAAAAACATGCTCTACCTCCAGATGAATAGCTTGAAGCCGGAGGATACCGCAATGTACTATTGTGCCGCGATGGAGAGACGCTCCGGTCGGCGTCGCATGACTGAAAATGCCGAGTACAAGTACTGGGGGCAGGGGACTCAGGTGACCGTGAGCAGC | 358. |
| hIL12Rb1_VHH19 | CAAGTTCAGCTCCAGGAGAGTGGAGGCGGTTCCGTACAGGCTGGCGGAAGTCTGCGCCTCTCCTGCGCCGTCTCCGGTTACGACTATTGTGGGTACGACGTGCGCTGGTATAGACAGGCTCCTGGAAAGGAGCGTGAGTTTGTGAGTGGCATCAACTCCGACGGTAGCACCTCCTATGCTGATTCTGTGAAGGGTCGCTTTACAATCTCACAGGACAACGCCGAAAACACTTCCTATCTGCACATGTTCAGCCTCAAGCCCGAAGACACCGCAATGTACTATTGTAAGACTGAAGGTCCAGCTGGCGAGAGTGCATGGTGCAGGAATTTTAGGGGCATGGACTACTGGGGCAAGGGCACCCAGGTCACCGTGTCTTCA | 359. |
| hIL12Rb1_VHH20 | CAGGTGCAGTTGCAGGAATCAGGAGGCGGTTCTGTGCAGGCCGGAGGCAGCCTGCGTCTGAGCTGCACCGCTTCTGGGTACACCTACTCAAGTGCCTCATGGCCTGGTTTCGGCAAGCGCCCGGCAAGGAACGCGAGGGAGTTGCGGCCATCTACACCAGGGACGGCAGTCCCGTGTACGCTGACTCCCTGAAGGGCCGTTTCACCATCAGCCAGGATAACGCAAAGAACACCCTGCACCTCCAGATGAACAGCCTGAAACCTGAGGACACAGCTATGTATTACTGCGCGGCCAAAATCCCTGAGCCTGGAAGAATCAGCCTCCTTGACTCCCAGACCTACGACTACTGGGGTCACGGCACTCAGGTGACTGTGTCTTCT | 360. |
| hIL12Rb1_VHH21 | CAGGTTCAACTCCAAGAGTCTGGAGGCGGGTCCGTGCAGGCTGGGGGCTCCCTCAGACTGTCCTGTACTGCGTCAGGGTACACCTACAGCTCCGCTTTCATGGCTTGGTTCCGGCAAGCTCCGGGCAAGGAGCGCGAGGGCGTGGCCGCGATGTATACCCGCGACGGTGGCACCGTGTACGCCGACTCTGTTAAAGGCCGCTTCACCATCTCCCAGGATAACGCCAAGAACACCCTGTACCTCCAGATGAACTCTTTGAAGACCGAGGATACCGCTATGTACTATTGCGCCGCAAAATTCCCCAGCCGGGCCGTGCTTCCCTTCTGGACAGCCAAACCTATGATTACTGGGGCCAGGGCACACAGGTGACCGTGTCCTCC | 361. |

TABLE 10-continued anti-IL12Rb1 sdAb VHH DNA SEQUENCE HUMAN

| Name | Sequence | SEQ ID NO: |
|---|---|---|
| hIL12Rb1_VHH22 | CAGGTGCAACTTCAGGAATCTGGCGGTGGCAGCGTGCAGGCTGGTGGCTCCCT GCGCCTGAGCTGTACTGCTTCCGGCTACACATACTCTAGTGCGTTCATGGCCT GGTTCAGGCAAGCTCCGGGAAAGGAGCGCGAGGGTGTGGCGGCCATTTATACA CGCGACGGAGGCACCGTGTACGCTGACTCTGTCAAGGGCCGCTTCACCATCTC ACAGGACAATGCAAAAAATACCCTCTACCTTCAGATGAACAGCCTGAAGGCAG AGGACACAGCAATGTATTACTGTGCAGCCAAGATCCCACAACCCGGACGCGCG TCCCTCCTGGATTCACAGACCTACGACTACTGGGGCCAGGGCACGCAGGTTAC TGTATCAAGC | 362. |

TABLE 11 anti-mIL12Rb1 sdAb VHH DNA SEQUENCE

| Name | DNA Sequence | SEQ ID NO |
|---|---|---|
| mIL12Rb1_VHH1 | CAGGTGCAGCTCCAGGAAAGCGGGGGAGGTTCCGTCCAGGCC GGTGGCTCCCTCCGCCTGTCATGCACAGCGAGCGGTTACACGT ATAGCTCCGCCTTTATGGCCTGGTTTAGACAGGCCCCAGGGAA AGAACGTGAGGGAGTGGCTGCAATTTACACCCGCGATGCGG GACTGTTTACGCCGATAGCGTCAAGGGTCGCTTTACCATCAGC CAGGACAACGCTAAAAACACCCTCTATCTCCAGATGAATAGC CTGAAGGCCGAGGACACTGCGATGTATTACTGCGCCGCTAAG ATCCCTCAACCTGGCCGCGCCAGCTTGCTGGATAGCCAGACAT ACGATTACTGGGTCAGGGAACACAAGTGACGGTCAGCAGC | 363. |
| mIL12Rb1_VHH2 | CAGGTGCAGCTCCAGGAGAGCGGCGGGGGCTCCGTACAGGCC GGTGGATCACTCCGCCTGAGCTGTGCTGTGAGCGGGTACGAC TATTGCGGATACGACGTGCGCTGGTATCGCCAAGCTCCAGGG AAGGAAAGGGAGTTCGTGAGCGGAATTGATTCCGATGGCTCC ACCAGTTATGCCGACTCCGTTAAAGGAAGGTTTACCATCTCCC AAGATAACGCCGAGAACACCTCCTATCTGCATATGTTTTCCCT GAAACCCGAGGATACCGCTATGTATTACTGTAAGACAGAGAG CCCTGCCGGAGAGTCCGCCTGGTGCCGCAACTTTCGGGGCAT GGACTACTGGGGAAAGGGCACCCAGGTGACAGTGTCTAGC | 364. |
| mIL12Rb1_VHH3 | CAGGTGCAGCTGCAAGAATCAGGAGGTGGATCTGTGCAAGCT GGGGGGCTCTTTGCGCCTGTCCTGTGTCGCCTCCGGCTATAGCT ATTGCGGCTATGACATGATGTGGTACAGGCAAGCCCCAGGTA AGGAGAGGGAGTTTGTGGCTCTCATCACCTCCGACTACAGCA TTCGCTATGAAGATAGTGTCGAGGGACGCTTCTCCATTTCTCG CGACAACGCGAAGAACACTGGCTATTTGCTGATGAGTAACCT CACCCCCGCCGACACCGCGATCTACTATTGCAAAACATCTACC GCCGCTCGGGAAAGTAGCTGGTGTAGGTCACGTTATAGGGTC GCTTCCTGGGGTCAGGGCACGCAGGTGACCGTCTCATCC | 365. |
| mIL12Rb1_VHH4 | CAGGTGCAGTTGCAGGAGAGCGGAGGCGGATCTGTGCAGGCA GGCGGAAGCCTCCGCCTGTCTTGCGCCGCTTCCCGGTACACCT ACACAAATAACTTTATGGCATGGTTCCGCCAAGCGCCCGGCA AGGAGCGCGAGGGTGTCGCGGCCATTTACACAGGTGATGGCT ACGCCTATTACTTCGACTCCGTGAAAGGCAGGTTCACGATCTC CCAGGATAACGACAAGAATATGTTGTATCTTCAGATGAACTCT CTGAAACCTGAGGACACCGCTATGTACTATTGTGCAGCTATGG AACGCAGGTCAGGCAGGCGCAGGATGACCGAGAACGCCGAG TACAAGTACTGGGGCCAGGGCACCCAGGTGACCGTGTCTTCA | 366. |
| mIL12Rb1_VHH5 | CAGGTGCAGCTCCAGGAGTCTGGAGGCGGTTCCGTCCAGGCC GGGGAAACGCTCCGGCTTAGCTGCACCGTCTCCGGTTTCACCA TTGATGACTCCGAAATGGGTTGGTATCGCCAAGCGCCCGGCC ATGAGTGCGAACTGGTGGCCAGCGGAAGTTCCGACGATGACA CCTATTACGTGGACTCAGTGAAGGGTCGCTTTACGATCTCTCT GGATAACGCCAAAAACATGGTGTACCTCCAGATGAACTCACT CAAGCCAGAGGATACAGCAGTTTATTACTGTGCCACTGGACC TACATACCCTCCCAAGGATGGTGACTGCGCACACTGGGGTCA AGGCACCCAGGTCACTGTCTCCTCC | 367. |
| mIL12Rb1_VHH6 | CAAGTCCAGCTCCAGGAGTCTGGGGGAGGCTCAGTGCAAGCT GGTGGATCTCTTCGCCTGTCTTGCACCGCTTCTGGGTACACCT ATAGCTCTGCCTTCATGGCCTGGTTTAGGCAAGCGCCTGGCAA GGAGCGGGAGGGCGTCGCCGCTATCTACACCCGCGACGGCAG TCCGGTTTATGCCGACTCCCTGAAGGGTAGATTTACTATCTCT CAGGATAATGCAAAGAATACGCTGCACTTGCAGATGAACTCC CTCAAACCCGAGGACACGGCCATGTATTACTGTGCTGCAAAA | 368. |

TABLE 11-continued anti-mIL12Rb1 sdAb VHH DNA SEQUENCE

| Name | DNA Sequence | SEQ ID NO |
|---|---|---|
| | ATCCCAGAGCCTGGTCGGATCTCCCTCCTGGATTCACAGACCT ACGACTACTGGGGCCACGGCACCCAGGTGACAGTCTCTTCC | |
| mIL12Rb1_VHH7 | CAGGTGCAGCTCCAGGAGTCCGGTGGCGGAAGCGTGCAGGCC GGTGGCTCCCTGCGGTTGAGTTGCGCGGTCTCAGGTTACGATT ATTGTGGCTACGACGTGCGCTGGTATAGACGCGCTCCTGGCA AGGAGCGTGAGTTCGTGTCTGGCATCGACTCCGATGGCTCTAC TTCATACGCTGATTCCGTCAAAGGCCGTTTCACCATCTCTCAG GATAACGCCGAGAACACCTCCTACCTTCACATGTTCTCTCTGA AGCCCGAGGATACTGCAATGTATTACTGTAAGACTGAGTCTCC TGCCGGAGAATCCGCCTGGTGTCGTAACTTTCGTGGCATGGAC TACTGGGGTAAGGGAACCCAGGTGACTGTATCTTCC | 369. |
| mIL12Rb1_VHH8 | CAGGTCCAGTTGCAGGAGTCTGGTGGAGGCTCCGTCCAAGCT GGGGGCTTTCTTAGGCTGTCATGTGTGGCATCCGGCTATGGGT ATTGTGGCTATGATATGTCCTGGTATAGACAAGCGCCCGGCA AGGAGCGCGAGTTCGTGGCGCTGATTACCAGCGAGCGCGTTA TCAGCTACGAGGACTCCGTCAAAGGCAGATTCTCCATCTCACG CGACAACGCCGAGAACACAGGCTATCTGGAAATGAATCGTTT GACACCTGATGACACCGCTATCTACTATTGCAAGACCTCTGCG GCTGCGCGTGAGTCTAGCTGGTGCCGTTCCCGCTATAGAGTGG CTTCTTGGGGTCAGGGAACCCAGGTGACAGTCTCCAGC | 370. |
| mIL12Rb1_VHH9 | CAGGTACAGCTCCAGGAGTCTGGAGGCGGGAGCGTGCAGGCA GGCGGTTCCCTGCGTCTGTCCTGCGTCGCCTCTGGGTATGGGT ACTGCGGCTACGATATGTCCTGGTATCGTCAGGCTCCCGGCAA AGAAAGAGAGTTCGTAGCCCTCATCACATCTGACCGGAGCAT TCCTACGAAGACTCCGTCAAGGCCCGCTTCATTATCTCACGG GATAACGCAGCCAACACCGGATACCTGGACATGACTCGCCTG ACCCCCGATGACACTGCTATCTATTACTGCAAGACGAGCGCG GCAGCTCGCGAGAGTTCTTGGTGCCGGTCCCGGTACAGGGTG GCGTCCTGGGGCCAGGGGACTCAGGTCACCGTCTCCTCC | 371. |
| mIL12Rb1_VHH10 | CAGGTGCAACTCCAGGAGAGTGGAGGTGGCTCAGTACAGGCC GGGGGAAGCCTCCGTCTGAGCTGTGCCGTGTCCGGCTACGATT ACTGTGGTTACGACGTGCGGTGGATCGCCAGGCCCCTGGTA AGGAAAGAGAGTTCGTGTCCGGCATCGACAGCGATGGTAGCA CATCTTACGCCGACTCCGTGAAGGGCCGCTTCACAATCTCCCA GGACAACGCCGAAAACACGTCTTACCTCCATATGTTTTCCCTG AAACCTGAAGACACCGCTATGTATTACTGCAAGACCGAGTCT CCCGCTGGCGAGTCAGCATGGTGTAGGAACTTTCGCGGCATG GACTATTGGGGTAAGGGCACCCAGGTGACGGTGAGTTCT | 372. |
| mIL12Rb1_VHH11 | CAGGTGCAGCTCCAGGAAAGCGGCGGGGAAGCGTGCAGGC AGGAGGCTCCCTTCGGTTGAGCTGCGTGGCCAGCGGCTACAG CTACTGCGGCTACGACATGATGTGGTATCGCCAAGCTCCGGG GAAGGAGCGCGAGTTCGTCGCCCTCATCACCAGTGATTATTCT ATCCGCTACGAAGACTCTGTGGAAGGTAGGTTCTCCATTAGCA GAGACAACGCAAAGAACACTGGATACCTGCTTATGAGCAACC TCACACCCGCCGACACTGCCATCTACTATTGTAAGACCTCTAC CGCCGCTCGCGAAAGCTCCTGGTGCAGGTCCCGCTATCGCGTG GCCAGTTGGGGTCAGGGAACCCAGGTGACGGTATCTAGC | 373. |
| mIL12Rb1_VHH12 | CAGGTTCAGTTGCAGGAGTCTGGAGGTGGCAGTGTGCAAGCT GGAGGCTCCCTCCGCCTGAGTTGCGCTGCCAGCAGATATACCT ATACGAATAACTTTATGGCTTGGTTTAGACAGGCCCCCGGTAA AGAGCGGGAAGGTGTGGCCGCGATTTACACCGGCGATGGCTA CGCCTATTACTTTTACAGCGTGAAGGGACGTTTCACCATTTCT CAGGATAACGATGAAAACATGCTGTATCTCCAAATGAACTCT CTGAAGCCTGAAGACACCGCTATGTATTACTGCGCGGCTATG GAGCGCAGGATCGGAACAAGACGCATGACTGAGAACGCTGA GTATAAATATTGGGGACAAGGCACACAGGTGACAGTTAGCTC C | 374. |
| mIL12Rb1_VHH13 | CAGGTCCAACTCCAGGAGTCCGGGGAGGGTCTGTGCAGGCG GGTGGCTCCCTGCGCCTGAGCTGTGTCGCGTCTGGTTACTCCT ACTGTGGATATGATATGATGTGGTATAGACAGGCCCCAGGTA AGGAGCGCGAGTTTGTGGCCCTGATTACCAGCGACTACAGTA TCCGCTATGAGGATTCCGTGGAGGGCCGCTTCTCTATCTCACG CGACAACGCCAAGAATCAGGCTACCTCCTGATGAGCAACCT GACCCCTGCCGACACAGCCATTTATTACTGCAAGACCTCCACC GCCGCGCGTGAATCCGGCTGGTGCAGGTCACGCTATCGTGTC GCCAGCTGGGGTCAGGGGACACAGGTGACGGTGTCATCT | 375. |

TABLE 11-continued anti-mIL12Rb1 sdAb VHH DNA SEQUENCE

| Name | DNA Sequence | SEQ ID NO |
|---|---|---|
| mIL12Rb1_VHH14 | CAAGTGCAGTTGCAAGAATCAGGAGGCGGGTCCGTGCAGGCG<br>GGCGGATCTCTGCGTCTGTCTTGTGCTGTCTCCGGTTATGACT<br>ACTGTGGTTACGACGTGCGCTGGTATCGCCAGGCCCCTGGTAA<br>GGAACGTGAGTTCGTGAGCGGGATCAATAGCGACGGCTCCAC<br>CTCTTATGCCGACAGTGTGAAGGGTAGGTTTACCATCAGTCAA<br>GACAACGCCGAGAACACATCCTACCTTCATATGTTCTCTCTCA<br>AGCCTGAGGATACCGCAATGTACTATTGCAAGACGGAGTCCC<br>CAGCAGGTGAGTCCGCTTGGTGCAGAAACTTTCGCGGCATGG<br>ATTATTGGGGGAAGGGAACCCAGGTCACCGTGTCTTCC | 376. |
| mIL12Rb1_VHH15 | CAGGTGCAACTTCAGGAATCCGGTGGCGGATCTGTTCAGGCT<br>GGCGGATTCCTGCGCCTGTCTTGCGTGGCCAGTGGCTACGGCT<br>ACTGCGGCTATGATATGTCATGGTATCGCCAAGTGCCCGGCA<br>AGGAGCGCGAGTTTGTAGCCCTCATCACATCTGATCGTTCTGT<br>CAGCTACGAAGACAGTGTCAAGGGCCGCTTTTCCATCAGCCG<br>CGATAATGCGAAGAACACGGCCTACCTGGAGATGAACAGACT<br>GACACCGGATGACACCGCTGTATATTACTGTAAGACCTCAAC<br>GGCTGCCAGAGAATAATTGGTGCCGTTCTCGCTACCGCATC<br>GCTTATTGGGGCCAGGGAACACAGGTCACAGTCTCCTCC | 377. |
| mIL12Rb1_VHH16 | CAGGTGCAACTCCAGGAGAGCGGGGGAGGTTCCGTTCAGGCC<br>GGGGGTTCCCTCAGATTGTCTTGTGCCGTCTCCGGGTACGATT<br>ACTGTGGCTATGACGTGCGCTGGTATCGGCAGGCTCCTGGGA<br>AGGAGCGGGAGTTCGTGAGTGGCATTAACTCAGACGGGTCTA<br>CCTCCTATGCCGACAGCGTTAAGGGCAGGTTTACTATCAGTCA<br>GGACAATGCGGAGAATACCAGTTACCTGCACATGTTCAGCCT<br>CAAGCCCGAGGATACCGCCATGTATTACTGCAAGACAGAGGG<br>TCCAGCTGGCGAGTCCGCATGGTGCCGCAACTTCAGGGGTAT<br>GGACTACTGGGGCAAGGGTACTCAGGTGACTGTGTCCTCT | 378. |
| mIL12Rb1_VHH17 | CAGGTGCAGTTGCAGGAGTCAGGCGGGGGCTCTGTCCAGGCT<br>GGGGGCTCTCTGAGACTGTCTTGTACTGCGTCTGGTTACACGT<br>ACAGTTCTGCCTTTATGGCCTGGTTTCGGCAAGCGCCCGGAAA<br>GGAGCGCGAGGGTGTTGCTGCCATGTATACCCGTGATGGCGG<br>AACCGTCTACGCAGATTCTGTTAAGGGTCGTTTCACAATCTCC<br>CAGGACAATGCGAAAAATACCCTCTATCTCCAGATCCACACC<br>TTGAAGGCTGAGGACACCGCGATGTATTACTGTGCTGCCAAG<br>ATCCCGCAGCCTGGCCGCGCTTCCCTGCTCGACAGCCAGACAT<br>ACGACTACTGGGGTCAGGGCACACAGGTTACCGTGAGTAGT | 379. |
| mIL12Rb1_VHH18 | CAAGTCCAACTCCAGGAAAGCGGAGGTGGCAGCGTCCAGGCC<br>GGGGGCTCTCTGAGACTGTCTTGTACCGCTTCCGGCTATACAT<br>ATTCCTCTGCCTTTATGGCATGGTTCCGCCAAGCGCCAGGCAA<br>GGAGCGCGAGGGCGTCGCCGCTATGTATACCAGAGACGGAGG<br>CACCGTCTACGCTGACAGCGTCAAGGGACGCTTCACAATCTCC<br>CAGGACAACGCCAAGAATACTTTGTATCTCCAGATGAATAGC<br>CTCAAGACGGAGGACACCGCAATGTATTACTGCGCTGCAAAA<br>ATCCCTCAGCCAGGTCGCGCCTCCCTCCTGGACAGTCAGACCT<br>ATGATTATTGGGGCCAGGGGACCCAGGTGACTGTCTCCTCC | 380. |
| mIL12Rb1_VHH19 | CAGGTACAGTTGCAGGAGTCCGGCGGAGGCAGCGTTCAGGCC<br>GGTGGCTTCCTGAGGCTGTCCTGCGTCGCCAGCGGCTATGGAT<br>ATTGCGGCTACGATATGTCCTGGTACAGACAGGTCCCTGGGA<br>AAGAACGCGAGTTCGTGGCTCTTATCACATCCGACAGGTCCGT<br>GTCCTATGAGGACTCTGTCAAGGGCCGTTTCAGCATCAGCCGT<br>GACAACGCAAAAAACACGGCTTACTTGGAGATGAACCGGCTT<br>ACCCCCGACGATACCGCGATTTATTACTGCAAGACCAGCACA<br>GCAGCCAGGGAAAATAATTGGTGTCGGAGCCGTTATCGTATC<br>GCCTCTTGGGGACAGGGAACCCAGGTGACTGTCTCCTCA | 381. |
| mIL12Rb1_VHH20 | CAGGTGCAGCTCCAGGAGTCCGGCGGAGGCTCAGTACAAGCT<br>GGCGGTTCACTCAGGTTGAGTTGTGTCGCCAGTGGCTACGGCT<br>ATTGTGGCTATGATATGTCTTGGTATCGCCAGACCCCCGGCAA<br>GGAGCGTGAGTTCGTGGCACTCATCACGTCCGACCGGATCGC<br>CTCTTACGAAGACTCTGTCAAGGGCCGTTTTATTATCAGCCGC<br>GACAACGCAAAAAACACTGGTTATCTCGACATGACTCGGGTG<br>ACCCCCGATGACACTGCCATCTACTATTGCAAAACCTCTGCTG<br>CGGCCCGCGAGAACTCCTGGTGCCGTAGTCGCTACCGCGTCG<br>CCTCCTGGGGACAGGGTACACAGGTGACCGTTAGCTCC | 382. |
| mIL12Rb1_VHH21 | CAGGTCCAACTGCAAGAGTCTGGCGGTGGCTCCGTGCAGGCT<br>GGCGGTAGTCTGCGCCTGTCTTGTGCAGTCAGCGGGTACGACT<br>ACTGCGGTTATGATGTCAGATGGTATCGCGTGCTCCCGGCAA<br>GGAACGCGAGTTCGTCTCTGGCATTGACTCCGACGGCTCTACC<br>TCCTATGCCGATAGCGTAAAGGGAAGGTTCACCATCAGCCAG<br>GACAACGCTGAGAACACCAGCTACTTGCACATGTTCTCCCTTA | 383. |

TABLE 11-continued anti-mIL12Rb1 sdAb VHH DNA SEQUENCE

| Name | DNA Sequence | SEQ ID NO |
|---|---|---|
| | AACCTGAGGACACAGCTATGTATTACTGTAAAACTGAGAGCC<br>CGGCTGGCGAGAGCGCCTGGTGTCGCAACTTTCGTGGCATGG<br>ACTACTGGGGTAAGGGCACCCAGGTTACTGTCTCTAGT | |
| mIL12Rb1_<br>VHH22 | CAGGTGCAACTTCAGGAGAGCGGTGGCGGTTCAGTGCAGGCT<br>GGGGGAAGCCTGCGCCTGTCTTGCACCGCTTCCGGCTACACCT<br>ATTCCAGTGCCTTCATGGCCTGGTTCCGCCAGGCCCCTGGAAA<br>GGAACGCGAAGGCGTGGCTGCCATTTATACACGGGATGGGGG<br>AACCGTCTACGCGGACTCCGTCAAGGGAAGATTCACCATTAG<br>CCAGGATAATGCTAAGAACATCCTGTACCTCCAGATGAACTC<br>CCTCAAAGCCGAGGATACTGCTATGTACTATTGTGCCGCTAAG<br>ATTCCGCAGCCAGGCCGGGCATCCCTCCTGGACAGCCAGACC<br>TATGACTACTGGGGACAGGGGACCCAGGTGACCGTGTCTTCC | 384. |
| mIL12Rb1_<br>VHH23 | CAGGTGCAGCTCCAGGAGTCCGGCGGTGGCAGTGTCCAGGCA<br>GGAGGCAGTCTGCGTCTGTCTTGCACTGCCTCAGGCTACACAT<br>ACTCAAGCGCATTCATGGCCTGGTTCAGGCAGGCCCCTGGGA<br>AGGAGCGCGAGGGTGTGGCAGCTATCTACACCCGCGATGGCG<br>GTACTGTGTACGCCGATAGTGTCAAGGGGCGCTTTACCATTTC<br>TCAGGACAACGCGAAGAACACCCTGTACTTGCAGATGAACAG<br>CCTGAAGCCGGAGGATACTGCTATGTATTACTGCGCCGCAAA<br>AATGCCCCAGCCGGGCCGCGCGTCTTTGCTGGATTCCCAGACA<br>TACGACTACTGGGGCAGGGCACCCAGGTTACGGTTAGCTCC | 385. |

TABLE 12 anti-IL12Rb2 sdAb VHH DNA SEQUENCE

| Name | Sequence | SEQ ID NO: |
|---|---|---|
| hIL12Rb2_<br>VHH1 | CAGGTCCAGCTCCAGGAAAGCGGAGGTGGATCTGTGCAGGCCGGTGGATCACT<br>GCGGCTGAGTTGCGCCGCAAGCGGCTTTACCGTGACAAGATATTGCATGGGT<br>GGTTGCGCCAGGCACCCGGCAAACAGCGTGAAGGCGTGGCTATCATTGAGCGC<br>GACGGTCGGACCGGCTATGCGGATAGCGTCAAGGGCAGATTCACCATCAGCAA<br>GGACAACGCGAAAAATACCCTGTACCTGCAAATGAACTCCCTCAAGCCCGAGG<br>ATACGGCGATGTACTATTGCGGCGCGATTGAGGGTTCTTGTCGGCCTGATTTC<br>GGTTATCGCGGGCAGGGAACCCAAGTGACCGTCTCCTCT | 386. |
| hIL12Rb2_<br>VHH2 | CAGGTACAGTTGCAGGAGAGTGGCGGAGGTAGCGTCCAAGCGGGCGGGAGCCT<br>GCGCCTGAGTTGTGCTGCCAGCGGTTTTACCATCTCTCGCTACTGTATGGGAT<br>GGCTGCGGCAAGCGCCTGGCAAGCAGAGGGAAGGAGTGGCCATTATCGAGAGG<br>GATGGCCGCACCGGATACGCCGACTCCGTGAAGGGACGCTTCACGATCTCAAA<br>GGATAACGCTAAGAACACTCTCTACCTCCAGATGAACAGTCTGAAGCCGGAGG<br>ATACTGCTATGTATTACTGTGGGGCCATTGAGGGTAGCTGTCGGCCTGACTTT<br>GGTTATCGCGGACAGGGAACGCAGGTAACCGTGTCATCC | 387. |
| hIL12Rb2_<br>VHH3 | CAGGTGCAGCTCCAGGAGAGCGGCGGGGGTTCCGTTCAGGCTGGAGGTTCTCT<br>GCGCCTTAGTTGTACTGCCAGCGGCCTGACTTTCGACGATGTCGAGATGGCAT<br>GGTATCGCCAAGGTCCCGGCGACGATTACGATCTGGTGTCCAGTATCAATACC<br>GATAGCAGGGTCTATTACGTCGATAGCGTCAAGGACAGATTCACCATCAGCCG<br>GGACAACGCCAAGAACACCCTCTACTTGCAGATGAATAACCTGAAGCCGGAGG<br>ATACAGCTGTTTATTACTGTGCCGCAGACCCTTGGGGTGGCGACCTCAGGGGC<br>TACCCGAACTATTGGGGCCAGGGCACACAGGTGACCGTTAGCTCT | 388. |
| hIL12Rb2_<br>VHH4 | CAGGTGCAGTTGCAGGAGAGCGGGGGAGGTAGCGTGCAGGCGGGCGGTTCCCT<br>GCGCTTGTCTTGTGTCGCCTCCGGTTTTACCATCTCCGTTATTGTATGGGCT<br>GGTTGCGCCAGGCACCCGGCAAGCAGCGGGAGGGGGTGGCTATTATCGAGAGG<br>GATGGCCGTACTGGATATGCCGACTCCGTGAAGGGCCGTTTCACAATCTCCAA<br>AGACAATGCAAAGAATACTCTGTATCTTCAGATGAACTCCCTGAAGCCCGGCG<br>ACACTGCTATGTACTATTGCGGGGCCATCGAGGGTTCCTGTCGGCCCGACTTC<br>GGCTACCGTGGCCAGGGCACCCAGGTCACCGTTAGTTCC | 389. |
| hIL12Rb2_<br>VHH5 | CAGGTTCAGCTCCAGGAGTCTGGCGGAGGCCTGGTTCAGCCTGGAGGTAGCCT<br>GAAGCTGTCTTGCGCCGCTTCTGGTTTTACCTTCTCTACCTACGCTATGTCTT<br>GGGTGAGGCAGGCACCTGGCAAGGAGCCTGAGTGGATCAGCGTATCTCTTCC<br>GGCGGGGGCAATACATATTACGCTGACGCTGTTAAGGGGCGCTTCGCCATCAG<br>TCGCGATAATGCCAAGAACACTCTGTATCTCCAGCTGAACAGCCTGAAGACAG<br>AGGACACTGCAATTTATGTATGTACTATGGACGATTACTATGGGGGCTCCTGG<br>CATCCCATCTCCAGAGGGCATGGGACCCAGGTAACCGTGTCCTCT | 390. |

TABLE 12-continued anti-IL12Rb2 sdAb VHH DNA SEQUENCE

| Name | Sequence | SEQ ID NO: |
|---|---|---|
| hIL12Rb2_VHH6 | CAGGTGCAGCTCCAGGAAAGCGGCGGTGGGCTTGTGCAGGCAGGTGGCTCCCTGAGGGCTGTCCTGCCAGGCCAGCGGGTACACATACGGCTTGTTCTGTATGGGCTGGTTCCGTCAGGTCAGCGGTAAAAAGCGCGAAGGGGTTGCGTCGTGGATAGCCCAGGAGGCCGCCACGTGGCCGACAGCCTGAAGGGCCGTTTCACCATCTCCAAGGACAACGCCAATAACATCTTGTATCTGGACATGACCAATCTGAAGTCCGAGGACACCGCAACCTATTACTGCGCCGCTGACCCTGAGAAGTATTGCTTTCTCTTCTCCGATGCTGGCTATCAGTACTGGGGACAAGGCACACAGGTTACAGTATCCTCC | 391. |
| hIL12Rb2_VHH7 | CAAGTACAGCTTCAGGAATCTGGGGGTGGCTCCGTCCAGGCAGGAGGCTCCCTTAGACTGTCCTGTGCGGCCAGCGGGGTCACCTACTCCAGATATTGTATGGGGTGGTTCCGGCAGGCCCCTGGACTGGAACGCGAACGTGTGGCCTATCTACTCCAGGGGCATTATCACATATTACACAGACAGCGTTAAGGGAAGGTTTACCATTTCCCAGGACAGTGCTAAAAAGACCGTCTACTTGCAGATGAACTCCTTGAAGCCTGAGGACACGGCAATGTACTATTGTGCCGCGACTCGCGAGACTTACGGTGGATCTGGCGACTGTGACTACGAGTCTGTCTACAACTACTGGGCTCAAGGCACCCAGGTGACAGTCTCAAGC | 392. |
| hIL12Rb2_VHH8 | CAGGTGCAACTGCAAGAATCTGGGGGCGGTTCCGTTCAGGCCGGAGGTAGCCTGCGCCTGAGCTGCGCGGCTTCAGGCTTCACCGTGAGCAGATACTGTATGGGCTGGTTGAGGCAAGCTCCTGGAAAGCAACGCGAAGGGGTCGCCATTATCGAGCGTGAGGGACGTACCGGCTACGCCGATAGCGTTAAGGGACGTTTTACCATCTCTAAGGACAACGCCAAGAACACGCTGTATTTGCAGATGAACAGTCTCAAGCCCGAAGATACAGCTATGTATTACTGCGGCGCAATCGAAGGCTCTTGCAGGCCCGACTTTGGATATCGCGGCCAAGGTACACAGGTTACTGTGTCTTCC | 393. |
| hIL12Rb2_VHH9 | CAGGTGCAGCTGCAAGAGTCAGGTGGCGGGAGCGTGCAGGCGGGAGGCAGCCTTCGCCTGAGTTGCGCAGCCTCCGGCTTCACCATCTCACGCTACTGTATGGGTGGCTGCGCCAAGCGCCTGGAAAACAGCGCAAGGTGTGGCTATCATTGAACGCGACGGAAGGACCGGCTACGCAGATTCAGTGAAGGGCCGCTTCACCATCAGCAAGGATAACGCTAAGAACACTCTTTATCTCCAGATGAACTCCTTGAAACCAGAGGATACTGCGATGTACTTCTGCGCGCTATTGAGGGTTCCTGCCGCCCCGATTTTGGCTATCGCGGGCAGGGCACCCAGGTCACCGTGAGCAGT | 394. |
| hIL12Rb2_VHH10 | CAGGTGCAGCTTCAGGAGAGCGGGGGAGGCAGCGTGCAAGCTGGTGGCTCCTTGCGCTTGAGCTGTGCAGCGTCTGGATTCACCGTTACAAGATATTGCATGGGATGGCTCCGTCAAGCGCCTGGCAAGCAGCGCGAGGGCGTGGCCATCATTGAGAGGGACGGAAGGACAGGTTACGCCGATAGTGTGAAGGGACGGTTCACTATCAGCAAGGATAATGCCAAGAATACGCTTTATCTTCAGATGAACTCCCTTAAACCAGAGACACCGCTATGTATTACTGTGGGCTATCGAAGGCAGCTGTAGGCCGGACTTCGGATATCGCGGCCAGGGAACTCAGGTTACCGTAAGCTCC | 395. |
| hIL12Rb2_VHH11 | CAAGTGCAGCTTCAGGAGTCTGGGGGCGGTTCCGTGCAAGCCGGAGGCAGCCTGCGCCTGAGCTGCGCCGCAAGCGGATTTACAGTGAGCCGCTATTGTATGGGGTGGCTGCGGCAGGCCCCAGGAAAGCAGCGCGAGGGGGTGGCCATCATTGAGAGATGGAAGGACCGGCTATGCCGATAGCGTCAAAGGCCGTTTTACCATCAGTAAAGATGACGCCAAGAACACACTGTATCTTCAGATGAACTCCCTCAAGCCTGAGGACACCGCCATGTATTACTGTGGCGCAATCGAAGGCAGCTGTCGCCCCGATTTTGGTTACAGAGGCCAGGGCACTCAGGTGACCGTCAGCAGC | 396. |
| hIL12Rb2_VHH12 | CAGGTGCAGCTTCAGGAGTCTGGGGGAGGCTCTGTCCAGGCTGGAGGCTCCCTGCGCCTGTCCTGTGCAGCCTCTGGCGTGACCTATTCCCGCTACTGCATGGGCTGGTTTCGTCAGGCCCCAGGGCTGGAGAGAGAGCGGGTGGCCACGATCTACTCTCGCGGGATTATCACCTATTACACTGACTCCGTGAAGGGCAGATTCACCATCTCCCAGGATTCCGCGAAAAAGACCGTGTACCTTCAAATGAACATGCTGAAGCCCGAGGATACAGCCATGTATTACTGCGCCGCTACAAGGGAGACCTACGGCGGAAGCGGTGACTGCGACTATGAAAGCGTTTACAACTACTGGGCTCAGGGCACGCAGGTGACCGTAAGCTCT | 397. |
| hIL12Rb2_VHH13 | CAGGTGCAGCTCCAAGAGTCTGGAGGCGGGTCCGTGCAAGCCGGGGGCTCACTGCGCCTGTCCTGCGCTGCGAGCGGTTTTACTATTAGCAAGTACTGCATGGGATGGCTCCGCCAAGCACCGGGCAAACAGCGCGAAGGCGTGGCGATTATCGAGAGAGATGGCCGTACCGGGTACGCCGACTCCGTCAAGGGCCGCTTCACCATCAGCAAGGACAATGCTAAGAACACCCTGTATTTGCAGATGAACAGTCTGAAGCCGGAGACACTGCTATGTATTACTGCGGTGCCATTGAGGGTTCTTGCCGTCCAGACTTCGGCTATCGCGGACAGGGCACGCAAGTCACTGTTTCTAGT | 398. |
| hIL12Rb2_VHH14 | CAGGTGCAGCTGCAAGAATCAGGTGGCGGTTCTGTGCAGGCTGGAGGCAGCCTGAGGCTGTCCTGTGCTGCCAGTGGTGTAACATACTCCCGCTACTGTATGGGTTGGTTTCGCCAGGCTCCGGGCCTGGAGAGGGAGCGCGTCGCCCATATCTATAGCCGTGGCATTATCACCTATTACACCGACAGCGTGAAGGGTCGTTTCACCATCAGCCAGGACTCTGCTAAGAAAACCGTGTATCTCCAGATGAACAGCCTGAAGCCTGAGGATACCGCCATGTATTACTGCGCAGCGACTAGAGAGACCTACGGTGGGTCCGGGGATTGCGGATACGAGAGCGTCTACAACTACTGGGCTCAGGGCACCCAAGTCACCGTGTCCTCT | 399. |

TABLE 12-continued anti-IL12Rb2 sdAb VHH DNA SEQUENCE

| Name | Sequence | SEQ ID NO: |
|---|---|---|
| hIL12Rb2_VHH15 | CAGGTGCAGTTGCAGGAGTCCGGCGGTGGCTCTGTGCAGGCCGGGGGCTCCCT TCGCCTGTCCTGCGCAGCCAGTGGTTTCACCATCTCCCGTTACTGCATGGGCT GGCTGCGCCAAGCCCCCGGCAAGCAGCGGGAGGGGGTTGCAATTATCGAGCGT GACGGTAGGACCGGATACGCTGATTCCGTGAAAGGCAGGTTTACAATTAGTAA AGATAATGCTAAGAACACCCTTTACCTCCAGATGAACTCCCTTAAACCAGAGG ATACTGCTATGTATTACTGCGGGGCCATTGAGGGTAGTTGTCGCCCTGACCTG GGCTACAGAGGCCAGGGAACTCAGGTGACCGTGTCCAGT | 400. |
| hIL12Rb2_VHH16 | CAGGTGCAGCTTCAGGAATCCGGTGGCGGGTCTGTGCAGGCCGGTGGCAGCCT GCGGCTGTCCTGCGCTGCCTCTGGCGTGACATACTCTCGTTATTGTATGGGCT GGTTCCGCCAGGCTCCCGGCCTGGAGCGTGAGAGAGTTGCACACATTTATTCT AGGGGCATTATCACGTACTATACCGATTCTGTGAAGGGACGCTTCACCATTTC CCAGGACAGCGCGAAAAAGACGGTTTACCTCCAGATGAACTCACTGAAACCTG AGGATACCGCCATGTATTACTGCGCTGCCACCCGTGAGACCTACGGTGGCTCT GGTGATTGTAGCTACGAGTCTGTTTACAACCATTGGGCACAGGGAACCCAGGT GACCGTGTCAAGC | 401. |
| hIL12Rb2_VHH17 | CAGGTTCAGTTGCAGGAGTCAGGAGGGGGCTCAGTGCAGGCGGGCGGTAGCTT GCGTCTGAGTTGCGCTGCCAGTGGATTGACGATTTCTCGCTACTGCATGGGTT GGCTTCGCCAGGCCCCTGGTAAACAACGGGAAGGTGTAGCAATTATCGAGCGC GATGGCCGGACGGGGTACGCCGATAGCGTGAAGGGCCGCTTCACTATTAGCAA GGACAACGCCAAAAACACCCTGTACTTGCAGATGAACAGCTTGAAGCCTGAGG ATACTGCCATGTATTACTGCGGAGCTATCGAGGGCTCCTGCCGCCCGGATTTC GGATACAGGGGCCAAGGCACTCAGGTGACAGTGAGTAGT | 402. |
| hIL12Rb2_VHH18 | CAGGTCCAGCTCCAGGAATCTGGCGGAGGCTCAGTCCAAGCCGGTGGCAGCTT GCGCCTGTCTTGCTCAGCCTCCGGTTTCACCGTGGATGACTTTGCTATGGGAT GGTATCGCCAGGCACCGGGTAACGAGTGTGAGCTGGTGTCCACTATCTCCTCT GGGGGCAGCACCTATTACGCGGACTCTGTGAAGGGAAGATTTACAATTTCTCA GGATTCCGCGAAGAACACCGTCTATCTTCAGATGAACAGCCTGAAGCCTGAAG ACACAGCCGTGTACTATTGTGCGCCATCCTCTGTAGGGTGTCCATTGGGGTAC TGGGGCCAGGGTACACAAGTCACTGTGTCAAGC | 403. |

TABLE 13 anti-mIL12Rb2 sdAb VHH DNA SEQUENCE

| Name | DNA Sequence | SEQ ID NO. |
|---|---|---|
| mIL12Rb2 VHH1 | CAGGTGCAGCTTCAGGAGAGTGGCGGAGGCAGTGTTCAGGCTGGTGGATCATT GCGCCTGTCCTGTGCGGCTTCCGGCTACACATATTCTAACCGCCACATGGGCT GGTTTAGGCAGGCCCCTGGCAAGGAACGCGAGGGTGTGGCGGCAATCTACACT GGGGGTGGCTCCACATATTACGCGGACTCCGTGAAGGACCGCTTCACCATTTC CCAGGATAACGCGAAGAACACGTTGTACTTGCAGATGAACAGTCTGACTCCCG AAGACACCGCCATGTATTACTGCGCAGCCGATTTGACACGTTGGTATAGTGGT GGCTGGCGCGATCCCAGGGGTTACAAATACTGGGGCCAGGGCACGCAGGTAAC GGTGTCA | 404. |
| mIL12Rb2 VHH2 | CAAGTTCAGCTTCAGGAGAGTGGAGGTGGCAGCGTGCAGGCCGGTGGGTCCCT GAGGCTGTCCTGTGCTGCCAGCGGAGTTACCTACGGCAGCTATTACATGGCAG CTTGGTTTAGGCAGGCCCCAGGTAAGGAGCGCGAAGGCGTCGCCTCCATCTAT GGCGGTAGCGACTCCACCTATTACGCAGACTCTGTCCTGGGCCGTTTCACCAT CTCTCAGGACAATGGAAAGAACACCCTCTACTTGCAGATGAACTCACTGAAGC CAGATGACACCGCGATGTATTATTGTGCTGCCGCTCCTCCGGGCAAGTGGTTC CTGAAGCGTCTGGAAGGCCACAACTACAGTTATTGGGTCAGGGCACTCAGGT AACCGTGTCATCT | 405. |
| mIL12Rb2 VHH3 | CAGGTCCAGCTCCAGGAGAGCGGAGGGGGCTCTGTTCAGGTGGGTGGCTCCCT GCGCCTGTCTTGTGCCGCGTCTGGTTTCACTTATAGCTCTTCCTGCCTGGGCT GGTTCCGGCAGGCTCCTGGGAAGGAGCGTGAAGGAGTGGCCACCATCTATCCC GCAGGTGGCAACATCTTTTACGCCGACAGTGTGAAGGGCCGCTTCACCATTTC CCAGGATAACGCTAAGAACACTGTTTACCTCCAGATGGATTCTCTGAAACCGG AGGACACCGCGATGTATTACTGCGCTGCACGGGAGGTCAGACCTGGGGGTCC GGCGGAAATAGATGTTCTTTGTGGCTCCCAGCTTACAACTATTGGGGCCAGGG CACCCAGGTCACTGTTTCCTCT | 406. |
| mIL12Rb2 VHH4 | CAGGTCCAGCTCCAGGAGTCCGGGGTGGCTCTGTGCAGGTCGGTGGCAGCCT GCGGCTGTCTTGCGCCCGTTAGCGGCAAGCTGTACGGAGGGGCCTGGTTCCGGC AGGCCCAGGGCAAGGGGCGTGAAGGAGTGGCGGCAATCTGGATTGGCACCGGA ACAACCTTCTACGCCGACAGTGTGAAGGACGCTTCACTATCAGCCGCGACAA | 407. |

TABLE 13-continued anti-mIL12Rb2 sdAb VHH DNA SEQUENCE

| Name | DNA Sequence | SEQ ID NO. |
|---|---|---|
| | CGCGAAGAACACCGTCTATCTGCAAATGGATGGGCTGAAGCCCGAGGACACCG CTCTGTACTATTGTGCTGCCGATGATCGCCCAGGTTATCGGGACCCTCTGGCC CCCGTGTCTTACAATCACTGGGGTCAGGGCACCCAGGTGACAGTGTCTAGT | |
| mIL12Rb2 VHH5 | CAGGTGCAGCTTCAGGAGAGCGGTGGGGGTAGCGTGCAGGCAGGCGGAAGTCT GAGGTTGTCTTGTGCCGCTAGTGGAATCACTTATCGCGGGGTCTGGATGGGAT GGTTCCGGCAAGCGCCCGGTAAGGAAAGAAGGAGTGGCGACTATCTATACA GGCTCCGGTCATACATATTACGCAGATTCTGTTAAGGGCCGCTTCACCATCTC TCAAGACAACGCCAAGAACACTGTCTATCTCCAGATGAACTCCCTGAAGCCCG AGGACACAGCTATGTATTACTGCGCCGCTAGGACCGTCGGGGGTACTTTTTAC ACTCTCGCGGCTGACTCATTTAACACATGGGGTCAGGGCACCCAAGTGACAGT GTCCAGT | 408. |
| mIL12Rb2 VHH6 | CAGGTCCAGTTGCAGGAGAGCGGTGGAGGTTCCGTTCAGGCAGGTGGAAGCCT CCGGCTGTCCTGTGCTGTGTCTGGCAAGGCCTACGGAGGTGCCTGGTTCCGTC AGGCTCAAGGCAAAGGCCGGGAAGGCGTCGCTGCAATCTGGATTGGTACTGGA ACCACATTCTATGCAGACTCCGTGAAGGGCAGATTTACCATTTCTCGTGACAA CGCGAAAAACACCGTTTACTTGCAGATGGACGGGCTGAAGCCTGAGGATACCG CTGTCTATTACTGCGCGGCAGATGACAGACCGGGCTACCGCGACCCTCTGGCC CCGGTGTCTTATAACCATTGGGGCAAGGCACCCAGGTGACCGTTTCTTCC | 409. |
| mIL12Rb2 VHH7 | CAGGTCCAGCTCCAGGAGTCCGGCGGGGAAGTGTCCAAGCTGGTGGGTCCCT CAAACTTTCTTGTGCGGTGTCCGGTAACCCTTACGGTGGAGCCTGGTTCCGCC AGGCCCAGGGCAAGTCTCGCGAAGGGGTGGCTGCCATTTGGCTGGGAACTGGC ACCACTTTTTACGCTGACTCCGTGAAGGGCCGCTTCACCATTTCCAGAGACAA CGCTAAGAACACCGTGTATGTCCAGATCGACGGGTTGAAACCTGAGGATACCG CCATGTATTACTGCGCCGCTGATGATCGCCCCGGCTATCGCGATCCGCTCGCT CCCGTCAGTTACAACCACTGGGGTCAGGGCACCCAGGTGACCGTTTCCTCC | 410. |
| mIL12Rb2 VHH8 | CAAGTGCAGCTTCAGGAAAGTGGAGGCGGGAGCGTGCAGGCGGGCGGTTCCCT GAGACTTAGCTGTGTCGTGTCTGGCAAAGCGTATGGGGGTGCTTGGTTCCGCC AGGCCCAGGGCAAATCTAGGGAGGGCGTGGCTGCCATCTGGATCGGCACCGGA ACGACCTTTTACGCCGACTCCGTAAAGGGACGTTTCACCATCTCTCGGATAAA TGCCAAGAATACCGTCTACCTTCAGATGGACGGGCTGAAGCCTGAGGATACCG CCATGTATTACTGTGCCGCTGATGACAGGCCAGGATACCGCGATCCTCTGGCT CCTGTCTCTTATAACCACTGGGGCCAAGGTACTCAAGTTACCGTCTCTTCC | 411. |
| mIL12Rb2 VHH9 | CAGGTGCAGTTGCAGGAGAGCGGCGGAGGCTCTGTTCAGGCTGGCGGGAGCCT CACACTGTCCTGCGTTGTGTCCGGCAAGGCCTTTGGTGGCGCTTGGTTTCGTC AGGCGCAGGGTAAGGGACGCGAGGGCGTCGCGGCTATCTGGATCGGCACCGGG ACCACATTTTATGCCGACAGTGTGAAAGGCCGTTTCACGATCAGCCGCGACAA CGCAAAGAATACCGTGTATCTGCAAATGGACGGTCTGAAGCCGGATGACACTG CAATGTACTATTGCGCTGCCGACGATAGGCCGGGCTATAGAGACCCCCTTGCC CCAGTGAGCTACAACCACTGGGGACAGGGCACTCAGGTAACTGTCTCTAGT | 412. |
| mIL12Rb2 VHH10 | CAGGTTCAGCTCCAGGAGAGTGGTGGCGGGAGTGTGCAGGCTGGTGGCAGTCT GAGGCTGTCATGCGCCGCTTCCGGTTACACGTTCAGTAATCATCACATGGGGT GGTTTCGGCAGGCCCCTGGTAAGGAGCGTGAGGGTGTGGCGGCCATCTACACC GGCGCTGGCAACATCTATTACGCGGACAGTGTGAAAGATCGGTTTACTATCTC CAAGGACACCGCGAAGAACACCCTGTACCTTCAGATGAACTCTCTCACCCCTG AGGATACCGGCATGTACTATTGCGCAGCCGATCTCACTCGCTGGTACTCCGGT GGGTGGCGTGACCCGAGGGGCTACAAATACTGGGGTCAGGGGACGCAGGTAAC AGTCTCTTCA | 413. |
| mIL12Rb2 VHH11 | CAGGTGCAGCTCCAGGAGAGCGGGGTGGCCCAGTCCAGGCGGGAGGTTCCCT TCGGCTGTCCTGCGCGGCTTCAGGCTACACGTTTAGCAATCATCACATGGGCT GGTTTCGTCAAGCACCAGGAAAGGAGCGTGAGGGTGTGGCAGCTATTTATACC GGCGCTGGGAACATCTATTACGCCGACTCCGTGAAGGATCGGTTCACCATCTC CAAAGACACCGCCAAGAACACCCTGTATCTCCAGATGAACTCACTGACACCCG AGGACACAGGTATGTATTACTGCGCTGCCGATCTGACCCGTTGGTACAGCGGG GGTTGGAGAGACCCTCGCGGTTATAAATATTGGGGCCAGGGCACCCAGGTGAC CGTCTCCAGC | 414. |
| mIL12Rb2 VHH12 | CAGGTGCAGTTGCAGGAGTCCGGGGCGGGTCGTGCAACCTGGGGGCTCCCT CAGACTGAGCTGTGCTGCCAGCGGGTATACTTTCTCCAACCATCACATGGGAT GGTTCAGGCAGGCCCCTGGTAAGGAACGGGAAGGCGTCGCTGCCATCTACACT GGTGCTGGTAACATCTATTACGCAGACAGCGTCAAAGATCGCTTTACTATCAG CAAGGACACAGCCAAGAATACCCTGTATCTGCAAATGAACTCTCTGACCCCAG AGGACACGGGTATGTATTACTGTGCCGCAGACCTGACTCGGTGGTATAGCGGG GGCTGGAGAGACCCACGGGGCTACAAATACTGGGGTCAGGGCACCCAGGTTAC TGTGAGCAGC | 415. |
| mIL12Rb2 VHH13 | CAAGTGCAACTCCAGGAGTCCGGTGGAGGCAGCGTTCAGGCGGGCGGTAGCCT GCGTCTGTCTTGCGCCGTGAGCGGCTATACCTTTAGCAACCATCACATGGGAT GGTTCCGCCAGGCTCCCGGAAAGGAGAGAGAGGGGGTTGCTGCCATCTACACC | 416. |

TABLE 13-continued anti-mIL 12Rb2 sdAb VHH DNA SEQUENCE

| Name | DNA Sequence | SEQ ID NO. |
|---|---|---|
| | GGAGCCGGTAACATCTACTATGCCGACAGCGTCAAGGACCGTTTCACTATTTC<br>TAAGGACACCGCTAAGAATACTCTCTATCTGCAAATGAACTCTCTTACTCCCG<br>AGGACACCGGCATGTATTACTGCGCTGCCGACCTCACCCGCTGGTATTCAGGG<br>GGCTGGCGCGACCCGCGCGGGTACAAGTATTGGGGACAGGGAACTCAAGTGAC<br>AGTCTCCAGC | |
| mIL12Rb2 VHH14 | CAAGTGCAGCTCCAGGAAAGCGGGGGCGGTAGTGTGCAGGCTGGTGGCAGCCT<br>GAGACTGAGCTGCGCCGCTTCTGGGGCCACTAATTCCAACAGACACATGGGAT<br>GGTTCCGTCAGGCTCCCGGTAAGGAGCGCGAAGGCGTGGCGGCTATTTACACC<br>GGATACACTGGTGGGGGCAACACATATTACGCAGACAGCGTTCGGGATCGGTT<br>CACCATTAGCCAGGATAACGCTAAAAACACACTGTATCTCCAGATGAATAGCC<br>TGACCCCCGAGGACACCGCTATGTATTACTGTGCCGCAGACCTCACACGTTGG<br>TACTCTGGAGGCTGGCGCGACCCTCGTGGCTACAAGTATTGGGGACAGGGCAC<br>ACAAGTGACTGTAAGCTCC | 417. |
| mIL12Rb2 VHH15 | CAGGTCCAGCTCCAGGAGTCTGGCGGTGGCAGCGTACAGGACGGGGGATCACT<br>GCGCCTGTCCTGCGCTGCCAGCGGCGACATTTACGCGAGGAACTGTATGGGAT<br>GGTTCCGCCAGGCCCCCGGCAAAGAGCGCGAAAAGATTGCGGTCGCCGACACA<br>GGCGGGCGTTCTCCCTATTACGCTGACTCCGTGAAGGGACGCTTTACCATCAG<br>TAGGGACAATGCCAAGAACACCGTGGACCTGCAAATGAACTCCCTCAAGCCCG<br>AGGACACCGCCGTGTATTACTGCGCCGCTGGCCCACTGGTGCCTGTGGTCAAT<br>ACAGCTGCCCGCTGCGTGTACGAGTATTGGGGCCAGGGAACCCAGGTGACAGT<br>CTCCTCC | 418. |
| mIL12Rb2 VHH16 | CAGGTGCAGCTCCAAGAGTCCGGTGGAGGCAGTGTGCAGGCCGGGGGCAGTCT<br>GAGGCTTAGCTGTGCAGCGTCCGGTGCCACCAACTCCAATAGGCACATGGGTT<br>GGTTCCGGCAGGCTCCGGGGAAGGAGCGCGAGGGCGTCGCCGCAATCTACACC<br>GGCTACACCGGCGGTGGGAATACATATTACGCCGATTCTGTGAAGGACAGGTT<br>CACAATCTCCCAGGACAACGCCAAGAACACTCTGTATCTCCAGATGAACTCCT<br>TGACCCCCGAGGATACTGCGATGTATTACTGCGCCGCTGACCTGACCAGATGG<br>TACTCTGGCGGATGGCGTGACCCTCGCGGATATAAATACTGGGGGCAGGGCAC<br>CCAGGTCACCGTCTCTAGC | 419. |

It is understood that the embodiments described herein are for illustrative purposes only and that various modifications or changes in light thereof will be suggested to persons skilled in the art and are to be included within the spirit and purview of this application and scope of the appended claims. All publications, patents, patent applications, and the sequences of the sequence accession numbers cited herein are hereby incorporated by reference.

What is claimed is:

1. An IL12 receptor binding molecule that specifically binds to IL12Rb1 and IL12Rb2, wherein the binding molecule comprises a single-domain antibody (sdAb) that specifically binds to IL12Rb1 (an anti-IL12Rb1 sdAb) and a sdAb that specifically binds to IL12Rb2 (an anti-IL12Rb2 sdAb), wherein the anti-IL12Rb1 sdAb and the anti-IL12Rb2 sdAb are joined by a peptide linker that comprises between 1 and 50 amino acids or a covalent bond, or wherein the C-terminus of the anti-IL12Rb1 sdAb is conjugated to a first Fc monomer of an Fc domain and the C-terminus of the anti-IL12Rb2 sdAb is conjugated to a second Fc monomer of the Fc domain, and wherein one of the first and second Fc monomers comprises a knob and the other of the first and second Fc monomers comprises a hole, and wherein the knob and the hole form a knob-into-hole interface and non-covalently associate with each other, wherein the anti-IL12Rb1 sdAb comprises a CDR1, a CDR2, and a CDR3 in a single row of the following table:

| Name | CDR1 | SEQ ID NO: |
|---|---|---|
| hIL12Rb1_VHH1 | YGYCGYDMS | 25 |
| hIL12Rb1_VHH2 | YTYSSAFMA | 26 |
| hIL12Rb1_VHH3 | YSYCGYDMM | 27 |

-continued

| Name | CDR1 | SEQ ID NO: |
|---|---|---|
| hIL12Rb1_VHH4 | YGYCGYDMS | 28 |
| hIL12Rb1_VHH5 | YGYCGYDMS | 29 |
| hIL12Rb1_VHH6 | YTYTNNFMA | 30 |
| hIL12Rb1_VHH7 | YDYCGYDVR | 31 |
| hIL12Rb1_VHH8 | YSYCGYDMM | 32 |
| hIL12Rb1_VHH9 | YSYCGYDMM | 33 |
| hIL12Rb1_VHH10 | YDYCGYDVR | 34 |
| hIL12Rb1_VHH11 | YDYCGYDVR | 35 |
| hIL12Rb1_VHH12 | YTYSSAFMA | 36 |
| hIL12Rb1_VHH13 | YGYCGYDMS | 37 |
| hIL12Rb1_VHH14 | YDYCGYDVR | 38 |
| hIL12Rb1_VHH15 | YDYCGYDVR | 39 |
| hIL12Rb1_VHH16 | YTYSSAFMA | 40 |
| hIL12Rb1_VHH17 | YGYCGYDMS | 41 |
| hIL12Rb1_VHH18 | YTYTNNFMA | 42 |
| hIL12Rb1_VHH19 | YDYCGYDVR | 43 |
| hIL12Rb1_VHH20 | YTYSSAFMA | 44 |
| hIL12Rb1_VHH21 | YTYSSAFMA | 45 |
| hIL12Rb1_VHH22 | YTYSSAFMA | 46 |

| Name | CDR2 | SEQ ID NO: |
|---|---|---|
| hIL12Rb1_VHH1 | LITSDRSISYEDSVKA | 47 |
| hIL12Rb1_VHH2 | AIYTRDGGTVYADSVKG | 48 |
| hIL12Rb1_VHH3 | LITSDYSIRYEDSVEG | 49 |
| hIL12Rb1_VHH4 | LITSDRIASYEDSVKG | 50 |
| hIL12Rb1_VHH5 | LITSDRSVSYEDSVKG | 51 |
| hIL12Rb1_VHH6 | AIYTGDGYAYYFYSVKG | 52 |
| hIL12Rb1_VHH7 | GIDSDGSTSYADSVKG | 53 |
| hIL12Rb1_VHH8 | LITSDYSIRYEDSVEG | 54 |
| hIL12Rb1_VHH9 | LITSDYSIRYEDSVEG | 55 |
| hIL12Rb1_VHH10 | GIDSDGSTSYADSVKG | 56 |
| hIL12Rb1_VHH11 | GIDSDGSTSYADSVKG | 57 |
| hIL12Rb1_VHH12 | AIYTRDGGTVYADSVKG | 58 |
| hIL12Rb1_VHH13 | LITSERVISYEDSVKG | 59 |
| hIL12Rb1_VHH14 | GIDSDGSTSYADSVKG | 60 |
| hIL12Rb1_VHH15 | GINSDGSTSYADSVKG | 61 |
| hIL12Rb1_VHH16 | AMYTRDGGTVYADSVKG | 62 |
| hIL12Rb1_VHH17 | LITSDRSVSYEDSVKG | 63 |
| hIL12Rb1_VHH18 | AIYTGDGYAYYFDSVKG | 64 |
| hIL12Rb1_VHH19 | GINSDGSTSYADSVKG | 65 |
| hIL12Rb1_VHH20 | AIYTRDGSPVYADSLKG | 66 |
| hIL12Rb1_VHH21 | AMYTRDGGTVYADSVKG | 67 |
| hIL12Rb1_VHH22 | AIYTRDGGTVYADSVKG | 68 |

| Name | CDR3 | SEQ ID NO: |
|---|---|---|
| hIL12Rb1_VHH1 | SAAARESSWCRSRYRVAS | 69 |
| hIL12Rb1_VHH2 | KIPQPGRASLLDSQTYDY | 70 |
| hIL12Rb1_VHH3 | STAARESSWCRSRYRVAS | 71 |
| hIL12Rb1_VHH4 | SAAARENSWCRSRYRVAS | 72 |
| hIL12Rb1_VHH5 | STAARENNWCRSRYRIAY | 73 |
| hIL12Rb1_VHH6 | MERRIGTRRMTENAEYKY | 74 |
| hIL12Rb1_VHH7 | ESPAGESAWCRNFRGMDY | 75 |
| hIL12Rb1_VHH8 | STAARESSWCRSRYRVAS | 76 |
| hIL12Rb1_VHH9 | STAARESGWCRSRYRVAS | 77 |
| hIL12Rb1_VHH10 | ESPAGESAWCRNERGMDY | 78 |
| hIL12Rb1_VHH11 | ESPAGESAWCRNFRGMDY | 79 |
| hIL12Rb1_VHH12 | KMPQPGRASLLDSQTYDY | 80 |
| hIL12Rb1_VHH13 | SAAARESSWCRSRYRVAS | 81 |
| hIL12Rb1_VHH14 | ESPAGESAWCRNFRGMDY | 82 |
| hIL12Rb1_VHH15 | ESPAGESAWCRNFRGMDY | 83 |
| hIL12Rb1_VHH16 | KIPQPGRASLLDSQTYDY | 84 |
| hIL12Rb1_VHH17 | STAARENNWCRSRYRIAS | 85 |
| hIL12Rb1_VHH18 | MERRSGRRRMTENAEYKY | 86 |
| hIL12Rb1_VHH19 | EGPAGESAWCRNFRGMDY | 87 |
| hIL12Rb1_VHH20 | KIPEPGRISLLDSQTYDY | 88 |
| hIL12Rb1_VHH21 | KIPQPGRASLLDSQTYDY | 89 |
| hIL12Rb1_VHH22 | KIPQPGRASLLDSQTYDY | 90 | and wherein the anti-IL12Rb2 sdAb comprises a CDR1, a CDR2, and a CDR3 in a single row of the following table:

| Name | CDR1 | SEQ ID NO: |
|---|---|---|
| hIL12Rb2_VHH1 | FTVTRYCMG | 160 |
| hIL12Rb2_VHH2 | FTISRYCMG | 161 |
| hIL12Rb2_VHH3 | LTFDDVEMA | 162 |
| hIL12Rb2_VHH4 | FTISRYCMG | 163 |
| hIL12Rb2_VHH5 | FTFSTYAMS | 164 |
| hIL12Rb2_VHH6 | YTYGLFCMG | 165 |
| hIL12Rb2_VHH7 | VTYSRYCMG | 166 |

| Name | CDR2 | SEQ ID NO: |
|---|---|---|
| hIL12Rb2_VHH8 | FTVSRYCMG | 167 |
| hIL12Rb2_VHH9 | FTISRYCMG | 168 |
| hIL12Rb2_VHH10 | FTVTRYCMG | 169 |
| hIL12Rb2_VHH11 | FTVSRYCMG | 170 |
| hIL12Rb2_VHH12 | VTYSRYCMG | 171 |
| hIL12Rb2_VHH13 | FTISKYCMG | 172 |
| hIL12Rb2_VHH14 | VTYSRYCMG | 173 |
| hIL12Rb2_VHH15 | FTISRYCMG | 174 |
| hIL12Rb2_VHH16 | VTYSRYCMG | 175 |
| hIL12Rb2_VHH17 | LTISRYCMG | 176 |
| hIL12Rb2_VHH18 | FTVDDFAMG | 177 |

| Name | CDR2 | SEQ ID NO: |
|---|---|---|
| hIL12Rb2_VHH1 | IIERDGRTGYADSVKG | 178 |
| hIL12Rb2_VHH2 | IIERDGRTGYADSVKG | 179 |
| hIL12Rb2_VHH3 | SINTDSRVYYVDSVKD | 180 |
| hIL12Rb2_VHH4 | IIERDGRTGYADSVKG | 181 |
| hIL12Rb2_VHH5 | RISSGGGNTYYADAVKG | 182 |
| hIL12Rb2_VHH6 | VVDSPGGRHVADSLKG | 183 |
| hIL12Rb2_VHH7 | TIYSRGIITYYTDSVKG | 184 |
| hIL12Rb2_VHH8 | IIEREGRTGYADSVKG | 185 |
| hIL12Rb2_VHH9 | IIERDGRTGYADSVKG | 186 |
| hIL12Rb2_VHH10 | IIERDGRTGYADSVKG | 187 |
| hIL12Rb2_VHH11 | IIERDGRTGYADSVKG | 188 |
| hIL12Rb2_VHH12 | TIYSRGIITYYTDSVKG | 189 |
| hIL12Rb2_VHH13 | IIERDGRTGYADSVKG | 190 |
| hIL12Rb2_VHH14 | HIYSRGIITYYTDSVKG | 191 |
| hIL12Rb2_VHH15 | IIERDGRTGYADSVKG | 192 |
| hIL12Rb2_VHH16 | HIYSRGIITYYTDSVKG | 193 |
| hIL12Rb2_VHH17 | IIERDGRTGYADSVKG | 194 |
| hIL12Rb2_VHH18 | TISSGGSTYYADSVKG | 195 |

| Name | CDR3 | SEQ ID NO: |
|---|---|---|
| hIL12Rb2_VHH1 | IEGSCRPDFGY | 196 |
| hIL12Rb2_VHH2 | IEGSCRPDFGY | 197 |
| hIL12Rb2_VHH3 | DPWGGDLRGYPNY | 198 |
| hIL12Rb2_VHH4 | IEGSCRPDFGY | 199 |
| hIL12Rb2_VHH5 | DDYYGGSWHPIS | 200 |
| hIL12Rb2_VHH6 | DPEKYCFLESDAGYQY | 201 |
| hIL12Rb2_VHH7 | TRETYGGSGDCDYESVYNY | 202 |
| hIL12Rb2_VHH8 | IEGSCRPDFGY | 203 |
| hIL12Rb2_VHH9 | IEGSCRPDFGY | 204 |
| hIL12Rb2_VHH10 | IEGSCRPDFGY | 205 |
| hIL12Rb2_VHH11 | IEGSCRPDFGY | 206 |
| hIL12Rb2_VHH12 | TRETYGGSGDCDYESVYNY | 207 |
| hIL12Rb2_VHH13 | IEGSCRPDFGY | 208 |
| hIL12Rb2_VHH14 | TRETYGGSGDCGYESVYNY | 209 |
| hIL12Rb2_VHH15 | IEGSCRPDLGY | 210 |
| hIL12Rb2_VHH16 | TRETYGGSGDCSYESVYNH | 211 |
| hIL12Rb2_VHH17 | IEGSCRPDFGY | 212 |
| hIL12Rb2_VHH18 | SSVGCPLGY | 213. |

2. The IL12 receptor binding molecule of claim 1, wherein the peptide linker comprises a sequence of GGGS (SEQ ID NO:13).

3. The IL12 receptor binding molecule of claim 1, wherein the binding molecule comprises an anti-IL12Rb1 sdAb linked to the N-terminus of the peptide linker and an anti-IL12Rb2 sdAb linked to the C-terminus of the peptide linker.

4. The IL12 receptor binding molecule of claim 3, wherein the anti-IL12Rb1 sdAb comprises a sequence having at least 90% sequence identity to a sequence of the following table:

| Name | Sequence | SEQ ID NO: |
|---|---|---|
| hIL12Rb1_VHH1 | QVQLQESGGGSVQAGGSLRLSCVASGYGYCGYDMSWYRQAPGKEREFVALITSDRSISY EDSVKARFIISRDNAANTGYLDMTRLTPDDTAIYYCKTSAAARESSWCRSRYRVASWGQ GTQVTVSS | 262 |
| hIL12Rb1_VHH2 | QVQLQESGGGSVQAGGSLRLSCTASGYTYSSAFMAWFRQAPGKEREGVAAIYTRDGGTV YADSVKGRFTISQDNAKNILYLQMNSLKAEDTAMYYCAAKIPQPGRASLLDSQTYDYWG QGTQVTVSS | 263 |
| hIL12Rb1_VHH3 | QVQLQESGGGSVQAGGSLRLSCVASGYSYCGYDMMWYRQAPGKEREFVALITSDYSIRY EDSVEGRESISRDNAKNTGYLLMSNLTPADTAIYYCKTSTAARESSWCRSRYRVASWGQ GTQVTVSS | 264 |

-continued

| Name | Sequence | SEQ ID NO: |
|---|---|---|
| hIL12Rb1_VHH4 | QVQLQESGGGSVQAGGSLRLSCVASGYGYCGYDMSWYRQTPGKEREFVALITSDRIASYEDSVKGRFIISRDNAKNTGYLDMTRVTPDDTAIYYCKTSAAARENSWCRSRYRVASWGQGTQVTVSS | 265 |
| hIL12Rb1_VHH5 | QVQLQESGGGSVQAGGFLRLSCVASGYGYCGYDMSWYRQVPGKEREFVALITSDRSVSYEDSVKGRFSISRDNAKNTAYLEMNRLTPDDTAVYYCKTSTAARENNWCRSRYRIAYWGQGTQVTVSS | 266 |
| hIL12Rb1_VHH6 | QVQLQESGGGSVQAGGSLRLSCAASRYTYTNNFMAWFRQAPGKEREGVAAIYTGDGYAYYFYSVKGRFTISQDNDENMLYLQMNSLKPEDTAMYYCAAMERRIGTRRMTENAEYKYWGQGTQVTVSS | 267 |
| hIL12Rb1_VHH7 | QVQLQESGGGSVQAGGSLRLSCAVSGYDYCGYDVRWYRRAPGKEREFVSGIDSDGSTSYADSVKGRFTISQDNAENTSYLHMFSLKPEDTAMYYCKTESPAGESAWCRNFRGMDYWGKGTQVTVSS | 268 |
| hIL12Rb1_VHH8 | QVQLQESGGGSVQAGGSLRLSCVASGYSYCGYDMMWYRQAPGKEREFVALITSDYSIRYEDSVEGRESISRDNAKNTGYLLMSNLTPADTAIYYCKTSTAARESSWCRSRYRVASWGQGTQVTVSS | 269 |
| hIL12Rb1_VHH9 | QVQLQESGGGSVQAGGSLRLSCVASGYSYCGYDMMWYRQAPGKEREFVALITSDYSIRYEDSVEGRFSISRDNAKNTGYLLMSNLTPADTAIYYCKTSTAARESGWCRSRYRVASWGQGTQVTVSS | 270 |
| hIL12Rb1_VHH10 | QVQLQESGGGSVQAGGSLRLSCAVSGYDYCGYDVRWYRQAPGKEREFVSGIDSDGSTSYADSVKGRFTISQDNAENTSYLHMFSLKPEDTAMYYCKTESPAGESAWCRNFRGMDYWGKGTQVTVSS | 271 |
| hIL12Rb1_VHH11 | QVQLQESGGGSVQAGGSLRLSCAVSGYDYCGYDVRWYRQAPGKEREFVSGIDSDGSTSYADSVKGRFTISQDNAENTSYLHMFSLKPEDTAMYYCKTESPAGESAWCRNFRGMDYWGKGTQVTVSS | 272 |
| hIL12Rb1_VHH12 | QVQLQESGGGSVQAGGSLRLSCTASGYTYSSAFMAWFRQAPGKEREGVAAIYTRDGGTVYADSVKGRFTISQDNAKNTLYLQMNSLKPEDTAMYYCAAKMPQPGRASLLDSQTYDYWGQGTQVTVSS | 273 |
| hIL12Rb1_VHH13 | QVQLQESGGGSVQAGGFLRLSCVASGYGYCGYDMSWYRQAPGKEREFVALITSERVISYEDSVKGRFSISRDNAENTGYLEMNRLTPDDTAIYYCKTSAAARESSWCRSRYRVASWGQGTQVTVSS | 274 |
| hIL12Rb1_VHH14 | QVQLQESGGGSVQAGGSLRLSCAVSGYDYCGYDVRWYRRAPGKEREFVSGIDSDGSTSYADSVKGRFTISQDNAENTSYLHMFSLKPEDTAMYYCKTESPAGESAWCRNFRGMDYWGKGTQVTVSS | 275 |
| hIL12Rb1_VHH15 | QVQLQESGGGSVQAGGSLRLSCAVSGYDYCGYDVRWYRQAPGKEREFVSGINSDGSTSYADSVKGRFTISQDNAENTSYLHMFSLKPEDTAMYYCKTESPAGESAWCRNFRGMDYWGKGTQVTVSS | 276 |
| hIL12Rb1_VHH16 | QVQLQESGGGSVQAGGSLRLSCTASGYTYSSAFMAWFRQAPGKEREGVAAMYTRDGGTVYADSVKGRFTISQDNAKNTLYLQIHTLKAEDTAMYYCAAKIPQPGRASLLDSQTYDYWGQGTQVTVSS | 277 |
| hIL12Rb1_VHH17 | QVQLQESGGGSVQAGGFLRLSCVASGYGYCGYDMSWYRQVPGKEREFVALITSDRSVSYEDSVKGRFSISRDNAKNTAYLEMNRLTPDDTAIYYCKTSAAARENNWCRSRYRIASWGQGTQVTVSS | 278 |
| hIL12Rb1_VHH18 | QVQLQESGGGSVQAGGSLRLSCAASRYTYTNNFMAWFRQAPGKEREGVAAIYTGDGYAYYFDSVKGRFTISQDNDKNMLYLQMNSLKPEDTAMYYCAAMERRSGRRRMTENAEYKYWGQGTQVTVSS | 279 |
| hIL12Rb1_VHH19 | QVQLQESGGGSVQAGGSLRLSCAVSGYDYCGYDVRWYRQAPGKEREFVSGINSDGSTSYADSVKGRFTISQDNAENTSYLHMFSLKPEDTAMYYCKTEGPAGESAWCRNFRGMDYWGKGTQVTVSS | 280 |
| hIL12Rb1_VHH20 | QVQLQESGGGSVQAGGSLRLSCTASGYTYSSAFMAWFRQAPGKEREGVAAIYTRDGSPVYADSLKGRFTISQDNAKNTLHLQMNSLKPEDTAMYYCAAKIPEPGRISLLDSQTYDYWHGTQVTVSS | 281 |
| hIL12Rb1_VHH21 | QVQLQESGGGSVQAGGSLRLSCTASGYTYSSAFMAWFRQAPGKEREGVAAMYTRDGGTVYADSVKGRFTISQDNAKNTLYLQMNSLKTEDTAMYYCAAKIPQPGRASLLDSQTYDYWGQGTQVTVSS | 282 |

| Name | Sequence | SEQ ID NO: |
|---|---|---|
| hIL12Rb1_VHH22 | QVQLQESGGGSVQAGGSLRLSCTASGYTYSSAFMAWERQAPGKEREGVAAIYTRDGGTVYADSVKGRFTISQDNAKNTLYLQMNSLKAEDTAMYYCAAKIPQPGRASLLDSQTYDYWGQGTQVTVSS. | 283 |

5. The IL12 receptor binding molecule of claim 4, wherein the anti-IL12Rb1 sdAb comprises a sequence of any one of SEQ ID NOS: 262-283.

6. The IL12 receptor binding molecule of claim 3, wherein the anti-IL12Rb2 sdAb comprises a sequence having at least 90% sequence identity to a sequence of the following table:

| Name | Sequence | SEQ ID NO: |
|---|---|---|
| hIL12Rb2_VHH1 | QVQLQESGGGSVQAGGSLRLSCAASGFTVTRYCMGWLRQAPGKQREGVAIIERDGRTGYADSVKGRFTISKDNAKNTLYLOMNSLKPEDTAMYYCGAIEGSCRPDFGYRGQGTQVTVSS | 307 |
| hIL12Rb2_VHH2 | QVQLQESGGGSVQAGGSLRLSCAASGFTISRYCMGWLRQAPGKQREGVAIIERDGRTGYADSVKGRFTISKDNAKNTLYLQMNSLKPEDTAMYYCGAIEGSCRPDFGYRGQGTQVTVSS | 308 |
| hIL12Rb2_VHH3 | QVQLQESGGGSVQAGGSLRLSCTASGLTEDDVEMAWYRQGPGDDYDLVSSINTDSRVYYVDSVKDRFTISRDNAKNTLYLQMNNLKPEDTAVYYCAADPWGGDLRGYPNYWGQGTQVTVSS | 309 |
| hIL12Rb2_VHH4 | QVQLQESGGGSVQAGGSLRLSCVASGFTISRYCMGWLRQAPGKQREGVAIIERDGRTGYADSVKGRFTISKDNAKNTLYLQMNSLKPGDTAMYYCGAIEGSCRPDFGYRGQGTQVTVSS | 310 |
| hIL12Rb2_VHH5 | QVQLQESGGGLVQPGGSLKLSCAASGFTESTYAMSWVRQAPGKEPEWISRISSGGGNTYYADAVKGRFAISRDNAKNTLYLQLNSLKTEDTAIYVCTMDDYYGGSWHPISRGHGTQVTVSS | 311 |
| hIL12Rb2_VHH6 | QVQLQESGGGLVQAGGSLRLSCQASGYTYGLFCMGWFRQVSGKKREGVAVVDSPGGRHVADSLKGRFTISKDNANNILYLDMTNLKSEDTATYYCAADPEKYCFLFSDAGYQYWGQGTQVTVSS | 312 |
| hIL12Rb2_VHH7 | QVQLQESGGGSVQAGGSLRLSCAASGVTYSRYCMGWFRQAPGLERERVATIYSRGIITYYTDSVKGRFTISQDSAKKTVYLQMNSLKPEDTAMYYCAATRETYGGSGDCDYESVYNYWAQGTQVTVSS | 313 |
| hIL12Rb2_VHH8 | QVQLQESGGGSVQAGGSLRLSCAASGFTVSRYCMGWLRQAPGKQREGVAIIEREGRTGYADSVKGRFTISKDNAKNTLYLQMNSLKPEDTAMYYCGAIEGSCRPDFGYRGQGTQVTVSS | 314 |
| hIL12Rb2_VHH9 | QVQLQESGGGSVQAGGSLRLSCAASGFTISRYCMGWLRQAPGKQREGVAIIERDGRTGYADSVKGRFTISKDNAKNTLYLOMNSLKPEDTAMYFCGAIEGSCRPDFGYRGQGTQVTVSS | 315 |
| hIL12Rb2_VHH10 | QVQLQESGGGSVQAGGSLRLSCAASGFTVTRYCMGWLRQAPGKQREGVAIIERDGRTGYADSVKGRFTISKDNAKNTLYLQMNSLKPEDTAMYYCGAIEGSCRPDFGYRGQGTQVTVSS | 316 |
| hIL12Rb2_VHH11 | QVQLQESGGGSVQAGGSLRLSCAASGFTVSRYCMGWLRQAPGKQREGVAIIERDGRTGYADSVKGRFTISKDDAKNTLYLQMNSLKPEDTAMYYCGAIEGSCRPDFGYRGQGTQVTVSS | 317 |
| hIL12Rb2_VHH12 | QVQLQESGGGSVQAGGSLRLSCAASGVTYSRYCMGWFRQAPGLERERVATIYSRGIITYYTDSVKGRFTISQDSAKKTVYLQMNMLKPEDTAMYYCAATRETYGGSGDCDYESVYNYWAQGTQVTVSS | 318 |
| hIL12Rb2_VHH13 | QVQLQESGGGSVQAGGSLRLSCAASGFTISKYCMGWLRQAPGKQREGVAIIERDGRTGYADSVKGRFTISKDNAKNTLYLQMNSLKPEDTAMYYCGAIEGSCRPDFGYRGQGTQVTVSS | 319 |
| hIL12Rb2_VHH14 | QVQLQESGGGSVQAGGSLRLSCAASGVTYSRYCMGWFRQAPGLERERVAHIYSRGIITYYTDSVKGRFTISQDSAKKTVYLQMNSLKPEDTAMYYCAATRETYGGSGDCGYESVYNYWAQGTQVTVSS | 320 |

| Name | Sequence | SEQ ID NO: |
|---|---|---|
| hIL12Rb2_VHH15 | QVQLQESGGGSVQAGGSLRLSCAASGFTISRYCMGWLRQAPGKQREGVAIIER DGRTGYADSVKGRFTISKDNAKNTLYLQMNSLKPEDTAMYYCGAIEGSCRPDL GYRGQGTQVTVSS | 321 |
| hIL12Rb2_VHH16 | QVQLQESGGGSVQAGGSLRLSCAASGVTYSRYCMGWFRQAPGLERERVAHIYS RGIITYYTDSVKGRFTISQDSAKKTVYLQMNSLKPEDTAMYYCAATRETYGGS GDCSYESVYNHWAQGTQVTVSS | 322 |
| hIL12Rb2_VHH17 | QVQLQESGGGSVQAGGSLRLSCAASGLTISRYCMGWLRQAPGKQREGVAIIER DGRTGYADSVKGRFTISKDNAKNTLYLQMNSLKPEDTAMYYCGAIEGSCRPDF GYRGQGTQVTVSS | 323 |
| hIL12Rb2_VHH18 | QVQLQESGGGSVQAGGSLRLSCSASGFTVDDFAMGWYRQAPGNECELVSTISS GGSTYYADSVKGRFTISQDSAKNTVYLQMNSLKPEDTAVYYCAPSSVGCPLGY WGQGTQVTVSS. | 324 |

7. The IL12 receptor binding molecule of claim 6, wherein the anti-IL12Rb2 sdAb comprises a sequence of any one of SEQ ID NOS: 307-324.

8. The IL12 receptor binding molecule of claim 3, wherein the anti-IL12Rb1 sdAb comprises a sequence having at least 90% sequence identity to a sequence of the following table:

| Name | Sequence | SEQ ID NO: |
|---|---|---|
| hIL12Rb1_VHH1 | QVQLQESGGGSVQAGGSLRLSCVASGYGYCGYDMSWYRQAPGKEREFVALITSDRSISY EDSVKARFIISRDNAANTGYLDMTRLTPDDTAIYYCKTSAAARESSWCRSRYRVASWGQ GTQVTVSS | 262 |
| hIL12Rb1_VHH2 | QVQLQESGGGSVQAGGSLRLSCTASGYTYSSAFMAWFRQAPGKEREGVAAIYTRDGGTV YADSVKGRFTISQDNAKNILYLQMNSLKAEDTAMYYCAAKIPQPGRASLLDSQTYDYWG QGTQVTVSS | 263 |
| hIL12Rb1_VHH3 | QVQLQESGGGSVQAGGSLRLSCVASGYSYCGYDMMWYRQAPGKEREFVALITSDYSIRY EDSVEGRFSISRDNAKNTGYLLMSNLTPADTAIYYCKTSTAARESSWCRSRYRVASWGQ GTQVTVSS | 264 |
| hIL12Rb1_VHH4 | QVQLQESGGGSVQAGGSLRLSCVASGYGYCGYDMSWYRQTPGKEREFVALITSDRIASY EDSVKGRFIISRDNAKNTGYLDMTRVTPDDTAIYYCKTSAAARENSWCRSRYRVASWGQ GTQVTVSS | 265 |
| hIL12Rb1_VHH5 | QVQLQESGGGSVQAGGFLRLSCVASGYGYCGYDMSWYRQVPGKEREFVALITSDRSVSY EDSVKGRESISRDNAKNTAYLEMNRLTPDDTAVYYCKTSTAARENNWCRSRYRIAYWGQ GTQVTVSS | 266 |
| hIL12Rb1_VHH6 | QVQLQESGGGSVQAGGSLRLSCAASRYTYTNNEMAWFRQAPGKEREGVAAIYTGDGYAY YFYSVKGRFTISQDNDENMLYLQMNSLKPEDTAMYYCAAMERRIGTRRMTENAEYKYWG QGTQVTVSS | 267 |
| hIL12Rb1_VHH7 | QVQLQESGGGSVQAGGSLRLSCAVSGYDYCGYDVRWYRRAPGKEREFVSGIDSDGSTSY ADSVKGRFTISQDNAENTSYLHMFSLKPEDTAMYYCKTESPAGESAWCRNFRGMDYWGK GTQVTVSS | 268 |
| hIL12Rb1_VHH8 | QVQLQESGGGSVQAGGSLRLSCVASGYSYCGYDMMWYRQAPGKEREFVALITSDYSIRY EDSVEGRESISRDNAKNTGYLLMSNLTPADTAIYYCKTSTAARESSWCRSRYRVASWGQ GTQVTVSS | 269 |
| hIL12Rb1_VHH9 | QVQLQESGGGSVQAGGSLRLSCVASGYSYCGYDMMWYRQAPGKEREFVALITSDYSIRY EDSVEGRESISRDNAKNTGYLLMSNLTPADTAIYYCKTSTAARESGWCRSRYRVASWGQ GTQVTVSS | 270 |
| hIL12Rb1_VHH10 | QVQLQESGGGSVQAGGSLRLSCAVSGYDYCGYDVRWYRQAPGKEREFVSGIDSDGSTSY ADSVKGRFTISQDNAENTSYLHMFSLKPEDTAMYYCKTESPAGESAWCRNFRGMDYWGK GTQVTVSS | 271 |
| hIL12Rb1_VHH11 | QVQLQESGGGSVQAGGSLRLSCAVSGYDYCGYDVRWYRQAPGKEREFVSGIDSDGSTSY ADSVKGRFTISQDNAENTSYLHMFSLKPEDTAMYYCKTESPAGESAWCRNFRGMDYWGK GTQVTVSS | 272 |

-continued

| Name | Sequence | SEQ ID NO: |
|---|---|---|
| hIL12Rb1_VHH12 | QVQLQESGGGSVQAGGSLRLSCTASGYTYSSAFMAWFRQAPGKEREGVAAIYTRDGGTVYADSVKGRFTISQDNAKNTLYLQMNSLKPEDTAMYYCAAKMPQPGRASLLDSQTYDYWGQGTQVTVSS | 273 |
| hIL12Rb1_VHH13 | QVQLQESGGGSVQAGGFLRLSCVASGYGYCGYDMSWYRQAPGKEREFVALITSERVISYEDSVKGRESISRDNAENTGYLEMNRLTPDDTAIYYCKTSAAARESSWCRSRYRVASWGQGTQVTVSS | 274 |
| hIL12Rb1_VHH14 | QVQLQESGGGSVQAGGSLRLSCAVSGYDYCGYDVRWYRRAPGKEREFVSGIDSDGSTSYADSVKGRFTISQDNAENTSYLHMFSLKPEDTAMYYCKTESPAGESAWCRNFRGMDYWGKGTQVTVSS | 275 |
| hIL12Rb1_VHH15 | QVQLQESGGGSVQAGGSLRLSCAVSGYDYCGYDVRWYRQAPGKEREFVSGINSDGSTSYADSVKGRFTISQDNAENTSYLHMFSLKPEDTAMYYCKTESPAGESAWCRNFRGMDYWGKGTQVTVSS | 276 |
| hIL12Rb1_VHH16 | QVQLQESGGGSVQAGGSLRLSCTASGYTYSSAFMAWFRQAPGKEREGVAAMYTRDGGTVYADSVKGRFTISQDNAKNTLYLQIHTLKAEDTAMYYCAAKIPQPGRASLLDSQTYDYWGQGTQVTVSS | 277 |
| hIL12Rb1_VHH17 | QVQLQESGGGSVQAGGFLRLSCVASGYGYCGYDMSWYRQVPGKEREFVALITSDRSVSYEDSVKGRFSISRDNAKNTAYLEMNRLTPDDTAIYYCKTSTAARENNWCRSRYRIASWGQGTQVTVSS | 278 |
| hIL12Rb1_VHH18 | QVQLQESGGGSVQAGGSLRLSCAASRYTYTNNEMAWFRQAPGKEREGVAAIYTGDGYAYYFDSVKGRFTISQDNDKNMLYLQMNSLKPEDTAMYYCAAMERRSGRRRMTENAEYKYWGQGTQVTVSS | 279 |
| hIL12Rb1_VHH19 | QVQLQESGGGSVQAGGSLRLSCAVSGYDYCGYDVRWYRQAPGKEREFVSGINSDGSTSYADSVKGRFTISQDNAENTSYLHMFSLKPEDTAMYYCKTEGPAGESAWCRNFRGMDYWGKGTQVTVSS | 280 |
| hIL12Rb1_VHH20 | QVQLQESGGGSVQAGGSLRLSCTASGYTYSSAFMAWFRQAPGKEREGVAAIYTRDGSPVYADSLKGRFTISQDNAKNTLHLQMNSLKPEDTAMYYCAAKIPEPGRISLLDSQTYDYWHGTQVTVSS | 281 |
| hIL12Rb1_VHH21 | QVQLQESGGGSVQAGGSLRLSCTASGYTYSSAFMAWFRQAPGKEREGVAAMYTRDGGTVYADSVKGRFTISQDNAKNTLYLOMNSLKTEDTAMYYCAAKIPQPGRASLLDSQTYDYWGQGTQVTVSS | 282 |
| hIL12Rb1_VHH22 | QVQLQESGGGSVQAGGSLRLSCTASGYTYSSAFMAWFRQAPGKEREGVAAIYTRDGGTVYADSVKGRFTISQDNAKNTLYLOMNSLKAEDTAMYYCAAKIPQPGRASLLDSQTYDYWGQGTQVTVSS | 283 | and the anti-IL12Rb2 sdAb comprises a sequence having at least 90% sequence identity to a sequence of the following table:

| Name | Sequence | SEQ ID NO: |
|---|---|---|
| hIL12Rb2_VHH1 | QVQLQESGGGSVQAGGSLRLSCAASGFTVTRYCMGWLRQAPGKQREGVAIIERDGRTGYADSVKGRFTISKDNAKNTLYLQMNSLKPEDTAMYYCGAIEGSCRPDFGYRGQGTQVTVSS | 307 |
| hIL12Rb2_VHH2 | QVQLQESGGGSVQAGGSLRLSCAASGFTISRYCMGWLRQAPGKQREGVAIIERDGRTGYADSVKGRFTISKDNAKNTLYLQMNSLKPEDTAMYYCGAIEGSCRPDFGYRGQGTQVTVSS | 308 |
| hIL12Rb2_VHH3 | QVQLQESGGGSVQAGGSLRLSCTASGLTFDDVEMAWYRQGPGDDYDLVSSINTDSRVYYVDSVKDRFTISRDNAKNTLYLQMNNLKPEDTAVYYCAADPWGGDLRGYPNYWGQGTQVTVSS | 309 |
| hIL12Rb2_VHH4 | QVQLQESGGGSVQAGGSLRLSCVASGFTISRYCMGWLRQAPGKQREGVAIIERDGRTGYADSVKGRFTISKDNAKNTLYLQMNSLKPGDTAMYYCGAIEGSCRPDFGYRGQGTQVTVSS | 310 |
| hIL12Rb2_VHH5 | QVQLQESGGGLVQPGGSLKLSCAASGFTESTYAMSWVRQAPGKEPEWISRISSGGGNTYYADAVKGRFAISRDNAKNTLYLQLNSLKTEDTAIYVCTMDDYYGGSWHPISRGHGTQVTVSS | 311 |

-continued

| Name | Sequence | SEQ ID NO: |
|---|---|---|
| hIL12Rb2_VHH6 | QVQLQESGGGLVQAGGSLRLSCQASGYTYGLFCMGWFRQVSGKKREGVAVVDS PGGRHVADSLKGRFTISKDNANNILYLDMTNLKSEDTATYYCAADPEKYCFLF SDAGYQYWGQGTQVTVSS | 312 |
| hIL12Rb2_VHH7 | QVQLQESGGGSVQAGGSLRLSCAASGVTYSRYCMGWFRQAPGLERERVATIYS RGIITYYTDSVKGRFTISQDSAKKTVYLQMNSLKPEDTAMYYCAATRETYGGS GDCDYESVYNYWAQGTQVTVSS | 313 |
| hIL12Rb2_VHH8 | QVQLQESGGGSVQAGGSLRLSCAASGFTVSRYCMGWLRQAPGKQREGVAIIER EGRTGYADSVKGRFTISKDNAKNTLYLQMNSLKPEDTAMYYCGAIEGSCRPDF GYRGQGTQVTVSS | 314 |
| hIL12Rb2_VHH9 | QVQLQESGGGSVQAGGSLRLSCAASGFTISRYCMGWLRQAPGKQREGVAIIER DGRTGYADSVKGRFTISKDNAKNTLYLQMNSLKPEDTAMYFCGAIEGSCRPDF GYRGQGTQVTVSS | 315 |
| hIL12Rb2_VHH10 | QVQLQESGGGSVQAGGSLRLSCAASGFTVTRYCMGWLRQAPGKQREGVAIIER DGRTGYADSVKGRFTISKDNAKNTLYLQMNSLKPEDTAMYYCGAIEGSCRPDF GYRGQGTQVTVSS | 316 |
| hIL12Rb2_VHH11 | QVQLQESGGGSVQAGGSLRLSCAASGFTVSRYCMGWLRQAPGKQREGVAIIER DGRTGYADSVKGRFTISKDDAKNTLYLQMNSLKPEDTAMYYCGAIEGSCRPDF GYRGQGTQVTVSS | 317 |
| hIL12Rb2_VHH12 | QVQLQESGGGSVQAGGSLRLSCAASGVTYSRYCMGWERQAPGLERERVATIYS RGIITYYTDSVKGRFTISQDSAKKTVYLQMNMLKPEDTAMYYCAATRETYGGS GDCDYESVYNYWAQGTQVTVSS | 318 |
| hIL12Rb2_VHH13 | QVQLQESGGGSVQAGGSLRLSCAASGFTISKYCMGWLRQAPGKQREGVAIIER DGRTGYADSVKGRFTISKDNAKNTLYLQMNSLKPEDTAMYYCGAIEGSCRPDF GYRGQGTQVTVSS | 319 |
| hIL12Rb2_VHH14 | QVQLQESGGGSVQAGGSLRLSCAASGVTYSRYCMGWFRQAPGLERERVAHIYS RGIITYYTDSVKGRFTISQDSAKKTVYLQMNSLKPEDTAMYYCAATRETYGGS GDCGYESVYNYWAQGTQVTVSS | 320 |
| hIL12Rb2_VHH15 | QVQLQESGGGSVQAGGSLRLSCAASGFTISRYCMGWLRQAPGKQREGVAIIER DGRTGYADSVKGRFTISKDNAKNTLYLQMNSLKPEDTAMYYCGAIEGSCRPDL GYRGQGTQVTVSS | 321 |
| hIL12Rb2_VHH16 | QVQLQESGGGSVQAGGSLRLSCAASGVTYSRYCMGWFRQAPGLERERVAHIYS RGIITYYTDSVKGRFTISQDSAKKTVYLQMNSLKPEDTAMYYCAATRETYGGS GDCSYESVYNHWAQGTQVTVSS | 322 |
| hIL12Rb2_VHH17 | QVQLQESGGGSVQAGGSLRLSCAASGLTISRYCMGWLRQAPGKQREGVAIIER DGRTGYADSVKGRFTISKDNAKNTLYLQMNSLKPEDTAMYYCGAIEGSCRPDF GYRGQGTQVTVSS | 323 |
| hIL12Rb2_VHH18 | QVQLQESGGGSVQAGGSLRLSCSASGFTVDDFAMGWYRQAPGNECELVSTISS GGSTYYADSVKGRFTISQDSAKNTVYLQMNSLKPEDTAVYYCAPSSVGCPLGY WGQGTQVTVSS. | 324 |

9. The IL12 receptor binding molecule of claim 8, wherein the anti-IL12Rb1 sdAb comprises a sequence of any one of SEQ ID NOS: 262-283 and the anti-IL12Rb2 sdAb comprises a sequence of any one of SEQ ID NOS: 307-324.

10. The IL12 receptor binding molecule of claim 1, wherein the binding molecule comprises an anti-IL12Rb2 sdAb linked to the N-terminus of the peptide linker and an anti-IL12Rb1 sdAb linked to the C-terminus of the peptide linker.

11. A pharmaceutical composition comprising the IL12 receptor binding molecule of claim 1 and a pharmaceutically acceptable carrier.

12. The IL12 receptor binding molecule of claim 1, wherein the anti-IL12Rb1 sdAb and the anti-IL12Rb2 sdAb are joined by a peptide linker that comprises between 1 and 50 amino acids.

* * * * *